(12) United States Patent
Srinivasan et al.

(10) Patent No.: US 11,491,152 B2
(45) Date of Patent: *Nov. 8, 2022

(54) METHODS OF TREATING LUNG CANCER WITH CYP3A4 SUBSTRATE DRUGS

(71) Applicant: BOW RIVER LLC, Corona Del Mar, CA (US)

(72) Inventors: Sundar Srinivasan, Corona Del Mar, CA (US); Christina Chow Wallen, Seattle, WA (US)

(73) Assignee: BOW RIVER LLC, Corona Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/700,947

(22) Filed: Mar. 22, 2022

(65) Prior Publication Data

US 2022/0211685 A1  Jul. 7, 2022

Related U.S. Application Data

(60) Continuation of application No. 17/469,628, filed on Sep. 8, 2021, now Pat. No. 11,351,160, which is a continuation-in-part of application No. 17/244,065, filed on Apr. 29, 2021, now Pat. No. 11,154,545, which is a continuation of application No. 17/150,467, filed on Jan. 15, 2021, now Pat. No. 11,052,077, which is a continuation of application No. 17/082,902, filed on Oct. 28, 2020, which is a continuation of application No. 16/408,931, filed on May 10, 2019, now Pat. No. 10,857,144, which is a continuation-in-part of application No. 15/596,585, (Continued)

(51) Int. Cl.
| | | |
|---|---|---|
| A61K 31/496 | (2006.01) | |
| A61P 35/00 | (2006.01) | |
| A61P 35/02 | (2006.01) | |
| A61P 25/18 | (2006.01) | |
| A61P 25/16 | (2006.01) | |
| A61P 35/04 | (2006.01) | |
| A61K 9/00 | (2006.01) | |
| A61K 9/08 | (2006.01) | |
| A61K 9/10 | (2006.01) | |
| A61K 9/20 | (2006.01) | |
| A61K 9/48 | (2006.01) | |
| A61K 31/00 | (2006.01) | |
| A61K 31/397 | (2006.01) | |
| A61K 31/407 | (2006.01) | |
| A61K 31/4468 | (2006.01) | |
| A61K 31/454 | (2006.01) | |
| A61K 31/4745 | (2006.01) | |
| A61K 31/497 | (2006.01) | |
| A61K 31/498 | (2006.01) | |
| A61K 31/4995 | (2006.01) | |
| A61K 31/506 | (2006.01) | |
| A61K 31/519 | (2006.01) | |
| A61K 31/5383 | (2006.01) | |
| A61K 31/5395 | (2006.01) | |

(52) U.S. Cl.
CPC .......... *A61K 31/496* (2013.01); *A61K 9/0019* (2013.01); *A61K 9/0053* (2013.01); *A61K 9/0056* (2013.01); *A61K 9/0078* (2013.01); *A61K 9/0095* (2013.01); *A61K 9/08* (2013.01); *A61K 9/10* (2013.01); *A61K 9/2004* (2013.01); *A61K 9/4841* (2013.01); *A61K 31/00* (2013.01); *A61K 31/397* (2013.01); *A61K 31/407* (2013.01); *A61K 31/4468* (2013.01); *A61K 31/454* (2013.01); *A61K 31/4745* (2013.01); *A61K 31/497* (2013.01); *A61K 31/498* (2013.01); *A61K 31/4995* (2013.01); *A61K 31/506* (2013.01); *A61K 31/519* (2013.01); *A61K 31/5383* (2013.01); *A61K 31/5395* (2013.01); *A61P 25/16* (2018.01); *A61P 25/18* (2018.01); *A61P 35/02* (2018.01); *A61P 35/04* (2018.01)

(58) Field of Classification Search
CPC .............................. A61K 31/496; A61P 35/00
USPC ...................................................... 514/254.05
See application file for complete search history.

(56) References Cited

U.S. PATENT DOCUMENTS

| 10,376,507 B2 | 8/2019 | Srinivasan et al. |
| 10,835,529 B2 | 11/2020 | Srinivasan et al. |

(Continued)

FOREIGN PATENT DOCUMENTS

| WO | WO 2007/140299 A2 | 12/2007 |
| WO | WO 2017/165635 A1 | 9/2017 |

(Continued)

OTHER PUBLICATIONS

[Author Unknown] "Sirolimus severe overdosage following co-treatment with the new tablet formulation of posaconazole (Noxafil): a case report". Fundamental and Clinical Pharmacology (2016); vol. 30, Supp. 1, pp. 26, Abstract No. PM1-007, 2 pages.

(Continued)

*Primary Examiner* — Raymond J Henley, III
(74) *Attorney, Agent, or Firm* — Cooley LLP

(57) ABSTRACT

The present disclosure provides for methods of treating a patient with a CYP3A4 substrate drug, wherein the patient is treated with posaconazole. In some embodiments, the patient stops posaconazole treatment, waits for at least 2 days, and then is treated with the CYP3A4 substrate drug as soon as it is safe to do so. In some embodiments, treatment with the CYP3A4 substrate drug is delayed for about 2-42 days after stopping posaconazole. In some embodiments, the patient is treated with a reduced dose of the CYP3A4 substrate drug for about 2-42 days.

30 Claims, 14 Drawing Sheets

Related U.S. Application Data filed on May 16, 2017, now Pat. No. 10,376,507, and a continuation-in-part of application No. 17/407,440, filed on Aug. 20, 2021, which is a continuation of application No. 17/099,298, filed on Nov. 16, 2020, now Pat. No. 11,123,346, which is a division of application No. 16/191,351, filed on Nov. 14, 2018, now Pat. No. 10,835,529, which is a continuation-in-part of application No. 15/596,585, filed on May 16, 2017, now Pat. No. 10,376,507.

(56) References Cited

U.S. PATENT DOCUMENTS

| | | | |
|---|---|---|---|
| 10,857,144 | B2 | 12/2020 | Srinivasan et al. |
| 11,052,077 | B2 | 7/2021 | Srinivasan et al. |
| 11,123,346 | B2 | 9/2021 | Srinivasan et al. |
| 11,154,545 | B2 | 10/2021 | Srinivasan et al. |
| 2010/0179169 | A1 | 7/2010 | Davis |
| 2014/0221424 | A1 | 8/2014 | Zha |
| 2014/0350060 | A1 | 11/2014 | Bradford et al. |
| 2017/0100331 | A1 | 4/2017 | Klein et al. |
| 2017/0258720 | A1 | 9/2017 | Pottier et al. |
| 2018/0333409 | A1 | 11/2018 | Srinivasan et al. |
| 2018/0333410 | A1 | 11/2018 | Srinivasan et al. |
| 2018/0333411 | A1 | 11/2018 | Srinivasan et al. |
| 2019/0076425 | A1 | 3/2019 | Srinivasan et al. |
| 2019/0255043 | A1 | 8/2019 | Srinivasan et al. |
| 2019/0262328 | A1 | 8/2019 | Srinivasan et al. |
| 2021/0128543 | A1 | 5/2021 | Srinivasan et al. |
| 2021/0154181 | A1 | 5/2021 | Srinivasan et al. |
| 2021/0154189 | A1 | 5/2021 | Srinivasan et al. |
| 2021/0260048 | A1 | 8/2021 | Srinivasan et al. |
| 2021/0283119 | A1 | 9/2021 | Srinivasan et al. |
| 2021/0379041 | A1 | 12/2021 | Srinivasan et al. |
| 2021/0401820 | A1 | 12/2021 | Srinivasan et al. |

FOREIGN PATENT DOCUMENTS

| | | |
|---|---|---|
| WO | WO 2018/089687 A1 | 5/2018 |
| WO | WO 2018/212764 A1 | 11/2018 |
| WO | WO 2020/018136 A1 | 1/2020 |

OTHER PUBLICATIONS

"Drug Development and Drug Interactions: Table of Substrates, Inhibitors, and Inducers." US Food and Drug Administration. Available at: https://www.fda.gov/drugs/developmentapprovalprocess/developmentresources/druginteractionslabeling/ucm093664.htm Accessed Dec. 13, 2017, 16 pages.

ADVAIR DISKUS (fluticasone propionate and salmeterol inhalation powder), Inhalation powder: Inhaler containing a combination of fluticasone propionate (100, 250, or 500 mcg) and salmeterol (50 mcg) as a powder formulation for oral inhalation; Highlights of Prescribing Information, Label; Patient Information; Revised: Jan. 2019 (Jan. 2019), Initial U.S. Approval: 2000, Reference ID: 4372031, GlaxoSmithKline, Research Triangle Park, NC 27709, USA, 63 pages.

ADVAIR DISKUS (fluticasone propionate and salmeterol inhalation powder), Inhalation powder: Inhaler containing a combination of fluticasone propionate (100, 250, or 500 mcg) and salmeterol (50 mcg) as a powder formulation for oral inhalation; Highlights of Prescribing Information, Label; Patient Information; Revised: Dec. 2017 (Dec. 2017), Initial U.S. Approval: 2000, Reference ID: 4198047, GlaxoSmithKline, Research Triangle Park, NC 27709, USA, 62 pages.

AFINITOR® (everolimus) tablets for oral administration—2.5 mg, 5 mg, 7.5 mg, and 10 mg tablets; AFINITOR DISPERZ Tablets, for oral suspension—2 mg, 3 mg, and 5 mg tablets; Label; Highlights of Prescribing Information, Patient Information approved by the U.S. Food and Drug Administration, Revised: Jun. 2016 (Jun. 2016), Initial U.S. Approval: 2009, Reference ID: 3944879, Manufactured by: Novartis Pharma Stein AG Stein, Switzerland, Distributed by: Novartis Pharmaceuticals Corporation, East Hanover, NJ, USA, 44 pages.

AFINITOR® (everolimus), Highlights of Prescribing Information, Label; Patient Information; NDA203985, Novartis Pharmaceuticals Corporation, Initial U.S. Approval: 2009, Revised Jun. 2016, 79 pages.

AFINITOR® Prescribing Information, published 2010 (Year: 2010), 25 pages.

Agarwal, et al., "Management of Venetoclax-Posaconazole Interaction in Acute Myeloid Leukemia Patients: Evaluation of Dose Adjustments", Clinical Therapeutics (Feb. 2017); 39(2): 359-367. Epub Feb. 1, 2017.

ALUNBRIG™ (brigatinib) Tablets: 30 mg and 90 mg, Label; Highlights of Prescribing Information, Patient Information approved by the U.S. Food and Drug Administration; Revised: Apr. 2017 (Apr. 2017), Initial U.S. Approval: 2017, Reference ID: 4090797, Manufactured for: ARIAD Pharmaceuticals, Inc., a wholly owned subsidiary of Takeda Pharmaceutical Company Limited, Cambridge, MA, USA, 18 pages.

Bawa and Scarff, "Lurasidone: A New Treatment Option for Bipolar Depression—A Review." Innov Clin Neurosci. (Feb. 2015); 12(1-2): 21-23.

Bogenberger, et al., "Combined venetoclax and alvocidib in acute myeloid leukemia", Oncotarget (Dec. 5, 2017); 8(63): 107206-107222.

BOSULIF® (bosutinib) Tablets: 100 mg and 500 mg, Label; Highlights of Prescribing Information, Patient Information approved by the U.S. Food and Drug Administration; Revised: Apr. 2017 (Apr. 2017), Initial U.S. Approval: 2012, Reference ID: 4083804, Distributed by: Pfizer Labs, New York, NY, USA, 17 pages.

BRAFTOVI™ (encorafenib) Capsules: 50 mg and 75 mg, for oral use, Label; Highlights of Prescribing Information; Revised: Jun. 2018 (Jun. 2018), Initial U.S. Approval: 2018, Reference ID: 4283598, Array BioPharma Inc., 19 pages.

BRILINTA® (ticagrelor) Tablets: 60 mg and 90 mg, Label; Highlights of Prescribing Information, Patient Information approved by the U.S. Food and Drug Administration; Revised: Apr. 2019 (Apr. 2019), Initial U.S. Approval: 2011, Reference ID: 4413689, Distributed by: AstraZeneca Pharmaceuticals LP, Wilmington, DE 19850, USA, 29 pages.

Brill, M.J.E., et al., "Impact of Obesity on Drug Metabolism and Elimination in Adults and Children." Clinical Pharmacokinetics (2012); 51(5): 277-304.

CABOMETYX™ (cabozantinib) Tablets: 20 mg, 40 mg, and 60 mg, Label; Highlights of Prescribing Information, Patient Information approved by the U.S. Food and Drug Administration; Revised: Apr. 2016 (Apr. 2016), Initial U.S. Approval: 2012, Reference ID: 3924269, Manufactured for Exelixis, Inc. South San Francisco, CA, USA, 21 pages.

CABOMETYX™ (cabozantinib) Tablets: 20 mg, 40 mg, and 60 mg, Label; Highlights of Prescribing Information, Patient Information approved by the U.S. Food and Drug Administration; Revised: Jan. 2019 (Jan. 2019), Initial U.S. Approval: 2012, Reference ID: 4375294, Manufactured for Exelixis, Inc. South San Francisco, CA, USA, 32 pages.

CALQUENCE® (acalabrutinib) capsules, Label; Highlights of Prescribing Information, Capsules: 100 mg, Patient Information approved by the U.S. Food and Drug Administration; Revised: Oct. 2017 (Oct. 2017), Issued Oct. 2017 (Oct. 2017), Initial U.S. Approval: 2017, Reference ID: 4174611, Distributed by: AstraZeneca Pharmaceuticals LP, Wilmington, DE 19850, USA; Under license of Acerta Pharma B.V., 17 pages.

CAMPTOSAR® (Irinotecan) Injection, intravenous infusion, Initial U.S. Approval: 1996, Revised: Dec. 2014 (Dec. 2014), U.S. Approval: 1996, Reference ID: 3674813, Distributed by: Pfizer Inc., New York, NY 10017, USA, 39 pages.

Center for Drug Research and Evaluation, Food and Drug Administration. Application No. 207500Orig1s000 / 207501Orig1s000. Clinical Pharmacology and Biopharmaceutics Review(s). NDA 207500 (Trade Name: Cresemba, Generic Name: Isavuconazonium sulfate), Dosage Form/Strength: Capsules/186.3 mg of isavuconazonium

(56) References Cited

OTHER PUBLICATIONS sulfate (equivalent to 100 mg isavuconazole), Submission Date: Jul. 8, 2014 (Original Submission), Sep. 26, 2014 (Sequence 0006), Oct. 8, 2014 (Sequence 0008), Dec. 11, 2014 (Sequence 0015), Dec. 18, 2014 (Sequence 0017), Date of Review: Dec. 23, 2014, Reference ID: 3606431. Available at: https://www.accessdata.fda.gov/drugsatfda_docs/nda/2015/207500Orig1207501Orig1s000ClinPharmR.pdf Accessed Dec. 13, 2017, 78 pages.
Chiu, et al., "Lurasidone drug-drug interaction studies: a comprehensive review." Drug Metab Drug Interact (2014); 29(3): 191-202.
Chow, et al., "Persistence of a Posaconazole-Mediated Drug-Drug Interaction With Ranolazine After Cessation of Posaconazole Administration: Impact of Obesity and Implications for Patient Safety." J Clin Pharmacol. (Nov. 2018); 58(11):1436-1442. Epub May 11, 2018.
Citrome, L., "Lurasidone for schizophrenia: a review of the efficacy and safety profile for this newly approved second-generation antipsychotic," Clinical Schizophrenia & Related Psychoses (Jan. 2011); vol. 4(4), pp. 251-257. Epub Dec. 3, 2010.
COMETRIQ® (cabozantinib) Capsules: 20 mg and 80 mg, Label; Highlights of Prescribing Information, Patient Information approved by the U.S. Food and Drug Administration; Revised: Jan. 2018 (Jan. 2018), Initial U.S. Approval: 2012, Reference ID: 4206685, Manufactured for Exelixis, Inc. South San Francisco, CA, USA, 22 pages.
COMETRIQ® (cabozantinib) Capsules: 20 mg and 80 mg, Label; Highlights of Prescribing Information, Patient Information approved by the U.S. Food and Drug Administration; Revised: May 2016 (May 2016), Initial U.S. Approval: 2012, Reference ID: 3934582, Manufactured for Exelixis, Inc. South San Francisco, CA, USA, 22 pages.
COTELLIC® (cobimetinib) Tablets: 20 mg, Label; Highlights of Prescribing Information, Patient Information approved by the U.S. Food and Drug Administration; Revised: Jan. 2018 (Jan. 2018), Initial U.S. Approval: 2015, Reference ID: 3938960, Distributed by: Genentech USA, Inc., A Member of the Roche Group, South San Francisco, CA 94080, USA, 20 pages.
COTELLIC® (cobimetinib) Tablets: 20 mg, Label; Highlights of Prescribing Information, Patient Information approved by the U.S. Food and Drug Administration; Revised: May 2016 (May 2016), Initial U.S. Approval: 2015, Reference ID: 4212951, Distributed by: Genentech USA, Inc., A Member of the Roche Group, South San Francisco, CA 94080, USA, 19 pages.
CRESEMBA® (isavuconazonium sulfate), Highlights of Prescribing Information, Label; Patient Information approved by the U.S. Food and Drug Administration; Astellas Pharma US, Inc. (Licensed from Basilea Pharmaceutica International Ltd.), Illinois, USA, Initial U.S. Approval: Mar. 2015, Reference ID: 3712237, 28 pages.
DIFLUCAN® (fluconazole), Label; Patient Information, Reference ID: 3650838, Roerig, Division of Pfizer Inc., New York, NY, Revised Mar. 2013, 35 pages.
ELIQUIS® (apixaban), Tablets: 2.5 mg and 5 mg, Highlights of Prescribing Information / Package Insert / Label, Revised: Feb. 2018 (Feb. 2018), Initial U.S. Approval: 2012, Reference ID: 4218935, Marketed by: Bristol-Myers Squibb Company Princeton, New Jersey 08543 USA and Pfizer Inc., New York, New York 10017, USA, 43 pages.
ENHERTU® (fam-trastuzumab deruxtecan-nxki), Highlights of Prescribing Information, Label; Patient Information; Injection 100 mg lyophilized powder in a single-dose vial; Revised: Jan. 2021 (Jan. 2021), Initial U.S. Approval: 2019, Reference ID: 4732117, Manufactured by: Daiichi Sankyo, Inc., Basking Ridge, NJ 07920, Marketed by: Daiichi Sankyo, Inc., Basking Ridge, NJ 07920 and AstraZeneca Pharmaceuticals LP, Wilmington, DE 19850, 21 pages.
ENVARSUS XR® (tacrolimus extended-release tablets), Extended-release tablets: 0.75 mg, 1 mg, 4 mg, Highlights of Prescribing Information / Package Insert / Label, Initial U.S. Approval: 1994, Revised: Dec. 2018 (Dec. 2018), Reference ID: 4365084, Manufactured by: Rottendorf Pharma GmbH, 59320 Ennigerloh, North Rhine-Westphalia, Germany, Manufactured for: Veloxis Pharmaceuticals, Inc., Cary, North Carolina 27513, USA, 31 pages.
ESBRIET® (pirfenidone) capsules, product label, Highlights of Prescribing Information, Dosage Forms and Strengths—Capsules: 267 mg, Initial U.S. Approval: 2014, Revised: Oct. 2014, Issued: Oct. 2014, © 2014 InterMune, Inc., Reference ID: 3643926, 21 pages.
Extended European Search Report for European Application No. 17897227.9 dated Apr. 7, 2020, 5 pages.
Extended European Search Report for European Application No. 18926463.3 dated Jan. 20, 2021, 6 pages.
FARYDAK® (panobinostat), Capsules: 10 mg, 15 mg, and 20 mg, Label; Highlights of Prescribing Information, Patient Information approved by the U.S. Food and Drug Administration; Revised: Feb. 2015 (Feb. 2015), Initial U.S. Approval: 2015, Reference ID: 3699607, Distributed by: Novartis Pharmaceuticals Corporation, East Hanover, NJ, USA, 23 pages.
Greenblatt, et al., "Sustained Impairment of Lurasidone Clearance After Discontinuation of Posaconazole." J. Clin. Psychopharmacol. (2018); 38(4): 289-295.
IBRANCE® (palbociclib) Capsules: 125 mg, 100 mg, and 75 mg, for oral use, Revised: Feb. 2018 (Feb. 2018), Initial U.S. Approval: 2015, Reference ID: 4217399, Distributed by: Pfizer Inc., New York, NY 10017, USA, 24 pages.
IBRANCE® (palbociclib), Capsules: 125 mg, 100 mg, and 75 mg, Label; Highlights of Prescribing Information, Patient Information approved by the U.S. Food and Drug Administration; Revised: Mar. 31, 2017 (Mar. 31, 2017), Initial U.S. Approval: 2015, Reference ID: 4078038, Distributed by: Pfizer Labs, New York, NY, USA, 23 pages.
ICLUSIG® (ponatinib), Tablets: 15 mg, 30 mg and 45 mg, Label; Highlights of Prescribing Information, Patient Information approved by the U.S. Food and Drug Administration; Revised: Nov. 2016 (Nov. 2016), Initial U.S. Approval: 2012, Reference ID: 4019587, Manufactured for: ARIAD Pharmaceuticals, Inc., Cambridge, MA, USA, 26 pages.
IMBRUVICA® (ibrutinib) Capsules for oral use, IMBRUVICA® (ibrutinib) Tablets for oral use, Capsules: 70 mg and 140 mg, Tablets: 140 mg, 280 mg, 420 mg, and 560 mg; Highlights of Prescribing Information / Package Insert / Label, Revised: Aug. 2018 (Aug. 2018), Initial U.S. Approval: 2013, Reference ID: 4311953, Distributed and Marketed by: Pharmacyclics LLC Sunnyvale, CA 94085, USA, Marketed by: Janssen Biotech, Inc. Horsham, PA 19044, USA, 45 pages.
IMBRUVICA® (ibrutinib) Capsules: 140 mg, Label; Highlights of Prescribing Information, Patient Information approved by the U.S. Food and Drug Administration; Revised: Jan. 2017 (Jan. 2017), Initial U.S. Approval: 2013, Reference ID: 4043198, Distributed and Marketed by: Pharmacyclics LLC Sunnyvale, CA, USA, 37 pages.
IMBRUVICA® (ibrutinib), Capsule: 70 mg and 140 mg; Highlights of Prescribing Information, Label; Patient Information approved by the U.S. Food and Drug Administration, Initial U.S. Approval: 2013; Revised: Dec. 2017; Distributed and Marketed by: Pharmacyclics LLC Sunnyvale, CA USA 94085; Marketed by: Janssen Biotech, Inc. Horsham, PA USA 19044; Reference ID: 4198358, 40 pages.
IMBRUVICA® Prescribing Information, Initial U.S. Approval: 2013; Revised Mar. 2016, (Year: 2016); Distributed and Marketed by: Pharmacyclics LLC Sunnyvale, CA USA 94085, and Marketed by: Janssen Biotech, Inc. Horsham, PA USA 19044; Reference ID: 3896712, 32 pages.
INLYTA® (axitinib) Tablets: 1 mg and 5 mg, for oral administration, Label; Highlights of Prescribing Information; Revised: Aug. 2018 (Aug. 2018), Initial U.S. Approval: 2012, Distributed by: Pfizer Inc., New York, NY 10017, USA, 19 pages.
INLYTA® (axitinib) Tablets: 1 mg and 5 mg, Label; Highlights of Prescribing Information, Patient Information approved by the U.S. Food and Drug Administration; Revised: Aug. 2014 (Aug. 2014), Initial U.S. Approval: 2012, Reference ID: 3603361, Distributed by: Pfizer Labs, New York, NY, USA, 21 pages.
International Preliminary Reporton Patentability in International Application No. PCT/US2017/032924, dated Nov. 19, 2019, 6 pages.
International Preliminary Reporton Patentability in International Application No. PCT/US2018/061141, dated Jan. 19, 2021, 7 pages.

(56) References Cited

OTHER PUBLICATIONS

International Search Report and Written Opinion in International Application No. PCT/US2017/032924, dated Aug. 28, 2017, 11 pages.
International Search Report and Written Opinion in International Application No. PCT/US2018/061141, dated Jan. 25, 2019, 14 pages.
JAKAFI® (ruxolitinib), Tablets: 5 mg, 10 mg, 15 mg, 20 mg and 25 mg, Label; Highlights of Prescribing Information, Patient Information approved by the U.S. Food and Drug Administration; Revised: Mar. 2016 (Mar. 2016), Initial U.S. Approval: 2011, Reference ID: 3899946, Manufactured for: Incyte Corporation, Wilmington, DE, USA, 34 pages.
Jerling et al., "Studies to Investigate the Pharmacokinetic Interactions Between Ranolazine and Ketoconazole, Diltiazem, or Simvastatin During Combined Administration in Healthy Subjects." The Journal of Clinical Pharmacology (2005); 45(4): 422-433.
JEVTANA® (cabazitaxel) injection, for intravenous use; Single dose vial 60 mg/1.5 mL, Label; Highlights of Prescribing Information, Patient Information approved by the U.S. Food and Drug Administration; Revised: Sep. 2016 (Sep. 2016), Initial U.S. Approval: 2010, Reference ID: 3984498, Manufactured by: sanofi-aventis U.S. LLC Bridgewater, NJ, USA, 25 pages.
JYNARQUE (tolvaptan) Tablets: 15 mg, 30 mg, 45 mg, 60 mg and 90 mg, Label; Highlights of Prescribing Information, Patient Information approved by the U.S. Food and Drug Administration; Revised: Apr. 2018 (Apr. 2018), Initial U.S. Approval: 2009, Reference ID: 4252782, Manufactured by Otsuka Pharmaceutical Co., Ltd., Tokyo, 101-8535 Japan, Distributed and marketed by Otsuka America Pharmaceutical, Inc., Rockville, MD 20850, USA, 20 pages.
KADCYLA® (ado-trastuzumab emtansine) for injection, for intravenous use; Lyophilized powder in single-use vials containing 100 mg per vial or 160 mg per vial, Label; Highlightsof Prescribing Information, Revised: Jul. 2016 (Jul. 2016), Initial U.S. Approval: 2013, Reference ID: 3963399, Manufactured by: Genentech USA, Inc., San Francisco, CA, USA, 24 pages.
KISQALI® FEMARA® Co-Pack (ribociclib tablets; letrozole tablets), Tablets—KISQALI: 200 mg, FEMARA: 2.5 mg, Label; Highlights of Prescribing Information, Patient Information approved by the U.S. Food and Drug Administration; Revised: May 2017 (May 2017), Initial U.S. Approval: 2017, Reference ID: 4093616, Distributed by: Novartis Pharmaceuticals Corporation East Hanover, NJ, USA, 21 pages.
Krishna, G., et al., "Effects of oral posaconazole on the pharmacokinetic properties of oral and intravenous midazolam: A phase I, randomized, open-label, crossover study in healthy volunteers." Clinical Therapeutics (2009); 31(2): 286-298.
Kubiak, D.W., et al., "Safety of Posaconazole and Sirolimus Coadministration in Allogeneic Hematopoietic Stem Cell Transplants," Biology of Blood and Marrow Transplantation (Sep. 2012); vol. 18(9), pp. 1462-1465. Epub May 4, 2012.
LATUDA (lurasidone hydrochloride),Tablets: 20 mg, 40 mg, 60 mg, 80 mg and 120 mg, Highlights of Prescribing Information / Package Insert / Label, Initial U.S. Approval: 2010, Revised Sep. 2017 (Sep. 2017), Reference ID: 4157569, Manufactured for: Sunovion Pharmaceuticals Inc., Marlborough, MA 01752, USA, 57 pages.
LATUDA (lurasidone), 18.5 mg film-coated tablets, 37 mg film-coated tablets, 74 mg film-coated tablets; Package Leaflet, Information for the patient, European Medicines Agency, Revised: Mar. 2018; Marketed by Aziende Chimiche Riunite Angelini Francesco—A.C.R.A.F. S.p.A., Rome, Italy, Manufactured by AndersonBrecon (UK) Ltd., 7 pages.
Lempers, et al., "Inhibitory Potential of Antifungal Drugs on ATP-Binding Cassette Transporters P-Glycoprotein, MRP1 to MRP5, BCRP, and BSEP." Antimicrob. Agents Chemother. (2016); 60(6): 3372-3379.
Li, et al., "Pharmacokinetic/pharmacodynamic profile of posaconazole." Clin Pharmacokinet. (2010); 49(6): 379-396.
Lipp, Hans-Peter, "Clinical pharmacodynamics and pharmacokinetics of the antifungal extended-spectrum triazole posaconazole: an overview." British Journal of Pharmacology (2010); 70(4): 471-480.
Loebel, A., et al., "Lurasidone Monotherapy in the Treatment of Bipolar I Depression: A Randomized, Double-Blind, Placebo-Controlled Study." The American Journal of Psychiatry (2014); 171(2): 160-168.
LORBRENA® (lorlatinib) Tablets: 25 mg or 100 mg, for oral use, Revised: Nov. 2018 (Nov. 2018), Initial U.S. Approval: 2018, Reference ID: 4344940, Distributed by: Pfizer Inc., New York, NY 10017, USA, 21 pages.
LYNPARZA™ (olaparib), Capsules: 50 mg, Label; Highlights of Prescribing Information, Patient Information approved by the U.S. Food and Drug Administration; Revised: Jan. 2017 (Jan. 2017), Initial U.S. Approval: 2014, Reference ID: 4047222, Distributed by: AstraZeneca Pharmaceuticals LP, Wilmington, DE, USA, 16 pages.
Masters, J.C., et al., "Drug Interaction between Sirolimus and Ranolazine in a Kidney Transplant Patient." Case Reports in Transplantation (Jan. 2014); vol. 2014, Article ID 548243, 4 pages.
Miceli, M.H., et al., "Serum posaconazole levels among haematological cancer patients taking extended release tablets is affected by body weight and diarrhoea: single centre retrospective analysis." Mycoses (2015); 58(7): 432-436.
Moore, et al., "Pharmacologic and clinical evaluation of posaconazole". Expert Rev Clin Pharmacol. (May 2015); 8(3): 321-334.
Nash and Nash, "Ranolazine for chronic stable angina." Lancet (2008); 372(9646): 1335-1341.
NEXAVAR (sorafenib), Tablets: 200 mg, Label; Highlights of Prescribing Information, Patient Information approved by the U.S. Food and Drug Administration; Revised: Nov. 2013 (Nov. 2013), Initial U.S. Approval: 2005, Reference ID: 3411803, Distributed and marketed by: Bayer Healthcare Pharmaceuticals Inc. Whippany, NJ, USA, Marketed by: Onyx Pharmaceuticals, Inc., South San Francisco, CA, USA, 30 pages.
NIZORAL® (ketoconazole)Label; Patient Information approved by the U.S. Food and Drug Administration, Reference ID: 3458324, Copyright 2014 Janssen Pharmaceuticals, Inc., New Jersey, USA, Revised Feb. 2014, 23 pages.
NOXAFIL® (posaconazole) injection 18 mg/mL; delayed-release tablets 100mg; oral suspension 40 mg/mL, Highlights of Prescribing Information, FDA Label; Revised Nov. 2015 (Nov. 2015), Reference ID: 3847805, Initial U.S. Approval: 2006 (oral suspension), Copyright 2006, 2010, 2013, 2014, Merck Sharp & Dohme Corp., a subsidiary of Merck & Co., Inc., New Jersey, USA, 39 pages.
NOXAFIL® (posaconazole), Highlights of Prescribing Information, Label; Patient Information approved by the U.S. Food and Drug Administration; Copyright © 2006, 2010, 2013, 2014 Merck Sharp & Dohme Corp., a subsidiary of Merck & Co., Inc., New Jersey, USA, Revised Sep. 2016, Reference ID: 3983525, 37 pages.
ODOMZO® (sonidegib), Capsules: 200 mg capsules, Label; Highlights of Prescribing Information, Patient Information approved by the U.S. Food and Drug Administration; Revised: May 2016 (May 2016), Initial U.S. Approval: 2015, Reference ID: 3930636, Distributed by: Novartis Pharmaceuticals Corporation East Hanover, NJ, USA, 13 pages.
ONIVYDE™ (irinotecan liposome injection), Injection: 43 mg/10 mL single dose vial, Label; Highlights of Prescribing Information, Revised: Oct. 2015 (Oct. 2015), Initial U.S. Approval: 1996, Reference ID: 3836766, Manufactured for: Merrimack Pharmaceuticals, Inc., Cambridge, MA, USA, 18 pages.
ORAVIG® (miconazole), Highlights of Prescribing Information, Label; Patient Information approved by the U.S. Food and Drug Administration; Copyright 2012 Praelia Pharmaceuticals, Inc., North Carolina, USA (Manufactured for: Vestiq Pharmaceuticals, Inc., North Carolina, USA), Initial U.S. Approval: Jan. 1974, Revised Aug. 2012, Reference ID: 3270873, 2 pages.
Payne and Hall, "Dosing of antifungal agents in obese people." Expert Review of Anti-infective Therapy (2016); 14(2): 257-267.
POMALYST® (pomalidomide), Capsules: 1 mg, 2 mg, 3 mg, and 4 mg, Label; Highlights of Prescribing Information, Patient Information approved by the U.S. Food and Drug Administration;

(56) References Cited

OTHER PUBLICATIONS

Revised: Jun. 2016 (Jun. 2016), Initial U.S. Approval: 2013, Reference ID: 3953274, Manufactured for: Celgene Corporation, Summit, NJ, USA, 31 pages.
RANEXA (Ranolazine), Ranexa 375 mg prolonged-release tablets, Ranexa 500 mg, and Ranexa 750 mg prolonged-release tablets, Patient Information, Label and Package Leaflet, 62 pages. European Medicines Agency, First Published Sep. 14, 2009, Last Updated Oct. 6, 2017. http://www.ema.europa.eu/ema/index.jsp?curl=pages/medicines/human/medicines/000805/human_med_001009.jsp&mid=WC0b01ac058001d124.
RANEXA® (ranolazine), Extended-release tablets: 500 mg, Highlights of Prescribing Information, Label; Patient Information approved by the U.S. Food and Drug Administration; Copyright © 2016 Gilead Sciences, Inc., Foster City, CA 94404, Revised Jan. 2016, Initial U.S. Approval: 2006, Reference ID: 3869690, 23 pages.
Roberts, et al., "Targeting BCL2 with Venetoclax in Relapsed Chronic Lymphocytic Leukemia", N Engl J Med (Jan. 2016); 374: 311-322.
*Roxane Laboratories, Inc.* v. *Vanda Pharmaceuticals Inc.*, Case IPR2016-00690 (U.S. Pat. No. 9,138,432 B2), PTAB decision, Aug. 30, 2016, 24 pages.
RYDAPT® (midostaurin) Capsules: 25 mg, Label; Highlights of Prescribing Information, Patient Information approved by the U.S. Food and Drug Administration; Revised: Apr. 2017 (Apr. 2017), Initial U.S. Approval: 2017, Reference ID: 4090671, Distributed by: Novartis Pharmaceuticals Corporation, East Hanover, NJ, USA, 20 pages.
Sandherr and Maschmeyer, "Pharmacology and metabolism of voriconazole and posaconazole in the treatment of invasive aspergillosis—review of the literature." European Journal of Medical Research (2011); 16: 139-144.
SPORANOX® (itraconazole), Label; Patient Information approved by the U.S. Food and Drug Administration, Reference ID: 4071289, Copyright 2001 Janssen Pharmaceutical Companies, New Jersey, USA, Revised Mar. 2017, 40 pages.
STIVARGA® (regorafenib), Tablets: 40 mg, Label; Highlights of Prescribing Information, Patient Information approved by the U.S. Food and Drug Administration; Revised: Apr. 2017 (Apr. 2017), Initial U.S. Approval: 2012, Reference ID: 4090114, Bayer Healthcare Pharmaceuticals Inc., Whippany, NJ, USA, 28 pages.
SUTENT® (sunitinib malate), Capsules: 12.5 mg, 25 mg, 37.5 mg, 50 mg, Label; Highlights of Prescribing Information, Patient Information approved by the U.S. Food and Drug Administration; Revised: Apr. 2015 (Apr. 2015), Initial U.S. Approval: 2006, Reference ID: 3846154, Distributed by: Pfizer Labs, Div of Pfizer Inc., NY, NY 10017, USA, 32 pages.
SUTENT® (sunitinib malate), Capsules: 12.5 mg, 25 mg, 37.5 mg, 50 mg, Label; Highlights of Prescribing Information, Patient Information approved by the U.S. Food and Drug Administration; Revised: May 2019 (May 2019), Initial U.S. Approval: 2006, Reference ID: 4429764, Distributed by: Distributed by: Pfizer Labs, Div of Pfizer Inc., NY, NY 10017, USA, 39 pages.
Ta, C., et al., "Predicting Interactions with PDE5 Inhibitors." Pharmacy Times (2005); pp. 16 and 28, 2 pages.
TACROLIMUS, Capsules RX only, Prescribing Information / Medication Guide / Package Insert / Label (May 27, 2009), Iss May 2009, Manufactured in India by Sandoz Private Limited for Sandoz Inc; Princeton NJ 08540, USA, 4 pages.
TAFINLAR® (dabrafenib) Capsules: 50 mg, 75 mg, Label; Highlights of Prescribing Information, Patient Information approved by the U.S. Food and Drug Administration; Revised: Jun. 2016 (Jun. 2016), Initial U.S. Approval: 2013, Reference ID: 3946597, Distributed by: Novartis Pharmaceuticals Corporation, East Hanover, NJ 07936, USA, 31 pages.
TAFINLAR® (dabrafenib) Capsules: 50 mg, 75 mg, Label; Highlights of Prescribing Information, Patient Information approved by the U.S. Food and Drug Administration; Revised: May 2018 (May 2018), Initial U.S. Approval: 2013, Reference ID: 4258092, Distributed by: Novartis Pharmaceuticals Corporation, East Hanover, NJ 07936, USA, 40 pages.
TARCEVA (erlotinib) Tablets: 25 mg, 100 mg, and 150 mg, Label; Highlights of Prescribing Information, Revised: Oct. 2016 (Oct. 2016), Initial U.S. Approval: 2004, Reference ID: 4000318, Manufactured for: OSI Pharmaceuticals, LLC, Northbrook, IL 60062 an affiliate of Astellas Pharma US, Inc., Distributed by: Genentech USA, Inc., A Member of the Roche Group, South San Francisco, CA, USA, 19 pgs.
TARCEVA® (erlotinib), Highlights of Prescribing Information, Label; Patient Information; NDA021743, Copyright © 2016 Astellas Pharma US, Inc., and Genentech, Inc., Initial U.S. Approval: 2004, Revised Oct. 2016, 29 pages.
TARCEVA® Prescribing Information, published 2010. (Year: 2010), 24 pages.
TASIGNA® (nilotinib), 150 mg and 200 mg hard capsules, Label; Highlights of Prescribing Information, Patient Information approved by the U.S. Food and Drug Administration; Revised: Feb. 2017 (Feb. 2017), Initial U.S. Approval: 2007, Reference ID: 4058928, Distributed by: Novartis Pharmaceuticals Corporation, East Hanover, NJ, USA, 29 pages.
U.S. Department of Health and Human Services, Food and Drug Administration. Guidance for Industry. "E14 Clinical Evaluation of QT/QTc Interval Prolongation and Proarrhythmic Potential for Non-Antiarrhythmic Drugs." (Oct. 2005); 20 pages. Available at: https://www.fda.gov/downloads/Drugs/GuidanceComplianceRegulatoryInformation/Guidances/UCM073153.pdf. (Accessed: Jan. 31, 2018).
VENCLEXTA® (venetoclax) tablets, Highlights of Prescribing Information, FDA Label, Insert and Packaging, Tablets: 10 mg, 50 mg, 100 mg; Revised: Sep. 2018 (Sep. 2018), Initial U.S. Approval: 2016, Reference ID: 4316460, Manufactured and Marketed by: AbbVie Inc., Chicago, IL, USA, Marketed by: Genentech USA, Inc., San Francisco, CA, USA, 35 pages.
VENCLEXTA® (venetoclax) tablets, Prescribing Information, Tablets: 10 mg, 50 mg, 100 mg; Initial U.S. Approval: Apr. 2016 (Apr. 2016), Revised Jun. 2018 (Jun. 2018), Reference ID: 4275193, Manufactured and Marketed by: AbbVie Inc., Chicago, IL, USA, Marketed by: Genentech USA, Inc., San Francisco, CA, USA, 32 pages.
VENCLEXTA™ (venetoclax) tablets, Highlights of Prescribing Information, FDA Label, Tablets: 10 mg, 50 mg, 100 mg; Issued: Apr. 2016 (Apr. 2016), Initial U.S. Approval: 2016, Reference ID: 3915259, Manufactured and Marketed by: AbbVie Inc., Chicago, IL, USA, Marketed by: Genentech USA, Inc., San Francisco, CA, USA, 25 pages.
VERZENIO™ (abemaciclib) Tablets: 50 mg, 100 mg, 150 mg, and 200 mg, for oral use, Highlights of Prescribing Information, Label; Patient Information; Revised: Feb. 2018 (Feb. 2018), Initial U.S. Approval: 2017, Reference ID: 4226487, Marketed by: Lilly USA, LLC, Indianapolis, IN 46285, USA, 25 pages.
VERZENIO™ (abemaciclib), Tablets: 50 mg, 100 mg, 150 mg, and 200 mg; Highlights of Prescribing Information, Label; Patient Information approved by the U.S. Food and Drug Administration, Initial U.S. Approval: 2017; Revised: Sep. 2017; Marketed by Lilly USA, LLC, Indianapolis, IN 46285, USA, Reference ID: 4160137, 21 pages.
VESIcare® (solifenacin succinate), Highlights of Prescribing Information, Label; Patient Information; NDA021518, Astellas Pharma US, Inc., Initial U.S. Approval: 2004, Revised Mar. 2017, 22 pages.
VESIcare® (solifenacin succinate), Prescribing Information, Revised: Apr. 2010, published 2009, 16 pages.
VFEND® (voriconazole), Highlights of Prescribing Information, Label; Patient Information approved by the U.S. Food and Drug Administration, Roerig, Division of Pfizer Inc., New York, NY, Initial U.S. Approval: 2002, Revised Feb. 2015, Reference ID: 3696601, 42 pages.
VITRAKVI® (larotrectinib) capsules, VITRAKVI® (larotrectinib) oral solution, Capsules: 25 mg, 100 mg, Oral Solution: 20 mg/mL, Revised: Nov. 2018 (Nov. 2018), Initial U.S. Approval: 2018, Reference ID: 4354324, Manufactured for: Loxo Oncology, Inc., Stamford, CT 06901, USA, 20 pages.

(56) References Cited

OTHER PUBLICATIONS

VOTRIENT (pazopanib), Highlights of Prescribing Information 200 mg tablets (3), Initial U.S. Approval: 2009, Reference ID: 3823458, Revised Sep. 2015, 27 pages.

VOTRIENT (pazopanib), Tablets: 200 mg, Label; Highlights of Prescribing Information, Patient Information approved by the U.S. Food and Drug Administration; Revised: Aug. 2016 (Aug. 2016), Initial U.S. Approval: 2009, Reference ID: 3968512, GlaxoSmithKline, Research Triangle Park, NC, USA, 29 pages.

VRAYLAR® (cariprazine) Capsules: 1.5 mg, 3 mg, 4.5 mg, and 6 mg, Label; Highlights of Prescribing Information, Revised: Nov. 2017 (Nov. 2017), Initial U.S. Approval: 2015, Reference ID: 4179057, Licensed from Gedeon Richter Plc., Manufactured by: Forest Laboratories Ireland Limited, Dublin, IE, Distributed by: Allergan USA, Inc., Irvine, CA 92612, USA, 32 pages.

XALKORI® (crizotinib) Capsules: 250 mg and 200 mg, Label; Highlights of Prescribing Information, Patient Information approved by the U.S. Food and Drug Administration; Revised: Apr. 2017 (Apr. 2017), Initial U.S. Approval: 2011, Reference ID: 4090872, Distributed by: Pfizer Labs, New York, NY, USA, 27 pages.

XARELTO® (rivaroxaban), Tablets: 2.5 mg, 10 mg, 15 mg, and 20 mg, Highlights of Prescribing Information / Package Insert / Label/ Full Prescribing Information, Initial U.S. Approval: 2011, Revised: Jan. 2019 (Jan. 2019), Reference ID: 4376293, Janssen Pharmaceuticals, Inc., Titusville, NJ, USA, 58 pages.

XELJANZ® (tofacitinib) tablets, for oral use, XELJANZ® XR (tofacitinib) extended-release tablets for oral use, XELJANZ Tablets: 5 mg, 10 mg tofacitinib, XELJANZ XR Tablets: 11 mg tofacitinib, Highlights of Prescribing Information, Initial U.S. Approval: 2012; Revised Oct. 2018 (Oct. 2018), Reference ID: 4337031, Pfizer Labs, New York, NY 10017, USA, 53 pages.

YONDELIS (trabectedin), injection, for intravenous use; 1 mg sterile lyophilized powder in a single-dose vial, Label; Highlights of Prescribing Information, Patient Information approved by the U.S. Food and Drug Administration; Revised: Jul. 2016 (Jul. 2016), Initial U.S. Approval: 2015, Reference ID: 3960738, Manufactured by: Baxter Oncology GmbH, Halle/Westfalen Germany, Manufactured for: Janssen Products, LP, Horsham, PA, 20 pages.

ZELBORAF® (vemurafenib), Tablets: 240 mg, Label; Highlights of Prescribing Information, Patient Information approved by the U.S. Food and Drug Administration; Revised: Apr. 2017 (Apr. 2017), Initial U.S. Approval: 2011, Reference ID: 4084937, Distributed by: Genentech USA, Inc., A Member of the Roche Group, South San Francisco, CA, USA, 21 pages.

ZORTRESS® (everolimus), Highlights of Prescribing Information, Label; Patient Information; NDA021560, Novartis Pharmaceuticals Corporation, Initial U.S. Approval: 2010, Revised Oct. 2016, 42 pages.

FIG 5
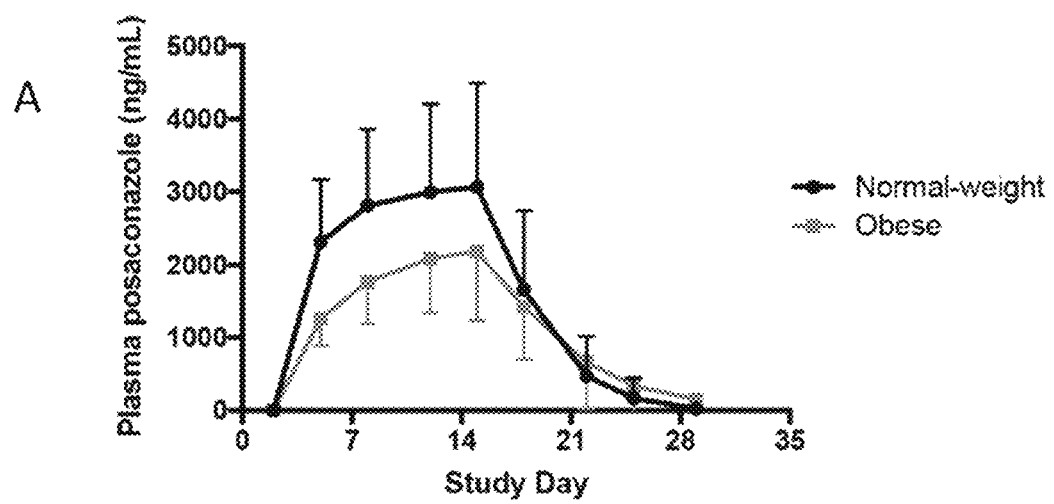
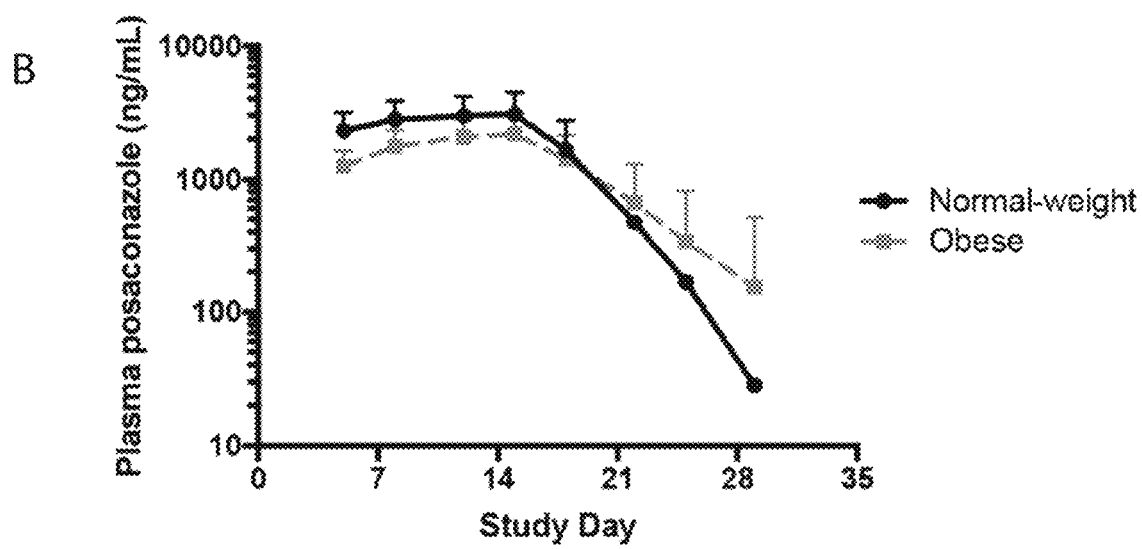

FIG 6
a)
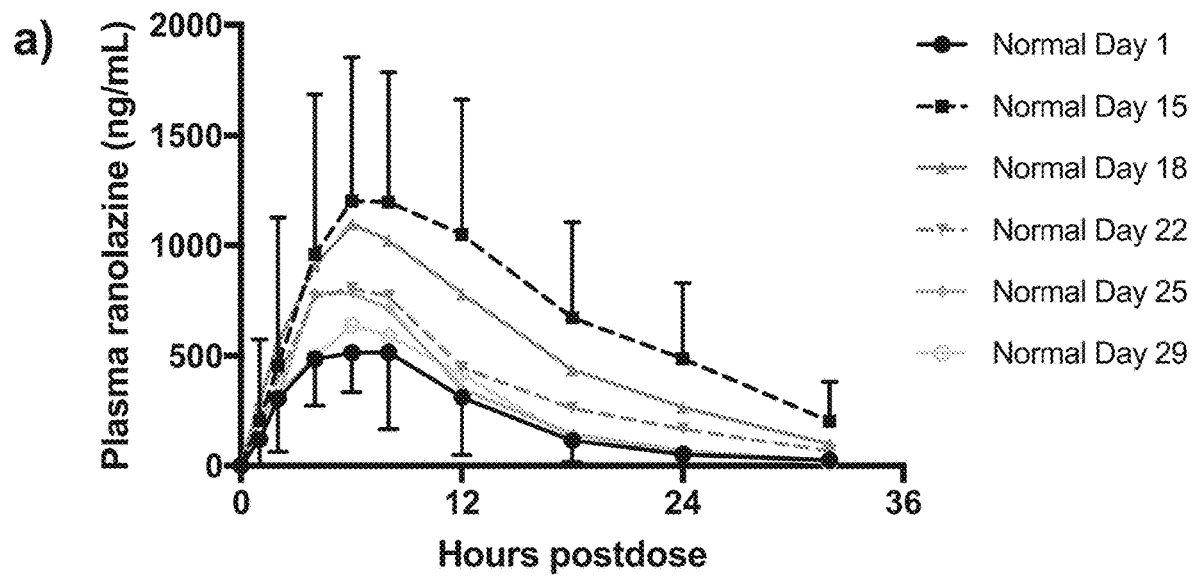
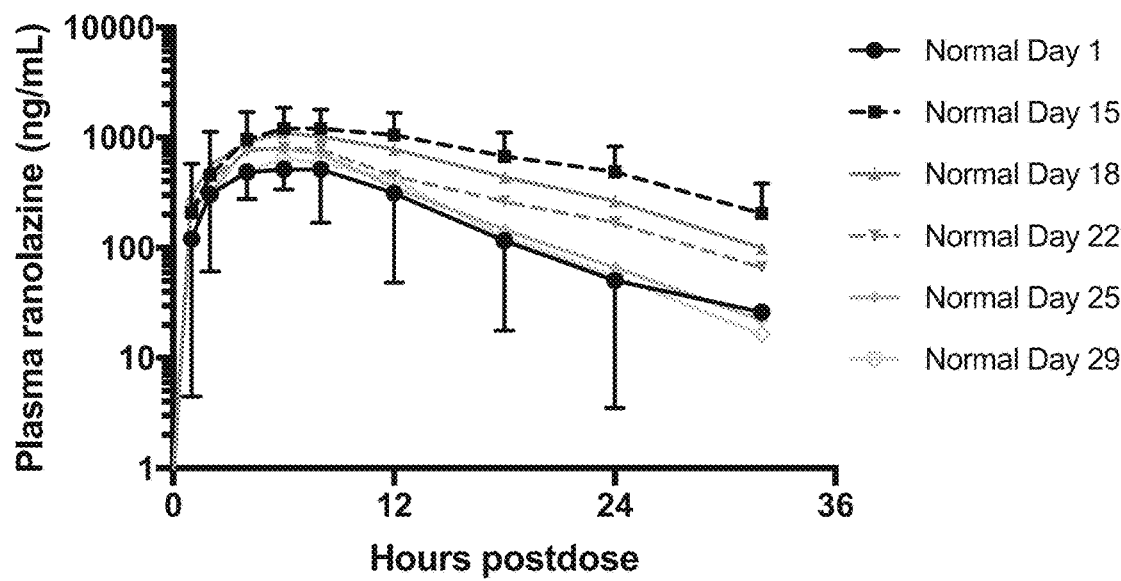

FIG. 6 (cont.)
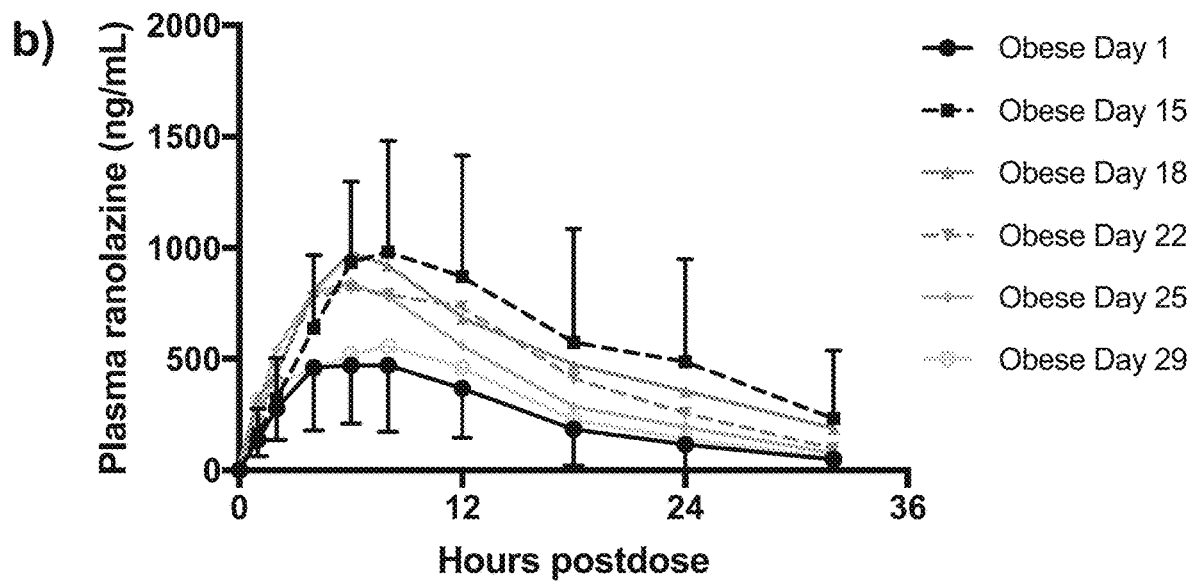
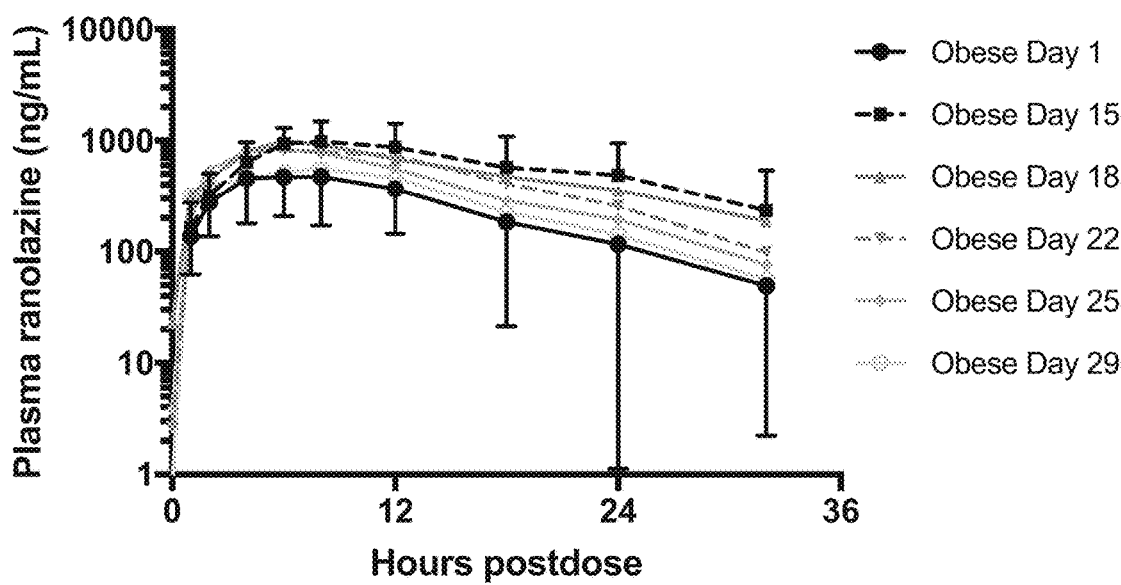

METHODS OF TREATING LUNG CANCER WITH CYP3A4 SUBSTRATE DRUGS

CROSS-REFERENCE TO RELATED APPLICATIONS

This application is a continuation of U.S. application Ser. No. 17/469,628, filed Sep. 8, 2021 (now U.S. Pat. No. 11,351,160), which is a continuation of U.S. application Ser. No. 17/244,065, filed Apr. 29, 2021 (now U.S. Pat. No. 11,154,545), which is a continuation of U.S. application Ser. No. 17/150,467, filed Jan. 15, 2021 (now U.S. Pat. No. 11,052,077), which is a continuation of U.S. application Ser. No. 17/082,902, filed Oct. 28, 2020, which is a continuation of U.S. application Ser. No. 16/408,931, filed May 10, 2019 (now U.S. Pat. No. 10,857,144), which is a continuation-in-part of U.S. application Ser. No. 15/596,585, filed May 16, 2017 (now U.S. Pat. No. 10,376,507); this application is also a continuation-in-part of Ser. No. 17/407,440, filed Aug. 20, 2021, which is a continuation of Ser. No. 17/099,298, filed Nov. 16, 2020, (now U.S. Pat. No. 11,123,346), which is a division of Ser. No. 16/191,351, filed Nov. 14, 2018, (now U.S. Pat. No. 10,835,529), which is a continuation-in-part of U.S. patent application Ser. No. 15/596,585, filed May 16, 2017, (now U.S. Pat. No. 10,376,507), the entire contents of each of which are incorporated by reference in their entireties for all purposes.

BACKGROUND

Posaconazole, also called Noxafil and Posanol, is indicated for the prophylaxis of invasive *Aspergillus* and *Candida* infections in patients who are at high risk of developing these infections due to being severely immunocompromised, such as hematopoietic stem cell transplant (HSCT) recipients with graft-versus-host disease (GVHD) or those with hematologic malignancies with prolonged neutropenia from chemotherapy, for the treatment of oropharyngeal candidiasis (OPC), including OPC refractory (rOPC) to itraconazole and/or fluconazole, the treatment of invasive aspergillosis, and the treatment of zygomycosis. Posaconazole has also been used "off-label" for treating allergic bronchopulmonary aspergillosis; prophylaxis or treatment of recurrent candidiasis for the esophagus, secondary to HIV infection; *Fusarium* infections mycosis; and chronic or cavitary necrotizing pulmonary aspergillosis.

Posaconazole is a strong inhibitor of the CYP3A4 enzyme, a member of the cytochrome P450 family of oxidizing enzymes found in the liver. These Cytochrome P450 enzymes, such as CYP3A4, oxidize small organic molecules in the body, such as toxins or certain drugs, thereby deactivating and/or degrading them. Organic molecules in the body (such as a drug) which are primarily oxidized by a particular enzyme can be referred to as "substrates" for the relevant enzyme. A drug which is primarily oxidized by the CYP3A4 enzyme can be referred to as a "CYP3A4 substrate drug."

The Noxafil label specifically contraindicates the co-administration of CYP3A4 substrate drug with specific drugs metabolized by CYP3A4 such as sirolimus, CYP3A4 substrates such as pimozide and quinidine, HMG-CoA Reductase Inhibitors primarily metabolized through CYP3A4, and ergot alkaloids, and indicates that dosage adjustments should be considered when concomitantly administering posaconazole with other drugs metabolized by CYP3A4, including tacrolimus, cyclosporine, *Vinca* alkaloids such as vincristine and vinblastine, and calcium channel blockers such as verapamil, diltiazem, nifedipine, nicardipine, and felodipine. However, while the Noxafil label does identify specific drug-drug interactions related to concomitant administration of posaconazole and CYP3A4 substrate drugs, it does not indicate any concerns regarding the administration of CYP3A4 substrate drugs after ceasing the administration of posaconazole.

The present inventors have surprisingly discovered that a delay in administration of a CYP3A4 substrate drug, or in some instances a dose adjustment of a CYP3A4 substrate drug for a specified time interval is required after ceasing the administration of posaconazole in order to prevent or reduce the incidence of dangerous side effects of the CYP3A4 substrate drug.

SUMMARY OF THE INVENTION

The present disclosure provides for methods of treating a patient with a CYP3A4 substrate drug contraindicated for concomitant administration with a strong CYP3A4 inhibitor, wherein the patient was previously administered a therapeutically effective regimen of posaconazole.

Applicants have discovered that although CYP3A4 substrate drugs are generally only contraindicated for coadministration with strong CYP3A4 inhibitors, such as posaconazole, CYP3A4 substrate drugs cannot always be safely administered immediately after a patient has stopped posaconazole treatment. Applicants have discovered that posaconazole accumulation in the body of patients, particularly for specific patient populations as described herein, can result in serious and potentially life-threatening side effects if a CYP3A4 substrate drug is administered too soon, subsequent to the cessation of a posaconazole regimen. Accordingly, for CYP3A4 substrate drugs, particularly those contraindicated for coadministration with a strong CYP3A4 inhibitor (including but not limited to posaconazole), a washout or delay period of about 2-42 days (e.g., 2-21 days) between ceasing administration of the posaconazole regimen and starting administration of the CYP3A4 substrate drug is required in order to avoid or reduce the incidence of side effects resulting from administration of the CYP3A4 substrate drug. Alternatively, rather than delaying administering the CYP3A4 substrate drug after ceasing administration of the posaconazole regimen, in some embodiments, the Applicants have discovered that patients can safely be administered a reduced dose of the CYP3A4 substrate drug (reduced relative to the recommended dose of the CYP3A4 substrate drug) for a period of time (about 2-42 days (e.g., 2-21 days)) following cessation of the posaconazole regimen, after which the dose of the CYP3A4 substrate drug can be safely increased to the recommended level.

In certain embodiments, the disclosed methods of delaying treatment with a CYP3A4 substrate drug, or reducing the dose of a CYP3A4 substrate drug, for about 2-42 days (e.g., 2-21 days) after ceasing administration of a posaconazole regimen are directed to a normal patient, e.g., non-obese patients and normal CYP3A4 metabolizers. In certain embodiments, the disclosed methods of delaying treatment of a CYP3A4 substrate drug, or reducing the dose of a CYP3A4 substrate drug, for about 2-42 days (e.g., 2-21 days) after ceasing administration of a posaconazole regimen are directed to patients having specific physiological characteristics as described herein. Such patients can exhibit a substantially greater exposure to the CYP3A4 substrate drug after ceasing administration of a posaconazole regimen than was previously known, and therefore after ceasing administration of posaconazole, require substantially longer "washout" periods prior to starting treatment of a CYP3A4 substrate drug, or require treatment of a reduced dose of the CYP3A4 substrate drug for a substantially longer period in order to avoid or reduce the incidence of side effects associated with treatment of the CYP3A4 substrate drug. More specifically, the present applicants have found that patients having specific physiological characteristics as described herein exhibit higher than expected exposure to a CYP3A4 substrate drug dosed after ceasing administration of a posaconazole regimen, compared to "normal" patients (e.g., a patient who is otherwise the same except for having specific physiological characteristics as described herein). For example, patients with e.g., BMI values in the "normal" range (about 18.5-24.9) can exhibit substantially reduced CYP3A4 substrate drug elimination; such patients may be described as poor or intermediate CYP3A4 metabolizers. Thus, as disclosed herein, the present inventors have found that specific patient populations may require substantially different and longer washout periods after ceasing administration of posaconazole and prior to starting treatment with a CYP3A4 substrate drug, or alternatively treating with a reduced dose of a CYP3A4 substrate drug for a particular period of time after stopping posaconazole treatment.

In various embodiments, the present disclosure provides for methods of treating a patient by delaying a first use of a CYP3A4 substrate drug until about 2-42 days (e.g., 2-21 days) after stopping administration of posaconazole. In embodiments, the CYP3A4 substrate drug is a drug contraindicated for concomitant use with a strong CYP3A4 inhibitor, such as but not limited to posaconazole. Accordingly, in various embodiments, the present disclosure provides for methods of treating a patient who has previously been treated with multiple doses of posaconazole, with a CYP3A4 substrate drug contraindicated for concomitant treatment with a strong CYP3A4 inhibitor, said method comprising first treating the patient, or prescribing the first treatment to begin, with a dose of the CYP3A4 substrate drug at least 2-42 days (e.g., 2-21 days) after stopping a posaconazole treatment.

In various embodiments, the present disclosure provides for methods of treating a patient, or prescribing the first treatment to begin, with a CYP3A4 substrate drug at a dose which is less than or equal to about 50% of the reference dose, e.g., for a period of at least about 2-42 days (e.g., 2-21 days) after stopping posaconazole treatment. Accordingly, in various embodiments, the methods include treating, or prescribing the first treatment to begin, with a therapeutically effective amount of a CYP3A4 substrate drug contraindicated for concomitant use with a strong CYP3A4 inhibitor to a patient in need thereof. In some embodiments, the patient has previously been treated with posaconazole. In some embodiments, the patient is treated, or prescribed to be treated, with a CYP3A4 substrate drug at a dose which is no more than about 50% of the reference dose for at least about 2-42 days (e.g., 2-21 days) after discontinuation of the posaconazole regimen.

In some embodiments, after the delay described herein (e.g., at least 2 days, including 2-42 days), the CYP3A substrate drug is administered the CYP3A4 substrate drug as soon as it is safe. In some embodiments, the CYP3A4 substrate drug is administered in step (d) as soon as at least one of the AUC, Cmax, GMR AUC, or GMR Cmax of the CYP3A4 substrate drug does not exceed a maximum level where benefits of treating the patient outweigh risks of elevated exposure to the CYP3A4 substrate drug. In some embodiments, the maximum level where benefits of treating the patient outweigh risks of elevated exposure to the CYP3A4 substrate drug is a target safe level listed in Table A. In some embodiments, the CYP3A4 substrate drug is administered to achieve a AUC, Cmax, GMR AUC, or GMR Cmax of the CYP3A4 substrate drug that is above the baseline but does not exceed a target safe level listed in Table A for the CYP3A4 substrate drug. In some embodiments, the CYP3A4 substrate drug is administered to achieve an AUC or Cmax of the CYP3A4 substrate drug that is at least about 105% of a predicted AUC or Cmax for the day on which that CYP3A4 substrate drug is administered. In some embodiments, the CYP3A4 substrate drug is administered to achieve an AUC or Cmax of the CYP3A4 substrate drug that is at least about 105% of a predicted AUC or Cmax for the day on which that CYP3A4 substrate drug is administered but does not exceed a target safe level listed in Table A for the CYP3A4 substrate drug. In some embodiments, the CYP3A4 substrate drug is administered to achieve a GMR AUC or GMR Cmax of the CYP3A4 substrate drug that is at least about 1.05-fold of the expected AUC or Cmax. In some embodiments, the CYP3A4 substrate drug is administered to achieve a GMR AUC or GMR Cmax of the CYP3A4 substrate drug that is at least about 1.05-fold of the expected AUC or Cmax but does not exceed a target safe level listed in Table A for the CYP3A4 substrate drug.

In some embodiments, the CYP3A4 substrate drug is selected from the group consisting of abemaciclib, ivacaftor, olaparib, ruxolitinib phosphate, brexpiprazole, ivacaftor/tezacaftor, regorafenib, daclatasvir, crizotinib, naloxegol oxalate, dabrafenib, elbasvir/grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, upadacitinib, roxadustat, AR101, trastuzumab deruxtecan, VK2809, MGL-3196 (resmetirom), and MGL-3745.

In some embodiments, the methods providing for treating patients having a disease or condition selected from the group consisting of: non-metastatic castration-resistant prostate cancer; anaplastic lymphoma kinase (ALK)-positive metastatic non-small cell lung cancer (NSCLC) who have progressed on or are intolerant to crizotinib; seizures associated with Lennox-Gastaut syndrome or Dravet syndrome in patients 2 years of age and older; relapsed follicular lymphoma (FL) in adults who have received at least two prior systemic therapies; adults with relapsed or refractory chronic lymphocytic leukemia (CLL) or small lymphocytic lymphoma (SLL) after at least two prior therapies; adult patients with relapsed or refractory follicular lymphoma (FL) after at least two prior systemic therapies, in combination with binimetinib; unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use; adult patients with relapsed or refractory acute myeloid leukemia (AML) with a susceptible IDH1 mutation as detected by an FDA-approved test; multiple myeloma who have received at least 2 prior regimens, including bortezomib and an immunomodulatory agent; adult patients with locally advanced basal cell carcinoma (BCC) that has recurred following surgery or radiation therapy, or those who are not candidates for surgery or radiation therapy; unresectable or metastatic melanoma with BRAF V600E mutation as detected by an FDA-approved test; Erdheim-Chester Disease with BRAF V600 mutation; non-metastatic castration-resistant prostate cancer; anaplastic lymphoma kinase (ALK)-positive metastatic non-small cell lung cancer (NSCLC) who have progressed on or are intolerant to crizotinib; seizures associated with Lennox-Gastaut syndrome or Dravet syndrome in patients 2 years of age and older; adult patients with relapsed follicular lymphoma (FL) who have received at least two prior systemic therapies; adult patients with relapsed or refractory chronic lymphocytic leukemia (CLL) or small lymphocytic lymphoma (SLL) after at least two prior therapies; adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test; premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance; to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use; adult patients with relapsed or refractory acute myeloid leukemia (AML) with a susceptible IDH1 mutation as detected by an FDA-approved test; patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy; patients with unresectable or metastatic melanoma with BRAF V600E mutation as detected by an FDA-approved test; and the treatment of patients with Erdheim-Chester Disease with BRAF V600 mutation; adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment; relapsing forms of multiple sclerosis (MS), to include clinically isolated syndrome, relapsing-remitting disease, and active secondary progressive disease, in adults; adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy thrombocytopenia in adult patients with chronic immune thrombocytopenia (ITP) who have had an insufficient response to a previous treatment; management of moderate to severe pain associated with endometriosis; treatment of patients with anaplastic lymphoma kinase (ALK)-positive metastatic non-small cell lung cancer (NSCLC) whose disease has progressed on crizotinib and at least one other ALK inhibitor for metastatic disease; anaplastic lymphoma kinase (ALK)-positive metastatic non-small cell lung cancer (NSCLC) whose disease has progressed on alectinib as the first ALK inhibitor therapy for metastatic disease; anaplastic lymphoma kinase (ALK)-positive metastatic non-small cell lung cancer (NSCLC) whose disease has progressed on ceritinib as the first ALK inhibitor therapy for metastatic disease; in combination with low-dose cytarabine, for the treatment of newly-diagnosed acute myeloid leukemia (AML) in adult patients who are ≥75 years old or who have comorbidities that preclude use of intensive induction chemotherapy; adult patients who have relapsed or refractory acute myeloid leukemia (AML) with a FLT3 mutation as detected by an FDA-approved test; opioid-induced constipation (OIC) in adult patients with chronic non-cancer pain, including patients with chronic pain related to prior cancer or its treatment who do not require frequent (e.g., weekly) opioid dosage escalation; adults with tardive dyskinesia; adult patients with newly diagnosed acute myeloid leukemia (AML) that is FLT3 mutation-positive as detected by an FDA-approved test, in combination with standard cytarabine and daunorubicin induction and cytarabine consolidation; adult patients with aggressive systemic mastocytosis (ASM), systemic mastocytosis with associated hematological neoplasm (SM-AHN), or mast cell leukemia (MCL); extended adjuvant treatment of adult patients with early stage HER2-overexpressed/amplified breast cancer, to follow adjuvant trastuzumab-based therapy; adult patients with mantle cell lymphoma (MCL) who have received at least one prior therapy; moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients; ulcerative colitis; psoriatic arthritis; Crohn's disease; atopic dermatitis; ankylosing spondylitis; and giant cell arteritis; CKD-related anemia in patients dependent on kidney dialysis and not on kidney dialysis; to reduce peanut allergy in children and adolescents aged from 4 to 17, and children aged between 1 and 3 years; as monotherapy or as part of a combination with HER2-expressing cancers, including breast cancer, gastric cancer, non-small cell lung cancer, and colorectal cancer; non-alcoholic fatty liver disease (NAFLD); elevated low-density lipoprotein cholesterol (LDL-C); Glycogen storage disease type I (GSD I); non-alcoholic steatohepatitis (NASH); hypercholesterolemia; non-alcoholic steatohepatitis (NASH); dyslipidemias, including heterozygous familial hypercholesterolemia (HeFH); in combination with fluorouracil and leucovorin, for the treatment of patients with metastatic adenocarcinoma of the pancreas after disease progression following gemcitabine-based therapy; first-line therapy in combination with 5-fluorouracil and leucovorin for patients with metastatic carcinoma of the colon or rectum; metastatic carcinoma of the colon or rectum whose disease has recurred or progressed following initial fluorouracil-based therapy; hallucinations and delusions associated with Parkinson's disease psychosis; and unresectable or metastatic liposarcoma or leiomyosarcoma who received a prior anthracycline-containing regimen.

In various embodiments, the present disclosure provides for methods of treating patients, or prescribing treatment for patients, having a disease or condition selected from the group consisting of schizophrenia in adults and adolescents (13 to 17 years), depressive episodes associated with Bipolar I Disorder (bipolar depression) in adults and pediatric patients (10-17 years) as monotherapy or adjunctive therapy with lithium or valproate, moderate bipolar depression, severe bipolar depression, and severe bipolar depression with acute suicidal idealation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever, antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, hormone receptor (HR)-positive, human epidermal growth factor receptor 2 (HER2)-negative advanced or metastatic breast cancer with disease progression following endocrine therapy in women in combination with fulvestrant, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, chronic HCV genotype 1 or 3 infection with sofosbuvir and with or without ribavirin, metastatic non-small cell lung cancer (NSCLC) in patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma in patients with BRAF V600E mutation as detected by an FDA-approved test, in combination with trametinib, for the treatment of unresectable or metastatic melanoma in patients with BRAF V600E or V600K mutations as detected by an FDA-approved test, melanoma in patients with BRAF V600E or V600K mutations, as detected by an FDA-approved test, and involvement of lymph node(s), following complete resection, metastatic non-small cell lung cancer (NSCLC) in patients with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, and the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

In some embodiments, the methods include treating the disease or condition with a CYP3A4 substrate drug which is contraindicated for concomitant use with a strong CYP3A4 inhibitor, wherein the patient is also in need of treatment with a strong CYP3A4 inhibitor (i.e., posaconazole). In some embodiments, the methods include (a) delaying a first treatment of the CYP3A4 substrate drug for at least about 2-42 days after stopping posaconazole; and then (b) treating, or prescribing a first treatment, with the CYP3A4 substrate drug. In other embodiments, the methods include (a) delaying a first treatment of the CYP3A4 substrate drug for at least about 2-21 days after stopping administration of the posaconazole regimen, and then (b) treating or prescribing a first treatment the CYP3A4 substrate drug at a dose which is less than or equal to about 50% of the reference dose for at least about 2-42 days after stopping administration of the posaconazole regimen.

BRIEF DESCRIPTION OF THE DRAWINGS

FIGS. 2A and 2C show the 72-hour duration of the study with a logarithmic concentration axis. FIGS. 2B and 2D show the first 24 hours after dosage with a linear concentration axis. (Data for Days 20 and 26 is not shown).

FIG. 5 shows the mean (±SD) and log-transformed plasma posaconazole concentrations in normal-weight subjects and obese subjects during the period of posaconazole administration and after discontinuation. FIG. 5A shows a linear concentration axis. FIG. 5B shows a logarithmic concentration axis.

FIG. 6 shows the mean (±SD) plasma ranolazine concentrations in normal-weight subjects (FIG. 6A) and obese subjects (FIG. 6B) alone (day 1), with posaconazole coadministration (day 15), and after posaconazole discontinuation (days 18-29). See Table 10 for kinetic analysis. Top is linear concentration axes. Bottom is logarithmic concentration axes.

DETAILED DESCRIPTION

Figure 1:
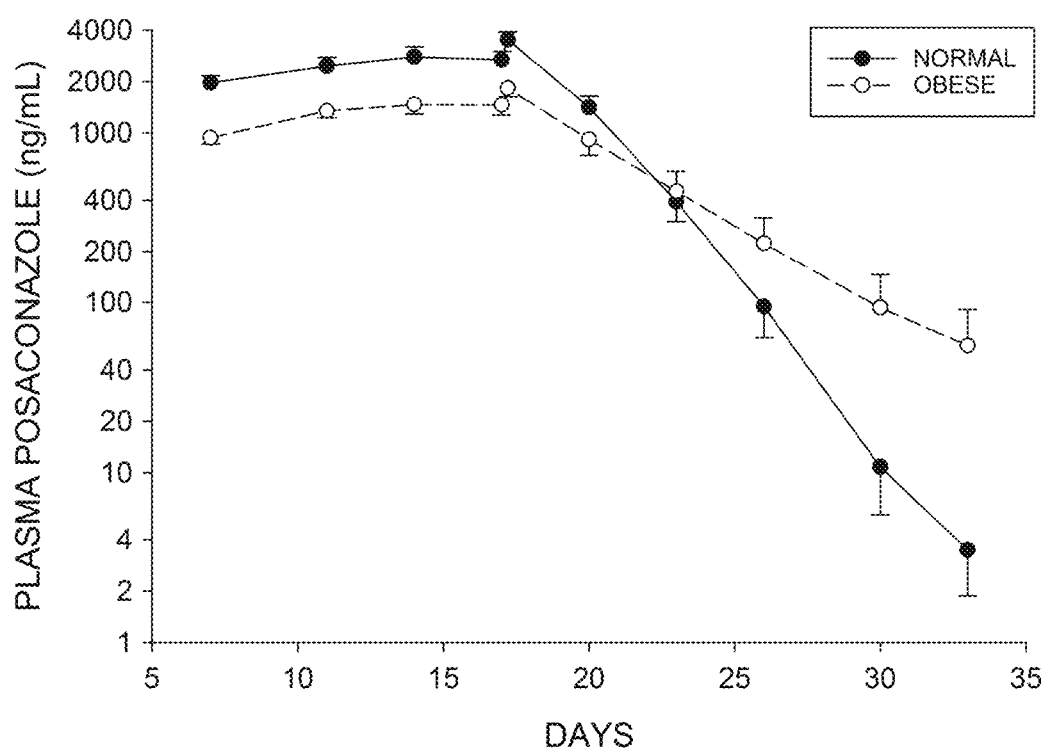
FIG. 1 shows mean (±standard error) plasma posaconazole concentrations in normal-weight subjects, and in obese subjects during the period of posaconazole administration and after discontinuation. See Table 2 for kinetic analysis.

All documents, including patents, applications, and non-patent publications cited herein are incorporated herein in their entireties for all purposes.

As used herein, the term "about" refers to an amount somewhat more or less than the stated parameter value, for example plus or minus five or ten percent of the object that "about" modifies, or as one of skill in the art would recognize from the context (e.g., approximately 50% of the interval between values). The term "about" also includes the value referenced. For example, a BMI of about 40 includes 40, as well as values somewhat below or above 40.

As used herein, the term "patient" refers to a human subject. In some embodiments, the patient can be a male or a female. In some embodiments, the patient can be an adult, or a pediatric patient.

As used herein "treating or "prescribing" as it pertains to the CYP3A substrate drug during the 2-42 day period after ceasing posaconazole treatment, refers to the overall therapeutic regimen of the CYP3A4 substrate drug. For example, a patient may be prescribed or administered (including self-administering) a reduced dose of the CYP3A4 substrate drug (e.g., no more than about 50% of the reference dose of the CYP3A4 substrate drug) during this period. In some embodiments, the patient would not be administered, or would, in the physician's prescribed dosing regimen, be advised not to take the CYP3A4 substrate drug during the 2-42 day period; afterwards, the patient could (or would be prescribed to) resume taking e.g., the reference amount of the CYP3A4 substrate drug.

As used herein, the terms "treating," "treatment" and "treat" include (i) preventing a particular disease or disorder from occurring in a subject who may be predisposed to the disease or disorder but has not yet been diagnosed as having it; (ii) curing, treating, or inhibiting the disease, i.e., arresting its development; or (iii) ameliorating the disease by reducing or eliminating symptoms, conditions, and/or by causing regression of the disease. In some embodiments, "treating," "treatment" and "treat" may include administering a therapeutically effective regimen as defined herein.

As used herein, a "therapeutically effective regimen" refers to a treatment regimen of a duration and dosage sufficient to treat a disease or condition for which a drug is prescribed.

As used herein, a "patient" refers to human subject that has an indication amenable to treatment with posaconazole and is also in need of treatment with a CYP3A4 substrate drug. For example, the patient, prior to being treated with or prescribed posaconazole, can simultaneously have a first indication amenable to treatment with posaconazole and a second indication amenable to treatment the CYP3A4 substrate drug. In some such embodiments, the patient is first treated with posaconazole, and then, after stopping the posaconazole regimen, the patient is switched to a treatment described herein for the CYP3A4 substrate drug. In other embodiments, the patient, while being treated with posaconazole, develops an indication amenable to treatment with a CYP3A4 substrate drug. In some such embodiments, after stopping the posaconazole regimen, the patient is switched to a treatment descried herein for the CYP3A4 substrate drug. As used herein, a "patient" does not include a subject that, at some point after stopping posaconazole treatment, subsequently develops an indication which is amenable to treatment with a CYP3A4 substrate drug.

As used herein, a "patient treated with posaconazole" or a "patient previously on posaconazole" refers to a patient having an indication which was amenable to treatment with posaconazole.

As used herein, the term "normal baseline $C_{max}$" or "baseline $C_{max}$" refers to the average $C_{max}$ of a drug measured at the same dosage in an otherwise identical patient population that was not previously treated with the strong CYP3A4 inhibitor (e.g., posaconazole). For example, when the CYP3A4 substrate drug is ranolazine, the "normal baseline $C_{max}$" of ranolazine refers to the average $C_{max}$ of ranolazine measured at the same dosage of ranolazine in an otherwise identical patient population that was not previously treated with the strong CYP3A4 inhibitor (e.g., posaconazole). As another example, when the CYP3A4 substrate drug is lurasidone, the "normal baseline $C_{max}$" of lurasidone refers to the average $C_{max}$ of lurasidone measured at the same dosage of lurasidone in an otherwise identical patient which was not previously treated with the strong CYP3A4 inhibitor (e.g., posaconazole). As another example, when the CYP3A4 substrate drug is tadalafil, the "normal baseline $C_{max}$" of tadalafil refers to the average $C_{max}$ of tadalafil measured at the same dosage of tadalafil in an otherwise identical patient which was not previously treated with the strong CYP3A4 inhibitor (e.g., posaconazole).

As used herein, the term "normal baseline AUC" or "baseline AUC" refers to the average AUC of a drug measured at the same dosage in an otherwise identical patient population that was not previously treated with the strong CYP3A4 inhibitor (e.g., posaconazole). For example, when the CYP3A4 substrate drug is ranolazine, the "normal baseline AUC" of ranolazine refers to the average AUC of ranolazine measured at the same dosage of ranolazine in an otherwise identical patient population that was not previously treated with the strong CYP3A4 inhibitor (e.g., posaconazole). As another example, when the CYP3A4 substrate drug is lurasidone, the "normal baseline AUC" of lurasidone refers to the average AUC of lurasidone measured at the same dosage of lurasidone in an otherwise identical patient population that was not previously treated with the strong CYP3A4 inhibitor (e.g., posaconazole). As another example, when the CYP3A4 substrate drug is tadalafil, the "normal baseline AUC" of tadalafil refers to the average AUC of tadalafil measured at the same dosage of tadalafil in an otherwise identical patient population that was not previously treated with the strong CYP3A4 inhibitor (e.g., posaconazole).

As used herein, "normal," "reference," or other derivations or variations thereof refers to a non-obese state in a person who can have at least one of the following characteristics: BMI less than about 35, % IBW less than about 150%, waist size less than about 42, % body fat less than about 40%, % android body fat less than about 40%, % gynoid body fat less than about 40%, and total body fat less than about 40 kg. Unless otherwise modified "normal metabolizer" also means an extensive CYP3A4 metabolizer.

As used herein, a "reference dose" refers to the dosage of a particular CYP3A4 substrate drug, as indicated on the manufacture's FDA-approved label (e.g., the most recent FDA-approved label for the particular CYP3A4 drug in effect as of May 7, 2019, prescribed for an identical patient not previously treated with the strong CYP3A4 inhibitor (e.g., posaconazole). It is common for a particular drug to be approved for multiple different indications, and each indication may have a different reference dose. Similarly, drugs are commonly approved for different age groups, and each age group may have a different reference dose. In some embodiments, the reference dose is selected based on the patient's age and condition. Furthermore, some drug labels may recommend a range of doses to treat a particular indication; however, for an individual patient, a specific dose within the recommended range will be safe and therapeutically effective. In such embodiments, the safe and therapeutically effective dose for a particular patient is the "reference dose" for that patient. Specific reference doses for CYP3A4 substrate drugs are provided herein.

Any reference to a CYP3A4 substrate drug herein also encompasses all of the pharmaceutically acceptable isomers (e.g., stereoisomers), solvates, hydrates, polymorphs, salts, and prodrugs (e.g., esters and phosphates). For example, a reference to solifenacin herein also includes its pharmaceutically acceptable salts, such as a succinate salt. As another example, a reference to naloxegol herein also includes its pharmaceutically acceptable salts, such as an oxalate salt. As another example, a reference to aripiprazole herein also includes its pharmaceutically acceptable prodrugs, such as aripiprazole lauroxil.

As used herein, "stereoisomer" is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The CYP3A4 substrate drugs of the present invention may have asymmetric centers and occur as racemates, racemic mixtures, individual diastereoisomers, or enantiomers, or may exist as geometric isomers, with all isomeric forms of said compounds being included in the present invention. Further, the CYP3A4 substrate drug may include any ratio for a mixture of stereoisomers, e.g., from about 1:99 to about 99:1 including all ratios and subranges in between, such as about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, and about 95:5.

The present disclosure also encompasses combinations of the CYP3A4 substrate drugs described herein. Therefore, in accordance of any of the embodiments of the present disclosure, a patient may be treated with more than one CYP3A4 substrate drug, such as lurasidone and ranolazine.

Disclosed herein are methods of treating, or prescribing treatment for, a patient with a CYP3A4 substrate drug contraindicated for concomitant administration with a strong CYP3A4 inhibitor, wherein the patient was previously treated with posaconazole, particularly when patients having one or more of the physiological characteristics described herein are subsequently treated with a CYP3A4 substrate drug. That is, the disclosure provides for methods of treating different patient populations—e.g., "normal" patients, obese patients, and/or intermediate or worse (e.g., poor) CYP3A4 metabolizers—with a CYP3A4 substrate drug contraindicated for concomitant administration with a strong CYP3A4 inhibitor after said patient has ceased posaconazole treatment. Methods of initiating treatment with a CYP3A4 substrate drug intended to treat various conditions or disorders in patients previously treated with posaconazole are also described herein. The present disclosure also provides methods of preventing or decreasing the risk of side effects associated with overexposure to a CYP3A4 substrate drug in normal patients, obese patients and/or patients with impaired CYP3A4 function (e.g., poor or intermediate CYP3A4 metabolizers) and who had previously been treated with a posaconazole regimen prior to treating or prescribing a CYP3A4 substrate drug to said patient. (including those for treating conditions described herein).

In various embodiments, the present disclosure provides methods for treating, or prescribing treatment for, a patient who had been treated with a therapeutically effective posaconazole regimen with a CYP3A4 substrate drug, after a "washout" period of about 2-42 days after ceasing administration of posaconazole. This washout period allows for the blood plasma concentrations of posaconazole to be reduced to appropriate levels after which a CYP3A4 substrate drug can be administered without creating an elevated risk of serious side effects from the CYP3A4 substrate drug. As described herein, the present Applicants have found that CYP3A4 substrate drugs can be safely administered to a patient previously treated with posaconazole, by first treating, or prescribing a first treatment, with the CYP3A4 substrate drug (i.e., initiating the treatment with the CYP3A4 substrate drug) following a "washout" period of about 2-42 days starting at the time the patient has stopped posaconazole treatment. However, the need for such a washout period has been hitherto unknown, as such CYP3A4 substrate drugs are conventionally contraindicated for concomitant administration with posaconazole. As also described herein, in some embodiments the present Applicants have found that instead of a washout period, the CYP3A4 substrate drug can potentially be safely administrated to a patient previously treated with posaconazole, at a dose which is no more than about 50% of the reference dose of the CYP3A4 substrate drug for a period of about 2-42 days after ceasing the posaconazole treatment. Similarly, such a dosing regime has been hitherto unknown.

Cytochrome P450 3A4 (CYP3A4) is an enzyme that modifies small organic molecules, such as particular drugs (specifically including drugs referred to herein as "CYP3A4 substrate drugs"), so that the molecules are metabolized and eliminated from the body. Some substances, termed "CYP3A4 inhibitors," reduce the activity of the CYP3A4 enzyme, and therefore these CYP3A4 inhibitors can increase the exposure of a patient to CYP3A4 substrate drugs. Strong CYP3A4 inhibitors can deactivate CYP3A4 if administered in an appropriate dose, which can result in excessive and potentially dangerous blood plasma levels of a concomitantly administered CYP3A4 substrate drugs. Consequently, concomitant administration of CYP3A4 substrate drugs is contraindicated with strong CYP3A4 inhibitors.

As used herein, a "strong CYP3A4 inhibitor" refers to a drug deemed so by the FDA and/or which causes at least about a 5-fold increase in the AUC of a sensitive CYP3A4 substrate drug, or more than about an 80% decrease in the clearance of a sensitive CYP3A4 substrate drug. The methods disclosed herein can be applied to treat a patient with any CYP3A4 substrate drug which is contraindicated for concomitant administration with any strong CYP3A4 inhibitor, wherein the patient has been treated with a strong CYP3A4 inhibitor, such as posaconazole.

Co-administration of posaconazole and CYP3A4 substrate drugs known to prolong the $QT_c$ interval are contraindicated. The presence of concomitant and clinically significant plasma levels of posaconazole and such CYP3A4 substrate drugs can result in significantly elevated levels of the CYP3A4 substrate drug, which creates a risk of prolonging QT. Consequences of prolonged QT include arrhythmias, rapid heartbeat, abnormal heart rhythm, heart palpitations, dizziness, lightheadedness, sudden fainting, seizure, torsades de pointes, and cardiac death.

For example, according to the drug label for posaconazole (NOXAFIL® label, revised September 2016), patients are advised not to co-administer specific CYP3A4 substrate drugs such as serolimus, pimozide, quinidine, HMG-CoA reductase inhibitors, ergot alkaloids, or drugs known to prolong the $QT_c$ interval and cause cases of TdP, with posaconazole. The NOXAFIL® label also warns that dose adjustments should be considered for concomitant administration of posaconazole and other drugs metabolized by CYP3A4 such as tacrolimus, cyclosporine, *Vinca* alkaloids, and calcium channel blockers. However, the drug label of posaconazole does not recognize that any washout period or any stratification of the patient populations are required after ceasing administration of posaconazole and before initiating administration of a CYP3A4 substrate.

In some embodiments, the strong CYP3A4 inhibitor is posaconazole (i.e., Noxafil, Posanol). Posaconazole is currently formulated as an oral suspension solution (40 mg/mL), and intravenous solution (18 mg/mL), and delayed release tablets (100 mg). According to the drug label (Merck & Co., Inc.), current recommended dosing levels for prophylaxis of invasive *Aspergillus* and *Candida* infections by intravenous injection or by delayed-release tablet are 300 mg twice a day on the first day and 300 mg once a day thereafter, or 200 mg three times a day by oral suspension. Current recommended dosing levels for treatment of oropharyngeal candidiasis by oral suspension are 100 mg twice a day on the first day and 100 mg once a day for 13 days. Current recommended dosing levels for treatment of oropharyngeal candidiasis refractory to itraconazole and/or fluconazole by oral suspension is 400 mg twice a day.

In some embodiments, posaconazole can be indicated for the treatment of fungal infections. In one embodiment, posaconazole can be indicated for the treatment of infections caused by *Candida*, e.g., oropharyngeal candidiasis. In one embodiment, posaconazole can be indicated for the treatment of oropharyngeal candidiasis which is refractory to itraconazole and/or fluconazole. In one embodiment, posaconazole can be indicated for the treatment of infections caused by *Aspergillus*. In one embodiment, posaconazole can be indicated for the treatment of infections caused by Zygomycetes. In some embodiments, posaconazole can be indicated for the prophylaxis of *Aspergillus* or *Candida* infections, e.g., in immunocompromised patients at high risk of developing such infections, such as hematopoietic stem cell transplant (HSCT) recipients with graft-versus-host disease (GVHD) or patients with hematologic malignancies with prolonged neutropenia from chemotherapy. In one embodiment, posaconazole can be indicated for the treatment of zygomycosis. In one embodiment, posaconazole can be indicated for the treatment of allergic bronchopulmonary aspergillosis. In one embodiment, posaconazole can be indicated for the treatment or prophylaxis of recurrent candidiasis for the esophagus, secondary to HIV infections. In one embodiment, posaconazole can be indicated for the treatment of *Fusarium* infections mycosis. In one embodiment, posaconazole can be indicated for the treatment of and chronic or cavitary necrotizing pulmonary aspergillosis.

As used herein, a "CYP3A4 substrate drug" refers to any drug which is primarily metabolized by the CYP3A4 enzyme which is administered in any pharmaceutically acceptable formulation (e.g. tablet, capsule, oral solution, injection, infusion, or delayed or extended release formulations thereof). In some embodiments, the CYP3A4 drug is lurasidone (Latuda). In some embodiments, the CYP3A4 is ranolazine (Ranexa). In some embodiments, the CYP3A4 substrate drugs can include lumacaftor/ivacaftor (Orkambi). In some embodiments, the CYP3A4 substrate drugs can include venetoclax (Venclexta). In some embodiments, the CYP3A4 substrate drugs can include trabectedin (Yondelis). In some embodiments, the CYP3A4 substrate drugs can include ribociclib succinate (Kisqali). In some embodiments, the CYP3A4 substrate drugs can include deflazacort (Emflaza). In some embodiments, the CYP3A4 substrate drugs can include cinacalcet hydrochloride (Sensipar). In some embodiments, the CYP3A4 substrate drugs can include pimavanserin tartrate (Nuplazid). In some embodiments, the CYP3A4 substrate drugs can include aripiprazole lauroxil (Aristada). In some embodiments, the CYP3A4 substrate drugs can include cariprazine hydrochloride (Vraylar). In some embodiments, the CYP3A4 substrate drugs can include simeprevir sodium (Olysio). In some embodiments, the CYP3A4 substrate drugs can include everolimus (Afinitor, Afinitor Disperz, Zortress). In some embodiments, the CYP3A4 substrate drugs can include saxagliptin hydrochloride (Onglyza). In some embodiments, the CYP3A4 substrate drugs can include saxagliptin/metformin hydrochloride (Kombiglyze XR). In some embodiments, the CYP3A4 substrate drugs can include ticagrelor (Brilinta). In some embodiments, the CYP3A4 substrate drugs can include vilazodone hydrochloride (Viibryd). In some embodiments, the CYP3A4 substrate drugs can include apixaban (Eliquis). In some embodiments, the CYP3A4 substrate drugs can include tofacitinib citrate (Xeljanz). In some embodiments, the CYP3A4 substrate drugs can include eletriptan hydrobromide (Relpax). In some embodiments, the CYP3A4 substrate drugs can include nilotinib hydrochloride monohydrate (Tasigna). In some embodiments, the CYP3A4 substrate drugs can include dronedarone hydrochloride (Multaq). In some embodiments, the CYP3A4 substrate drugs can include fluticasone propionate/salmeterol xinafoate (Advair Diskus). In some embodiments, the CYP3A4 substrate drugs can include rivaroxaban (Xarelto). In some embodiments, the CYP3A4 substrate drugs can include tadalafil (Cialis, Adcirca). In some embodiments, the CYP3A4 substrate drugs can include colchicine (Colcrys). In some embodiments, the CYP3A4 substrate drugs can include ibrutinib (Imbruvica). In some embodiments, the CYP3A4 substrate drugs can include cobimetinib (Cotellis).

In some embodiments, the CYP3A4 substrate drugs can include cabazitaxel (Jevtana). In some embodiments, the CYP3A4 substrate drugs can include tolvaptan (Samsca). In some embodiments, the CYP3A4 substrate drugs can include fosaprepitant dimeglumine (Emend). In some embodiments, the CYP3A4 substrate drugs can include aprepitant (Emend). In some embodiments, the CYP3A4 substrate drugs can include solifenacin succinate (VESIcare). In some embodiments, the CYP3A4 substrate drugs can include erlotinib hydrochloride (Tarceva). In some embodiments, the CYP3A4 substrate drugs can include ado-trastuzumab ematansine (Kadcycla). In some embodiments, the CYP3A4 substrate drugs can include bosutinib monohydrate (Bosulif). In some embodiments, the CYP3A4 substrate drugs can include sunitinib malate (Sutent). In some embodiments, the CYP3A4 substrate drugs can include fesoterodine fumarate (Toviaz). In some embodiments, the CYP3A4 substrate drugs can include maraviroc (Selzentry). In some embodiments, the CYP3A4 substrate drugs can include pazopanib hydrochloride (Votrient). In some embodiments, the CYP3A4 substrate drugs can include aripiprazole (Abilify). In some embodiments, the CYP3A4 substrate drugs can include axitinib (Inlyta). In some embodiments, the CYP3A4 substrate drugs can include dapagliflozin/saxagliptin (Farxiga/Onglyza). In some embodiments, the CYP3A4 substrate drugs can include cabozantinib S-malate (Cabometyx). In some embodiments, the CYP3A4 substrate drugs can include ponatinib hydrochloride (Iclusig). In some embodiments, the CYP3A4 substrate drugs can include isavuconazonium sulfate (Cresemba). In some embodiments, the CYP3A4 substrate drugs can include lomitapide mesylate (Juxtapid). In some embodiments, the CYP3A4 substrate drugs can include iloperidone (Fanapt). In some embodiments, the CYP3A4 substrate drugs can include palbociclib (Ibrance). In some embodiments, the CYP3A4 substrate drugs can include levomilnacipran hydrochloride (Fetzima). In some embodiments, the CYP3A4 substrate drugs can include pimozide (Orap). In some embodiments, the CYP3A4 substrate drugs can include pomalidomide (Pomalyst). In some embodiments, the CYP3A4 substrate drugs can include abemaciclib (Verzenio). In some embodiments, the CYP3A4 substrate drugs can include ivacaftor (Kalydeco). In some embodiments, the CYP3A4 substrate drugs can include ruxolitinib phosphate (Jakafi). In some embodiments, the CYP3A4 substrate drugs can include brexpiprazole (Rexulti). In some embodiments, the CYP3A4 substrate drugs can include ivacaftor/tezacaftor (Symdeko). In some embodiments, the CYP3A4 substrate drugs can include regorafenib (Stivarga). In some embodiments, the CYP3A4 substrate drugs can include daclatasvir (Daklinza). In some embodiments, the CYP3A4 substrate drugs can include crizotinib (Xalkori). In some embodiments, the CYP3A4 substrate drugs can include naloxegol oxalate (Movantik). In some embodiments, the CYP3A4 substrate drugs can include dabrafenib (Tafinlar). In some embodiments, the CYP3A4 substrate drugs can include elbasvir and grazoprevir (Zepatier). In some embodiments, the CYP3A4 substrate drugs can include olaparib (Lynparza). In some embodiments, the CYP3A4 substrate drugs can include apalutamide (Erleada). In some embodiments, the CYP3A4 substrate drugs can include brigatinib (Alunbrig). In some embodiments, the CYP3A4 substrate drugs can include cannabidiol (Epidiolex). In some embodiments, the CYP3A4 substrate drugs can include copanlisib (Aliqopa). In some embodiments, the CYP3A4 substrate drugs can include duvelisib (Copiktra). In some embodiments, the CYP3A4 substrate drugs can include encorafenib (Braftovi). In some embodiments, the CYP3A4 substrate drugs can include flibanserin (Addyi). In some embodiments, the CYP3A4 substrate drugs can include ivabradine (Corlanor). In some embodiments, the CYP3A4 substrate drugs can include ivosidenib (Tibsovo). In some embodiments, the CYP3A4 substrate drugs can include panobinostat (Farydak). In some embodiments, the CYP3A4 substrate drugs can include sonidegib (Odomzo). In some embodiments, the CYP3A4 substrate drugs can include vemurafenib (Zelboraf). In some embodiments, the CYP3A4 substrate drugs can include larotrectinib (Vitrakvi). In some embodiments, the CYP3A4 substrate drugs can include irinotecan (Onivyde, Camptosar). In some embodiments, the CYP3A4 substrate drugs can include siponimod (Mayzent). In some embodiments, the CYP3A4 substrate drugs can include erdafitinib (Balversa). In some embodiments, the CYP3A4 substrate drugs can include fostamatinib disodium (Tavalisse). In some embodiments, the CYP3A4 substrate drugs can include elagolix sodium (Orlissa). In some embodiments, the CYP3A4 substrate drugs can include lorlatinib (Lorbrena). In some embodiments, the CYP3A4 substrate drugs can include glasdegib (Daurismo). In some embodiments, the CYP3A4 substrate drugs can include gilteritinib (Xospata). In some embodiments, the CYP3A4 substrate drugs can include naldemedine (Symproic). In some embodiments, the CYP3A4 substrate drugs can include valbenazine (Ingrezza). In some embodiments, the CYP3A4 substrate drugs can include midostaurin (Rydapt). In some embodiments, the CYP3A4 substrate drugs can include neratinib (Nerlynx). In some embodiments, the CYP3A4 substrate drugs can include acalabrutinib (Calquence). In some embodiments, the CYP3A4 substrate drugs can include pimavanserin (Nuplazid). In some embodiments, the CYP3A4 substrate drugs can include trabectedin (Yondelis). In some embodiments, the CYP3A4 substrate drugs can include upadacitinib. In some embodiments, the CYP3A4 substrate drugs can include roxadustat. In some embodiments, the CYP3A4 substrate drugs can include AR-101. In some embodiments, the CYP3A4 substrate drugs can include trastuzumab deruxtecan. In some embodiments, the CYP3A4 substrate drugs can include VK2809. In some embodiments, the CYP3A4 substrate drugs can include MGL-3196. In some embodiments, the CYP3A4 substrate drugs can include MGL-3745. Other non-limiting examples of CYP3A4 substrate drugs include HIV protease inhibitors, such as amprenavir (Agenerase), atazanavir (Reyataz), darunavir (Prezista), fosamprenavir (Lexiva, Telzir), indinavir (Crixivan), lopinavir (Kaletra), nelfinavir (Viracept), ritonavir (Norvir), saquinavir (Invirase, Forovase), and tipranavir (Aptivus), benzodiazepines, such as alprazolam (Xanax), clonazepam (Klonopin), and diazepam (Valium), calcium channel blockers such as amlodipine (Norvasc), aranidipine (Sapresta), azelnidipine (Calblock), barnidipine (HypoCa), benidipine (Coniel), cilnidipine (Atelec, Cinalong, Siscard), clevidipine (Cleviprex), isradipine (DynaCirc, Prescal), efonidipine (Landel), felodipine (Plendil), lacidipine (Motens, Lacipil), lercanidipine (Zanidip), manidipine (Calslot, Madipine), nicardipine (Cardene, Carden SR), nifedipine (Procardia, Adalat), nilvadipine (Nivadil), nimodipine (Nimotop), nisoldipine (Baymycard, Sular, Syscor), nitrendipine (Cardif, Nitrepin, Baylotensin), and pranidipine (Acalas), hydroxymethylglutaryl coenzyme A-reductase inhibitors, such as atorvastatin (Lipitor, Ator), lovastatin (Mevacor, Altocor, Altoprev), mevastatin (Compactin) and simvastatin (Zocor, Lipex), antineoplastic drugs, such as sorafenib (Nexavar) and sunitinib (Sutent), nonsedating antihistamines, such as fexofenadine (Allegra), loratadine (Claritin), desloratadine (Clarinex), cetirizine (Zyrtec), levocetirizine (Xyza) and immunosuppressants, such as cyclosporin.

In some embodiments, the CYP3A4 substrate drug used in the methods disclosed herein can be any drug metabolized by CYP3A4, in particular drugs metabolized by CYP3A4 and which are contraindicated for use with strong CYP3A4 inhibitors or include dose adjustment recommendations for concomitant administration with CYP3A4 inhibitors. In some embodiments, the methods described herein can be applied to any therapeutic regimen in which one or more CYP3A4 substrate drug(s) described herein are used to treat a patient previously on posaconazole, including therapeutic regimens that entail treating a patient with a CYP3A4 substrate drug in combination with other drugs.

In some embodiments, the CYP3A4 substrate drug can be indicated for the treatment of disease or condition selected from the group consisting of schizophrenia in adults and adolescents (13 to 17 years), depressive episodes associated with Bipolar I Disorder (bipolar depression) in adults and pediatrics (10 to 17 years) as monotherapy or adjunctive therapy with lithium or valproate, moderate bipolar depression, severe bipolar depression, and severe bipolar depression with acute suicidal idealation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, advanced hormone receptor-positive, HER2-negative breast cancer (advanced HR+ BC) in postmenopausal women in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever, antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, and treatment of multiple myeloma in patients who have received at least two prior therapies including lenalidomide and a proteasome inhibitor and have demonstrated disease progression on or within 60 days of completion of the last therapy allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, hormone receptor (HR)-positive, human epidermal growth factor receptor 2 (HER2)-negative advanced or metastatic breast cancer with disease progression following endocrine therapy in women in combination with fulvestrant, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, chronic HCV genotype 1 or 3 infection with sofosbuvir and with or without ribavirin, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma in patients with BRAF V600E mutation as detected by an FDA-approved test, in combination with trametinib, unresectable or metastatic melanoma in patients with BRAF V600E or V600K mutations as detected by an FDA-approved test, adjuvant treatment of patients with melanoma in patients BRAF V600E or V600K mutations, as detected by an FDA-approved test, and involvement of lymph node(s), following complete resection, metastatic non-small cell lung cancer (NSCLC) in patients with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

In some embodiments, the CYP3A4 substrate drug can be indicated for the treatment of schizophrenia in adults and adolescents (13 to 17 years), depressive episodes associated with Bipolar I Disorder (bipolar depression) in adults and pediatrics (10-17 years) as monotherapy or as adjunctive therapy with lithium or valproate, moderate bipolar depression, severe bipolar depression, and severe bipolar depression with acute suicidal ideation and behavior (ASIB).

In one embodiment, the CYP3A4 substrate drug can be indicated for the treatment of chronic angina.

In one embodiment, the CYP3A4 substrate drug can be indicated for the treatment of cystic fibrosis, e.g., in patients 6 years and older who are homozygous for the F508del mutation in the CFTR gene.

In one embodiment, the CYP3A4 substrate drug can be indicated for the treatment of chronic lymphocytic leukemia, e.g., in patients with 17p deletion, who have received at least one prior therapy.

In one embodiment, the CYP3A4 substrate drug can be indicated for the treatment of unresectable or metastatic liposarcoma or leiomyosarcoma, e.g., in patients who received a prior anthracycline-containing regimen.

In one embodiment, the CYP3A4 substrate drug can be indicated for the treatment of advanced or metastatic breast cancer, e.g., in postmenopausal women with hormone receptor (HR)-positive, human epidermal growth factor receptor 2 (HER2)-negative advanced or metastatic breast cancer. In a further embodiment, the CYP3A4 substrate drug can be indicated for a treatment of negative advanced or metastatic breast cancer in postmenopausal women e.g., in combination with an aromatase inhibitor as initial endocrine-based therapy.

In one embodiment, the CYP3A4 substrate drug can be indicated for the treatment of Duchenne muscular dystrophy (DMD).

In one embodiment, the CYP3A4 substrate drug can be indicated for the treatment of secondary hyperparathyroidism (HPT), e.g., in patients with chronic kidney disease (CKD) on dialysis. In one embodiment, the CYP3A4 substrate drug can be indicated for the treatment of hypercalcemia, e.g., in patients with parathyroid carcinoma. In one embodiment, the CYP3A4 substrate drug can be indicated for the treatment of hypercalcemia, e.g., in patients with primary HPT for who parathyroidectomy would be indicated on the basis of serum calcium levels, but who are unable to undergo parathyroidectomy.

In one embodiment, the CYP3A4 substrate drug can be indicated for the treatment of hallucinations and delusions associated with Parkinson's disease psychosis.

In one embodiment, the CYP3A4 substrate drug can be indicated for the treatment of schizophrenia.

In one embodiment, the CYP3A4 substrate drug can be indicated for the acute treatment of manic or mixed episodes associated with bipolar I disorder.

In one embodiment, the CYP3A4 substrate drug can be indicated for the treatment of chronic hepatitis C (CHC) infection, e. g., as a component of a combination antiviral treatment regimen with peginterferon alfa and ribavirin in HCV genotype 1 infected subjects with compensated liver disease.

In one embodiment, the CYP3A4 substrate drug can be indicated for the treatment of postmenopausal women with advanced hormone receptor-positive, HER2-negative breast cancer (advanced HR+ BC), e.g., in combination with exemestane after failure of treatment with letrozole or anastrozole. In one embodiment, the CYP3A4 substrate drug can be indicated for the treatment of patients with progressive neuroendocrine tumors of pancreatic origin (PNET). In one embodiment, the CYP3A4 substrate drug can be indicated for the treatment of patients with progressive, well-differentiated, non-functional neuroendocrine tumors (NET) of gastrointestinal (GI) or lung origin that are unresectable, locally advanced or metastatic. In one embodiment, the CYP3A4 substrate drug can be indicated for the treatment of patients with advanced renal cell carcinoma (RCC), e.g., after failure of treatment with sunitinib or sorafenib. In one embodiment, the CYP3A4 substrate drug can be indicated for the treatment of patients with renal angiomyolipoma and tuberous sclerosis complex (TSC), not requiring immediate surgery. In one embodiment, the CYP3A4 substrate drug can be indicated for the treatment of patients with TSC who have subependymal giant cell astrocytoma (SEGA) that require therapeutic intervention but are not candidates for surgical resection.

In one embodiment, the CYP3A4 substrate drug can be indicated for the treatment of type 2 diabetes mellitus, e.g., as an adjunct to diet and exercise to improve glycemic control in adults.

In one embodiment, the CYP3A4 substrate drug can be indicated to reduce the rate of thrombotic cardiovascular events (e.g., cardiovascular death, myocardial infarction, or stroke) in patients with acute coronary syndrome (ACS).

In one embodiment, the CYP3A4 substrate drug can be indicated for the treatment of major depressive disorder (MDD).

In one embodiment, the CYP3A4 substrate drug can be indicated to reduce the risk of stroke and systemic embolism in patients with nonvalvular atrial fibrillation. In one embodiment, the CYP3A4 substrate drug can be indicated for the prophylaxis of deep vein thrombosis (DVT), which may lead to pulmonary embolism (PE), e.g., in patients who have undergone hip or knee replacement surgery. In one embodiment, the CYP3A4 substrate drug can be indicated for the treatment of DVT or PE. In one embodiment, the CYP3A4 substrate drug can be indicated to reduce the risk of recurrent DVT and PE following initial therapy.

In one embodiment, the CYP3A4 substrate drug can be indicated for the treatment of moderate to severe active rheumatoid arthritis, e.g., in patients who have had inadequate response or tolerance to methotrexate.

In one embodiment, the CYP3A4 substrate drug can be indicated for the acute treatment of migraine with or without aura.

In one embodiment, the CYP3A4 substrate drug can be indicated for the treatment of chronic phase and accelerated phase Philadelphia chromosome positive chronic myeloid leukemia (Ph+ CML), e.g., in newly diagnosed patients or in patients resistant to or intolerant to prior therapy that included imatinib.

In one embodiment, the CYP3A4 substrate drug can be indicated to reduce the risk of hospitalization for atrial fibrillation (AF), e.g., in patients with a history of paroxysmal or persistent AF or atrial flutter (AFK), who are in sinus rhythm or will be cardioverted.

In one embodiment, the CYP3A4 substrate drug can be indicated for maintenance treatment of asthma, e.g., in patients aged 4 years and older. In one embodiment, the CYP3A4 substrate drug can be indicated for maintenance treatment of airflow obstruction and reducing exacerbations in patients with chronic obstructive pulmonary disease.

In one embodiment, the CYP3A4 substrate drug can be indicated for the treatment of erectile dysfunction (ED). In one embodiment, the CYP3A4 substrate drug can be indicated for the treatment of benign prostatic hyperplasia (BPH). In one embodiment, the CYP3A4 substrate drug can be indicated for treatment of pulmonary arterial hypertension (PAH) (WHO Group 1) to improve exercise ability.

In one embodiment, the CYP3A4 substrate drug can be indicated for the treatment of gout flares. In one embodiment, the CYP3A4 substrate drug can be indicated for the treatment of Familial Mediterranean fever.

In one embodiment, the CYP3A4 substrate drug can be indicated for mantle cell lymphoma in patients who have received at least one prior therapy. In one embodiment, the CYP3A4 substrate drug can be indicated for chronic lymphocytic leukemia/small lymphocytic lymphoma. In one embodiment, the CYP3A4 substrate drug can be indicated for chronic lymphocytic leukemia/small lymphocytic lymphoma with 17p deletion.

In one embodiment, the CYP3A4 substrate drug can be indicated for Waldenström's macroglobulinemia.

In one embodiment, the CYP3A4 substrate drug can be indicated for marginal zone lymphoma who require systemic therapy and have received at least one prior anti-CD20-based therapy.

In one embodiment, the CYP3A4 substrate drug can be indicated for unresectable or metastatic melanoma with a BRAF V600E or V600K mutation.

In one embodiment, the CYP3A4 substrate drug can be indicated for the treatment of hormone-refractory metastatic prostate cancer previously treated with a docetaxel-containing treatment regimen.

In one embodiment, the CYP3A4 substrate drug can be indicated for treatment of clinically significant hypervolemic and euvolemic hyponatremia; including patients with heart failure and Syndrome of Inappropriate Antidiuretic Hormone (SIADH).

In one embodiment, the CYP3A4 substrate drug can be indicated for the prevention of acute and delayed nausea and vomiting associated with initial and repeat courses of highly emetogenic cancer chemotherapy (HEC) including high-dose cisplatin.

In one embodiment, the CYP3A4 substrate drug can be indicated for the prevention of delayed nausea and vomiting associated with initial and repeat courses of moderately emetogenic cancer chemotherapy (MEC).

In one embodiment, the CYP3A4 substrate drug can be indicated for treatment of over-active bladder with symptoms of urge urinary incontinence, urgency, and urinary frequency.

In one embodiment, the CYP3A4 substrate drug can be indicated for the treatment of patients with metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression.

In one embodiment, the CYP3A4 substrate drug can be indicated for the first-line treatment of patients with locally advanced, unresectable or metastatic pancreatic cancer, in combination with gemcitabine.

In one embodiment, the CYP3A4 substrate drug can be indicated for the treatment of patients with HER2-positive, metastatic breast cancer who previously received trastuzumab and a taxane, separately or in combination in patients who have either: received prior therapy for metastatic disease or developed disease recurrence during or within six months of completing adjuvant therapy.

In one embodiment, the CYP3A4 substrate drug can be indicated for the treatment of adult patients with chronic, accelerated, or blast phase Ph+ chronic myelogenous leukemia (CML) with resistance or intolerance to prior therapy.

In one embodiment, the CYP3A4 substrate drug can be indicated for the treatment of gastrointestinal stromal tumor (GIST) after disease progression on or intolerance to imatinib mesylate.

In one embodiment, the CYP3A4 substrate drug can be indicated for the treatment of advanced renal cell carcinoma (RCC); progressive, well-differentiated pancreatic neuroendocrine tumors (pNET) in patients with unresectable locally advanced or metastatic disease.

In one embodiment, the CYP3A4 substrate drug can be indicated for the treatment of only CCR5-tropic HIV-1 infection in patients 2 years of age and older weighing at least 10 kg in combination with other antiretroviral agents.

In one embodiment, the CYP3A4 substrate drug can be indicated for the treatment of patients with advanced renal cell carcinoma.

In one embodiment, the CYP3A4 substrate drug can be indicated for the treatment of patients with advanced soft tissue sarcoma who have received prior chemotherapy.

In one embodiment, the CYP3A4 substrate drug can be indicated for the acute treatment of manic and mixed episodes associated with Bipolar I.

In one embodiment, the CYP3A4 substrate drug can be indicated for the adjunctive treatment of Major Depressive Disorder.

In one embodiment, the CYP3A4 substrate drug can be indicated for the treatment of irritability associated with Autistic Disorder.

In one embodiment, the CYP3A4 substrate drug can be indicated for the treatment of Tourette's disorder.

In one embodiment, the CYP3A4 substrate drug can be indicated for the treatment of agitation associated with schizophrenia or bipolar mania.

In one embodiment, the CYP3A4 substrate drug can be indicated for the treatment of advanced renal cell carcinoma after failure of one prior systemic therapy.

In one embodiment, the CYP3A4 substrate drug can be indicated to improve glycemic control in adults with type 2 diabetes mellitus (T2DM) who have inadequate control with dapagliflozin or who are already treated with dapagliflozin and saxagliptin.

In one embodiment, the CYP3A4 substrate drug can be indicated for the treatment of patients with progressive, metastatic medullary thyroid cancer (MTC).

In one embodiment, the CYP3A4 substrate drug can be indicated for the treatment of patients with advanced renal cell carcinoma (RCC) who have received prior anti-angiogenic therapy.

In one embodiment, the CYP3A4 substrate drug can be indicated for the treatment of adult patients with chronic phase, accelerated phase, or blast phase chronic myeloid leukemia (CML) or Ph+ ALL for whom no other tyrosine kinase inhibitor (TKI) therapy is indicated.

In one embodiment, the CYP3A4 substrate drug can be indicated for the treatment of adult patients with T315I-positive CML (chronic phase, accelerated phase, or blast phase) or T315I-positive Philadelphia chromosome positive acute lymphoblastic leukemia (Ph+ ALL).

In one embodiment, the CYP3A4 substrate drug can be indicated for the treatment of invasive aspergillosis.

In one embodiment, the CYP3A4 substrate drug can be indicated for the treatment of invasive mucormycosis; to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH).

In one embodiment, the CYP3A4 substrate drug can be indicated for the treatment of schizophrenia in adults.

In one embodiment, the CYP3A4 substrate drug can be indicated for the treatment of hormone receptor (HR)-positive; human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy.

In one embodiment, the CYP3A4 substrate drug can be indicated for the treatment of Major Depressive Disorder (MDD).

In one embodiment, the CYP3A4 substrate drug can be indicated for the suppression of motor and phonic tics in patients with Tourette's Disorder who have failed to respond satisfactorily to standard treatment.

In one embodiment, the CYP3A4 substrate drug can be indicated for the treatment of multiple myeloma in patients who have received at least two prior therapies including lenalidomide and a proteasome inhibitor and have demonstrated disease progression on or within 60 days of completion of the last therapy.

In one embodiment, the CYP3A4 substrate drug can be indicated for the treatment of non-small cell lung cancer (NSCLC) whose disease has not progressed after four cycles of platinum-based first-line chemotherapy.

In one embodiment, the CYP3A4 substrate drug can be indicated for the treatment of locally advanced or metastatic NSCLC after failure of at least one prior chemotherapy regimen.

In one embodiment, the CYP3A4 substrate drug can be indicated for the treatment of locally advanced, unresectable or metastatic pancreatic cancer.

In one embodiment, the CYP3A4 substrate drug can be indicated for the treatment of overactive bladder with symptoms of urge urinary incontinence, urgency, and urinary frequency.

In one embodiment, the CYP3A4 substrate can be indicated for the treatment of advanced renal cell carcinoma (RCC) after failure of treatment with sunitinib or sorafenib.

In one embodiment, the CYP3A4 substrate drug can be indicated for the treatment of subependymal giant cell astrocytoma (SEGA) associated with tuberous sclerosis complex (TSC) who require therapeutic intervention but are not candidates for curative surgical resection.

In one embodiment, the CYP3A4 substrate drug can be indicated for the treatment of renal angiomyolipoma and tuberous sclerosis complex.

In one embodiment, the CYP3A4 substrate drug can be indicated for the treatment of hormone receptor (HR)-positive, human epidermal growth factor receptor 2 (HER2)-negative advanced or metastatic breast cancer with disease progression following endocrine therapy in women in combination with fulvestrant.

In one embodiment, the CYP3A4 substrate drug can be used as monotherapy for the treatment of adult patients with HRpositive, HER2-negative advanced or metastatic breast cancer with disease progression following endocrine therapy and prior chemotherapy in the metastatic setting.

In one embodiment, the CYP3A4 substrate drug can be indicated for the treatment of cystic fibrosis (CF) in patients age 2 years and older who have one mutation in the CFTR gene that is responsive to ivacaftor based on clinical and/or in vitro assay data.

In one embodiment, the CYP3A4 substrate drug can be indicated for the treatment of deleterious or suspected deleterious germline BRCA-mutated advanced ovarian cancer in adult patients who have been treated with three or more prior lines of chemotherapy.

In one embodiment, the CYP3A4 substrate drug can be indicated for the treatment of intermediate or high-risk myelofibrosis, including primary myelofibrosis, post-polycythemia vera myelofibrosis and post-essential thrombocythemia myelofibrosis.

In one embodiment, the CYP3A4 substrate drug can be indicated for the treatment of polycythemia vera patients who have had an inadequate response to or are intolerant of hydroxyurea.

In one embodiment, the CYP3A4 substrate drug can be indicated as an adjunctive therapy to antidepressants for the treatment of major depressive disorder (MDD).

In one embodiment, the CYP3A4 substrate drug can be indicated for the treatment of schizophrenia.

In one embodiment, the CYP3A4 substrate drug can be indicated for the treatment of cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence.

In one embodiment, the CYP3A4 substrate drug can be indicated for the treatment of metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy.

In one embodiment, the CYP3A4 substrate drug can be indicated for the treatment of locally advanced, unresectable or metastatic gastrointestinal stromal tumor (GIST) patients who have been previously treated with imatinib mesylate and sunitinib malate.

In one embodiment, the CYP3A4 substrate drug can be indicated for the treatment of hepatocellular carcinoma (HCC) in patients who have been previously treated with sorafenib.

In one embodiment, the CYP3A4 substrate drug can be indicated for the use with sofosbuvir, with or without ribavirin, for the treatment of chronic HCV genotype 1 or 3 infection.

In one embodiment, the CYP3A4 substrate drug can be indicated for the treatment of metastatic non-small cell lung cancer (NSCLC) patients whose tumors are anaplastic lymphoma kinase (ALK) or ROS1-positive as detected by an FDA-approved test.

In one embodiment, the CYP3A4 substrate drug can be indicated for the treatment of opioid induced constipation (OIC) in adult patients with chronic non-cancer pain, including patients with chronic pain related to prior cancer or its treatment who do not require frequent (e.g., weekly) opioid dosage escalation.

In one embodiment, the CYP3A4 substrate drug can be indicated for the treatment of unresectable or metastatic melanoma with BRAF V600E mutation as detected by an FDA-approved test.

In one embodiment, the CYP3A4 substrate drug can be indicated in combination with trametinib, for the treatment of patients with unresectable or metastatic melanoma with BRAF V600E or V600K mutations as detected by an FDA-approved test.

In one embodiment, the CYP3A4 substrate drug can be indicated in combination with trametinib, for the treatment of patients with melanoma with BRAF V600E or V600K mutations, as detected by an FDA-approved test, and involvement of lymph node(s), following complete resection.

In one embodiment, the CYP3A4 substrate drug can be indicated in combination with trametinib, for the treatment of metastatic non-small cell lung cancer (NSCLC) with BRAF V600E mutation as detected by an FDA-approved test.

In one embodiment, the CYP3A4 substrate drug can be indicated in combination with trametinib, for the treatment of locally advanced or metastatic anaplastic thyroid cancer (ATC) with BRAF V600E mutation and with no satisfactory locoregional treatment options.

In one embodiment, the CYP3A4 substrate drug can be indicated with or without ribavirin for treatment of chronic HCV genotypes 1 or 4 infection in adults.

In some embodiments, the CYP3A4 substrate drug can be indicated in adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment.

In some embodiments, the CYP3A4 substrate drug can be indicated for relapsing forms of multiple sclerosis (MS), to include clinically isolated syndrome, relapsing-remitting disease, and active secondary progressive disease in adults.

In some embodiments, the CYP3A4 substrate drug can be indicated in adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy.

In some embodiments, the CYP3A4 substrate drug can be indicated for treatment of thrombocytopenia in adult patients with chronic immune thrombocytopenia (ITP) who have had an insufficient response to a previous treatment.

In some embodiments, the CYP3A4 substrate drug can be indicated for management of moderate to severe pain associated with endometriosis.

In some embodiments, the CYP3A4 substrate drug can be indicated for treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease.

In some embodiments, the CYP3A4 substrate drug can be indicated, in combination with low-dose cytarabine, for the treatment of newly-diagnosed acute myeloid leukemia (AML) in adult patients who are ≥75 years old or who have comorbidities that preclude use of intensive induction chemotherapy.

In some embodiments, the CYP3A4 substrate drug can be indicated for treatment of adult patients who have relapsed or refractory acute myeloid leukemia (AML) with a FLT3 mutation as detected by an FDA-approved test.

In some embodiments, the CYP3A4 substrate drug can be indicated in adults with tardive dyskinesia.

In some embodiments, the CYP3A4 substrate drug can be indicated in adult patients with newly diagnosed acute myeloid leukemia (AML) that is FLT3 mutation-positive as detected by an FDA-approved test.

In some embodiments, the CYP3A4 substrate drug can be indicated, in combination with standard cytarabine and daunorubicin induction and cytarabine consolidation, in adult patients with aggressive systemic mastocytosis (ASM), systemic mastocytosis with associated hematological neoplasm (SM-AHN), or mast cell leukemia (MCL).

In some embodiments, the CYP3A4 substrate drug can be indicated in extended adjuvant treatment of adult patients with early stage HER2-overexpressed/amplified breast cancer, to follow adjuvant trastuzumab-based therapy.

In some embodiments, the CYP3A4 substrate drug can be indicated for treatment of adult patients with mantle cell lymphoma (MCL) who have received at least one prior therapy.

In some embodiments, the CYP3A4 substrate drug can be indicated for treatment of moderate to severe rheumatoid arthritis, including patients not responding adequately to conventional synthetic disease-modifying anti-rheumatic drugs (DMARDs), patients not adequately responding to or intolerant of biologic DMARDs.

In some embodiments, the CYP3A4 substrate drug is indicated in patients switching from methotrexate monotherapy after inadequate responses, in combination with methotrexate, in patients with inadequate responses, and in methotrexate-naive patients with ulcerative colitis, psoriatic arthritis, Crohn's disease, atopic dermatitis, ankylosing spondylitis, and giant cell arteritis.

In some embodiments, the CYP3A4 substrate drug is indicated for CKD-related anemia in patients dependent on kidney dialysis and not on kidney dialysis.

In some embodiments, the CYP3A4 substrate drug is indicated to reduce peanut allergy in children and adolescents aged from 4 to 17, and children aged between 1 and 3 years.

In some embodiments, the CYP3A4 substrate drug is indicated as monotherapy or as part of a combination with HER2-expressing cancers, including breast cancer, gastric cancer, non-small cell lung cancer, and colorectal cancer.

In some embodiments, the CYP3A4 substrate drug is indicated for treatment of non-alcoholic fatty liver disease (NAFLD), elevated low-density lipoprotein cholesterol (LDL-C), or Glycogen storage disease type I (GSD I).

In some embodiments, the CYP3A4 substrate drug is indicated for treatment of non-alcoholic steatohepatitis (NASH), hypercholesterolemia, or non-alcoholic steatohepatitis (NASH), dyslipidemias, including heterozygous familial hypercholesterolemia (HeFH).

In some embodiments, the CYP3A4 substrate drug is indicated, in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy.

In some embodiments, the CYP3A4 substrate drug is indicated for treatment of hallucinations and delusions associated with Parkinson's disease psychosis.

In some embodiments, the CYP3A4 substrate drug is indicated for treatment of unresectable or metastatic liposarcoma or leiomyosarcoma who received a prior anthracycline-containing regimen.

Other non-limiting examples of conditions or diseases for which CYP3A4 substrate drugs are prescribed include anti-retroviral therapy, e.g., for the treatment of HIV/AIDS, anxiety disorders, panic disorders, seizures, insomnia, hypertension, cardiovascular disease (e.g., myocardial infarction, stroke, and angina), hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, allergies, and transplantation.

As discussed above, after stopping treatment with a strong CYP3A4 inhibitor (including but not limited to posaconazole), posaconazole accumulates in the body of patients, and reduces or prevents metabolism of CYP3A4 substrate drugs. Thus, patients previously on posaconazole that are concomitantly treated with CYP3A4 substrate drugs may have plasma levels of the CYP3A4 substrate drug that exceed the plasma levels of an otherwise identical patient that was not previously treated with posaconazole. Described herein, in various embodiments, are treatment regimens for CYP3A4 substrate drugs which are applicable to patients who previously received multiple doses of a strong CYP3A4 inhibitor (e.g., posaconazole) for a period of about 2-21 days after stopping treatment with the strong CYP3A4 inhibitor. In some embodiments, the treatment regimen provides for treating or prescribing a dose which is less than about 50% of the reference dose of the CYP3A4 substrate drug for a period of about 2-21 days after stopping posaconazole treatment. As used herein, a dose that is less than 50% of the reference dose of the CYP3A4 inhibitor can include any amount from 0% (i.e., no dose) to about 50% of the CYP3A4 inhibitor for the period of 2-21 days. Therefore, the treatment regimen disclosed herein can include, in some embodiments, delaying a first dose of a CYP3A4 substrate drug for about 2-21 days after stopping posaconazole treatment, or alternatively, treating with a reduced dose of the CYP3A4 substrate drug for about 2-21 days after stopping posaconazole treatment. The methods described herein can be applied to any patient that was previously on posaconazole and having an indication amenable to treatment with a CYP3A4 substrate drug, including normal patients (non-obese and normal metabolizers), obese patients, and poor or intermediate metabolizers, or combinations thereof.

In some embodiments, between about 2 and about 42 days, e.g., about 2, about 3, about 4, about 5, about 6, about 7, about 8, about 9, about 10, about 11, about 12 days, about 13, about 14, about 15, about 16, about 17, about 18, about 19, about 20, about 21 days, about 22 days, about 23, about 24, about 25, about 26, about 27, about 28, about 29, about 30, about 31 days, about 32 days, about 33, about 34, about 35, about 36, about 37, about 38, about 39, about 40, about 41 days, or about 42 days inclusive of all ranges and subranges therebetween, should elapse between discontinuation of posaconazole (i.e., the last dose in a posaconazole regimen) and initiation of treatment with a CYP3A4 substrate drug (i.e., the first dose in a CYP3A4 regimen of any of the CYP3A4 substrate drugs described herein). In some embodiments, the patient is a "normal" patient (i.e., a patient with "normal" CYP3A4 enzyme function, often termed an "extensive metabolizer" in the art; and having a normal weight—e.g., a BMI in the range of about 18.5-24.9), and in other embodiments the patient has one of the physiological characteristics described herein, e.g., is considered obese and/or has a level of CYP3A4 enzyme activity termed in the art as poor or intermediate.

This "delay" or waiting period between ceasing or stopping the treatment of posaconazole and initiating treatment with a CYP3A4 substrate drug can equivalently be characterized as the time that elapses between stopping treatment of posaconazole and treating with the first dose of CYP3A4 substrate drug. The skilled artisan will recognize that additional doses of the CYP3A4 substrate drug are typically administered or prescribed subsequently, but the "delay" or "washout" period as described herein is the time that elapses between stopping treatment of posaconazole and the first dose that initiates treatment with a CYP3A4 substrate drug.

In alternative embodiments, rather than delaying the treatment of the CYP3A4 substrate drug, after stopping treatment of posaconazole the CYP3A4 substrate drug is treated or prescribed at a dose which is no more than about 50% of a reference dose (the dose recommended for the patient on the FDA-approved label for the CYP3A4 substrate drug), including e.g., no more than about 50%, no more than about 49%, no more than about 48%, no more than about 47%, no more than about 46%, no more than about 45%, no more than about 44%, no more than about 43%, no more than about 42%, no more than about 41%, no more than about 40%, no more than about 39%, no more than about 38%, no more than about 37%, no more than about 36%, no more than about 35%, no more than about 34%, no more than about 33%, no more than about 32%, no more than about 31%, no more than about 30%, no more than about 29%, no more than about 28%, no more than about 27%, no more than about 26%, no more than about 25%, no more than about 24%, no more than about 23%, no more than about 22%, no more than about 21%, no more than about 20%, no more than about 19%, no more than about 18%, no more than about 17%, no more than about 16%, no more than about 15%, no more than about 14%, no more than about 13%, no more than about 12%, no more than about 11%, or no more than about 10% of the reference dose, inclusive of all ranges and subranges therebetween, for at least about 2-42 days after discontinuation of the posaconazole regimen, e.g., for about 2, about 3, about 4, about 5, about 6, about 7, about 8, about 9, about 10, about 11, about 12 days, about 13, about 14, about 15, about 16, about 17, about 18, about 19, about 20, about 21 days, about 22 days, about 23, about 24, about 25, about 26, about 27, about 28, about 29, about 30, about 31 days, about 32 days, about 33, about 34, about 35, about 36, about 37, about 38, about 39, about 40, about 41 days, or about 42 days, inclusive of all ranges and subranges therebetween.

In other alternative embodiments, depending on the CYP3A4 substrate drug, the patient can be treated with or prescribed a CYP3A4 substrate drug at a dose which is less than 100% of a reference dose (the dose recommended for the patient on the FDA-approved label for the CYP3A4 substrate drug), including e.g., about 95%, about 90%, about 85%, about 80%, about 75%, about 70%, about 65%, about 60%, about 55%, or about 50% of the reference dose, inclusive of all ranges and subranges therebetween, for at least about 2-42 days after discontinuation of the posaconazole treatment, e.g., for about 2, about 3, about 4, about 5, about 6, about 7, about 8, about 9, about 10, about 11, about 12 days, about 13, about 14, about 15, about 16, about 17, about 18, about 19, about 20, about 21 days, about 22 days, about 23, about 24, about 25, about 26, about 27, about 28, about 29, about 30, about 31 days, about 32 days, about 33, about 34, about 35, about 36, about 37, about 38, about 39, about 40, about 41 days, or about 42 days inclusive of all ranges and subranges therebetween.

In addition to providing methods of treating or prescribing treatment for "normal" patients (e.g., non-obese and normal CYP3A4 metabolizers), the present disclosure also provides methods for treating, or prescribing treatment for, patients with at least one of the physiological characteristics described herein, who had been treated with multiple doses of posaconazole, with a CYP3A4 substrate drug. The treatment with the CYP3A4 substrate drug is initiated or prescribed to be initiated (or the first dosing begins after stopping treatment with posaconazole) after a delay time as described herein, or is treated or prescribed at a reduced dose (e.g., any amount less than 100% of a reference dose, including but not limited to about ⅓, about ½, about ⅔, etc. of a reference dose) for a time period after treatment with posaconazole is stopped as described herein. The physiological characteristics of such patients include reduced hepatic enzyme function, specifically reduced CYP3A4 enzyme function (such patients are characterized in the art as intermediate or poor CYP3A4 metabolizers), and/or a weight or body fat status variously characterized as described herein. In some embodiments, the patients can have various characteristics of body fat status. The term "body fat status," "body fat characteristics," "obese status," "obese characteristics," or other derivations or variations thereof refer to at least seven characteristics (BMI, % IBW, waist size, % body fat, % android fat, % gynoid fat, and total body fat) as described herein. In some embodiments, the body fat status may be referred to as obesity, and the patients may be referred to as obese, or obese patients.

As described herein, the present Applicants have found that certain classes of patients, i.e., patients having the particular physiological characteristics described herein such as body fat and weight status and/or hepatic metabolizing enzyme status, after stopping treatment with posaconazole, may have substantially higher plasma levels of posaconazole and/or exhibit substantially longer elimination half-lives ($t_{1/2}$) of posaconazole than previously known or contemplated, e.g., in the NOXAFIL® label, and therefore require either a delay as described herein after stopping posaconazole treatment, before treating, or prescribing a first treatment to begin, with a CYP3A4 substrate drug, or a dose adjustment (reduction) of the CYP3A4 substrate drug for a time period after stopping posaconazole treatment, as described herein. In some embodiments, the duration of the delay period or dose adjustment period, or the degree of dose adjustment is greater than the corresponding delay or dose reduction period/amount compared to those considered to be "normal" patients. These classes of patients which exhibit substantially higher plasma levels of posaconazole, and/or exhibit substantially longer elimination half-lives ($t_{1/2}$) of posaconazole compared to the expected level (e.g., as embodied in the recommendations of the NOXAFIL® label), or who require a longer delay time, dose adjustment time, or dose adjustment level include obese patients who exhibit one or more of e.g., a BMI of at least about 35, % IBW of at least about 150%, waist size greater than about 42 inches, % body fat greater than about 40%, % android body fat greater than about 40%, % gynoid body fat greater than about 40%, total body fat greater than about 40 kg, optionally in combination with impaired hepatic function, e.g., intermediate or poor CYP3A4 metabolizers. Alternatively, patients who are not obese (e.g., have any of the various measures of body fat status described herein which are not considered as indicative of obesity, such as a BMI less than about 35, % IBW of less than about 150%, waist size less than about 42 inches, % body fat less than about 40%, % android body fat less than about 40%, % gynoid body fat less than about 40%, or total body fat less than about 40 kg) but have impaired hepatic metabolic function, e.g., are considered intermediate or poor CYP3A4 metabolizers, have also been found by the present Applicants to have substantially higher steady state plasma levels of posaconazole, and/or exhibit a substantially longer elimination half-lives ($t_{1/2}$) of posaconazole compared to those expected in "normal" patients—i.e., patients who do not exhibit the specific physiological characteristics described herein—or as embodied in the recommendations of the NOXAFIL® label may also require an extended washout period (as described herein) after stopping administration of posaconazole before beginning treatment with a CYP3A4 substrate drug. Alternatively, such patients may require an extended period (as described herein) after stopping administration of posaconazole before beginning treatment with a reduced dose (as described herein) relative to the reference dose of the CYP3A4 substrate drug in order to minimize or avoid adverse effects such as QTc prolongation or other side effects of the CYP3A4 substrate drug than has hitherto been recognized in the art. Conventionally, no such distinction between patients having such physiological characteristics has been recognized as requiring increased "washout" periods between dosing with posaconazole and a CYP3A4 substrate drug, or as requiring time periods during which a patient is treated, or prescribed to be treated, with a reduced reference dose of the CYP3A4 substrate drug after stopping administration of posaconazole, as the effects of such physiological characteristics on steady state plasma levels of posaconazole and/or elimination half-life was not previously known.

Each individual may have different activity levels of the CYP450 isozymes that metabolize drugs. Categorizations of metabolizers may include, but are not limited to, allelic heterogeneity in the CYP540 isozymes gene. For instance, the CYP3A4 gene can have allelic heterogeneity and expression of CYP3A4*22 allele can be used to classify individuals as reduced-expressers of CYP3A4 (i.e., individuals possessing one CYP3A4*22 allele), and normal-expressers of CYP3A4 (i.e., individuals not possessing any CYP3A4*22 allele).

In some embodiments, the class of patients treated by the methods of the present disclosure have a body mass index (BMI; expressed in units of kg/m² unless otherwise specified) of less than about 25, e.g., about 24.5, about 24, about 23.5, about 23, about 22.5, about 22, about 21.5, about 21, about 20.5, about 20, about 19.5, about 19, or about 18.5 or less, inclusive of all values and ranges therebetween.

In some embodiments, the class of patients treated by the methods of the present disclosure have a body mass index (BMI; expressed in units of kg/m² unless otherwise specified) of at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, at least about 141, at least about 142, at least about 143, at least about 144, at least about 145, at least about 146, at least about 147, at least about 148, at least about 149, at least about 150, at least about 151, at least about 152, at least about 153, at least about 154, at least about 155, at least about 156, at least about 157, at least about 158, at least about 159, at least about 160, at least about 161, at least about 162, at least about 163, at least about 164, at least about 165, at least about 166, at least about 167, at least about 168, at least about 169, at least about 170, at least about 171, at least about 172, at least about 173, at least about 174, at least about 175, at least about 176, at least about 177, at least about 178, at least about 179, at least about 180, at least about 181, at least about 182, at least about 183, at least about 184, at least about 185, at least about 186, at least about 187, at least about 188, at least about 189, at least about 190, at least about 191, at least about 192, at least about 193, at least about 194, at least about 195, at least about 195, at least about 196, at least about 197, at least about 198, at least about 199, at least about 200, at least about 201, at least about 202, at least about 203, at least about 204, at least about 205, at least about 206, at least about 207, at least about 208, at least about 209, or at least about 210, inclusive of all ranges and subranges therebetween, and any BMI described herein. In one embodiment, the patient has a body mass index (BMI) of at least about 35. In another embodiment, the patient has a body mass index (BMI) of at least about 40. In another embodiment, the patient has a body mass index (BMI) of at least 50.

In some embodiments, a patient treated according to the methods of the present invention has a BMI of at least about 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be termed overweight or pre-obese. In some embodiments, a patient with a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween can be considered obese. In some embodiments, a patient with a BMI of at least about 35 to at least about 39.9, at least about 35.5 to at least about 39, at least about 36 to at least about 38.5, at least about 36.5 to at least about 38, or at least about 37 to at least about 37.5, inclusive of all ranges and subranges therebetween, and any BMI described herein, can be considered obese. In other embodiments, a patient treated by the methods of the present disclosure has a BMI of at least about 35 or more, 40 or more, 50 or more, 60 or more, 70 or more, 80 or more, 90 or more, 100 or more, 110 or more, 120 or more, 130 or more, 140 or more, 150 or more, 160 or more, 170 or more, 180 or more, 190 or more, 200 or more, or 210 or more, inclusive of all ranges and subranges therebetween.

In some embodiments, the patient treated according to the methods of the present disclosure is a child or an adolescent with a BMI of at least about the 85$^{th}$ percentile to at least about 95$^{th}$ percentile, at least about the 86$^{th}$ percentile to at least about 94$^{th}$ percentile, at least about the 87$^{th}$ percentile to at least about 93$^{rd}$ percentile, at least about the 88$^{th}$ percentile to at least about 92$^{nd}$ percentile, at least about the 89$^{th}$ percentile to at least about 90$^{th}$ percentile, inclusive of all ranges and subranges therebetween, can be considered overweight or pre-obese. In some embodiments, the patient is a patient with a BMI of at least about the 95$^{th}$ percentile, at least about 96$^{th}$ percentile, at least about the 97$^{th}$ percentile, at least about 98$^{th}$ percentile, at least about 99$^{th}$ percentile, or at least about 100$^{th}$ percentile, inclusive of all ranges and subranges therebetween, and any BMI percentile described herein, and can be considered obese. In one embodiment, the patient is about 5 to about 19 years old or about 7 to about 18 years old.

In some embodiments, the patient treated according to the methods of the present disclosure is a female patient in the first trimester through third trimester of a pregnancy and has a BMI of at least 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be considered overweight or pre-obese. In some embodiments, the patient is a female patient in the first trimester through third trimester of a pregnancy and has a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween, and can be considered obese. In some embodiments, the patent treated according to the methods of the present invention is a female patient in the first trimester through third trimester of a pregnancy and has a BMI of at least about 35 to at least about 39.9, at least about 35.5 to at least about 39, at least about 36 to at least about 38.5, at least about 36.5 to at least about 38, at least about 37 to at least about 37.5, inclusive of all ranges and subranges therebetween, and can be considered severely obese.

In some embodiments, methods of calculating BMI may include, but are not limited to body weight in kilogram/(height in meters)$^2$, body weight in pounds/(height in inches)$^2$]×703, and the like.

In some embodiments, the patient treated according to the methods of the present disclosure can alternatively be described as having a % ideal body weight (% IBW) of at least about 110%, at least about 111%, at least about 112%, at least about 113%, at least about 114%, at least about 115%, at least about 116%, at least about 117%, at least about 118%, at least about 119%, at least about 120%, at least about 121%, at least about 122%, at least about 123%, at least about 124%, at least about 125%, at least about 126%, at least about 127%, at least about 128%, at least about 129%, at least about 130%, at least about 131%, at least about 132%, at least about 133%, at least about 134%, at least about 135%, at least about 136%, at least about 137%, at least about 138%, at least about 139%, at least about 140%, at least about 141%, at least about 142%, at least about 143%, at least about 144%, at least about 145%, at least about 146%, at least about 147%, at least about 148%, at least about 149%, at least about 150%, at least about 151%, at least about 152%, at least about 153%, at least about 154%, at least about 155%, at least about 156%, at least about 157%, at least about 158%, at least about 159%, at least about 160%, at least about 161%, at least about 162%, at least about 163%, at least about 164%, at least about 165%, at least about 166%, at least about 167%, at least about 168%, at least about 169%, at least about 170%, at least about 171%, at least about 172%, at least about 173%, at least about 174%, at least about 175%, at least about 176%, at least about 177%, at least about 178%, at least about 179%, at least about 180%, at least about 181%, at least about 182%, at least about 183%, at least about 184%, at least about 185%, at least about 186%, at least about 187%, at least about 188%, at least about 189%, at least about 190%, at least about 191%, at least about 192%, at least about 193%, at least about 194%, at least about 195%, at least about 196%, at least about 197%, at least about 198%, at least about 199%, at least about 200%, at least about 201%, at least about 202%, at least about 203%, at least about 204%, at least about 205%, at least about 206%, at least about 207%, at least about 208%, at least about 209%, at least about 210%, at least about 211%, at least about 212%, at least about 213%, at least about 214%, at least about 215%, at least about 216%, at least about 217%, at least about 218%, at least about 219%, at least about 220%, at least about 221%, at least about 222%, at least about 223%, at least about 224%, at least about 225%, at least about 226%, at least about 227%, at least about 228%, at least about 229%, at least about 230%, at least about 231%, at least about 232%, at least about 233%, at least about 234%, at least about 235%, at least about 236%, at least about 237%, at least about 238%, at least about 239%, at least about 240%, at least about 241%, at least about 242%, at least about 243%, at least about 244%, at least about 245%, at least about 246%, at least about 247%, at least about 248%, at least about 249%, at least about 250%, at least about 251%, at least about 252%, at least about 253%, at least about 254%, at least about 255%, at least about 256%, at least about 257%, at least about 258%, at least about 259%, at least about 260%, at least about 261%, at least about 262%, at least about 263%, at least about 264%, at least about 265%, at least about 266%, at least about 267%, at least about 268%, at least about 269%, at least about 270%, at least about 271%, at least about 272%, at least about 273%, at least about 274%, at least about 275%, at least about 276%, at least about 277%, at least about 278%, at least about 279%, or at least about 280%, inclusive of all ranges and subranges therebetween, and any % ideal body weight described herein. In one embodiment, the patient has % ideal body weight (IBW) of at least about 150%. In one embodiment, the patient has % ideal body weight (IBW) of at least about 250%. In other embodiments, the patient has % IBW of at least 150% and can be considered obese.

In some embodiments, the patient treated according to the present disclosure can alternatively be described as having a waist size or waist circumference greater than about 32, greater than about 33, greater than about 34, greater than about 35 inches, greater than about 36, greater than about 37, greater than about 38, greater than about 39, greater than about 40, greater than about 41, greater than about 42, greater than about 43, greater than about 44, greater than about 45, greater than about 46, greater than about 47, greater than about 48, greater than about 49, greater than about 50, greater than about 51, greater than about 52, greater than about 53, greater than about 54, greater than about 55, greater than about 56, greater than about 57, greater than about 58, greater than about 59, greater than about 60 inches, greater than about 61 inches, greater than about 62 inches, greater than about 63 inches, greater than about 64 inches, greater than about 65 inches, inclusive of all ranges and subranges therebetween, and any waist size or circumference described herein. In one embodiment, a patient having a waist size or waist circumference of about 42 inches can be considered obese. In another embodiment, the patient has waist size or waist circumference greater than about 48 inches. In other embodiment, the patient has waist or waist circumference of at least 42 inches.

In some embodiments, the patient treated according to the methods of the present disclosure can alternatively be described as having a % body fat greater than about 20%, greater than about 21%, greater than about 22%, greater than about 23%, greater than about 24%, greater than about 25%, greater than about 26%, greater than about 27%, greater than about 28%, greater than about 29%, greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, or greater than about 50%, inclusive of all ranges and subranges therebetween, and any % body fat described herein. In one embodiment, the patient has a % body fat greater than about 40%. In one embodiment, the patient has a % body fat of at least about 50%. In another embodiment, a patient having a % body fat greater than about 40% can be considered obese. In some embodiments, methods of calculating % body fat can include, but are not limited to total body fat expressed as a percentage of total body weight. Other standards for obesity can be used. For example, the American Council on Exercise suggests that an "average" percentage of body fat for women is about 25-31%, and for men, about 18-24%, and for obese women, about 32% and higher, and obese men, about 25% and higher.

In other embodiments, the patient can alternatively be described as having a android body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % android body fat described herein. In one embodiment, a patient having a % android body fat greater than about 40% can be considered obese. In one embodiment, a patient having a % android body fat greater than about 50% can be considered obese In other embodiments, the patient can alternatively be described as having a % android body fat of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%, inclusive of all ranges and subranges therebetween, and % android body fat described herein. In one embodiment, the patient has % android body fat of at least about 50%.

In other embodiments, the patient can alternatively be described as having a gynoid body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % gynoid body fat described herein. In one embodiment, a patient having a % gynoid body fat greater than about 40% can be considered obese. In one embodiment, a patient having a % gynoid body fat greater than about 50% can be considered obese.

In other embodiments, the patient can alternatively be described as having a total body fat content greater than about 30 kg, greater than about 31 kg, greater than about 32 kg, greater than about 33 kg, greater than about 34 kg, greater than about 35 kg, greater than about 36 kg, greater than about 37 kg, greater than about 38 kg, greater than about 39 kg, greater than about 40 kg, greater than about 41 kg, greater than about 42 kg, greater than about 43 kg, greater than about 44 kg, greater than about 45 kg, greater than about 46 kg, greater than about 47 kg, greater than about 48 kg, greater than about 49 kg, greater than about 50 kg, greater than about 51 kg, greater than about 52 kg, greater than about 53 kg, greater than about 54 kg, greater than about 55 kg, greater than about 56 kg, greater than about 57 kg, greater than about 58 kg, greater than about 59 kg, greater than about 60 kg, greater than about 61 kg, greater than about 62 kg, greater than about 63 kg, greater than about 64 kg, greater than about 65 kg, greater than about 66 kg, greater than about 67 kg, greater than about 68 kg, greater than about 69 kg, greater than about 70 kg, greater than about 71 kg, greater than about 72 kg, greater than about 73 kg, greater than about 74 kg, greater than about 75 kg, greater than about 76 kg, greater than about 77 kg, greater than about 78 kg, greater than about 79 kg, greater than about 80 kg, greater than about 81 kg, greater than about 82 kg, greater than about 83 kg, greater than about 84 kg, greater than about 85 kg, greater than about 86 kg, greater than about 87 kg, greater than about 88 kg, greater than about 89 kg, greater than about 90 kg, greater than about 91 kg, greater than about 92 kg, greater than about 93 kg, greater than about 94 kg, greater than about 95 kg, greater than about 96 kg, greater than about 97 kg, greater than about 98 kg, greater than about 99 kg, greater than about 100 kg, at least 101 kg, at least 102 kg, at least 103 kg, at least 104 kg, at least 105 kg, at least 106 kg, at least 107 kg, at least 108 kg, at least 109 kg, or at least 110 kg, inclusive of all ranges and subranges therebetween, and any total body fat described herein. In one embodiment, a patient having total body fat greater than about 40 kg can be considered obese. In one embodiment, a patient having total body fat greater than about 50 kg can be considered obese.

In other embodiments, the obesity status of patients treated with the methods of the present disclosure can be measured by waist-to-hip ratio. In other embodiments, the obesity status of patients can be measured by skinfold thickness. In other embodiments, the obesity status of patients can be measured by bioelectric impedance. In other embodiments, the obesity status of patients can be measured by underwater weighing or densitometry. In other embodiments, the obesity status of patients can be measured by air-displacement plethysmography. In other embodiments, the obesity status of patients can be measured by dilution method or hydrometry. In other embodiments, the obesity status of patients can be measured by dual energy X-ray absorptiometry. In other embodiments, the obesity status of patients can be measured by computerized tomography and magnetic resonance imaging. In some embodiments, the obesity status can be defined by, but is not limited to adopting the clinical standards, conventional standards, and/or the standards published by the World Health Organization and Center of Disease Control (both of which are herein incorporated by reference in their entireties for all purposes) when using the methods described herein. For example, the WHO defines an obese person as a person with a BMI of 30 or more, an overweight person is one with a BMI equal to or more than 25 (to less than 30). Similarly, the CDC defines normal as a BMI of 18.5 to less than 25, 25.0 to less than 30 as overweight, and 30.0 or higher as obese. The CDC further subdivides obesity into 3 classes: Class 1, a BMI of 30 to less than 35; Class 2, a BMI of 35 to less than 40; and Class 3, as a BMI of 40 or higher. The CDC sometimes refers to Class 3 obesity as "extreme" or "severe" obesity.

In some embodiments, the patient treated by the methods of the present disclosure can be characterized by two or more of the physiological characteristics described herein. For example the patient can have a BMI of at least about 35 and can have a % IBW of at least 150%. In some embodiments, the patient can have a BMI of at least about 35 and can have a waist size greater than about 42 inches. In some embodiments, the patient can have a BMI of at least about 35 and can have a % body fat greater than about 40%. In some embodiments, the patient can have a BMI of at least about 35 and can have a % android body fat greater than about 40%. In some embodiments, the patient can have a BMI of at least about 35 and can have a % gynoid body fat greater than about 40%. In some embodiments, the patient can have a BMI of at least about 35 and can have total body fat greater than about 40 kg. In various other embodiments, the patient can have any combination of two or more of any of the specific physiological parameters described herein.

In some embodiments, the patient can have three or more of the physiological parameters described herein, for example a BMI of at least about 35, a % IBW of at least 150%, and waist size greater than about 42 inches. In some embodiments, the patient can have a BMI of at least about 35, a % IBW of at least 150%, and a % body fat greater than about 40%. In some embodiments, the patient can have a BMI of at least about 35, a % IBW of at least 150%, and a % android body fat greater than about 40%. In some embodiments, the patient can have a BMI of at least about 35, a % IBW of at least 150%, and a % gynoid body fat greater than about 40%. In some embodiments, the patient can have a BMI of at least about 35, a % IBW of at least 150%, and total body fat greater than about 40 kg. In various other embodiments, the patient can have any combination of three or more of any of the specific physiological parameters described herein.

In some embodiments, the patient can have four or more of the physiological parameters described herein, for example the patient can have a BMI of at least about 35, a % IBW of at least 150%, waist size greater than about 42 inches, and a % body fat greater than about 40%. In some embodiments, the patient can have a BMI of at least about 35, a % IBW of at least 150%, waist size greater than about 42 inches, and a % android body fat greater than about 40%. In some embodiments, the patient can have a BMI of at least about 35, a % IBW of at least 150%, waist size greater than about 42 inches, and a % gynoid body fat greater than about 40%. In some embodiments, the patient can have a BMI of at least about 35, a % IBW of at least 150%, a waist size greater than about 42 inches, and total body fat greater than about 43 kg. In some embodiments, the patient can have a BMI of at least about 35, a % IBW of at least 150%, a waist size greater than about 42 inches, a % body fat greater than about 40%, and a % android body fat greater than about 40%. In some embodiments, the patient can have a BMI of at least about 35, a % IBW of at least 150%, a waist size greater than about 42 inches, a % body fat greater than about 40%, and a % gynoid body fat greater than about 40%. In some embodiments, the patient can have a BMI of at least about 35, a % IBW of at least 150%, a waist size greater than about 42 inches, a % body fat greater than about 40%, and total body fat greater than about 40 kg. In some embodiments, the patient can have a BMI of at least about 35, a % IBW of at least 150%, a waist size greater than about 42 inches, a % body fat greater than about 40%, a % android body fat greater than about 40%, in % gynoid body fat greater than about 40%, and total body fat greater than about 40 kg. In one embodiment, the patient who has a BMI of at least about 35, in % IBW of at least 150%, a waist size greater than about 42 inches, and a % body fat greater than about 40%, a % android body fat greater than about 40%, a % gynoid body fat greater than about 40%, and total body fat greater than about 40 kg. In various other embodiments, the patient can have any combination of any or all of the specific physiological parameters described herein.

In some embodiments, the patient can have a waist size greater than about 42 inches, a % body fat greater than about 40%, and a % android body fat greater than about 40%. In some embodiments, the patient can have a waist size greater than about 42 inches, a % body fat greater than about 40%, and a % gynoid body fat greater than about 40%. In some embodiments, the patient can have a waist size greater than about 42 inches, a % body fat greater than about 40%, and total body fat greater than about 40 kg.

In some embodiments, the patient can have a % body fat greater than about 40%, a % android body fat greater than about 40%, and a % gynoid body fat greater than about 40%. In some embodiments, the patient can have a % body fat greater than about 40%, a % android body fat greater than about 40%, and total body fat greater than about 40 kg. In some embodiments, the patient can have a % body fat greater than about 40%, a % gynoid body fat greater than about 40%, and total body fat greater than about 40 kg. In some embodiments, a % android body fat greater than about 40%, and a % gynoid body fat greater than about 40%, and total body fat greater than about 43 kg. In some embodiments, the patient can have any combinations of obesity characteristics described herein In some embodiments, patients with at least one of the obesity characteristics described herein can be an intermediate CYP3A4 metabolizer. In other embodiments, the patients with at least one of the obesity characteristics described herein can be a poor CYP3A4 metabolizer. In some embodiments, the patients with at least one of the obesity characteristics described herein can be an extensive CYP3A4 metabolizer. In still other embodiments, the patient is not obese, e.g., can have normal weight, and be an intermediate or poor CYP3A4 metabolizer.

Alternatively, in some embodiments, the CYP3A4 genotype can be tested by using targeted variant analysis. In some embodiments, the CYP3A4 genotype can be tested by using sequence analysis of select exons.

In various embodiments, the present disclosure also provides for methods of treating patients previously treated with posaconazole with a CYP3A4 substrate drug which is contraindicated for concomitant use with a strong CYP3A4 inhibitor, such as posaconazole, wherein the CYP3A4 substrate drug maintains an AUC which is no more than about 3000% of a normal baseline AUC (as defined above) of the CYP3A4 substrate drug, e.g., no more than about 2950%, no more than about 2900%, no more than about 2850%, no more than about 2800%, no more than about 2750%, no more than about 2700%, no more than about 2650%, no more than about 2600%, no more than about 2550%, no more than about 2500%, no more than about 2450%, no more than about 2400%, no more than about 2350%, no more than about 2300%, no more than about 2250%, no more than about 2200%, no more than about 2150%, no more than about 2100%, no more than about 2050%, no more than about 2000%, no more than about 1950%, no more than about 1900%, no more than about 1850%, no more than about 1800%, no more than about 1750%, no more than about 1700%, no more than about 1650%, no more than about 1600%, no more than about 1550%, no more than about 1500%, no more than about 1450%, no more than about 1400%, no more than about 1350%, no more than about 1300%, no more than about 1250%, no more than about 1200%, no more than about 1150%, no more than about 1100%, no more than about 1050%, no more than about 1000%, no more than about 950%, no more than about 900%, no more than about 850%, no more than about 800%, no more than about 750%, no more than about 700%, no more than about 650%, no more than about 600%, no more than about 550%, no more than about 500%, no more than about 450%, no more than about 445%, no more than about 440%, no more than about 435%, no more than about 430%, no more than about 425%, no more than about 420%, no more than about 415%, no more than about 410%, no more than about 405%, no more than about 400%, no more than about 395%, no more than about 390%, no more than about 385%, no more than about 380%, no more than about 375%, no more than about 370%, no more than about 365%, no more than about 360%, no more than about 355%, no more than about 350%, no more than about 345%, no more than about 340%, no more than about 335%, no more than about 330%, no more than about 325%, no more than about 320%, no more than about 315%, no more than about 310%, no more than about 305%, or no more than about 300%, no more than about 295%, no more than about 290%, no more than about 285%, no more than about 280%, no more than about 275%, no more than about 270%, no more than about 265%, no more than about 260%, no more than about 255%, no more than about 250%, no more than about 245%, no more than about 240%, no more than about 235%, no more than about 230%, no more than about 225%, no more than about 220%, no more than about 216%, no more than about 215%, no more than about 210%, no more than about 205%, no more than about 200%, no more than about 195%, no more than about 190%, no more than about 185%, no more than about 180%, no more than about 175%, no more than about 170%, no more than about 165%, no more than about 160%, no more than about 155%, no more than about 150%, no more than about 145%, no more than about 140%, no more than about 135%, no more than about 130%, no more than about 125%, no more than about 120%, no more than about 115%, no more than about 110%, no more than about 105%, or no more than about 100% of the normal baseline AUC of the CYP3A4 substrate drug, inclusive of all ranges and subranges therebetween. In particular embodiments, the CYP3A4 substrate drug is ranolazine, and the AUC of ranolazine is maintained at a level of no more than about 150% of a normal baseline AUC of ranolazine. As used herein, the "normal baseline AUC of ranolazine" refers to the steady state $AUC_{0-12}$ measured for a particular dose of ranolazine in the absence of other drugs. In some embodiments, the steady state $AUC_{0-12}$ (% CV) is 13,720 (67.0%) ng*h/mL measured after administration of 500 mg ranolazine. In some embodiments, the steady state $AUC_{0-12}$ (% CV) is 32,091 (42.2%) ng*h/mL measured after administration of 1,000 mg ranolazine. In other particular embodiments, the CYP3A4 substrate drug is lurasidone, and the AUC of lurasidone is maintained at a level of no more than about 216% of a normal baseline AUC of lurasidone. As used herein, the "normal baseline AUC of lurasidone" refers to the mean $AUC_{0-tau}$ measured for a particular dose of lurasidone in the absence of other drugs. In some embodiments, the mean $AUC_{0-tau}$ is about 743 ng*h/mL measured after administration of 120 mg lurasidone administered in the fed state after a 350 kcal meal. In other particular embodiments, the CYP3A4 drug is tadalafil, and the AUC of tadalafil is maintained at a level of no more than about 410% of a normal baseline AUC of tadalafil. As used herein, the "normal baseline AUC of tadalafil" refers to the mean $AUC_{0-\infty}$ (% CV) measured for a particular dose of tadalafil in the absence of other drugs. In some embodiments, the mean $AUC_{0-\infty}$ (% CV) is about 3647 (34.0%) µg*h/L measured after administration of 10 mg tadalafil. In some embodiments, the mean $AUC_{0-\infty}$ (% CV) is about 13,006 (43.9%) µg*h/L for 20 mg tadalafil. In some embodiments, the mean $AUC_{0-\infty}$ (% CV) is within the range of about 7,000 to about 13,000 (40.0%) µg*h/L for 20 mg tadalafil. In other particular embodiments, the CYP3A4 drug is erlotinib, and the AUC of erlotinib is maintained at a level of no more than about 164% of a normal baseline AUC of erlotinib at 150 mg. As used herein, the "normal baseline AUC of erlotinib" refers to the mean $AUC_{0-24}$ (% CV) measured for a particular dose of erlotinib in the absence of other drugs. In some embodiments, the mean $AUC_{0-24}$ (% CV) at steady state is about 15.2 (400.0%) µg*h/mL measured after administration of 150 mg erlotinib. The $AUC_{0-24}$ of erlotinib is highly variable and tends to increase in cancer patients relative to healthy volunteers. Thus, in some embodiments, the mean $AUC_{0-24}$ (% CV) can range from about 1 µg*h/mL to about 35 µg*h/mL, e.g., about 2 µg*h/mL, about 3 µg*h/mL, about 4 µg*h/mL, about 5 µg*h/mL, about 6 µg*h/mL, about 7 µg*h/mL, about 8 µg*h/mL, about 9 µg*h/mL, about 10 µg*h/mL, about 11 µg*h/mL, about 12 µg*h/mL, about 13 µg*h/mL, about 14 µg*h/mL, about 15 µg*h/mL, about 16 µg*h/mL, about 17 µg*h/mL, about 18 µg*h/mL, about 19 µg*h/mL, about 20 µg*h/mL, about 21 µg*h/mL, about 22 µg*h/mL, about 23 µg*h/mL, about 24 µg*h/mL, about 25 µg*h/mL, about 27 µg*h/mL, about 28 µg*h/mL, about 29 µg*h/mL, about 30 µg*h/mL, about 31 µg*h/mL, about 32 µg*h/mL, about 33 µg*h/mL, about 34 µg*h/mL, about 35 µg*h/mL, about 36 µg*h/mL, about 37 µg*h/mL, about 38 µg*h/mL, about 39 µg*h/mL, about 40 µg*h/mL, about 41 µg*h/mL, about 42 µg*h/mL, about 43 µg*h/mL, about 44 µg*h/mL, about 45 µg*h/mL, about 47 µg*h/mL, about 48 µg*h/mL, about 49 µg*h/mL, about 50 µg*h/mL, about 51 µg*h/mL, about 52 µg*h/mL, about 53 µg*h/mL, about 54

µg*h/mL, about 55 µg*h/mL, about 57 µg*h/mL, about 58 µg*h/mL, about 59 µg*h/mL, about 60 µg*h/mL, inclusive of all values and subranges therebetween. In other particular embodiments, the CYP3A4 drug is solifenacin succinate, and the AUC of solifenacin succinate is maintained at a level of no more than about 270% of a normal baseline AUC of solifenacin succinate. As used herein, the "normal baseline AUC of solifenacin succinate" refers to the mean $AUC_{0-24}$ (% CV) at steady state measured for a particular dose of solifenacin succinate in the absence of other drugs. In some embodiments, the mean $AUC_{0-24}$ (% CV) at steady state is about 463 (37%) ng*h/mL for 5 mg solifenacin succinate. In some embodiments, the mean $AUC_{0-24}$ (% CV) at steady state is about 749 (22%) ng*h/mL for 10 mg solifenacin succinate. In other particular embodiments, the CYP3A4 drug is everolimus, and the AUC of everolimus is maintained at a level of no more than about 440% of a normal baseline AUC of everolimus. As used herein, the "normal baseline AUC of everolimus" refers to the mean $AUC_{0-24} \pm SD$ measured at steady state conditions for a particular dose of everolimus in the absence of other drugs. In some embodiments, the mean $AUC_{0-24} \pm SD$ is about 536±7.7 ng*h/mL measured after administration of 10 mg everolimus.

In various other embodiments, the present disclosure provides for methods of treating patients previously treated with posaconazole, comprising treating or prescribing a reduced dose of a CYP3A4 substrate drug which is contraindicated for concomitant use with a strong CYP3A4 inhibitor (e.g., about 10%-90%, of the reference dose) for a period of about 2-42 days after stopping posaconazole treatment as described herein, wherein the CYP3A4 substrate drug is maintained an AUC which is no more than about 3000% of the baseline AUC of the CYP3A4 substrate drug, e.g., no more than about 2950%, no more than about 2900%, no more than about 2850%, no more than about 2800%, no more than about 2750%, no more than about 2700%, no more than about 2650%, no more than about 2600%, no more than about 2550%, no more than about 2500%, no more than about 2450%, no more than about 2400%, no more than about 2350%, no more than about 2300%, no more than about 2250%, no more than about 2200%, no more than about 2150%, no more than about 2100%, no more than about 2050%, no more than about 2000%, no more than about 1950%, no more than about 1900%, no more than about 1850%, no more than about 1800%, no more than about 1750%, no more than about 1700%, no more than about 1650%, no more than about 1600%, no more than about 1550%, no more than about 1500%, no more than about 1450%, no more than about 1400%, no more than about 1350%, no more than about 1300%, no more than about 1250%, no more than about 1200%, no more than about 1150%, no more than about 1100%, no more than about 1050%, no more than about 1000%, no more than about 950%, no more than about 900%, no more than about 850%, no more than about 800%, no more than about 750%, no more than about 700%, no more than about 650%, no more than about 600%, no more than about 550%, no more than about 500%, no more than about 450%, no more than about 445%, no more than about 440%, no more than about 435%, no more than about 430%, no more than about 425%, no more than about 420%, no more than about 415%, no more than about 410%, no more than about 405%, no more than about 400%, no more than about 395%, no more than about 390%, no more than about 385%, no more than about 380%, no more than about 375%, no more than about 370%, no more than about 365%, no more than about 360%, no more than about 355%, no more than about 350%, no more than about 345%, no more than about 340%, no more than about 335%, no more than about 330%, no more than about 325%, no more than about 320%, no more than about 315%, no more than about 310%, no more than about 305%, or no more than about 300%, no more than about 295%, no more than about 290%, no more than about 285%, no more than about 280%, no more than about 275%, no more than about 270%, no more than about 265%, no more than about 260%, no more than about 255%, no more than about 250%, no more than about 245%, no more than about 240%, no more than about 235%, no more than about 230%, no more than about 225%, no more than about 220%, no more than about 216%, no more than about 215%, no more than about 210%, no more than about 205%, no more than about 200%, no more than about 195%, no more than about 190%, no more than about 185%, no more than about 180%, no more than about 175%, no more than about 170%, no more than about 165%, no more than about 160%, no more than about 155%, no more than about 150%, no more than about 145%, no more than about 140%, no more than about 135%, no more than about 130%, no more than about 125%, no more than about 120%, no more than about 115%, no more than about 110%, no more than about 105%, or no more than about 100% of the normal baseline AUC of the CYP3A4 substrate drug, inclusive of all ranges and subranges therebetween. In particular embodiments, the CYP3A4 substrate drug is ranolazine, and the AUC of ranolazine is maintained at a level of no more than about 150% of the normal baseline AUC of ranolazine. In other particular embodiments, the CYP3A4 substrate drug is lurasidone, and the AUC of lurasidone is maintained at a level of no more than about 216% of the normal baseline AUC of lurasidone. In other particular embodiments, the CYP3A4 substrate drug is tadalafil, and the AUC of tadalafil is maintained at a level of no more than about 410% of the normal baseline AUC of tadalafil. In other particular embodiments, the CYP3A4 substrate drug is tadalafil, and the AUC of tadalafil is maintained at a level of no more than about 260% of the normal baseline AUC of tadalafil. In other particular embodiments, the CYP3A4 substrate drug is tadalafil, and the AUC of tadalafil is maintained at a level of no more than about 207% of the normal baseline AUC of tadalafil. In other particular embodiments, the CYP3A4 substrate drug is erlotinib, and the AUC of erlotinib is maintained at a level of no more than about 164% of the normal baseline AUC of erlotinib. In other particular embodiments, the CYP3A4 substrate drug is solifenacin succinate, and the AUC of solifenacin succinate is maintained at a level of no more than about 270% of the normal baseline AUC of solifenacin succinate. In other particular embodiments, the CYP3A4 substrate drug is everolimus, and the AUC of everolimus is maintained at a level of no more than about 440% of the normal baseline AUC of everolimus.

In various embodiments, the present disclosure also provides for methods of treating patients previously treated with posaconazole, with a CYP3A4 substrate drug which is contraindicated for concomitant use with a strong CYP3A4 inhibitor, such as posaconazole, wherein the CYP3A4 substrate drug maintains a $C_{max}$ which is no more than about 4000% of the normal baseline $C_{max}$ of the CYP3A4 substrate drug, e.g., 3950%, no more than about 3900%, no more than about 3850%, no more than about 3800%, no more than about 3750%, no more than about 3700%, no more than about 3650%, no more than about 3600%, no more than about 3550%, no more than about 3500%, no more than about 3450%, no more than about 3400%, no more than about 3350%, no more than about 3300%, no more than about 3250%, no more than about 3200%, no more than about 3150%, no more than about 3100%, no more than about 3050%, no more than about 3000%, no more than about 2950%, no more than about 2900%, no more than about 2850%, no more than about 2800%, no more than about 2750%, no more than about no more than about 2700%, no more than about 2650%, no more than about 2600%, no more than about 2550%, no more than about 2500%, no more than about 2450%, no more than about 2400%, no more than about 2350%, no more than about 2300%, no more than about 2250%, no more than about 2200%, no more than about 2150%, no more than about 2100%, no more than about 2050%, no more than about 2000%, no more than about 1950%, no more than about 1900%, no more than about 1850%, no more than about 1800%, no more than about 1750%, no more than about 1700%, no more than about 1650%, no more than about 1600%, no more than about 1550%, no more than about 1500%, no more than about 1450%, no more than about 1400%, no more than about 1350%, no more than about 1300%, no more than about 1250%, no more than about 1200%, no more than about 1150%, no more than about 1100%, no more than about 1050%, no more than about 1000%, no more than about 950%, no more than about 900%, no more than about 850%, no more than about 800%, no more than about 750%, no more than about 700%, no more than about 650%, no more than about 600%, no more than about 550%, no more than about 500%, no more than about 450%, no more than about 445%, no more than about 440%, no more than about 435%, no more than 430%, no more than about 425%, no more than about 420%, no more than about 415%, no more than about 410%, no more than about 405%, no more than about 400%, no more than about 395%, no more than about 390%, no more than about 385%, no more than about 380%, no more than about 375%, no more than about 370%, no more than about 365%, no more than about 360%, no more than about 355%, no more than about 350%, no more than about 345%, no more than about 340%, no more than about 335%, no more than 330%, no more than about 325%, no more than about 320%, no more than about 315%, no more than about 310%, no more than about 305%, or no more than about 300%, no more than about 295%, no more than about 290%, no more than about 285%, no more than about 280%, no more than about 275%, no more than about 270%, no more than about 265%, no more than about 260%, no more than about 255%, no more than about 250%, no more than about 245%, no more than about 240%, no more than about 235%, no more than 230%, no more than about 225%, no more than about 220%, no more than about 216%, no more than about 215%, no more than about 210%, no more than about 205%, no more than about 200%, no more than about 195%, no more than about 190%, no more than about 185%, no more than about 180%, no more than about 175%, no more than about 170%, no more than about 165%, no more than about 160%, no more than about 155%, no more than about 150%, no more than about 145%, no more than about 140%, no more than about 135%, no more than about no 130%, no more than about 125%, no more than about 120%, no more than about 115%, no more than about 110%, no more than about 105%, or no more than about 100% inclusive of all ranges and subranges therebetween. In particular embodiments, the CYP3A4 substrate drug is ranolazine, and the $C_{max}$ of ranolazine is maintained at a level of no more than about 150% of the normal baseline $C_{max}$ of ranolazine. As used herein, the "normal baseline $C_{max}$ of ranolazine" refers to the steady state $C_{max}$ measured for a particular dose of ranolazine in the absence of other drugs. In some embodiments, the steady state $C_{max}$ (% CV) is 1081 (49.1%) ng/mL measured after administration of 500 mg ranolazine. In some embodiments, the steady state $C_{max}$% CV) is 1955 (54.0%) ng/mL measured after administration of 1,000 mg ranolazine. In other particular embodiments, the CYP3A4 substrate drug is lurasidone, and the $C_{max}$ of lurasidone is maintained at a level of no more than about 210% of the normal baseline $C_{max}$ of lurasidone. As used herein, the "normal baseline $C_{max}$ of lurasidone" refers to the mean $C_{max}$ measured for a particular dose of lurasidone in the absence of other drugs. In some embodiments, the mean $C_{max}$ (% CV) is about 160 ng/mL measured after administration of 120 mg lurasidone in the fed state following a 350 kcal meal. In other particular embodiments, the CYP3A4 substrate drug is tadalafil, and the $C_{max}$ of tadalafil is maintained at a level of no more than about 120% of the normal baseline $C_{max}$ of tadalafil. As used herein, the "normal baseline $C_{max}$ of tadalafil" refers to the mean $C_{max}$ measured for a particular dose of tadalafil in the absence of other drugs. In some embodiments, the mean $C_{max}$ (% CV) is 190 (21.7%) µg/L measured after administration of 10 mg tadalafil. In some embodiments, the mean $C_{max}$ (% CV) is 548 (24.0%) µg/L measured after administration of 20 mg tadalafil. In other particular embodiments, the CYP3A4 substrate drug is erlotinib, and the $C_{max}$ of erlotinib is maintained at a level of no more than about 167% of the normal baseline $C_{max}$ of erlotinib at 150 mg. As used herein, the "normal baseline $C_{max}$ of erlotinib" refers to the mean $C_{max}$ measured at steady state conditions for a particular dose of erlotinib in the absence of other drugs. In some embodiments, the mean $C_{max}$ (% CV) is 1.7 (90%) µg/mL measured after administration of 150 mg erlotinib. The $C_{max}$ of erlotinib is highly variable and tends to increase in cancer patients relative to healthy volunteers. Thus, in some embodiments, the mean $AUC_{0-24}$ (% CV) can range from about 1 µg*h/mL to about 35 µg*h/mL, e.g., about 2 µg*h/mL, about 3 µg*h/mL, about 4 µg*h/mL, about 5 µg*h/mL, about 6 µg*h/mL, about 7 µg*h/mL, about 8 µg*h/mL, about 9 µg*h/mL, about 10 µg*h/mL, about 11 µg*h/mL, about 12 µg*h/mL, about 13 µg*h/mL, about 14 µg*h/mL, about 15 µg*h/mL, about 16 µg*h/mL, about 17 µg*h/mL, about 18 µg*h/mL, about 19 µg*h/mL, about 20 µg*h/mL, about 21 µg*h/mL, about 22 µg*h/mL, about 23 µg*h/mL, about 24 µg*h/mL, about 25 µg*h/mL, about 27 µg*h/mL, about 28 µg*h/mL, about 29 µg*h/mL, about 30 µg*h/mL, about 31 µg*h/mL, about 32 µg*h/mL, about 33 µg*h/mL, about 34 µg*h/mL, inclusive of all values and subranges therebetween. In other particular embodiments, the CYP3A4 substrate drug is solifenacin succinate, and the $C_{max}$ of solifenacin succinate is maintained at a level of no more than about 150% of the normal baseline $C_{max}$ of solifenacin succinate. As used herein, the "normal baseline $C_{max}$ of solifenacin" refers to the mean $C_{max}$ measured at steady state conditions for a particular dose of solifenacin succinate in the absence of other drugs. In some embodiments, the mean $C_{max}$ (% CV) is 24.01 (30%) ng/mL measured after administration of 5 mg solifenacin. In some embodiments, the mean $C_{max}$ (% CV) is 40.61 (21%) ng/mL measured after administration of 10 mg solifenacin succinate. In other particular embodiments, the CYP3A4 substrate drug is everolimus, and the $C_{max}$ of everolimus is maintained at a level of no more than about 200% of the normal baseline $C_{max}$ of everolimus. As used herein, the "normal baseline $C_{max}$ of everolimus" refers to the mean $C_{max}$ measured at steady state conditions for a particular dose of everolimus in the absence of other drugs. In some embodiments, the mean $C_{max}$ (% CV) is 59.7±16.9 (21.7%) ng/mL measured after administration of 10 mg everolimus.

In various other embodiments, the present disclosure provides for methods of treating patients previously administered posaconazole with a reduced dose of a CYP3A4 substrate drug (e.g., about 10%-50% of the reference dose) which is contraindicated for concomitant use with a strong CYP3A4 inhibitor, wherein the CYP3A4 substrate drug is maintained at a dose which provides a $C_{max}$ which is no more than about 4000% of the normal baseline $C_{max}$ of the CYP3A4 substrate drug for a period of at least about 2 to at least about 42 days after stopping posaconazole treatment, e.g., 3950%, no more than about 3900%, no more than about 3850%, no more than about 3800%, no more than about 3750%, no more than about 3700%, no more than about 3650%, no more than about 3600%, no more than about 3550%, no more than about 3500%, no more than about 3450%, no more than about 3400%, no more than about 3350%, no more than about 3300%, no more than about 3250%, no more than about 3200%, no more than about 3150%, no more than about 3100%, no more than about 3050%, no more than about 3000%, no more than about 2950%, no more than about 2900%, no more than about 2850%, no more than about 2800%, no more than about 2750%, no more than about no more than about 2700%, no more than about 2650%, no more than about 2600%, no more than about 2550%, no more than about 2500%, no more than about 2450%, no more than about 2400%, no more than about 2350%, no more than about 2300%, no more than about 2250%, no more than about 2200%, no more than about 2150%, no more than about 2100%, no more than about 2050%, no more than about 2000%, no more than about 1950%, no more than about 1900%, no more than about 1850%, no more than about 1800%, no more than about 1750%, no more than about 1700%, no more than about 1650%, no more than about 1600%, no more than about 1550%, no more than about 1500%, no more than about 1450%, no more than about 1400%, no more than about 1350%, no more than about 1300%, no more than about 1250%, no more than about 1200%, no more than about 1150%, no more than about 1100%, no more than about 1050%, no more than about 1000%, no more than about 950%, no more than about 900%, no more than about 850%, no more than about 800%, no more than about 750%, no more than about 700%, no more than about 650%, no more than about 600%, no more than about 550%, no more than about 500%, no more than about 450%, no more than about 445%, no more than about 440%, no more than about 435%, no more than 430%, no more than about 425%, no more than about 420%, no more than about 415%, no more than about 410%, no more than about 405%, no more than about 400%, no more than about 395%, no more than about 390%, no more than about 385%, no more than about 380%, no more than about 375%, no more than about 370%, no more than about 365%, no more than about 360%, no more than about 355%, no more than about 350%, no more than about 345%, no more than about 340%, no more than about 335%, no more than about 330%, no more than about 325%, no more than about 320%, no more than about 315%, no more than about 310%, no more than about 305%, or no more than about 300%, no more than about 295%, no more than about 290%, no more than about 285%, no more than about 280%, no more than about 275%, no more than about 270%, no more than about 265%, no more than about 260%, no more than about 255%, no more than about 250%, no more than about 245%, no more than about 240%, no more than about 235%, no more than about 230%, no more than about 225%, no more than about 220%, no more than about 216%, no more than about 215%, no more than about 210%, no more than about 205%, no more than about 200%, no more than about 195%, no more than about 190%, no more than about 185%, no more than about 180%, no more than about 175%, no more than about 170%, no more than about 165%, no more than about 160%, no more than about 155%, no more than about 150%, no more than about 145%, no more than about 140%, no more than about 135%, no more than about 130%, no more than about 125%, no more than about 120%, no more than about 115%, no more than about 110%, no more than about 105%, or no more than about 100% inclusive of all ranges and subranges therebetween. In particular embodiments, the CYP3A4 substrate drug is ranolazine, and the $C_{max}$ of ranolazine is maintained at a level of no more than about 150% of the normal baseline $C_{max}$ of ranolazine. In other particular embodiments, the CYP3A4 substrate drug is lurasidone, and the $C_{max}$ of lurasidone is maintained at a level of no more than about 210% of the normal baseline $C_{max}$ of lurasidone. In other particular embodiments, the CYP3A4 substrate drug is tadalafil, and the $C_{max}$ of tadalafil is maintained at a level of no more than about 120% of the normal baseline $C_{max}$ of tadalafil. In other particular embodiments, the CYP3A4 substrate drug is erlotinib, and the $C_{max}$ erlotinib is maintained at a level of no more than about 167% of the normal baseline $C_{max}$ of erlotinib. In other particular embodiments, the CYP3A4 substrate drug is solifenacin succinate, and the $C_{max}$ of solifenacin succinate is maintained at a level of no more than about 150% of the normal baseline $C_{max}$ of solifenacin succinate. In other particular embodiments, the CYP3A4 substrate drug is everolimus, and the $C_{max}$ of everolimus is maintained at a level of no more than about 200% of the normal baseline CYP3A4 substrate drugs (such as lurasidone and ranolazine) have labels which contraindicate their coadministration with strong CYP3A4 inhibitors, such as posaconazole. Thus, conventionally, it would be considered safe to administer the CYP3A4 substrate drug one day after the last dose of posaconazole (i.e., one day after discontinuing or "stopping" posaconazole). However, the interaction of posaconazole and many CYP3A4 substrate drugs had not been investigated previously. The Applicant's clinical research is the first work to observe the levels of certain CYP3A4 substrate drugs during both concomitant administration of posaconazole and for an extended period after posaconazole administration has been stopped. Applicant discovered that the inhibitory effects of posaconazole on CYP3A4 last substantially longer than would have been predicted from its half-life, and thus posaconazole inhibits the metabolism of CYP3A4 substrate drugs for substantially longer than would have been predicted from the prior art. Thus, actual blood plasma levels of CYP3A4 substrate drugs are in fact significantly higher after stopping posaconazole than would have been predicted from the prior art. Therefore, in order to achieve a "safe" blood plasma concentration profile for the CYP3A4 substrate drug (e.g., when the benefits of treating the patient for the condition or disease for which the CYP3A4 substrate drug is indicated outweigh the risks associated with the effects of a drug-drug interaction as described herein), Applicant discovered that patients must wait longer than previously believed (e.g., more than the 1 day contraindication period provided by the label), and/or administer a reduced dose of the CYP3A4 substrate drug.

For purposes of the present methods, the expected blood plasma levels of a CYP3A4 substrate drug after stopping coadministration with a strong CYP3A4 inhibitor such as posaconazole or ketoconazole can be calculated from the blood plasma levels of the CYP3A4 substrate drug during coadministration with the strong CYP3A4 inhibitor using conventional pharmacological methods as described below. Blood plasma levels may be described in various ways, such as area under the plasma concentration curve (AUC) and peak plasma concentration (Cmax). Baseline levels and posaconazole interaction levels for CYP3A4 substrate drugs may be compared using the geometric mean ratio (GMR) of AUC and Cmax. As used herein, "baseline" refers to the plasma concentration of the CYP3A4 substrate drug in an otherwise identical patient population who has not been administered a CYP3A4 inhibitor drug. GMR is the standard industry and regulatory method for assessing the ratio of change of a pharmacokinetic variable (such as AUC) relative to its own baseline value (e.g., in a patient that was not treated with posaconazole). Once the level of substrate drug (AUC or Cmax) during co-administration with posaconazole and a CYP3A4 substrate drug is known, a function can be derived using conventional pharmacological methods to estimate how the AUC or plasma level of the CYP3A4 substrate drug is expected to decay over time after stopping administration of posaconazole. Such a function can be used to provide a plot of the decay GMR of AUC (or Cmax) of the CYP3A4 substrate drug versus time due to its interaction with posaconazole, based on the stated half-life of posaconazole. As the GMR curve approaches the time when the known half-life of posaconazole predicts that essentially all of the posaconazole has been eliminated, the GMR approaches a value of 1.

One of ordinary skilled in the art would have understood that the expected DDI decay curve could be calculated using equation 1 (Rang, H., Dale, M., Ritter, J., and Flower R., Rang and Dale's Pharmacology, 6th ed. London: Elsevier, Ltd 2007. Chapter 8, p. 122) to provide the expected DDI decay curve:

$$AUC\ GMR\ \text{at day}\ (x) = 1 + [(AUC\ \text{during co-administration}) - 1] * e^{\wedge}(-K_{el} * x) \quad \text{(equation 1)}$$

Where $K_{el}=\ln(2)/(31\ \text{hours}/24\ \text{hours})$ or about 0.5366, based on the 31 hour half-life of posaconazole tablets (Noxafil® label updated September 2016) and Where x=the number of days after posaconazole discontinuation The expected DDI decay curve can also be calculated for $C_{max}$ GMR by substituting $C_{max}$ during co-administration for AUC during co-administration in equation 1. As used herein, "expected levels" and "predicted levels" and the like, refer to the AUC or $C_{max}$ GMR values calculated using equation 1.

Figure 9:
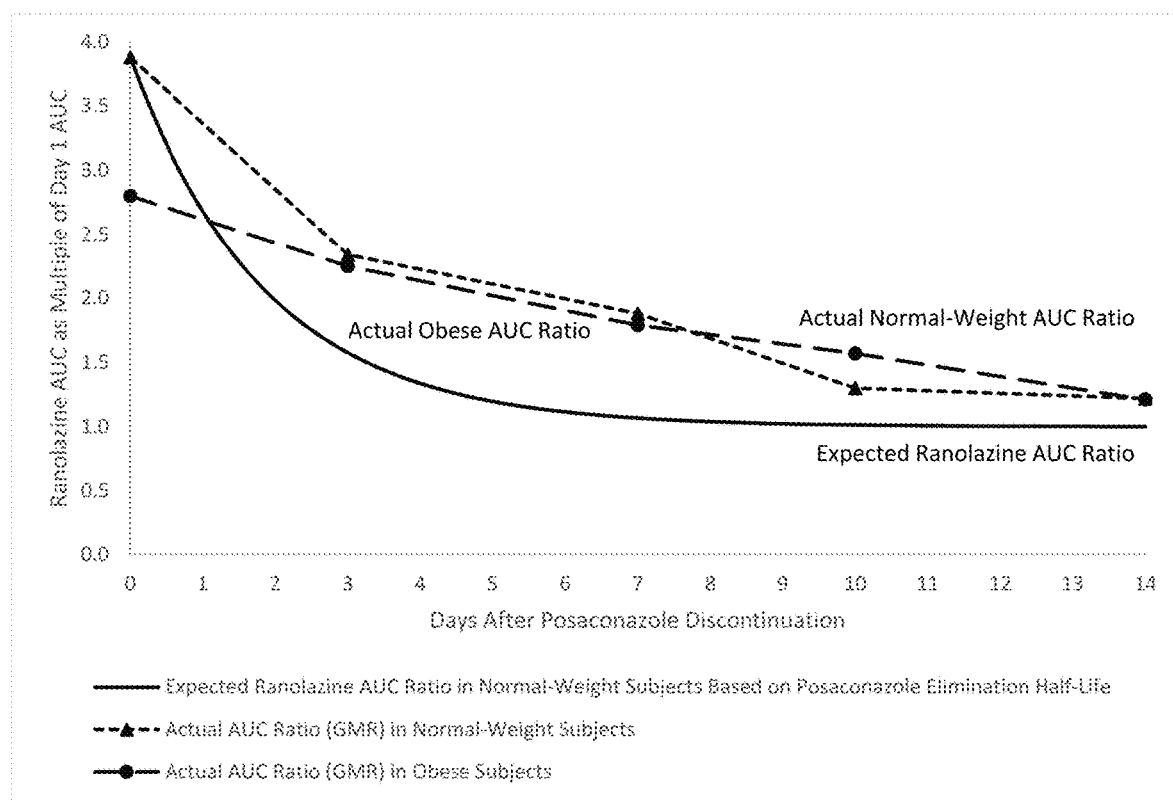
FIG. 9 shows actual ranolazine AUC ratios measured for normal-weight and obese subjects (dashed lines) compared to ranolazine AUC for the patients that would have been predicted from posaconazole half-life (expected ranolazine AUC ratios; solid line).
Figure 10:
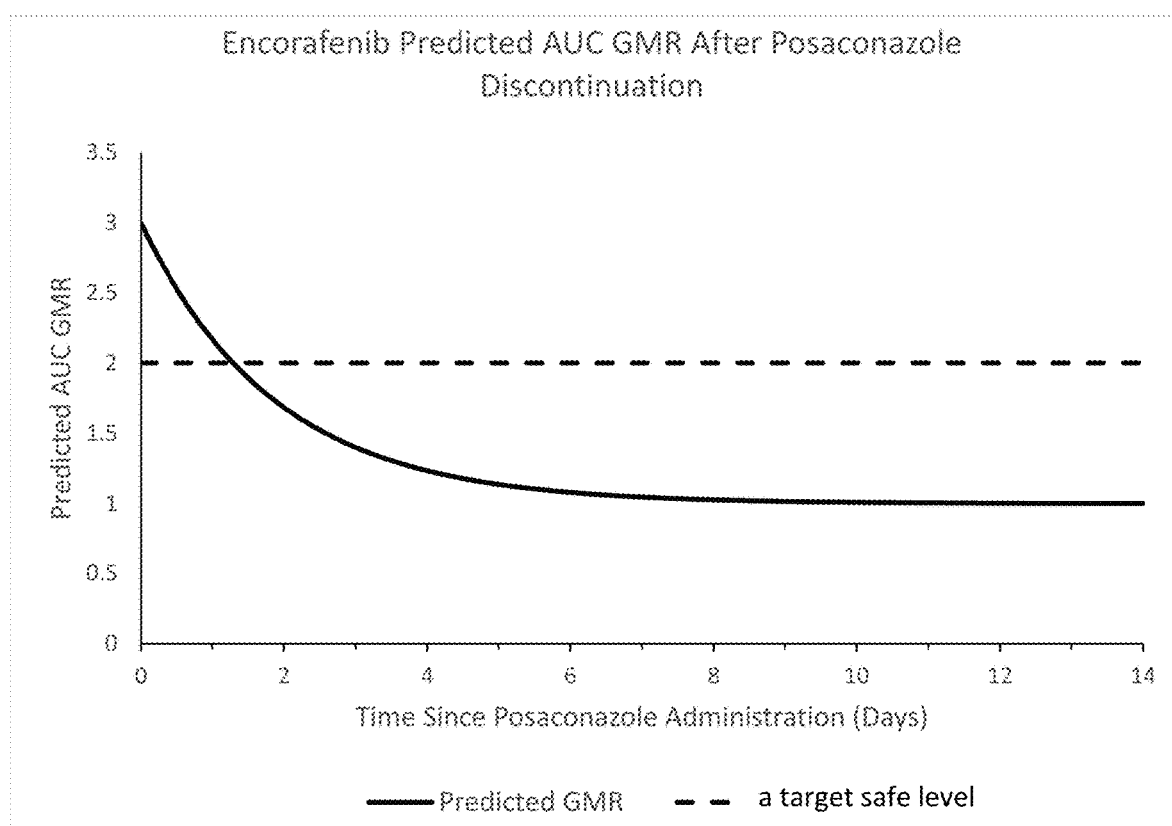
FIG. 10 shows the predicted decay curve for encorafenib (solid line) and a maximum ("target safe level") GMR of AUC level to be achieved by the methods disclosed herein.

Expected DDI curves have been prepared for lurasidone (FIG. 8; solid line) and ranolazine (FIG. 9; solid line), by applying equation 1 to AUC levels measured during coadministration with posaconazole. Clinically established coadministration levels have also been determined for encorafenib (BRAFTOVI®) in the presence of posaconazole. As shown in Table A, when coadministered with posaconazole, the drug-drug interaction with posaconazole elevates the baseline AUC of encorafenib by 300% (see column titled "AUC co-administration levels" "percent of baseline"). Equation 1 was applied to the coadministration AUC levels for encorafenib, and the predicted curve of posaconazole impact on encorafenib GMR of AUC was calculated as shown in FIG. 10.

Applicant surprisingly and unexpectedly discovered that blood plasma levels of CYP3A4 substrate drugs administered after stopping posaconazole, were significantly elevated compared to the expected levels of such drugs calculated using equation 1. Thus, Applicant discovered that the inhibitory effects of posaconazole on CYP3A4 substrate drugs persist far longer than were previously known, and that administering the full reference dose of the CYP3A4 substrate drug after stopping posaconazole (e.g., as taught in the labels of the CYP3A4 substrate drugs described herein) will actually achieve blood plasma levels of the CYP3A4 substrate drug that are greater than the expected levels, for example as calculated using equation 1 (see FIGS. 8 and 9; dashed lines). To address the clinical impact of this unexpected increase in blood plasma levels, Applicant discovered that: (i) a full reference dose of the CYP3A4 substrate drug should be administered two or more days (e.g., as described herein) after stopping posaconazole to achieve safe plasma levels that are higher than would have been predicted; or (ii) a reduced dose of the CYP3A4 substrate drug should be administered e.g. to achieve safe plasma levels of the drug that are approximately equivalent (e.g., about 80-125%) to those expected from a full reference dose of the CYP3A4 substrate drug based on the above equation. The reduced dose of the CYP3A4 substrate drug may be administered with posaconazole, the day after stopping posaconazole, or two or more days (e.g., as described herein) after stopping posaconazole.

In some embodiments (e.g., when a full dose is administered two or more days after stopping posaconazole or when a reduced dose is administered as described herein), the blood plasma levels of the CYP3A4 substrate drug are therapeutic, and are at or below the target levels that are considered safe (i.e., wherein inhibition of CYP3A4 by posaconazole would not present an unacceptable risk of serious side effects to the patient). Turning to FIG. 10, a line showing target AUC GMR levels of encorafenib that are considered safe according to some embodiments has been overlaid on this figure. The present disclosure provides for methods of administering encorafenib to achieve blood plasma levels that are greater than the expected levels but do not exceed the target safe levels. Accordingly, in various embodiments, the present methods comprise: (i) administering the reference dose of a CYP3A4 substrate drug (such as encorafenib) at least 2 days (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days) after stopping posaconazole to achieve blood plasma levels that are above those that would be predicted from the expected curve (e.g., above the predicted blood plasma level curve by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, or about 195% above predicted levels) but do not exceed the target safe levels) or (ii) administering a reduced dose to achieve the blood plasma levels that are greater than or equal to those calculated for the full reference dose but do not exceed the target safe levels.

As for lurasidone, ranolazine, and encorafenib, the expected DDI decay curves of the blood plasma levels for other CYP3A4 substrate drugs can be calculated using, e.g., Equation 1, from the blood plasma levels of the CYP3A4 substrate drugs obtained during co-administration with posaconazole, and the conventionally understood half-life of posaconazole. Table A, below, contains (a) the co-administration levels for CYP3A4 substrate drugs in the columns entitled "AUC co-administration levels" and "Cmax co-administration levels"; (b) "AUC target safe level" and "Cmax target safe level" (the levels at which benefits outweigh risks according to some embodiments); and (c) "baseline AUC" and "baseline Cmax" levels for CYP3A4 substrate drugs measured in a patient that was not previously treated with a strong CYP3A4 inhibitor (e.g., posaconazole). The columns entitled "Co-administration levels" provide the fold change or percent of baseline increase observed when the substrate drug was co-administered with a strong CYP3A4 inhibitor (e.g., ketoconazole). Because co-administration of many of these CYP3A4 substrate drugs with strong CYP3A4 inhibitors is contraindicated, the co-administration levels represent unsafe Cmax and AUC levels. In various embodiments, the "Target safe levels" are non-limiting examples of the upper limit of fold change or percent of baseline where in some embodiments the benefits of treating the patient for the condition or disease for which the CYP3A4 substrate drug is indicated outweigh the risks associated with the effects of a drug-drug interaction. While Table A provides one example of a target safe level for each CYP3A4 substrate drug, each drug may have more than one target safe level (e.g., depending on particular risk/benefit considerations for different patient populations). "Baseline AUC" or "Baseline Cmax" denotes the plasma concentrations of the CYP3A4 substrate drug in an otherwise identical patient who has not been administered a strong CYP3A4 inhibitor drug. The co-administration levels reported in Table A were measured with either posaconazole, itraconazole, ritonavir, or ketoconazole. For purposes of the present methods, the blood plasma levels measured during co-administration of the CYP3A4 substrate drug with ketoconazole may be used to estimate the posaconazole DDI decay curve, e.g., using equation 1. In some embodiments, the present disclosure provides for methods of administering a CYP3A4 substrate drug to achieve blood plasma levels that are less than or equal to the target safe AUC and Cmax shown in Table A. In order to determine when blood plasma levels will be within safe and effective levels, such that the proper delay period and/or reduced dosing period can be calculated, blood plasma levels of the CYP3A4 substrate drug can be measured using routine methods known in the art (e.g., obtaining blood samples from a patient and measuring the blood plasma concentration of the CYP3A4 substrate drug using mass spectrometry). The following sections discuss how Applicant's surprising and unexpected information about CYP3A4 inhibition by posaconazole gleaned from Applicant's clinical research inform dosing of CYP3A4 substrate drugs.

TABLE 1

Pharmacokinetic Parameters of CYP3A4 Substrate Drugs

| CYP3A4 drug | AUC co-administration levels | | AUC target safe level | | Baseline AUC (% CV) |
|---|---|---|---|---|---|
| | Fold change | Percent of baseline | Fold change | Percent of baseline | (ng*h/mL unless otherwise specified) |
| abemaciclib | 16 | 1600% | 1.3 | 130% | steady state $AUC_{0-24}$: 150 mg Q12H: 4280, 200 mg Q12H: 5520 |
| apalutamide | | | 1.24 | 124% | 60 mg steady state: 100 +/− 32 ug*h/mL |
| aripiprazole | | | 1.7 | 170% | $AUC_{0-24}$, 3 mg steady state: 678 +/− 413 |
| bosutinib | 2 | 200% | | | multiple 400 mg doses: 2720 +/− 442; multiple 500 mg doses: 3650 +/− 425 |
| brexpiprazole | | | 2 | 200% | $AUC_{inf}$ 1 mg tablet: 612 +/− 222; 2 mg: 1940 +/− 989; 4 mg: 2690 +/− 1710 |
| brigatinib | 2.01 | 201% | | | AUC0-t, steady state 90 mg: 8165 (57); 180 mg: 20276 (56) |
| cabazitaxel | 1.25 | 125% | | | 25 mg/m$^2$ q3w: 991 (34) |
| cariprazine | | | 4 | 400% | 3 mg steady state: 156 +/− 72; 6 mg steady state: 358 +/− 85.2 |
| cobimetinib | 6.7 | 670% | | | AUC0-24, steady state 60 mg: 4340 (61) |
| copanlisib | | | 1.53 | 153% | 0.8 mg/kg AUC0-25 steady state: 1570 +/− 338 |
| crizotinib | 1.57 | 157% | | | steady state at 250 mg BID: 3880 (36) |
| dabrafenib | 1.71 | 171% | | | day 15 150 mg BID: 2619 (76.7) |
| daclatasvir | | | 3 | 300% | AUC0-24, steady state 60 mg: 10973 +/− 5288 |

TABLE 1-continued

Pharmacokinetic Parameters of CYP3A4 Substrate Drugs

| | | | | | |
|---|---|---|---|---|---|
| dapagliflozin/ saxagliptin | saxagliptin: 3.67 | 367% | | | saxagliptin: 78 |
| deflazacort | | | 3 | 300% | single dose: 280 |
| duvelisib | | | 2 | 200% | steady state 25 mg bid: 7.9 (77) ug*h/mL |
| elbasvir/ grazoprevir | EBR: 1.8; GZR: 3.02 | EBR: 180%; GBR: 302% | | | AUC0-24 EBR: 1920, GZR: 1420 |
| encorafenib | 3 | 300% | | | median, 450 mg steady state: 12700 (range 9230-228000) |
| flibanserin | 1.4 | 140% | | | single 100 mg dose AUCinf: 1543 +/− 511 |
| fluticasone propionate/ salmeterol xinafoate | fluticasone propionate: 1.9; salmeterol: 15.76 | fluticasone propionate: 190%; salmeterol: 1576% | | | fluticasone: 230/21: 799 pg*h/mL after 2 inhalations, 115/21: 274 pg*h/mL, 45/21: 138 pg*h/mL with a spacer; salmeterol: 230/21: 317 pg*h/mL, 115/21: 53 pg*h/mL, 45/21: 103 pg*h/mL with a spacer |
| ibrutinib | 24 | 2400% | 3 | 300% | steady state: 560 mg with MCL: 865 (69%), MZL: 978 (82%); 420 mg with CLL/SLL 708 (71%), WM 707 (72%), cGVHD 1159 (50%) |
| ivabradine | 7 | 700% | 2.1 | 210% | |
| ivacaftor | | | 3 | 300% | single 150 mg dose: 10600 +/− 5260 |
| ivacaftor/ tezacaftor | | | ivacaftor: 2.95; tezacaftor: 2.0 | ivacaftor: 295%; tezacaftor 200% | AUC0-12 ivacaftor: 11.3 +/− 4.6; AUC0-24 tezacaftor: 84.5 +/− 27.8 |
| ivosidenib | 2.69 | 269% | 1.73 | 173% | 500 mg steady state: 117,348 (50) |
| naloxegol | 12.85 | 1285% | 3.41 | 341% | AUC0-12 steady state 25 mg: 363.9 +/− 151 |
| nilotinib | 3 | 300% | | | AUC0-12, 400 mg bid: 18000 (33); 300 mg bid: 13337 (46) |
| olaparib | 2.2 | 220% | | | AUC steady state: 300 mg tablets, 49 ug*h/mL; 400 mg capsules bid, 43.5 ug*h/mL |
| palbociclib | 1.87 | 187% | | | AUC0-10: 125 mg, 724 (38) |
| panobinostat | | | 1.73 | 173% | |
| pazopanib | 1.7 | 170% | | | 1037 ug*h/mL |
| regorafenib | 1.33 | 133% | | | steady state: 58.3 ug*h/mL |
| ribociclib | 3.2 | 320% | | | AUC0-6 after 8 days at 600 mg: 11173 +/− 1830 |
| rivaroxaban | 1.76 | 176% | 1.52 | 152% | AUC after a single dose: 2.5 mg, 321 (28.8); 10 mg fed, 1201 (21.3); 15 mg fed, 1801 (22.2); 20 mg fed, 2294 (19.0) |
| ruxolitinib | | | 1.91 | 191% | ranged from 862 to 30700 nM*h over a dose range of 5 to 200 mg |
| sonidegib | 2.2 | 220% | | | steady state AUC0-24: 22 ug/mL |
| sunitinib | | | 1.51 | 151% | single dose AUC0-inf: 1063 +/− 262 |
| tofacitinib | | | 1.75 | 175% | AUC0-24, ss: 5 mg bid rheumatoid arthritis: 504 (22); 5 mg bid psoriatic arthritis: 419 (34); 5 mg bid ulcerative colitis: 423 (23), 10 mg bid ulcerative colitis: 807 (25) |

TABLE 1-continued

Pharmacokinetic Parameters of CYP3A4 Substrate Drugs

| | | | | | |
|---|---|---|---|---|---|
| vemurafenib | | | | | AUC0-12 steady state 960 mg bid: 601 +/− 70 ug*h/mL |
| venetoclax | 1.78 | 178% | | | AUC0-24 400 mg: 32.8 +/− 16.9 ug*h/mL |
| larotrectinib | 4.3 | 430% | | | $AUC_{0-24\ hr}$ steady-state 100 mg BID: 4351 (97%) |
| irinotecan | | | | | single 90 min infusion Irinotecan 125 mg/m² $AUC_{0-24}$ = 10,200 ± 3,270 340 mg/m² $AUC_{0-24}$ = 20,604 ± 6,027 SN-38 125 mg/m² $AUC_{0-24}$ = 229 ± 108 340 mg/m² $AUC_{0-24}$ = 474 ± 245 |
| siponimod | 2 | 200% | 10.4 | 1040% | $AUC_{0-inf}$ after single 10 mg dose: 3226 +/− 1909 |
| erdafitinib | | | 1.34 | 134% | $AUC_{tau}$ steady state at 8 mg qd: 29,268 (60%) |
| fostamatinib disodium | | | R406: 2.02 | R406: 202% | R406: 7080 (±2670) |
| elagolix sodium | | | 2.2 | 220% | $AUC_\tau$ steady state at: 150 mg qd = 1292 (31) 200 mg BID = 1725 (57) |
| lorlatinib | 1.42 | 142% | | | $AUC_{0-24}$ steady state at 100 mg qd: 5650 (39%) |
| glasdegib | | | 2.4 | 240% | $AUC_{tau}$ steady state at 100 mg qd: 17210 (54%) |
| gilteritinib | | | 2.2 | 220% | $AUC_{24}$ steady state at 120 mg qd: 6943 (±3221) |
| naldemedine | | | 1.9 | 190% | $AUC_{inf}$ for single dose 0.1 mg G mean (CV) = 11.60 (25.4) A mean (SD) = 11.89 (2.75) 0.3 mg G mean (CV) = 32.53 (16.5) A mean (SD) = 32.90 (5.31) |
| valbenazine | | | val: 2.2 [+]-α-HTBZ: 2.1 | val: 220% [+]-α-HTBZ: 210% | $AUC_{0-inf}$ for single dose 50 mg val: 4,120 (1680) [+]-α-HTBZ: 575 (350) 75 mg val: 7,170 (1540) [+]-α-HTBZ: 1,150 (706) 100 mg val: 6,590 (1560) [+]-α-HTBZ: 872 (284) |
| midostaurin | | | mid: 10.4 CGP62221: 3.5 | mid: 1040% CGP62221: 350% | $AUC_{inf}$ single dose 50 mg Mido: 19,762.50 CGP62221: 31,366.63 |
| neratinib | 5.81 | 581% | | | $AUC_{0-24}$ single dose 180 mg: 734 ± 291 (40) 240 mg: 823 ± 291 (35) 320 mg: 1582 ± 800 (51) |
| acalabrutinib | 5.1 | 510% | 2.0 | 200% | 1111 |
| upadacitinib | | | | | $AUC_{inf}$ single dose at 3 mg: 103 ± 27.6 6 mg: 160 ± 37.6 |

TABLE 1-continued

Pharmacokinetic Parameters of CYP3A4 Substrate Drugs

| | | | | |
|---|---|---|---|---|
| roxadustat | | | | 12 mg: 331 ± 49.8<br>24 mg: 615 ± 78.1<br>$AUC_{inf}$ single 100 mg dose while fasted: 49,807 (15,111) |
| trastuzumab deruxtecan (DS-8201) | | | | $AUC_{last}$ (ug*day/mL) 21 day cycle at 0.8 mg/kg: 51.7 (13.1)<br>3.2 mg/kg: 325 (142)<br>8.0 mg/kg: 914 (235) |
| pimavanserin | | | 3 | 300% | $AUC0_{0-\infty}$ Single dose 100 mg: 3847 (16.2) |
| trabectedin | 1.66 | 166% | | | $AUC_{inf}$ one dose (24 hr infusion) at 600 ug/m²: 12 (±4.8)<br>900 ug/m² = 36 (±16)<br>1200 ug/m² = 32 (±13)<br>1500 ug/m² = 55 (±25) |

| | Cmax co-administration levels | | Cmax target safe level | | Baseline Cmax (% CV) |
|---|---|---|---|---|---|
| CYP3A4 drug | Fold change | Percent of baseline | Fold change | Percent of baseline | (ng/mL unless otherwise specified) |
| abemaciclib | | | | | 150 mg Q12H: 249, 200 mg Q12H: 298 |
| apalutamide | | | 1.38 | 138% | 6.0 +/− 1.7 ug/mL |
| aripiprazole | | | 1.4 | 140% | 3 mg steady state: 44.3 +/− 29.3 |
| bosutinib | 1.5 | 150% | | | multiple 400 mg doses: 146 +/− 20;<br>multiple 500 mg doses: 200 +/− 12 |
| brexpiprazole | | | 1.2 | 120% | 1 mg: 12.1 +/− 3.79;<br>2 mg: 24.6 +/− 5.58;<br>4 mg: 47.3 +/− 16.4 |
| brigatinib | 1.21 | 121% | | | steady state 90 mg: 552 (65); 180 mg 1452 (60) |
| cabazitaxel | | | | | 25 mg/m2 q3w: 226 (107) |
| cariprazine | | | 3.5 | 350% | 3 mg steady state: 10.2 +/− 4.69;<br>6 mg steady state: 22.7 +/− 4.18 |
| cobimetinib | 3.2 | 320% | | | 273 (60) |
| copanlisib | | | 1.03 | 103% | 463 +/− 584 |
| crizotinib | 1.33 | 133% | | | steady state at 250 mg BID: 411 (44) |
| dabrafenib | | | | | day 15 150 mg BID: 806 (95.1) |
| daclatasvir | | | 1.57 | 157% | steady state 60 mg: 182 +/− 137 |
| dapagliflozin/ saxagliptin | saxagliptin: 2.44 | saxagliptin: 244% | | | saxagliptin: 24 |
| deflazacort | | | | | single dose 30 mg: 116 |
| duvelisib | | | 1.7 | 170% | steady state 25 mg bid: 1.5 (64) ug/mL |
| elbasvir/ grazoprevir | EBR: 1.29;<br>GZR: 1.13 | EBR: 129%;<br>GBR: 113% | | | EBR: 121;<br>GZR: 165 |
| encorafenib | | | 1.45 | 145% | median, 450 mg steady state: 3800 (range 2870-7000) |
| flibanserin | | | 1.1 | 110% | single 100 mg dose: 419 +/− 206 |

TABLE 1-continued

Pharmacokinetic Parameters of CYP3A4 Substrate Drugs

| Drug | Col2 | Col3 | Col4 | Col5 | Col6 |
|---|---|---|---|---|---|
| fluticasone propionate/ salmeterol xinafoate | salmeterol: 1.4 | salmeterol: 140% | | | steady state fluticasone 45/21: 41 pg/mL, 115/21: 108 pg/mL, 230/21: 173 pg/mL; salmeterol: ranged from 220-470 pg/mL across dose range |
| ibrutinib | 29 | 2900% | 3.4 | 340% | |
| ivabradine | 3.25 | 325% | 1.6 | 160% | |
| ivacaftor | | | 2.7 | 270% | single 150 mg dose: 768 +/− 233 |
| ivacaftor/ tezacaftor | | | ivacaftor: 2.47; tezacaftor: not given | ivacaftor: 247%; tezacaftor: not given | ivacaftor: 1.17 +/− 0.424 ug/mL; tezacaftor: 5.95 +/− 1.5 ug/mL |
| ivosidenib | | | 1.52 | 152% | 500 mg steady state: 6551 (44) |
| naloxegol | 9.58 | 958% | 2.86 | 286% | steady state 25 mg: 96.87 +/− 55.38 |
| nilotinib | | | | | 400 mg bid: 2260 (35); 300 mg bid: 1540 (48) |
| olaparib | 1.1 | 110% | | | steady state: 300 mg tablets, 7.7 ug/mL; 400 mg capsules bid, 6.18 ug/mL |
| palbociclib | 1.34 | 134% | | | 125 mg, 86 (34) |
| panobinostat | | | 1.62 | 162% | 20 mg: 21.6 ng/mL |
| pazopanib | 1.5 | 150% | | | 58.1 ug/mL |
| regorafenib | | | | | steady state: 3.9 ug/mL |
| ribociclib | 1.7 | 170% | | | after 11 days at 600 mg: 2610 +/− 547 |
| rivaroxaban | 1.56 | 156% | | 0% | After a single dose: 2.5 mg, 52.0 (28.1); 10 mg fed, 161.7 (17.2); 15 mg fed, 234.2 (17.4); 20 mg fed, 294.4 (15.0) |
| ruxolitinib | | | 1.33 | 133% | ranged from 205 to 7100 nM over a dose range of 5 to 200 mg |
| sonidegib | 1.5 | 150% | | 0% | steady state: 1030 |
| sunitinib | | | 1.49 | 149% | single dose: 24.4 +/− 4 |
| tofacitinib | | | 1.1 | 110% | |
| vemurafenib | | | | | steady state 960 mg bid: 61 +/− 17 ug/mL |
| venetoclax | 1.06 | 106% | | | 400 mg: 2.1 +/− 1.1 ug/mL |
| larotrectinib | 2.8 | 280% | | | Steady state 100 mg BID: 788 (81%) |
| irinotecan | | | | | single 90 min infusion Irinotecan 125 mg/m$^2$: 1,660 ± 797 340 mg/m$^2$: 3,392 ± 874 SN-38 125 mg/m$^2$: 26.3 ± 11.9 340 mg/m$^2$: 56.0 ± 28.2 |
| siponimod | | | | | Single 10 mg dose: 80.4 +/− 19.6 |
| erdafitinib | | | 1.05 | 105% | Steady state at 8 mg qd: 1,399 (51%) |
| fostamatinib disodium | | | R406: 1.37 | R406: 137% | R406: 550 (±270) |
| elagolix sodium | | | 1.77 | 177% | Steady state at: 150 mg qd = 574 (29) 200 mg BID = 774 (68) |
| lorlatinib | 1.24 | 124% | | | Steady state at 100 mg qd 577 (42%) |
| glasdegib | | | 1.4 | 140% | steady state at 100 mg qd: 1252 (44%) |

TABLE 1-continued

Pharmacokinetic Parameters of CYP3A4 Substrate Drugs

| Drug | | | | | |
|---|---|---|---|---|---|
| gilteritinib | 1.20 | 120% | | | steady state at 120 mg qd: 374 (±190) |
| naldemedine | 1.38 | 138% | | | single dose 0.1 mg<br>G mean (CV) = 1.98 (30.9)<br>A mean (SD) = 2.05 (0.54)<br>0.3 mg<br>G mean (CV) = 4.47 (19.3)<br>A mean (SD) = 4.54 (0.83) |
| valbenazine | val: 1.6<br>[+]-α-HTBZ: 1.7 | val: 160%<br>[+]-α-HTBZ: 170% | | | Single dose<br>50 mg<br>val: 412 (236)<br>[+]-α-HTBZ: 20.4 (7.51)<br>75 mg<br>val: 788 (220)<br>[+]-α-HTBZ: 31.7 (11.4)<br>100 mg<br>val: 779 (293)<br>[+]-α-HTBZ: 31.9 (11.0) |
| midostaurin | | | | | Single dose 50 mg<br>Mido: 1,585.02<br>CGP62221: 586.78<br>CGP52421: 144.59 |
| neratinib | 4.21 | 421% | | | single dose<br>180 mg: 65.9 ± 34.7 (53)<br>240 mg: 75.9 ± 12.9 (17)<br>320 mg: 118 ± 47.6 (40) |
| acalabrutinib | 3.9 | 390% | 2.0 | 200% | 323 |
| upadacitinib | | | | | $AUC_{inf}$ single dose at<br>3 mg: 25.0 ± 6.88<br>6 mg: 38.9 ± 9.96<br>12 mg: 82.9 ± 12.1<br>24 mg: 158 ± 18.4 |
| roxadustat | | | | | single 100 mg dose while fasted: 8498 (2203) |
| trastuzumab deruxtecan (DS-8201) | | | | | Cmax (ug/mL) 21 day cycle at<br>0.8 mg/kg: 22.9 (3.8)<br>3.2 mg/kg: 78.2 (16.1)<br>8.0 mg/kg: 216 (52.0) |
| pimavanserin | | | 1.5 | 150% | Single dose 100 mg: 57.0 (18.0) |
| trabectedin | 1.22 | 122% | | | One dose (24 hr infusion) at<br>600 ug/m$^2$ = 0.56 (±0.22)<br>900 ug/m$^2$ = 0.95 (±0.20)<br>1200 ug/m$^2$ = 1.4 (±0.65)<br>1500 ug/m$^2$ = 1.8 (±1.1) |

The values in Table A are approximations. In some embodiments, the percent baseline for the AUC and Cmax target safe levels can vary by about ±25% (e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24% or about 25%, inclusive of all ranges therebetween). For example, when the target safe level in Table A is 130%, the AUC or Cmax level achieved may be 155% or 105%. Similarly, in some embodiments, the GMR of AUC or Cmax may vary by about ±25%.

Because the potentially adverse consequences of leaving a patient untreated with the CYP3A4 substrate drug must be balanced with potential risks associated with effects of a DDI between the CYP3A4 substrate drug and posaconazole (e.g., elevation of plasma levels and elevated exposure to the CYP3A4 substrate drug), a person of skill in the art (e.g., a physician) would administer a dose of the CYP3A4 substrate drug as soon as it would be safe to do so. For example, a physician would dose the CYP3A4 substrate drug as soon as doing so would not result in clinically significant, elevated plasma levels or exposure to the CYP3A4 drug that exceed the target levels considered safe. Such a physician would not wait for a longer period of time, as even though lower plasma levels of posaconazole would reduce the potentially adverse effects of a DDI, the patient would not receive the benefit of being treated with the CYP3A4 substrate drug (or alternatively, be exposed to risks associated with remaining untreated). For certain CYP3A4 substrate drugs, the CYP3A4 substrate drug is contraindicated for coadministration with posaconazole. A person of skill in the art would therefore construe such a contraindication to mean that only coadministration of the CYP3A4 substrate drug with the CYP3A4 inhibitor (e.g., posaconazole) is unsafe; but it would be safe to administer 100% of the reference dose (as defined herein) of the CYP3A4 substrate drug as soon as the day after the last dose of posaconazole (i.e., the day after "stopping" posaconazole).

However, Applicant discovered that the inhibitory effects of posaconazole on CYP3A4 last substantially longer than would have been predicted from its half-life. Applicant also discovered that posaconazole levels remain higher than expected for a longer period of time, particularly in obese patients (as defined herein). See FIG. 8, which shows that the actual lurasidone AUC levels (dashed lines) measured in a patient after stopping posaconazole are unexpectedly higher after stopping posaconazole than predicted in the prior art by posaconazole half-life (solid line); see also FIG. 9 which also shows that actual ranolazine AUC levels (dashed lines) are significantly higher the predicted AUC levels (solid line). This previously unknown persistence of posaconazole inhibition of CYP3A4 poses an increased risk of causing serious side effects upon subsequent administration of CYP3A4 substrate drugs, which was not previously appreciated. To mitigate this risk, in some embodiments the administration of the CYP3A4 substrate drug is contraindicated not just for co-administration with posaconazole, but the administration is also contraindicated for a period of time (e.g., 2 or more days) after stopping posaconazole beyond the label-prescribed delay of one day (i.e., contraindication for co-administration of the CYP3A4 substrate drug and posaconazole). In some embodiments, the present methods provide for administering the CYP3A4 substrate drug as soon as it is safe to do so, e.g., for time periods exceeding about 1 day, as described herein. Administering the CYP3A4 substrate drug "as soon as it is safe" does not mean waiting until all or almost all of the posaconazole is eliminated from the patient in order to minimize the DDI. Rather, administering the CYP3A4 substrate drug "as soon as it is safe" generally means administering the CYP3A4 substrate drug even when posaconazole plasma levels are such that an appreciable DDI effect is still present. The CYP3A4 substrate drug is administered as soon as the effects of the DDI are low enough such that the blood plasma levels of the CYP3A4 substrate drug do not exceed target safe levels. This accounts for the need to treat the patient with the CYP3A4 substrate drug with no more delay (after stopping posaconazole) than is necessary, so that the risks of leaving such a patient untreated are minimized as much as possible.

As used herein, "safe", such as usages in which the CYP3A4 substrate drug is administered "as soon as it is safe" and "safe level", means as soon as inhibition of CYP3A4 by posaconazole would not present an unacceptable risk of serious side effects to the patient (e.g., due to blood plasma levels of the CYP3A4 substrate drug). An "unacceptable risk of serious side effects" occurs e.g., when risks associated with elevated exposure to the CYP3A4 substrate drug are, on balance, greater than the risk of not treating the patient with the CYP3A4 substrate drug. In some embodiments, and as unexpectedly discovered by the Applicant, administering the CYP3A4 substrate drug "as soon as it is safe" requires waiting longer than would have been predicted by the prior art—i.e., waiting longer than 1 day after stopping posaconazole based on the label contraindication of coadministration of the CYP3A4 substrate drug and posaconazole. By implication, "unsafe" as used herein means when risks associated with treating a patient (e.g., elevated exposure to the CYP3A4 substrate drug) are greater than the risk of not treating the patient. Thus, the present methods account for the previously unknown magnitude and the unknown duration of the inhibitory effects of posaconazole on CYP3A4, as well as the need to treat the patient with the CYP3A4 substrate drug.

In some embodiments, the CYP3A4 substrate drug is administered as soon as treatment would provide a favorable risk/benefit profile. The risk/benefit profile weights the patient's risk(s) of potential adverse event(s) if treated compared to the benefit(s) of treatment. Non-limiting examples of factors used to assess the risk/benefit profile include: (i) the type of benefit(s) the patient would receive (e.g., treatment end points and the value of treatment to the patient); (ii) magnitude of the benefit(s); (iii) probability of the patient experiencing one or more benefit(s); (iv) duration of effect(s) and whether to duration is a benefit; (v) severity, types, number, and rates of harmful events (e.g., serious vs. non-serious adverse events); (vi) probability of a harmful event (e.g., the percentage of the patient population that would be expected to experience a harmful event; the incidence of each harmful event in the study population; degree of uncertainty in determination probability; patient's willingness to accept the probable risk of the harmful event, given the probable benefit); (vii) duration of harmful events (e.g., how long does the harmful event last and is it reversible; types of intervention required to address the harmful event); (viii) medical necessity (e.g., does the CYP3A4 substrate drug provide a benefit or address a need unmet by other therapies). In the context of a potential drug-drug interaction between a CYP3A4 inhibitor such as posaconazole and a CYP3A4 substrate drug (including those disclosed herein) appropriate dosing of the CYP3A4 substrate drug in the presence of a CYP3A4 inhibitor requires balancing the various risk and benefit factors (e.g., as described above). The appropriate dosing for a CYP3A4 substrate drug, resulting from an evaluation of the risk/benefit profile is conventionally incorporated into the FDA-approved drug label. To be clear, an elevation in PK (e.g., Cmax, AUC, or GMR of AUC or Cmax) is not the only factor that a person of skill in the art (e.g., a physician) would consider to be relevant in deciding whether to administer a CYP3A4 substrate drug. In some embodiments, the patient is administered the CYP3A4 substrate drug as soon as the benefit(s) outweigh the risk(s). In some embodiments, the patient is administered the full reference dose as soon as the benefit(s) outweigh the risk(s). In some embodiments, the patient is administered a reduced dose as soon as the benefit(s) outweigh the risk(s).

In some embodiments, the CYP3A4 substrate drug is administered as soon as least one or more of the Cmax, AUC, and GMR of AUC or Cmax of the CYP3A4 substrate drug, after such administration, would be at a safe level. In some embodiments, the safe levels are less than the coadministration Cmax, AUC, and/or GMR levels provided for CYP3A4 substrate drugs in Table A, e.g., about 5%, about 10%, about 15%, about 20%, about 25%, about 30%, about 25%, about 40%, about 45%, about 50%, about 55%, about 60%, about 65%, about 70%, about 75%, about 80%, about 85%, about 90%, or about 95% less than coadministration levels. In some embodiments, the CYP3A4 substrate drug is administered as soon as a time when one or more of the Cmax, AUC, average AUC, and GMR of AUC or Cmax of the CYP3A4 substrate drug is elevated to levels that would not have been predicted (e.g., higher than would have been predicted), and indeed would have been considered highly improbable, based on the prior art's understanding of the CYP3A4 inhibitor's (e.g., posaconazole's) impact on such levels for the CYP3A4 substrate drugs. In some embodiments, the CYP3A4 substrate drug can be safely administered as soon as the Cmax or AUC of the CYP3A4 substrate drug is about 3000%, about 2900%, about 2800%, about 2700%, about 2600%, about 2500%, about 2400%, about 2300%, about 2200%, about 2100%, about 2000%, about 1900%, about 1800%, about 1700%, about 1600%, about 1500, about 1400%, about 1300%, about 1200%, about 1100%, about 1000%, about 990%, about 980%, about 970%, about 960%, about 950%, about 940%, about 930%, about 920%, about 910%, about 900%, about 890%, about 880%, about 870%, about 860%, about 850%, about 840%, about 830%, about 820%, about 810%, about 800%, about 790%, about 780%, about 770%, about 760%, about 750%, about 740%, about 730%, about 720%, about 710%, about 700%, about 690%, about 680%, about 670%, about 660%, about 650%, about 640%, about 630%, about 620%, about 610%, about 600%, about 590%, about 580%, about 570%, about 560%, about 550%, about 540%, about 530%, about 520%, about 510%, about 500%, about 490%, about 480%, about 470%, about 460%, about 450%, about 440%, about 430%, about 420%, about 410%, about 400%, about 390%, about 380%, about 370%, about 360%, about 350%, about 340%, about 330%, about 320%, about 310%, about 300%, about 290%, about 280%, about 270%, about 260%, about 250%, about 240%, about 230%, about 220%, about 210%, about 200%, about 190%, about 180%, about 170%, about 160%, about 150%, about 140%, about 130%, about 120%, about 110%, and about 105% of the respective normal baseline values of such parameters (Table A) after stopping posaconazole (inclusive of all ranges in between). In some embodiments, the CYP3A4 substrate drug can be safely administered as soon as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days after stopping posaconazole, inclusive of ranges in between. In some embodiments, the CYP3A4 substrate drug can be safely administered as soon as the GMR of AUC or $C_{max}$ of the CYP3A4 substrate drug is about 30 fold, about 29 fold, about 28 fold, about 27 fold, about 26 fold, about 25 fold, about 24 fold, about 23 fold, about 22 fold, about 21 fold, about 20 fold, about 19 fold, about 18 fold, about 17 fold, about 16 fold, about 15 fold, about 14 fold, about 13 fold, about 12 fold, about 11 fold, about 10 fold, about 9.9 fold, about 9.8 fold, about 9.7 fold, about 9.6 fold, about 9.5 fold, about 9.4 fold, about 9.3 fold, about 9.2 fold, about 9.1 fold, about 9 fold, about 8.9 fold, about 8.8 fold, about 8.7 fold, about 8.6 fold, about 8.5 fold, about 8.4 fold, about 8.3 fold, about 8.2 fold, about 8.1 fold, about 8.0 fold, about 7.9 fold, about 7.8 fold, about 7.7 fold, about 7.6 fold, about 7.5 fold, about 7.4 fold, about 7.3 fold, about 7.2 fold, about 7.1 fold, about 7.0 fold, about 6.9 fold, about 6.8 fold, about 6.7 fold, about 6.6 fold, about 6.5 fold, about 6.4 fold, about 6.3 fold, about 6.2 fold, about 6.1 fold, about 6.0 fold, about 5.9 fold, about 5.8 fold, about 5.7 fold, about 5.6 fold, about 5.5 fold, about 5.4 fold, about 5.3 fold, about 5.2 fold, about 5.1 fold, about 5.0 fold, about 4.9 fold, about 4.8 fold, about 4.7 fold, about 4.6 fold, about 4.5 fold, about 4.4 fold, about 4.3 fold, about 4.2 fold, about 4.1 fold, about 4.0 fold, about 3.9 fold, about 3.8 fold, about 3.7 fold, about 3.6 fold, about 3.5 fold, about 3.4 fold, about 3.3 fold, about 3.2 fold, about 3.1 fold, about 3.0 fold, about 2.9 fold, about 2.8 fold, about 2.7 fold, about 2.6 fold, about 2.5 fold, about 2.4 fold, about 2.3 fold, about 2.2 fold, about 2.1 fold, about 2.0 fold, about 1.9 fold, about 1.8 fold, about 1.7 fold, about 1.6 fold, about 1.5 fold, about 1.4 fold, about 1.3 fold, about 1.2 fold, about 1.1 fold, and about 1.05 fold compared to the respective normal baseline values of such parameters, after stopping posaconazole (inclusive of all ranges in between). In some embodiments, the CYP3A4 substrate drug can be safely administered as soon as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days after stopping posaconazole, inclusive of all values and subranges therebetween. In some embodiments, the patient is administered the full reference dose of the CYP3A4 substrate drug to achieve any of the above $C_{max}$ or AUC values, or any of the above fold changes in GMR of $C_{max}$ or AUC. In some embodiments, after stopping posaconazole, the patient is administered a reduced dose of the CYP3A4 substrate drug to achieve any of the above $C_{max}$ or AUC values, or fold changes in GMR of $C_{max}$ or AUC.

Figure 8:
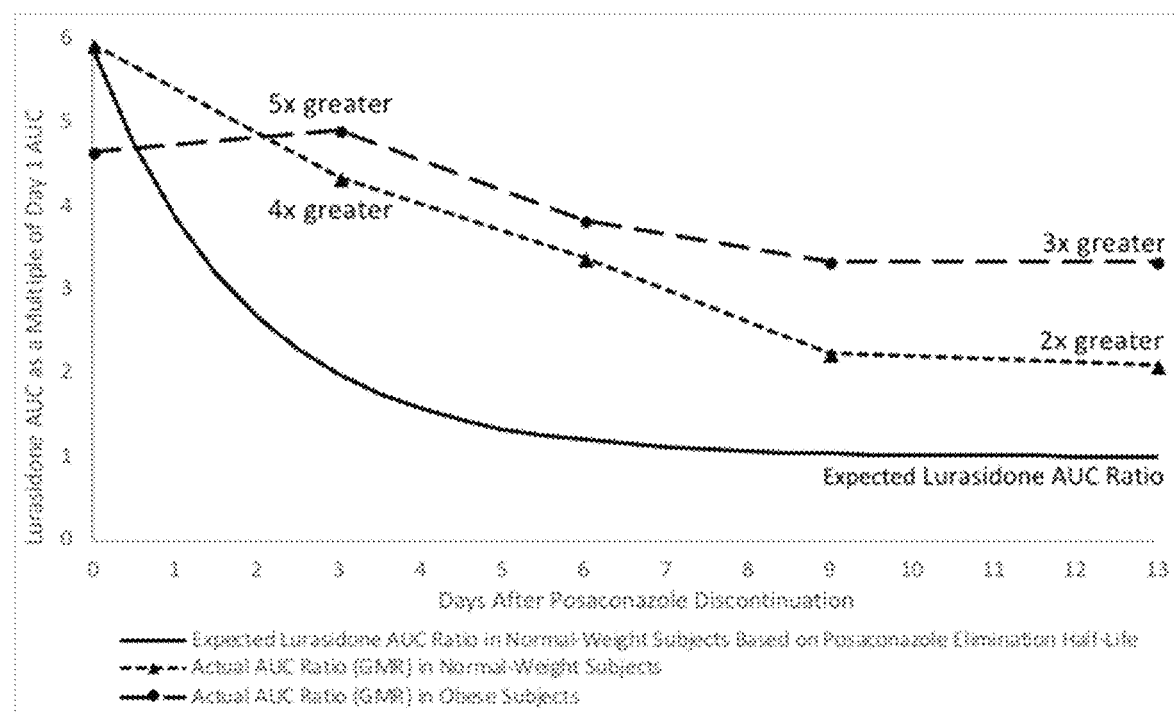
FIG. 8 shows actual lurasidone AUC ratios measured for normal-weight and obese subjects (dashed lines) compared to lurasidone AUC for the patients that would have been predicted from posaconazole half-life (expected lurasidone AUC ratios; solid line).

In some embodiments, the methods disclosed herein provide for administering a dose of CYP3A4 substrate to achieve one or more PK parameters (AUC, Cmax, and GMR of AUC or Cmax) that are above the respective values predicted for that dose of the CYP3A4 substrate drug, based on the conventionally understood posaconazole half-life of 27 hrs. (patients with normal hepatic function), 39 hrs. (patients with mild hepatic impairment), 27 hrs. (patients with moderate hepatic impairment), and 43 hrs. (patients with severe hepatic impairment), about 24 hours after dosing with posaconazole injection, about 31 hours after administration of posaconazole delayed-release tablets, and about 31-37 hours after administration of posaconazole oral suspension. Noxafil® label, revised September 2016. FIG. 8 depicts the actual lurasidone AUC levels (as a multiple of baseline AUC; dashed lines) resulting from administration of 100% of the reference dose in normal weight and obese patients at various times after stopping posaconazole as measured in Applicant's research compared to the lurasidone levels predicted from posaconazole's half-life as described in the Noxafil® label ("predicted levels"; solid line) using equation 1 and a posaconazole half-life of 31 hours. The solid line shows that predicted lurasidone AUC levels (reported as GMR) are about 400% (or about 4 fold) greater than baseline 1 day after stopping posaconazole, about 300% (or about 3 fold) greater than baseline 2 days after stopping posaconazole, about 200% (or about 2 fold) greater than baseline about 3 days after stopping posaconazole, and then tapering off to reach baseline around day 9 after stopping posaconazole. In contrast, Applicant's data shows that actual lurasidone AUC levels are significantly above predicted levels for at least 14 days after stopping posaconazole, e.g., about 2 fold greater than expected 2 days after stopping posaconazole; about 2-3 fold greater than expected 3 days after stopping posaconazole; about 2.5-3.5 fold greater than expected 4 days after stopping posaconazole, and remain about 2-3 fold above expected levels for at least about 14 days. The same studies were performed with ranolazine. Like FIG. 8, FIG. 9 depicts the actual ranolazine AUC levels (as a multiple of baseline AUC; dashed lines) for normal weight and obese patients resulting from administration of 100% of the reference dose at various times after stopping posaconazole as measured in Applicant's research, compared to the ranolazine levels predicted from posaconazole's half-life of 31 hours as described in the Noxafil® label ("predicted levels"; solid line). Applicant's data shows that the actual ranolazine AUC levels are significantly above predicted levels for at least 14 days after stopping posaconazole, e.g., about 0.5-1.5 fold greater than expected 2 days after stopping posaconazole; about 1.5 fold greater than expected 3 days after stopping posaconazole; about 1.5 fold greater than expected 4 days after stopping posaconazole, and remaining about 0.5-1.5 fold above expected levels for at least about 14 days. In some embodiments, the present methods administer a CYP3A4 substrate drug (e.g., lurasidone, ranolazine, or any other CYP3A4 substrate drug, such as those described herein) to achieve blood plasma levels above the expected levels measured for the reference dose.

In some embodiments, the present methods provide for administering lurasidone on a specified day after stopping posaconazole when at least one of the AUC, Cmax, and/or GMR of AUC or Cmax of lurasidone is above the predicted levels (e.g., the DDI decay curve calculated using equation 1 and the accepted half-life of posaconazole) on the specified day as depicted in FIG. 8. In some embodiments, lurasidone is administered when at least one of the AUC or Cmax of lurasidone are about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 210%, about 215%, about 216%, about 220%, about 225%, about 230%, about 235%, about 240%, about 245%, about 250%, about 255%, about 260%, about 265%, about 270%, about 275%, about 280%, about 285% about 290%, about 295%, about 300%, about 305%, about 310%, about 315%, about 320%, about 325%, about 330%, about 335%, about 340%, about 345%, about 350%, about 355%, about 360%, about 365%, about 370%, about 375%, about 380%, about 385%, about 390%, about 395%, or about 400% of baseline levels, inclusive of all values and ranges therebetween. In some embodiments, the CYP3A4 substrate drug is administered when at least one of the GMR of AUC or Cmax of lurasidone are increased by about 1.05 fold, about 1.1 fold, about 1.15 fold, about 1.2 fold, about 1.25 fold, about 1.3 fold, about 1.35 fold, about 1.4 fold, about 1.45 fold, about 1.50 fold, about 1.55 fold, about 1.60 fold, about 1.65 fold, about 1.7 fold, about 1.75 fold, about 1.8 fold, about 1.85 fold, about 1.9 fold, about 1.95 fold, about 2.0 fold, about 2.1 fold, about 2.15 fold, about 2.16 fold, about 2.2 fold, about 2.24 fold, about 2.25 fold, about 2.3 fold, about 2.35 fold, about 2.40 fold, about 2.45 fold, about 2.50 fold, about 2.55 fold, about 2.60 fold, about 2.65 fold, about 2.7 fold, about 2.75 fold, about 2.8 fold, about 2.85 fold, about 2.9 fold, about 2.95 fold, about 3.0 fold, about 3.05 fold, about 3.1 fold, about 3.15 fold, about 3.20 fold, about 3.25 fold, about 3.30 fold, about 3.35 fold, about 3.40 fold, about 3.45 fold, about 3.50 fold, about 3.55 fold, about 3.60 fold, about 3.65 fold, about 3.7 fold, about 3.75 fold, about 3.8 fold, about 3.85 fold, about 3.9 fold, about 3.95 fold, or about 4.0 fold, inclusive of all values and ranges therebetween. In some embodiments, lurasidone administration (e.g., 100% of the reference dose or a reduced dose) begins as soon as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days (inclusive of all values and subranges therebetween) after stopping posaconazole.

In some embodiments, the present methods provide for administering ranolazine on a specified day after stopping posaconazole when at least one of the AUC, Cmax, and/or GMR of AUC or Cmax of ranolazine is above the predicted levels (e.g., the DDI decay curve calculated using equation 1 and the accepted half-life of posaconazole) on the specified day as depicted in FIG. 9. In some embodiments, ranolazine is administered when at least one of the AUC or Cmax of ranolazine are about 105%, about 110%, about 115%, about 120%, about 125%, about 130%, about 135%, about 140%, about 145%, or about 150% of baseline levels, inclusive of all values and ranges therebetween. In some embodiments, ranolazine is administered when at least one of the GMR of AUC or Cmax of ranolazine are increased by about 1.05 fold, about 1.1 fold, about 1.15 fold, about 1.2 fold, about 1.25 fold, about 1.3 fold, about 1.35 fold, about 1.4 fold, about 1.45 fold, or about 1.50 fold. In some embodiments, ranolazine administration (e.g., 100% of the reference dose or a reduced dose) begins as soon as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days (inclusive of all values and subranges therebetween) after stopping posaconazole.

Applicant's observations from its clinical research with lurasidone and ranolazine indicates that dosing of other CYP3A4 substrate drugs should occur at least two days (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days) after stopping posaconazole. In some embodiments, Applicant discovered the CYP3A4 substrate drug can be administered after stopping posaconazole when one or more of the Cmax, AUC, and/or GMR of AUC or Cmax of the CYP3A4 substrate drug is elevated to levels that would not have been predicted (e.g., the DDI decay curve calculated using equation 1 and the accepted half-life of posaconazole), and indeed would have been considered highly improbable at a particular day after stopping posaconazole therapy. Because certain blood plasma levels may be unsafe, in some embodiments, the present methods provide for administering a CYP3A4 substrate drug when (e.g., as soon as) the at least one of the AUC, Cmax, or GMR of AUC or Cmax of the CYP3A4 substrate drug is at or below a maximum level, but above the predicted levels. In some embodiments, the maximum level is a blood plasma level of the CYP3A4 substrate drug when the benefits of treating the patient with the CYP3A4 substrate drug outweigh the risks. Above the maximum level, the risks of treatment outweigh the benefits. Non-limiting examples of maximum levels for various CYP3A4 substrate drugs are provided in Table A indicated as "target safe levels". In some embodiments, the CYP3A4 substrate drug is administered when at least one of the actual AUC or Cmax of the CYP3A4 substrate drug ranges from about 3000% to about 105% of the expected the AUC or Cmax, e.g., about 3000%, about 2900%, about 2800%, about 2700%, about 2600%, about 2500%, about 2400%, about 2300%, about 2200%, about 2100%, about 2000%, about 1900%, about 1800%, about 1700%, about 1600%, about 1500, about 1400%, about 1300%, about 1200%, about 1100%, about 1000%, about 950%, about 900%, about 850%, about 800%, about 750%, about 700%, about 650%, about 600%, about 550%, about 500%, about 450%, about 400%, about 350%, about 300%, about 250%, about 200%, about 195%, about 190%, about 185%, about 180%, about 175%, about 170%, about 165%, about 160%, about 155%, about 150%, about 145%, about 140%, about 135%, about 130%, about 125%, about 120%, about 115%, about 110%, and about 105%, and any ranges in between these values. In some embodiments, the CYP3A4 substrate drug is administered when at least one of the GMR of AUC or Cmax of the CYP3A4 substrate drug ranges from about 30 fold to about 1.05 fold of the baseline AUC or Cmax, e.g., about 30 fold, about 29 fold, about 28 fold, about 27 fold, about 26 fold, about 25 fold, about 24 fold, about 23 fold, about 22 fold, about 21 fold, about 20 fold, about 19 fold, about 18 fold, about 17 fold, about 16 fold, about 15 fold, about 14 fold, about 13 fold, about 12 fold, about 11 fold, about 10 fold, about 9.9 fold, about 9.8 fold, about 9.7 fold, about 9.6 fold, about 9.5 fold, about 9.4 fold, about 9.3 fold, about 9.2 fold, about 9.1 fold, about 9 fold, about 8.9 fold, about 8.8 fold, about 8.7 fold, about 8.6 fold, about 8.5 fold, about 8.4 fold, about 8.3 fold, about 8.2 fold, about 8.1 fold, about 8.0 fold, about 7.9 fold, about 7.8 fold, about 7.7 fold, about 7.6 fold, about 7.5 fold, about 7.4 fold, about 7.3 fold, about 7.2 fold, about 7.1 fold, about 7.0 fold, about 6.9 fold, about 6.8 fold, about 6.7 fold, about 6.6 fold, about 6.5 fold, about 6.4 fold, about 6.3 fold, about 6.2 fold, about 6.1 fold, about 6.0 fold, about 5.9 fold, about 5.8 fold, about 5.7 fold, about 5.6 fold, about 5.5 fold, about 5.4 fold, about 5.3 fold, about 5.2 fold, about 5.1 fold, about 5.0 fold, about 4.9 fold, about 4.8 fold, about 4.7 fold, about 4.6 fold, about 4.5 fold, about 4.4 fold, about 4.3 fold, about 4.2 fold, about 4.1 fold, about 4.0 fold, about 3.9 fold, about 3.8 fold, about 3.7 fold, about 3.6 fold, about 3.5 fold, about 3.4 fold, about 3.3 fold, about 3.2 fold, about 3.1 fold, about 3.0 fold, about 2.9 fold, about 2.8 fold, about 2.7 fold, about 2.6 fold, about 2.5 fold, about 2.4 fold, about 2.3 fold, about 2.2 fold, about 2.1 fold, about 2.0 fold, about 1.9 fold, about 1.8 fold, about 1.7 fold, about 1.6 fold, about 1.5 fold, about 1.4 fold, about 1.3 fold, about 1.2 fold, about 1.1 fold, and about 1.05 fold compared to the respective normal baseline values of such parameters, after stopping posaconazole (inclusive of all ranges in between). In some embodiments, administration begins 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days (inclusive of all values and subranges therebetween) after stopping posaconazole. For example, in some embodiments, lurasidone is administered such that the AUC is between about 400% and 105%, between about 300% and about 105%, or between about 216% and 105% of the normal baseline, and this could occur on 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days after stopping posaconazole. As another example, some embodiments administer ranolazine to provide an AUC between about 150% and 105% of the normal baseline, and this could occur on 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days after stopping posaconazole.

In some embodiments, the present methods require that the CYP3A4 substrate drug is not dosed when blood plasma levels of the substrate drug (i.e., at least one of AUC, Cmax, or GMR of AUC or Cmax) would otherwise exceed a specified maximum level (e.g., by about 25%) if said substrate drug were administered. That is, in some embodiments, the maximum level determines when to administer the CYP3A4 substrate drug—the CYP3A4 substrate drug is administered only when at least one of an AUC, Cmax, or GMR of AUC or Cmax would be at or below the maximum level. In some embodiments, the maximum level is less than at least one of the AUC, Cmax, or GMR of AUC or Cmax of the CYP3A4 substrate drug that would occur if said substrate drug was coadministered with posaconazole (See AUC and Cmax co-administration levels in Table A). In some embodiments, the maximum level is a blood plasma level at which the benefits of treating the patient with the CYP3A4 substrate drug outweigh the risks. In some embodiments, the maximum level is a target safe level provided in Table A. When administering the CYP3A4 substrate drug would cause at least one of the AUC, Cmax, or GMR of AUC or Cmax levels to exceed the target safe level, administration is delayed until at least one of the AUC, Cmax, or GMR of AUC or Cmax levels are at or below the target safe level.

In some embodiments, the maximum level is related to the incidence of an adverse event. In some embodiments, the incidence rate of the adverse event which establishes the maximum level is at least about 2%, at least about 5%, at least about 10%, at least about 15%, at least about 20%, at least about 25%, at least about 30%, at least about 35%, at least about 40%, at least about 45%, at least about 50% in a population of patients receiving the same treatments. In some embodiments, the determination of whether to dose the CYP3A4 substrate drug is based on a risk/benefit analysis (e.g., as discussed above).

Using lurasidone as an example, an increase of about 300% in the AUC of lurasidone (about 3 fold increase in GMR) is associated with somnolence, whereas an increase of 400% in AUC (or about 4 fold increase in GMR) is associated with akathisia. Because of the benefit of treating a patient, in some embodiments, lurasidone is administered when the AUC is increased by up to about 300% (about a 3 fold increase in GMR), but not when the AUC would be increased by about 400% (about a 4 fold increase in GMR). In some embodiments, the maximum level for lurasidone is a 216% increase in baseline AUC. In some embodiments, e.g., when the patient's need for treatment outweighs the risks, the maximum level may be about 500% increase in baseline AUC. In other embodiments, the maximum level may be any value in the range of less than 500% to 216% increase in baseline AUC, including any ranges in between those values. Accordingly, in some embodiments, the maximum level for lurasidone is 400%, about 300%, or about 216% of the normal baseline level of AUC. Thus, in some embodiments, lurasidone is administered as soon as the AUC is less than or equal to about 400%, about 350%, about 300%, about 275%, about 250%, about 225%, about 216%, about 215%, about 210%, about 205%, about 200%, about 195%, about 190%, about 185%, about 180%, about 175%, about 170%, about 165%, about 160%, about 155%, about 150%, about 145%, about 140%, about 135%, about 130%, about 125%, about 120%, about 115%, about 110%, about 105%, inclusive of all values and ranges therebetween, and this may occur on 2, 3, 4, 5, 6, 7, 8, 9, 10, 11, 12, 13, 14, 15, 16, 17, 18, 19, 20, 21, 22, 23, 24, 25, 26, 27, 28, 29, and 30 days after stopping posaconazole.

In some embodiments, the CYP3A4 substrate drug is not dosed when at least one of the AUC or Cmax would be greater than about 3000% of a normal baseline AUC (as defined above) of the CYP3A4 substrate drug, e.g., greater than about 2900%, greater than about 2800%, greater than about 2700%, greater than about 2600%, greater than about 2500%, greater than about 2400%, greater than about 2300%, greater than about 2200%, greater than about 2100%, greater than about 2000%, greater than about 1900%, greater than about 1800%, greater than about 1700%, greater than about 1600%, greater than about 1500%, greater than about 1400%, greater than about 1300%, greater than about 1200%, greater than about 1100%, greater than about 1000%, greater than about 950%, greater than about 900%, greater than about 850%, greater than about 800%, greater than about 750%, greater than about 700%, greater than about 650%, greater than about 600%, greater than about 550%, greater than about 500%, greater than about 450%, greater than about 400%, greater than about 350%, greater than about 300%, greater than about 250%, greater than about 200%, greater than about 190%, greater than about 180%, about 170%, greater than about 160%, greater than about 150%, greater than about 145%, greater than about 140%, greater than about 135%, greater than about 130%, greater than about 125%, greater than about 120%, greater than about 115%, or greater than about 110%, inclusive of all values and subranges therebetween. In some embodiments, the CYP3A4 substrate drug is not dosed when at least one of the GMR of AUC or $C_{max}$ would be greater than about 30 fold of a normal baseline AUC (as defined above) of the CYP3A4 substrate drug, e.g., greater than about 30 fold, greater than about 29 fold, greater than about 28 fold, greater than about 27 fold, greater than about 26 fold, greater than about 25 fold, greater than about 24 fold, greater than about 23 fold, greater than about 22 fold, greater than about 21 fold, greater than about 20 fold, greater than about 19 fold, greater than about 18 fold, greater than about 17 fold, greater than about 16 fold, greater than about 15 fold, greater than about 14 fold, greater than about 13 fold, greater than about 12 fold, greater than about 11 fold, greater than about 10 fold, greater than about 9.5 fold, greater than about 9 fold, greater than about 8.5 fold, greater than about 8.0 fold, greater than about 7.5 fold, greater than about 7.0 fold, greater than about 6.5 fold, greater than about 6.0 fold, greater than 5.5 fold, greater than about 5.0 fold, greater than about 4.5 fold, greater than about 4.0 fold, greater than about 3.5 fold, greater than about 3.0 fold, greater than about 2.5 fold, greater than about 2.0 fold, greater than about 1.9 fold, greater than about 1.8 fold, greater than about 1.7 fold, greater than about 1.6 fold, greater than about 1.5 fold, greater than about 1.4 fold, greater than about 1.3 fold, greater than about 1.2 fold, or greater than about 1.1 fold, inclusive of all values and subranges therebetween.

As discussed herein, Applicant discovered that the inhibitory effects of posaconazole on CYP3A4 last substantially longer than would have been predicted from its half-life. Accordingly, in some embodiments, the present methods provide for administering the CYP3A4 substrate drug as soon as sufficient posaconazole has been eliminated from the patient, such that the drug-drug interaction between posaconazole and the CYP3A4 substrate drug (e.g., clinically relevant adverse events associated with elevated levels of the CYP3A4 substrate drug) does not pose an unacceptable risk to the patient. As described in Examples 2 and 3, the elimination half-life of posaconazole is different in normal weight and obese patients, and therefore the delay period required to safely dose the CYP3A4 substrate drug after stopping posaconazole may be different in these patient populations. Specifically, Applicant measured the elimination half-life of posaconazole for normal weight patients at 33.6 hours, whereas the elimination half-life of posaconazole in obese patient was measured to be 58.3 hours. Table B shows the mean steady-state concentration of posaconazole measured for normal and obese patients measured in two separate clinical studies performed by Applicant (BOW-001 and BOW-002). The two clinical studies used the same protocol to measure posaconazole's elimination half-life, allowing for the data for normal patients from each study to be combined ("All Normal") and data for obese patients from each study to be combined ("All Obese").

TABLE B

Pooled Posaconazole Elimination Half-Life Data.

| | Css (ng/mL) | | t½ (h) | |
|---|---|---|---|---|
| | Mean | SD | Mean | SD |
| BOW-001 Normal | 3071 | 1422 | 35.7 | 11 |
| BOW-002 Normal | 2514 | 1435 | 30.9 | 7 |
| BOW-001 Obese | 2258 | 952 | 64.5 | 53 |
| BOW-002 Obese | 1462 | 649 | 52.5 | 31 |
| All Normal | 2864 | 1400 | 33.6 | 9 |
| All Obese | 1860 | 896 | 58.3 | 42 |

In some embodiments, the CYP3A4 substrate drug is dosed after at least about 2 half-lives of posaconazole have elapsed, e.g., about 2 half-lives, about 3 half-lives, about 4 half-lives, about 5 half-lives, about 6 half-lives, about 7 half-lives, about 8 half-lives, about 9 half-lives, about 10 half-lives, about 11 half-lives, about 12 half-lives, about 13 half-lives, about 14 half-lives, about 15 half-lives, about 16 half-lives, about 17 half-lives, about 18 half-lives, about 19 half-lives, about 20 half-lives, about 21 half-lives, about 22 half-lives, about 23 half-lives, about 24 half-lives, about 25 half-lives, about 26 half-lives, about 27 half-lives, about 28 half-lives, about 29 half-lives, or about 30 half-lives or more, inclusive of all values and subranges therebetween.

In some embodiments, the timing of administration of the CYP3A4 substrate drug is based on posaconazole levels as measured by applicant. In some embodiments, the CYP3A4 substrate drug is administered when posaconazole levels are reduced by at least about 50% of the steady state levels, e.g., reduced by about 55%, about 60%, about 65%, about 70%, about 75%, about 80%, about 85%, about 87.5%, about 90%, about 93.75%, about 95%, about 96.875%, about 98.4375%, or about 99%, inclusive of all values and subranges therebetween. In some embodiments, the CYP3A4 substrate drug is administered as soon as posaconazole levels about 50% of the steady state levels, e.g., about 45%, about 40%, about 35%, about 30%, about 25%, about 20%, about 15%, about 12.5%, about 10%, about 6.25%, about 5%, about 3.125%, about 1.5625%, or about 1% of the steady state levels, inclusive of all values and subranges therebetween.

In some embodiments, the CYP3A4 substrate drug is administered as soon as two conditions are met: (i) posaconazole levels are reduced by at least about 50% of the steady state levels (e.g., reduced by about 55%, about 60%, about 65%, about 70%, about 75%, about 80%, about 85%, about 87.5%, about 90%, about 93.75%, about 95%, about 96.875%, about 98.4375%, or about 99%, inclusive of all values and subranges therebetween); and (ii) the blood plasma levels of the CYP3A4 substrate drug are at or below a target level that is considered safe but above the expected levels for the CYP3A4 substrate drug. Expected levels of the CYP3A4 substrate drug may be calculated using equation 1. In some embodiments, the target level that is considered safe is the "target safe level" disclosed in Table A for the CYP3A4 substrate drug.

In some embodiments, the methods provide for administering a reduced dose (relative to the reference dose, as defined herein) of the CYP3A4 substrate drug to the patient. The reduced dose may be administered concurrently with posaconazole, the day after stopping posaconazole, or after any delay period described herein (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days after stopping posaconazole). In some embodiments, the reduced dose is administered for about 7 to about 42 days, e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 days, inclusive of all values and subranges therebetween. In some embodiments, the methods provide for selecting a reduced reference dose at that results in a maximum AUC that ranges from about 500% to about 100% (e.g., about 500%, about 475%, about 450%, about 425%, about 400%, about 375%, about 350%, about 325%, about 300%, about 275%, about 250%, about 225%, about 200%, about 175%, about 150%, about 125%, and about 100%, inclusive of all values and subranges therebetween) of the normal baseline AUC of the reference dose; and then, on the day that the reduced reference dose would provide an AUC that is less than 100% of the normal baseline, the patient is administered the reference dose. In some embodiments, the patient is administered the reference dose prior to the day that the reduced dose would provide an AUC that is less than 100% of the normal baseline, provided that when the reference dose is administered, the AUC would not exceed safe levels as described herein. In some embodiments, the AUC, Cmax, GMR AUC or GMR Cmax provided by administering a reduced dose of the CYP3A4 substrate drug is between the baseline value and a target safe value listed in Table A for the CYP3A4 substrate drug.

For example, in some embodiments, the methods of the present disclosure provide for administering a reduced reference dose of lurasidone at that provides a maximum GMR that is between about 4.34 and 1 of the patient's normal baseline; and then, on the day that the reduced reference dose would provide a GMR that is less than or equal to 1, the patient is administered the reference dose of lurasidone. In some embodiments, the reference dose of lurasidone may be about 120 mg. In some embodiments, the patient stops taking lurasidone while being treated with posaconazole; then the patient stops treatment with posaconazole and begins administering a reduced dose of lurasidone (e.g., about 60-80 mg) on any of days 1-3 after stopping posaconazole and for about 21-28 days; on a day ranging from about 21-28 days after stopping posaconazole, the patient begins administering the 120 mg reference dose of lurasidone. Alternatively, in some embodiments the patient may be administered 60 mg of lurasidone until about 9 days to about 12 days after stopping posaconazole, and then patient begins administering 120 mg reference dose.

In some embodiments, a reduced dose of the CYP3A4 substrate drug is administered as soon as posaconazole levels about 50% of the steady state levels, e.g., about 45%, about 40%, about 35%, about 30%, about 25%, about 20%, about 15%, about 12.5%, about 10%, about 6.25%, about 5%, about 3.125%, about 1.5625%, or about 1% of the steady state levels, inclusive of all values and subranges therebetween.

In some embodiments, a reduced dose of the CYP3A4 substrate drug is administered as soon as two conditions are met: (i) posaconazole levels are reduced by at least about 50% of the steady state levels (e.g., reduced by about 55%, about 60%, about 65%, about 70%, about 75%, about 80%, about 85%, about 87.5%, about 90%, about 93.75%, about 95%, about 96.875%, about 98.4375%, or about 99%, inclusive of all values and subranges therebetween); and (ii) the blood plasma levels of the CYP3A4 substrate drug are at or below a target level that is considered safe but above the expected levels for the CYP3A4 substrate drug. Expected levels of the CYP3A4 substrate drug may be calculated using equation 1. In some embodiments, the target level that is considered safe is the "target safe level" disclosed in Table A for the CYP3A4 substrate drug.

In some embodiments, the CYP3A4 substrate drug is ranolazine. In some embodiments, ranolazine is indicated for chronic angina. In some embodiments, the reference dose to treat chronic angina ranges from 500-1000 mg. In some embodiments, the reference dose is adminstered twice daily. In embodiments in which the CYP3A4 substrate drug is ranolazine, the daily dose of ranolazine is no more than about 500 mg, e.g., about 490 mg, about 480 mg, about 470 mg, about 460 mg, about 450 mg, about 440 mg, about 430 mg, about 420 mg, about 410 mg, about 400 mg, about 390 mg, about 380 mg, about 370 mg, 360 mg, about 350 mg, about 340 mg, about 330 mg, about 320 mg, about 310 mg, about 300 mg, about 290 mg, about 280 mg, about 270 mg, 260 mg, about 250 mg, about 240 mg, about 230 mg, about 220 mg, about 210 mg, about 100 mg, about 190 mg, about 180 mg, about 170 mg, 160 mg, about 150 mg, about 140 mg, about 130 mg, about 120 mg, about 110 mg, about 100 mg, about 90 mg, about 80 mg, about 70 mg, about 60 mg, or about 50 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments, the CYP3A4 substrate drug is lurasidone. In some embodiments, lurasidone is indicated for the treatment of schizophrenia in adults and adolescents (13 to 17 years), depressive episodes associated with Bipolar I Disorder (bipolar depression) in adults, monotherapy or adjunctive therapy with lithium or valproate, moderate bipolar depression, severe bipolar depression, severe bipolar depression with acute suicidal ideation and behavior (ASIB). In some embodiments, reference dose for treating schizophrenia in adults ranges from 40-160 mg per day (e.g., 40, 60, 80, 100, 120, 140, 160, or 180 mg). In some, the reference dose for treating schizophrenia in adolescents (13-17 years) ranges from 48-80 mg (e.g., 40, 60, or 80 mg). In some embodiments, the reference dose for treating bipolar depression in adults ranges from 20-120 mg (e.g., 20, 40, 60, 80, 100, or 120 mg). In some embodiments, the reference dose for treating bipolar depression in pediatric patients (10-17 years) ranges from 20-80 mg (e.g., 20, 40, 60, or 80 mg). In embodiments in which the CYP3A4 substrate drug is lurasidone, the daily dose of lurasidone is no more than about 80 mg, e.g., about 75, about 70 mg, about 65 mg, about 60 mg, about 55 mg, about 50 mg, about 45 mg, about 40 mg, about 35 mg, about 30 mg, about 25 mg, about 20 mg, about 15 mg, or about 10 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is tadalafil, the daily dose of tadalafil is no more than about 2.5 mg, e.g., about 2.25 mg, about 2.0 mg, about 1.75 mg, about 1.5 mg, about 1.25 mg, about 1.0 mg, about 0.75 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In other embodiments in which the CYP3A4 substrate drug is tadalafil, the 72 hr dose of tadalafil is no more than about 10 mg, e.g., about 9.5 mg, about 9.0 mg, about 8.5 mg, about 8.0 mg, about 7.5 mg, about 7.0 mg, about 6.5 mg, about 6.0 mg, about 5.5 mg, about 5.0 mg, about 4.5 mg, about 4.0 mg, about 3.5 mg, about 3.0 mg, about 2.5 mg, about 2.0 mg, about 1.5 mg, about 1.0 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In some embodiments, the CYP3A4 substrate drug is erlotinib. In some embodiments, the reference dose for treating non-small cell lung cancer (NSCLC) is 150 mg per day. In some embodiments, the reference dose for treating pancreatic cancer is 100 mg per day. In embodiments in which the CYP3A4 substrate drug is erlotinib, the daily dose of erlotinib is no more than about 150 mg, e.g., about 140 mg, about 130 mg, about 120 mg, about 110 mg, about 100 mg, about 90 mg, about 80 mg, about 70 mg, about 60 mg, about 50 mg, about 40 mg, about 30 mg, about 20 mg, or about 10 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is solifenacin succinate, the daily dose of solifenacin succinate is no more than about 10 mg, e.g., about 9 mg, about 8 mg, about 7 mg, about 6 mg, about 5 mg, about 4 mg, about 3 mg, about 2 mg, about 1 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is everolimus, the daily dose of everolimus is no more than about 10 mg, e.g., about 9 mg, about 8 mg, about 7 mg, about 6 mg, about 5 mg, about 4 mg, about 3 mg, about 2 mg, about 1.75 mg, about 1.5 mg, about 1.25 mg, about 1.0 mg, about 0.75 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is abemaciclib, the daily dose of abemaciclib is no more than about 400 mg, e.g., about 350 mg, about 300 mg, about 250 mg, about 225 mg, about 200 mg, about 175 mg, about 150 mg, about 125 mg, about 100 mg, about 75 mg, about 50 mg, about 25 mg, about 10 mg, about 5 mg, about 1.0 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is ivacaftor, the daily dose of ivacaftor is no more than about 300 mg, e.g., about 250 mg, about 225 mg, about 200 mg, about 175 mg, about 150 mg, about 125 mg, about 100 mg, about 75 mg, about 50 mg, about 25 mg, about 10 mg, about 5 mg, about 1.0 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is ruxolitinib, or a pharmaceutically acceptable salt thereof (e.g., ruxolitinib phosphate), the daily dose of ruxolitinib phosphate is no more than about 50 mg, e.g., about 48 mg, about 45 mg, about 40 mg, about 35 mg, about 30 mg, about 25 mg, about 20 mg, about 15 mg, about 10 mg, about 5 mg, about 1.0 mg, about 0.75 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is brexpiprazole, the daily dose of brexpiprazole is no more than about 4 mg, e.g., about 3 mg, about 2 mg, about 1.75 mg, about 1.5 mg, about 1.25 mg, about 1.0 mg, about 0.75 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is ivacaftor/tezacaftor, the daily dose of tezacaftor is no more than about 100 mg, e.g., about 90 mg, about 80 mg, about 70 mg, about 60 mg, about 50 mg, about 40 mg, about 30 mg, about 20 mg, about 17.5 mg, about 15 mg, about 12.5 mg, about 10 mg, about 7.5 mg, or about 5 mg, inclusive of all values and ranges therebetween, and the daily dose of ivacaftor is no more than about 300 mg, e.g., about 290 mg, about 280 mg, about 270 mg, about 260 mg, about 250 mg, about 240 mg, about 230 mg, about 220 mg, about 175 mg, about 150 mg, about 125 mg, about 100 mg, about 75 mg, or about 50 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is regorafenib, the daily dose of regorafenib is no more than about 160 mg, e.g., about 150 mg, about 140 mg, about 130 mg, about 120 mg, about 110 mg, about 100 mg, about 90 mg, about 80 mg, about 70 mg, about 60 mg, about 50 mg, about 25 mg, about 10 mg, or about 5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is daclatasvir, the daily dose of daclatasvir is no more than about 90 mg, e.g., about 80 mg, about 70 mg, about 60 mg, about 50 mg, about 40 mg, about 30 mg, about 20 mg, about 17.5 mg, about 15 mg, about 12.5 mg, about 10 mg, about 7.5 mg, or about 5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is crizotinib, the daily dose of crizotinib is no more than about 500 mg, e.g., about 450 mg, about 400 mg, about 350 mg, about 300 mg, about 250 mg, about 225 mg, about 200 mg, about 175 mg, about 150 mg, about 125 mg, about 100 mg, about 75 mg, about 50 mg, about 25 mg, about 10 mg, about 5 mg, about 1.0 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is naloxegol or a pharmaceutically acceptable salt thereof (e.g., naloxegol oxalate), the daily dose of naloxegol oxalate is no more than about 25 mg, e.g., about 22 mg, about 20 mg, about 18 mg, about 16 mg, about 15 mg, about 14 mg, about 13 mg, about 12 mg, about 10 mg, about 8 mg, about 5 mg, about 1 mg, about 0.75 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is dabrafenib, the daily dose of dabrafenib is no more than about 300 mg, e.g., about 250 mg, about 225 mg, about 200 mg, about 175 mg, about 150 mg, about 125 mg, about 100 mg, about 75 mg, about 50 mg, about 25 mg, about 10 mg, about 5 mg, about 1.0 mg, or about 0.5 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In embodiments in which the CYP3A4 substrate drug is elbasvir and grazoprevir, the daily dose of elbasvir is no more than about 1000 mg, e.g., about 900 mg, about 800 mg, about 700 mg, about 600 mg, about 500 mg, about 400 mg, about 300 mg, about 200 mg, about 175 mg, about 150 mg, about 125 mg, about 100 mg, about 75 mg, about 50 mg, or about 25 mg, inclusive of all values and ranges therebetween, and the daily dose of grazoprevir is no more than about 2000 mg, e.g., about 1500 mg, about 1250 mg, about 1000 mg, about 900 mg, about 800 mg, about 700 mg, about 600 mg, about 500 mg, about 400 mg, about 300 mg, about 200 mg, about 150 mg, about 100 mg, about 75 mg, or about 50 mg, inclusive of all values and ranges therebetween, and treatment is delayed for at least about 2-42 days after discontinuation of the posaconazole regimen, or reduced for the time period of about 2-42 days after discontinuation of the posaconazole regimen.

In addition to the preceding embodiments, the following embodiments further illustrate methods of administering certain CYP3A4 substrate drugs of the present disclosure.

In some embodiments, the CYP3A4 substrate drug is abemaciclib. The disease or condition treated with abemaciclib can include any disease or condition described herein or for which abemaciclib is indicated. For example, in some embodiments, abemaciclib is indicated in combination with an aromatase inhibitor as initial endocrine-based therapy for the treatment of postmenopausal women with hormone receptor (HR)-positive, human epidermal growth factor receptor 2 (HER2)-negative advanced or metastatic breast cancer. In some embodiments, abemaciclib is indicated in combination with fulvestrant for the treatment of women with hormone receptor (HR)-positive, human epidermal growth factor receptor 2 (HER2)-negative advanced or metastatic breast cancer with disease progression following endocrine therapy. In some embodiments, abemaciclib is indicated as monotherapy for the treatment of adult patients with HR-positive, HER2-negative advanced or metastatic breast cancer with disease progression following endocrine therapy and prior chemotherapy in the metastatic setting. Abemaciclib may be administered in a 50 mg, 100 mg, 150 mg, or 200 mg dosage form. In some embodiments, abemaciclib is administered twice daily up to a total daily dose of 400 mg. For example, when abemaciclib is indicated in combination with an aromatase inhibitor as initial endocrine-based therapy for the treatment of postmenopausal women with hormone receptor (HR)-positive, human epidermal growth factor receptor 2 (HER2)-negative advanced or metastatic breast cancer, the reference dose is 150 mg, administered twice daily (total daily reference dose is 300 mg). When abemaciclib is indicated in combination with fulvestrant for the treatment of women with hormone receptor (HR)-positive, human epidermal growth factor receptor 2 (HER2)-negative advanced or metastatic breast cancer with disease progression following endocrine therapy, the reference dose is 150 mg, administered twice daily (total daily reference dose is 300 mg). When abemaciclib is indicated as monotherapy for the treatment of adult patients with HR-positive, HER2-negative advanced or metastatic breast cancer with disease progression following endocrine therapy and prior chemotherapy in the metastatic setting, the reference dose is 200 mg, administered twice daily (total daily reference dose is 400 mg). Thus, in various embodiments, the total daily reference dose of abemaciclib may be, for example, 25 mg, 50 mg, 100 mg, 150 mg, 200 mg, 250 mg, 300 mg, 350 mg, or 400 mg. In accordance with certain embodiments of the present disclosure, when the total daily reference dose of abemaciclib is, for example, 400 mg, the patient will take a reduced total daily dose of abemaciclib (either concomitantly with posaconazole or after a delay period after stopping posaconazole). In some embodiments, the reduced total daily dose of abemaciclib is, for example, 25 mg, 50 mg, 75 mg, 100 mg, 125 mg, 150 mg, 175 mg, 200 mg, 225 mg, 250 mg, 275 mg, 300 mg, 325 mg, or 350 mg, including all integers and ranges therebetween. When the total daily reference dose of abemaciclib is 400 mg, the reduced total daily dose of abemaciclib is, for example, 25 mg, 50 mg, 75 mg, 100 mg, 125 mg, 150 mg, 175 mg, 200 mg, 225 mg, 250 mg, 275 mg, 300 mg, 325 mg, 350 mg, or 375 mg including all integers and ranges therebetween. When the total daily reference dose of abemaciclib is 350 mg, the reduced total daily dose of abemaciclib is, for example, 25 mg, 50 mg, 75 mg, 100 mg, 125 mg, 150 mg, 175 mg, 200 mg, 225 mg, 250 mg, 275 mg, 300 mg, or 325 mg including all integers and ranges therebetween. When the total daily reference dose of abemaciclib is 300 mg, the reduced total daily dose of abemaciclib is, for example, 25 mg, 50 mg, 75 mg, 100 mg, 125 mg, 150 mg, 175 mg, 200 mg, 225 mg, 250 mg, or 275 mg, including all integers and ranges therebetween. When the total daily reference dose of abemaciclib is 250 mg, the reduced total daily dose of abemaciclib is, for example, 25 mg, 50 mg, 75 mg, 100 mg, 125 mg, 150 mg, 175 mg, 200 mg, or 225 mg, including all integers and ranges therebetween. When the total daily reference dose of abemaciclib is 200 mg, the reduced total daily dose of abemaciclib is, for example, 25 mg, 50 mg, 75 mg, 100 mg, 125 mg, 150 mg, or 175 mg, including all integers and ranges therebetween. When the total daily reference dose of abemaciclib is 150 mg, the reduced total daily dose of abemaciclib is, for example, 25 mg, 50 mg, 75 mg, 100 mg, or 125 mg, including all integers and ranges therebetween. When the total daily reference dose of abemaciclib is 100 mg, the reduced total daily dose of abemaciclib is, for example, 25 mg, 50 mg or 75 mg, including all integers and ranges therebetween. Correspondingly, when the individual reference dose of abemaciclib is 200 mg, the reduced individual reference dose of abemaciclib is, for example, 25 mg, 50 mg, 75 mg, 100 mg, 125 mg, 150 mg, or 175 mg, including all integers and ranges therebetween. When the individual reference dose of abemaciclib is 150 mg, the reduced individual reference dose of abemaciclib is, for example, 25 mg, 50 mg, 75 mg, 100 mg, or 125 mg, including all integers and ranges therebetween.

In some embodiments, the CYP3A4 substrate drug is ado-trastuzumab emtansine. The disease or condition treated with ado-trastuzumab emtansine can include any disease or condition described herein or for which ado-trastuzumab emtansine is indicated. For example, in some embodiments, ado-trastuzumab emtansine is indicated as a single agent, for the treatment of patients with HER2-positive, metastatic breast cancer who previously received trastuzumab and a taxane, separately or in combination and the patients should have either received prior therapy for metastatic disease or developed disease recurrence during or within six months of completing adjuvant therapy. Ado-trastuzumab emtansine may be administered in via intravenous infusion in a 2.4 mg/kg, 3 mg/kg, or 3.6 mg/kg dosage form. In some embodiments, ado-trastuzumab emtansine is administered once every three weeks up to a total dose of 3.6 mg/kg every three weeks. For example, when ado-trastuzumab emtansine is indicated as a single agent, for the treatment of patients with HER2-positive, metastatic breast cancer who previously received trastuzumab and a taxane, separately or in combination and the patients should have either received prior therapy for metastatic disease or developed disease recurrence during or within six months of completing adjuvant therapy, the reference dose is 3.6 mg/kg every three weeks (total reference dose is 3.6 mg/kg every three weeks). Thus, in various embodiments, the total daily reference dose of ado-trastuzumab emtansine may be, for example, 0.3 mg/kg every three weeks, 0.6 mg/kg every three weeks, 0.9 mg/kg every three weeks, 1.2 mg/kg every three weeks, 1.5 mg/kg every three weeks, 1.8 mg/kg every three weeks, 2.1 mg/kg every three weeks, 2.4 mg/kg every three weeks, 2.7 mg/kg every three weeks, 3.0 mg/kg every three weeks, 3.3 mg/kg every three weeks, or 3.6 mg/kg every three weeks. In accordance with certain embodiments of the present disclosure, when the total daily reference dose of ado-trastuzumab emtansine is, for example, 3.6 mg/kg every three weeks, the patient will take a reduced total daily dose of ado-trastuzumab emtansine (either concomitantly with posaconazole or after a delay period after stopping posaconazole). In some embodiments, the reduced total daily dose of ado-trastuzumab emtansine is, for example, 0.3 mg/kg every three weeks, 0.6 mg/kg every three weeks, 0.9 mg/kg every three weeks, 1.2 mg/kg every three weeks, 1.5 mg/kg every three weeks, 1.8 mg/kg every three weeks, 2.1 mg/kg every three weeks, 2.4 mg/kg every three weeks, 2.7 mg/kg every three weeks, 3.0 mg/kg every three weeks, 3.3 mg/kg every three weeks, including all integers and ranges therebetween. When the total daily reference dose of ado-trastuzumab emtansine is 3.6 mg/kg every three weeks, the reduced total daily dose of ado-trastuzumab emtansine is, for example, 0.3 mg/kg every three weeks, 0.6 mg/kg every three weeks, 0.9 mg/kg every three weeks, 1.2 mg/kg every three weeks, 1.5 mg/kg every three weeks, 1.8 mg/kg every three weeks, 2.1 mg/kg every three weeks, 2.4 mg/kg every three weeks, 2.7 mg/kg every three weeks, 3.0 mg/kg every three weeks, 3.3 mg/kg every three weeks, including all integers and ranges therebetween. When the total daily reference dose of ado-trastuzumab emtansine is 3.0 mg/kg every three weeks, the reduced total daily dose of ado-trastuzumab emtansine is, for example, 0.3 mg/kg every three weeks, 0.6 mg/kg every three weeks, 0.9 mg/kg every three weeks, 1.2 mg/kg every three weeks, 1.5 mg/kg every three weeks, 1.8 mg/kg every three weeks, 2.1 mg/kg every three weeks, or 2.7 mg/kg every three weeks, including all integers and ranges therebetween. When the total daily reference dose of ado-trastuzumab emtansine is 2.4 mg/kg every three weeks, the reduced total daily dose of ado-trastuzumab emtansine is, for example, 0.3 mg/kg every three weeks, 0.6 mg/kg every three weeks, 0.9 mg/kg every three weeks, 1.2 mg/kg every three weeks, 1.5 mg/kg every three weeks, 1.8 mg/kg every three weeks, or 2.1 mg/kg every three weeks, including all integers and ranges therebetween.

In some embodiments, the CYP3A4 substrate drug is apalutamide. The disease or condition treated with apalutamide can include any disease or condition described herein or for which apalutamide is indicated. For example, in some embodiments, apalutamide is indicated for the treatment of patients with non-metastatic castration-resistant prostate cancer. Apalutamide may be administered in a 60 mg dosage form. In some embodiments, apalutamide is administered once daily up to a total daily dose of 240 mg. For example, when apalutamide is indicated for the treatment of patients with non-metastatic castration-resistant prostate cancer, the reference dose is 240 mg, administered once daily (total daily reference dose is 240 mg. Thus, in various embodiments, the total daily reference dose of apalutamide may be, for example, 30 mg, 60 mg, 90 mg, 120 mg, 150 mg, 180 mg, 210 mg, or 240 mg. In accordance with certain embodiments of the present disclosure, when the total daily reference dose of apalutamide is, for example, 240 mg, the patient will take a reduced total daily dose of apalutamide (either concomitantly with posaconazole or after a delay period after stopping posaconazole). In some embodiments, the reduced total daily dose of apalutamide is, for example, 30 mg, 60 mg, 90 mg, 120 mg, 150 mg, 180 mg, or 210 mg, including all integers and ranges therebetween. When the total daily reference dose of apalutamide is 240 mg, the reduced total daily dose of apalutamide is, for example, 30 mg, 60 mg, 90 mg, 120 mg, 150 mg, 180 mg, or 210 mg, including all integers and ranges therebetween. When the total daily reference dose of apalutamide is 180 mg, the reduced total daily dose of apalutamide is, for example, 30 mg, 60 mg, 90 mg, 120 mg, or 150 mg, including all integers and ranges therebetween. When the total daily reference dose of apalutamide is 120 mg, the reduced total daily dose of apalutamide is, for example, 30 mg, 60 mg, or 90 mg, including all integers and ranges therebetween. Correspondingly, when the individual reference dose of apalutamide is 60 mg, the reduced individual reference dose of apalutamide is, for example, 30 mg.

In some embodiments, the CYP3A4 substrate drug is aripiprazole)(ABILIFY®. The disease or condition treated with aripiprazole can include any disease or condition described herein or for which aripiprazole is indicated. For example, in some embodiments, aripiprazole is indicated orally for schizophrenia. In some embodiments, aripiprazole is indicated orally for Acute Treatment of Manic and Mixed Episodes associated with Bipolar I. In some embodiments, aripiprazole is indicated orally for Adjunctive Treatment of Major Depressive Disorder. In some embodiments, aripiprazole is indicated orally for Irritability Associated with Autistic Disorder. In some embodiments, aripiprazole is indicated orally for the Treatment of Tourette's Disorder. In some embodiments, aripiprazole is indicated for intramuscular injection for Agitation associated with schizophrenia or bipolar mania. Aripiprazole may be administered in a 2 mg, 5 mg, 10 mg, 15 mg, 20 mg, and 30 mg tablet dosage form or a 10 mg or 15 mg orally disintegrating tablet or a 1 mg/mL oral solution or a 9.75 mg/1.3 mL single-dose vial. In some embodiments, aripiprazole is administered once daily up to a total daily dose of 30 mg (orally or via injection). For example, when aripiprazole is indicated for schizophrenia in adults, the initial reference dose is 10-15 mg administered once daily (total daily reference dose is 10-15 mg). When aripiprazole is indicated for schizophrenia in adults, the recommended reference dose is 10-15 mg administered once daily (total daily reference dose is 10-15 mg). When aripiprazole is indicated for schizophrenia in adults, the maximum reference dose is 30 mg administered once daily (total daily reference dose is 30 mg). For example, when aripiprazole is indicated for schizophrenia in adolescents, the initial reference dose is 2 mg administered once daily (total daily reference dose is 2 mg). When aripiprazole is indicated for schizophrenia in adolescents, the recommended reference dose is 10 mg administered once daily (total daily reference dose is 10 mg). When aripiprazole is indicated for schizophrenia in adolescents, the maximum reference dose is 30 mg administered once daily (total daily reference dose is 30 mg). For example, when aripiprazole is indicated for bipolar mania in adults (monotherapy), the initial reference dose is 15 mg administered once daily (total daily reference dose is 15 mg). When aripiprazole is indicated for bipolar mania in adults (monotherapy), the recommended reference dose is 15 mg administered once daily (total daily reference dose is 15 mg). When aripiprazole is indicated for bipolar mania in adults (monotherapy), the maximum reference dose is 30 mg administered once daily (total daily reference dose is 30 mg). For example, when aripiprazole is indicated for bipolar mania in adults (adjunct to lithium or valproate), the initial reference dose is 10-15 mg administered once daily (total daily reference dose is 10-15 mg). When aripiprazole is indicated for bipolar mania in adults (adjunct to lithium or valproate), the recommended reference dose is 15 mg administered once daily (total daily reference dose is 15 mg). When aripiprazole is indicated for bipolar mania in adults (adjunct to lithium or valproate), the maximum reference dose is 30 mg administered once daily (total daily reference dose is 30 mg). For example, when aripiprazole is indicated for bipolar mania in pediatrics (monotherapy or adjunct to lithium or valproate), the initial reference dose is 2 mg administered once daily (total daily reference dose is 2 mg). When aripiprazole is indicated for bipolar mania in pediatrics (monotherapy or adjunct to lithium or valproate), the recommended reference dose is 10 mg administered once daily (total daily reference dose is 10 mg). When aripiprazole is indicated for bipolar mania in pediatrics (monotherapy or adjunct to lithium or valproate), the maximum reference dose is 30 mg administered once daily (total daily reference dose is 30 mg). For example, when aripiprazole is indicated for major depressive disorder in adults (adjunct to antidepressants), the initial reference dose is 2-5 mg administered once daily (total daily reference dose is 2-5 mg). When aripiprazole is indicated for major depressive disorder in adults (adjunct to antidepressants), the recommended reference dose is 5-10 mg administered once daily (total daily reference dose is 5-10 mg). When aripiprazole is indicated for major depressive disorder in adults (adjunct to antidepressants), the maximum reference dose is 15 mg administered once daily (total daily reference dose is 15 mg). For example, when aripiprazole is indicated for irritability associated with autistic disorder in pediatric patients, the initial reference dose is 2 mg administered once daily (total daily reference dose is 2 mg). When aripiprazole is indicated for irritability associated with autistic disorder in pediatric patients, the recommended reference dose is 5-10 mg administered once daily (total daily reference dose is 5-10 mg). When aripiprazole is indicated for irritability associated with autistic disorder in pediatric patients, the maximum reference dose is 15 mg administered once daily (total daily reference dose is 15 mg). For example, when aripiprazole is indicated for Tourette's disorder in patients <50 kg, the initial reference dose is 2 mg administered once daily (total daily reference dose is 2 mg). When aripiprazole is indicated for Tourette's disorder in patients <50 kg, the recommended reference dose is 5 mg administered once daily (total daily reference dose is 5 mg). When aripiprazole is indicated for Tourette's disorder in patients <50 kg, the maximum reference dose is 10 mg administered once daily (total daily reference dose is 10 mg). For example, when aripiprazole is indicated for Tourette's disorder in patients ≥50 kg, the initial reference dose is 2 mg administered once daily (total daily reference dose is 2 mg). When aripiprazole is indicated for Tourette's disorder in patients ≥50 kg, the recommended reference dose is 10 mg administered once daily (total daily reference dose is 10 mg). When aripiprazole is indicated for Tourette's disorder in patients ≥50 kg, the maximum reference dose is 20 mg administered once daily (total daily reference dose is 20 mg). For example, when aripiprazole is indicated for agitation associated with schizophrenia or bipolar mania in adults, the initial reference dose is 9.75 mg/1.3 mL administered intramuscularly once daily (total daily reference dose is 9.75 mg/1.3 mL). When aripiprazole is indicated for agitation associated with schizophrenia or bipolar mania in adults, the maximum reference dose is 30 mg administered intramuscularly once daily (total daily reference dose is 30 mg) Thus, in various embodiments, the total daily reference dose of aripiprazole may be, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, or 30 mg. In accordance with certain embodiments of the present disclosure, when the total daily reference dose of aripiprazole is, for example, 30 mg, the patient will take a reduced total daily dose of aripiprazole (either concomitantly with posaconazole or after a delay period after stopping posaconazole). In some embodiments, the reduced total daily dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, or 29 mg, including all integers and ranges therebetween. When the total daily reference dose of aripiprazole is 30 mg, the reduced total daily dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, or 29 mg, including all integers and ranges therebetween. When the total daily reference dose of aripiprazole is 20 mg, the reduced total daily dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the total daily reference dose of aripiprazole is 15 mg, the reduced total daily dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, or 14 mg, including all integers and ranges therebetween. When the total daily reference dose of aripiprazole is 10 mg, the reduced total daily dose of aripiprazole is, for example, 1 mg, 2 mg, 3 mg, 4 mg, 5 mg, 6 mg, 7 mg, 8 mg, or 9 mg, including all integers and ranges therebetween. When the total daily reference dose of aripiprazole is 5 mg, the reduced total daily dose of aripiprazole is, for example, 1 mg, 2 mg, 3 mg, or 4 mg, including all integers and ranges therebetween. When the total daily reference dose of aripiprazole is 2 mg, the reduced total daily dose of aripiprazole is, for example, 1 mg. Correspondingly, when the individual reference dose of aripiprazole is 30 mg, the reduced individual reference dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, or 29 mg, including all integers and ranges therebetween. When the individual reference dose of aripiprazole is 20 mg, the reduced individual reference dose of aripiprazole is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the individual reference dose of aripiprazole is 10 mg, the reduced individual reference dose of aripiprazole is, for example, 1 mg, 2 mg, 3 mg, 4 mg, 5 mg, 6 mg, 7 mg, 8 mg, or 9 mg, including all integers and ranges therebetween. When the individual reference dose of aripiprazole is 5 mg, the reduced individual reference dose of aripiprazole is, for example, 1 mg, 2 mg, 3 mg, or 4 mg, including all integers and ranges therebetween. When the individual reference dose of aripiprazole is 2 mg, the reduced individual reference dose of aripiprazole is, for example, 1 mg.

In some embodiments, the CYP3A4 substrate drug is aripiprazole (ARISTADA®). The disease or condition treated with aripiprazole can include any disease or condition described herein or for which aripiprazole is indicated. For example, in some embodiments, aripiprazole is indicated for the treatment of schizophrenia. Aripiprazole may be administered in a 441 mg, 662 mg, 882 mg, or 1064 single-use pre-filled syringe. In some embodiments, aripiprazole is administered once per month up to a total dose of 882 mg. In some embodiments, aripiprazole is administered once every 6 weeks up to a total dose of 882 mg. In some embodiments, aripiprazole is administered once every 2 months up to a total dose of 1064 mg. For example, when aripiprazole is indicated for the treatment of schizophrenia, the reference dose is 441 mg, 662 mg or 882 mg administered monthly, 882 mg dose every 6 weeks, or 1064 mg dose every 2 months, (total reference dose is 441 mg monthly, 662 mg monthly, 882 mg, monthly, 882 mg every 6 weeks, or 1064 mg every 2 months). Thus, in various embodiments, the total reference dose of aripiprazole may be, for example, 441 mg monthly, 662 mg monthly, 882 mg, monthly, 882 mg every 6 weeks, or 1064 mg every 2 months. In accordance with certain embodiments of the present disclosure, when the total daily reference dose of aripiprazole is, for example, 1064 mg every 2 months, the patient will take a reduced total daily dose of aripiprazole (either concomitantly with posaconazole or after a delay period after stopping posaconazole). In some embodiments, the reduced total daily dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 120 mg monthly, 140 mg monthly, 160 mg monthly, 180 mg monthly, 200 mg monthly, 220 mg monthly, 240 mg monthly, 260 mg monthly, 280 mg monthly, 300 mg monthly, 320 mg monthly, 340 mg monthly, 360 mg monthly, 380 mg monthly, 400 mg monthly, 420 mg monthly, 440 mg monthly, 460 mg monthly, 480 mg monthly, 500 mg monthly, 520 mg monthly, 540 mg monthly, 560 mg monthly, 580 mg monthly, 600 mg monthly, 620 mg monthly, 640 mg monthly, 660 mg monthly, 680 mg monthly, 700 mg monthly, 720 mg monthly, 740 mg monthly, 760 mg monthly, 780 mg monthly, 800 mg monthly, 820 mg monthly, 840 mg monthly, 860 mg monthly, or 880 mg monthly, including all integers and ranges therebetween; or 10 mg every 6 weeks, 20 mg every 6 weeks, 30 mg every 6 weeks, 40 mg every 6 weeks, 50 mg every 6 weeks, 60 mg every 6 weeks, 70 mg every 6 weeks, 80 mg every 6 weeks, 90 mg every 6 weeks, 100 mg every 6 weeks, 120 mg every 6 weeks, 140 mg every 6 weeks, 160 mg every 6 weeks, 180 mg every 6 weeks, 200 mg every 6 weeks, 220 mg every 6 weeks, 240 mg every 6 weeks, 260 mg every 6 weeks, 280 mg every 6 weeks, 300 mg every 6 weeks, 320 mg every 6 weeks, 340 mg every 6 weeks, 360 mg every 6 weeks, 380 mg every 6 weeks, 400 mg every 6 weeks, 420 mg every 6 weeks, 440 mg every 6 weeks, 460 mg every 6 weeks, 480 mg every 6 weeks, 500 mg every 6 weeks, 520 mg every 6 weeks, 540 mg every 6 weeks, 560 mg every 6 weeks, 580 mg every 6 weeks, 600 mg every 6 weeks, 620 mg every 6 weeks, 640 mg every 6 weeks, 660 mg every 6 weeks, 680 mg every 6 weeks, 700 mg every 6 weeks, 720 mg every 6 weeks, 740 mg every 6 weeks, 760 mg every 6 weeks, 780 mg every 6 weeks, 800 mg every 6 weeks, 820 mg every 6 weeks, 840 mg every 6 weeks, 860 mg every 6 weeks, or 880 mg every 6 weeks, including all integers and ranges therebetween; or 10 mg every 2 months, 20 mg every 2 months, 30 mg every 2 months, 40 mg every 2 months, 50 mg every 2 months, 60 mg every 2 months, 70 mg every 2 months, 80 mg every 2 months, 90 mg every 2 months, 100 mg every 2 months, 120 mg every 2 months, 140 mg every 2 months, 160 mg every 2 months, 180 mg every 2 months, 200 mg every 2 months, 220 mg every 2 months, 240 mg every 2 months, 260 mg every 2 months, 280 mg every 2 months, 300 mg every 2 months, 320 mg every 2 months, 340 mg every 2 months, 360 mg every 2 months, 380 mg every 2 months, 400 mg every 2 months, 420 mg every 2 months, 440 mg every 2 months, 460 mg every 2 months, 480 mg every 2 months, 500 mg every 2 months, 520 mg every 2 months, 540 mg every 2 months, 560 mg every 2 months, 580 mg every 2 months, 600 mg every 2 months, 620 mg every 2 months, 640 mg every 2 months, 660 mg every 2 months, 680 mg every 2 months, 700 mg every 2 months, 720 mg every 2 months, 740 mg every 2 months, 760 mg every 2 months, 780 mg every 2 months, 800 mg every 2 months, 820 mg every 2 months, 840 mg every 2 months, 860 mg every 2 months, or 880 mg every 2 months, 900 mg every 2 months, 920 mg every 2 months, 940 mg every 2 months, 960 mg every 2 months, 980 mg every 2 months, 1000 mg every 2 months, 1020 mg every 2 months, 1040 mg every 2 months or 1060 mg every 2 months, including all integers and ranges therebetween. When the total reference dose of aripiprazole is 1064 mg every 2 months, the reduced total daily dose of aripiprazole is, for example, 10 mg every 2 months, 20 mg every 2 months, 30 mg every 2 months, 40 mg every 2 months, 50 mg every 2 months, 60 mg every 2 months, 70 mg every 2 months, 80 mg every 2 months, 90 mg every 2 months, 100 mg every 2 months, 120 mg every 2 months, 140 mg every 2 months, 160 mg every 2 months, 180 mg every 2 months, 200 mg every 2 months, 220 mg every 2 months, 240 mg every 2 months, 260 mg every 2 months, 280 mg every 2 months, 300 mg every 2 months, 320 mg every 2 months, 340 mg every 2 months, 360 mg every 2 months, 380 mg every 2 months, 400 mg every 2 months, 420 mg every 2 months, 440 mg every 2 months, 460 mg every 2 months, 480 mg every 2 months, 500 mg every 2 months, 520 mg every 2 months, 540 mg every 2 months, 560 mg every 2 months, 580 mg every 2 months, 600 mg every 2 months, 620 mg every 2 months, 640 mg every 2 months, 660 mg every 2 months, 680 mg every 2 months, 700 mg every 2 months, 720 mg every 2 months, 740 mg every 2 months, 760 mg every 2 months, 780 mg every 2 months, 800 mg every 2 months, 820 mg every 2 months, 840 mg every 2 months, 860 mg every 2 months, or 880 mg every 2 months, 900 mg every 2 months, 920 mg every 2 months, 940 mg every 2 months, 960 mg every 2 months, 980 mg every 2 months, 1000 mg every 2 months, 1020 mg every 2 months, 1040 mg every 2 months or 1060 mg every 2 months, including all integers and ranges therebetween. When the total reference dose of aripiprazole is 882 mg every 6 weeks, the reduced total dose of aripiprazole is, for example, 10 mg every 6 weeks, 20 mg every 6 weeks, 30 mg every 6 weeks, 40 mg every 6 weeks, 50 mg every 6 weeks, 60 mg every 6 weeks, 70 mg every 6 weeks, 80 mg every 6 weeks, 90 mg every 6 weeks, 100 mg every 6 weeks, 120 mg every 6 weeks, 140 mg every 6 weeks, 160 mg every 6 weeks, 180 mg every 6 weeks, 200 mg every 6 weeks, 220 mg every 6 weeks, 240 mg every 6 weeks, 260 mg every 6 weeks, 280 mg every 6 weeks, 300 mg every 6 weeks, 320 mg every 6 weeks, 340 mg every 6 weeks, 360 mg every 6 weeks, 380 mg every 6 weeks, 400 mg every 6 weeks, 420 mg every 6 weeks, 440 mg every 6 weeks, 460 mg every 6 weeks, 480 mg every 6 weeks, 500 mg every 6 weeks, 520 mg every 6 weeks, 540 mg every 6 weeks, 560 mg every 6 weeks, 580 mg every 6 weeks, 600 mg every 6 weeks, 620 mg every 6 weeks, 640 mg every 6 weeks, 660 mg every 6 weeks, 680 mg every 6 weeks, 700 mg every 6 weeks, 720 mg every 6 weeks, 740 mg every 6 weeks, 760 mg every 6 weeks, 780 mg every 6 weeks, 800 mg every 6 weeks, 820 mg every 6 weeks, 840 mg every 6 weeks, 860 mg every 6 weeks, or 880 mg every 6 weeks, including all integers and ranges therebetween. When the total reference dose of aripiprazole is 882 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 120 mg monthly, 140 mg monthly, 160 mg monthly, 180 mg monthly, 200 mg monthly, 220 mg monthly, 240 mg monthly, 260 mg monthly, 280 mg monthly, 300 mg monthly, 320 mg monthly, 340 mg monthly, 360 mg monthly, 380 mg monthly, 400 mg monthly, 420 mg monthly, 440 mg monthly, 460 mg monthly, 480 mg monthly, 500 mg monthly, 520 mg monthly, 540 mg monthly, 560 mg monthly, 580 mg monthly, 600 mg monthly, 620 mg monthly, 640 mg monthly, 660 mg monthly, 680 mg monthly, 700 mg monthly, 720 mg monthly, 740 mg monthly, 760 mg monthly, 780 mg monthly, 800 mg monthly, 820 mg monthly, 840 mg monthly, 860 mg monthly, or 880 mg monthly, including all integers and ranges therebetween. When the total reference dose of aripiprazole is 662 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 120 mg monthly, 140 mg monthly, 160 mg monthly, 180 mg monthly, 200 mg monthly, 220 mg monthly, 240 mg monthly, 260 mg monthly, 280 mg monthly, 300 mg monthly, 320 mg monthly, 340 mg monthly, 360 mg monthly, 380 mg monthly, 400 mg monthly, 420 mg monthly, 440 mg monthly, 460 mg monthly, 480 mg monthly, 500 mg monthly, 520 mg monthly, 540 mg monthly, 560 mg monthly, 580 mg monthly, 600 mg monthly, 620 mg monthly, 640 mg monthly, or 660 mg monthly, including all integers and ranges therebetween. When the total reference dose of aripiprazole is 441 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 120 mg monthly, 140 mg monthly, 160 mg monthly, 180 mg monthly, 200 mg monthly, 220 mg monthly, 240 mg monthly, 260 mg monthly, 280 mg monthly, 300 mg monthly, 320 mg monthly, 340 mg monthly, 360 mg monthly, 380 mg monthly, 400 mg monthly, 420 mg monthly, or 440 mg monthly, including all integers and ranges therebetween.

In some embodiments, the CYP3A4 substrate drug is aripiprazole (ABILIFY MAINTENA®). The disease or condition treated with aripiprazole can include any disease or condition described herein or for which aripiprazole is indicated. For example, in some embodiments, aripiprazole is indicated for the treatment of schizophrenia in adults. In some embodiments, aripiprazole is indicated as a maintenance monotherapy treatment of bipolar I disorder in adults. Aripiprazole may be administered in 160, 200 mg, 300 mg or 400 mg injection. In some embodiments, aripiprazole is administered once monthly up to a total daily dose of 400 mg. For example, when aripiprazole is indicated for schizophrenia in adults, the reference dose is 400 mg, administered once monthly (total daily reference dose is 400 mg monthly). For example, when aripiprazole is indicated as a maintenance monotherapy treatment of bipolar I disorder in adults, the reference dose is 400 mg, administered once monthly (total daily reference dose is 400 mg monthly). Thus, in various embodiments, the total reference dose of aripiprazole may be, for example, 160 mg monthly, 200 mg monthly, 300 mg monthly, or 400 mg monthly. In accordance with certain embodiments of the present disclosure, when the total daily reference dose of aripiprazole is, for example, 400 mg monthly, the patient will take a reduced total daily dose of aripiprazole (either concomitantly with posaconazole or after a delay period after stopping posaconazole). In some embodiments, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 110 mg monthly, 120 mg monthly, 130 mg monthly, 140 mg monthly, 150 mg monthly, 160 mg monthly, 170 mg monthly, 180 mg monthly, 190 mg monthly, 200 mg monthly, 210 mg monthly, 220 mg monthly, 230 mg monthly, 240 mg monthly, 250 mg monthly, 260 mg monthly, 270 mg monthly, 280 mg monthly, 290 mg monthly, 300 mg monthly, 310 mg monthly, 320 mg monthly, 330 mg monthly, 340 mg monthly, 350 mg monthly, 360 mg monthly, 370 mg monthly, 380 mg monthly, or 390 mg monthly. When the total reference dose of aripiprazole is 400 mg monthly, the reduced total dose of aripiprazole is 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 110 mg monthly, 120 mg monthly, 130 mg monthly, 140 mg monthly, 150 mg monthly, 160 mg monthly, 170 mg monthly, 180 mg monthly, 190 mg monthly, 200 mg monthly, 210 mg monthly, 220 mg monthly, 230 mg monthly, 240 mg monthly, 250 mg monthly, 260 mg monthly, 270 mg monthly, 280 mg monthly, 290 mg monthly, 300 mg monthly, 310 mg monthly, 320 mg monthly, 330 mg monthly, 340 mg monthly, 350 mg monthly, 360 mg monthly, 370 mg monthly, 380 mg monthly, or 390 mg monthly, including all integers and ranges therebetween. When the total reference dose of aripiprazole is 300 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 110 mg monthly, 120 mg monthly, 130 mg monthly, 140 mg monthly, 150 mg monthly, 160 mg monthly, 170 mg monthly, 180 mg monthly, 190 mg monthly, 200 mg monthly, 210 mg monthly, 220 mg monthly, 230 mg monthly, 240 mg monthly, 250 mg monthly, 260 mg monthly, 270 mg monthly, 280 mg monthly, or 290 mg monthly, including all integers and ranges therebetween. When the total reference dose of aripiprazole is 200 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 110 mg monthly, 120 mg monthly, 130 mg monthly, 140 mg monthly, 150 mg monthly, 160 mg monthly, 170 mg monthly, 180 mg monthly, or 190 mg monthly, including all integers and ranges therebetween. When the total reference dose of aripiprazole is 160 mg monthly, the reduced total dose of aripiprazole is, for example, 10 mg monthly, 20 mg monthly, 30 mg monthly, 40 mg monthly, 50 mg monthly, 60 mg monthly, 70 mg monthly, 80 mg monthly, 90 mg monthly, 100 mg monthly, 110 mg monthly, 120 mg monthly, 130 mg monthly, 140 mg monthly, or 150 mg monthly, 160 mg monthly, including all integers and ranges therebetween.

In some embodiments, the CYP3A4 substrate drug is bosutinib. The disease or condition treated with bosutinib can include any disease or condition described herein or for which bosutinib is indicated. For example, in some embodiments, bosutinib is indicated for Newly-diagnosed chronic phase Ph+ chronic myelogenous leukemia (CML). In some embodiments, bosutinib is indicated for Chronic, accelerated, or blast phase Ph+ CML with resistance or intolerance to prior therapy. Bosutinib may be administered in a 100 mg, 400 mg, or 500 mg dosage form. In some embodiments, bosutinib is administered once daily up to a total daily dose of 600 mg. For example, when bosutinib is indicated for Newly-diagnosed chronic phase Ph+ chronic myelogenous leukemia (CML), the reference dose is 400 mg, administered once daily (total daily reference dose is 400 mg). For example, when bosutinib is indicated for Chronic, accelerated, or blast phase Ph+ CML with resistance or intolerance to prior therapy, the reference dose is 500 mg, administered once daily (total daily reference dose is 500 mg). In some embodiments, the dose is escalated by increments of 100 mg once daily to a maximum of 600 mg daily in patients who do not reach complete hematologic, cytogenetic, or molecular response and do not have Grade 3 or greater adverse reactions. Thus, in various embodiments, the total daily reference dose of bosutinib may be, for example, 50 mg, 100 mg, 150 mg, 200 mg, 250 mg, 300 mg, 350 mg, 400 mg, 450 mg, 500 mg, 550 mg, or 600 mg. In accordance with certain embodiments of the present disclosure, when the total daily reference dose of bosutinib is, for example, 600 mg the patient will take a reduced total daily dose of bosutinib (either concomitantly with posaconazole or after a delay period after stopping posaconazole). In some embodiments, the reduced total daily dose of bosutinib is, for example, 50 mg, 100 mg, 150 mg, 200 mg, 250 mg, 300 mg, 350 mg, 400 mg, 450 mg, 500 mg, or 550 mg, including all integers and ranges therebetween. When the total daily reference dose of bosutinib is 600 mg, the reduced total daily dose of bosutinib is, for example, 50 mg, 100 mg, 150 mg, 200 mg, 250 mg, 300 mg, 350 mg, 400 mg, 450 mg, 500 mg, or 550 mg, including all integers and ranges therebetween. When the total daily reference dose of bosutinib is 500 mg, the reduced total daily dose of bosutinib is, for example, 50 mg, 100 mg, 150 mg, 200 mg, 250 mg, 300 mg, 350 mg, 400 mg, or 450 mg, including all integers and ranges therebetween. When the total daily reference dose of bosutinib is 400 mg, the reduced total daily dose of bosutinib is, for example, 50 mg, 100 mg, 150 mg, 200 mg, 250 mg, 300 mg, or 350 mg, including all integers and ranges therebetween. Correspondingly, when the individual reference dose of bosutinib is 500 mg, the reduced individual reference dose of bosutinib is, for example, 50 mg, 100 mg, 150 mg, 200 mg, 250 mg, 300 mg, 350 mg, 400 mg, or 450 mg, including all integers and ranges therebetween. When the individual reference dose of bosutinib is 400 mg, the reduced individual reference dose of bosutinib is, for example, 50 mg, 100 mg, 150 mg, 200 mg, 250 mg, 300 mg, or 350 mg, including all integers and ranges therebetween.

In some embodiments, the CYP3A4 substrate drug is brexpiprazole. The disease or condition treated with brexpiprazole can include any disease or condition described herein or for which brexpiprazole is indicated. For example, in some embodiments, brexpiprazole is indicated for use as an adjunctive therapy to antidepressants for the treatment of major depressive disorder (MDD). In some embodiments, brexpiprazole is indicated for the treatment of schizophrenia. Brexpiprazole may be administered in a 0.25 mg, 0.5 mg, 1 mg, 2 mg, 3 mg, and 4 mg dosage form. In some embodiments, brexpiprazole is administered once daily up to a total daily dose of 8 mg. For example, when brexpiprazole is indicated for use as an adjunctive therapy to antidepressants for the treatment of major depressive disorder (MDD), the starting reference dose is 0.5 mg or 1 mg administered once daily (total daily reference dose is 0.5 mg or 1 mg). When brexpiprazole is indicated for use as an adjunctive therapy to antidepressants for the treatment of major depressive disorder (MDD), the recommended reference dose is 2 mg administered once daily (total daily reference dose is 2 mg). When brexpiprazole is indicated for use as an adjunctive therapy to antidepressants for the treatment of major depressive disorder (MDD), the maximum dose is 3 mg administered once daily (total daily reference dose is 3 mg). For example, when brexpiprazole is indicated for treating schizophrenia, the starting reference dose is 1 mg, administered once daily (total daily reference dose is 1 mg). When brexpiprazole is indicated for treating schizophrenia, the recommended reference dose is 2-4 mg (e.g. 2 mg, 3 mg, or 4 mg), administered once daily (total daily reference dose is 2-4 mg). When brexpiprazole is indicated for treating schizophrenia, the maximum dose is 4 mg, administered once daily (total daily reference dose is 4 mg). Thus, in various embodiments, the total daily reference dose of brexpiprazole may be, for example, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg or 8 mg. In accordance with certain embodiments of the present disclosure, when the total daily reference dose of brexpiprazole is, for example, 8 mg, the patient will take a reduced total daily dose of brexpiprazole (either concomitantly with posaconazole or after a delay period after stopping posaconazole). In some embodiments, the reduced total daily dose of brexpiprazole is 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, or 7.75 mg. When the total daily reference dose of brexpiprazole is 6 mg, the reduced total daily dose of brexpiprazole is, for example, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, or 5.75 mg, including all integers and ranges therebetween. When the total daily reference dose of brexpiprazole is 4 mg, the reduced total daily dose of brexpiprazole is, for example, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, or 3.75 mg, including all integers and ranges therebetween. When the total daily reference dose of brexpiprazole is 3 mg, the reduced total daily dose of brexpiprazole is, for example, 0.25 mg, 0.5 mg, 0.75 mg, 1 mg, 1.25 mg, 1.5 mg, 1.75 mg, 2 mg, 2.25 mg, 2.5 mg, or 2.75 mg, including all integers and ranges therebetween. When the total daily reference dose of brexpiprazole is 2 mg, the reduced total daily dose of brexpiprazole is, for example, 0.25 mg, 0.5 mg, 0.75 mg, 1 mg, 1.25 mg, 1.5 mg, or 1.75 mg, including all integers and ranges therebetween. When the total daily reference dose of brexpiprazole is 1 mg, the reduced total daily dose of brexpiprazole is, for example, 0.25 mg, 0.5 mg, or 0.75 mg, including all integers and ranges therebetween. When the total daily reference dose of brexpiprazole is 0.75 mg, the reduced total daily dose of brexpiprazole is, for example, 0.25 mg or 0.5 mg, including all integers and ranges therebetween. When the total daily reference dose of brexpiprazole is 0.5 mg, the reduced total daily dose of brexpiprazole is, for example, 0.125 or 0.25 mg, including all integers and ranges therebetween. When the total daily reference dose of brexpiprazole is 0.25 mg, the reduced total daily dose of brexpiprazole is, for example, 0.125 mg. Correspondingly, when the individual reference dose of brexpiprazole is 4 mg, the reduced individual reference dose of brexpiprazole is, for example, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, or 3.75 mg, including all integers and ranges therebetween. When the individual reference dose of brexpiprazole is 3 mg, the reduced individual reference dose of brexpiprazole is, for example, 0.25 mg, 0.5 mg, 0.75 mg, 1 mg, 1.25 mg, 1.5 mg, 1.75 mg, 2 mg, 2.25 mg, 2.5 mg, or 2.75 mg, including all integers and ranges therebetween. When the individual reference dose of brexpiprazole is 2 mg, the reduced individual reference dose of brexpiprazole is, for example, 0.25 mg, 0.5 mg, 0.75 mg, 1 mg, 1.25 mg, 1.5 mg, or 1.75 mg, including all integers and ranges therebetween. When the individual reference dose of brexpiprazole is 1 mg, the reduced individual reference dose of brexpiprazole is, for example, 0.25 mg, 0.5 mg, or 0.75 mg, including all integers and ranges therebetween. When the individual reference dose of brexpiprazole is 0.75 mg, the reduced individual reference dose of brexpiprazole is, for example, 0.25 mg or 0.5 mg, including all integers and ranges therebetween. When the individual reference dose of brexpiprazole is 0.5 mg, the reduced individual reference dose of brexpiprazole is, for example 0.125 or 0.25 mg, including all integers and ranges therebetween. When the individual reference dose of brexpiprazole is 0.25 mg, the reduced individual reference dose of brexpiprazole is, for example, 0.125 mg.

In some embodiments, the CYP3A4 substrate drug is brigatinib. The disease or condition treated with brigatinib can include any disease or condition described herein or for which brigatinib is indicated. For example, in some embodiments, brigatinib is indicated for the treatment of patients with anaplastic lymphoma kinase (ALK)-positive metastatic non-small cell lung cancer (NSCLC) who have progressed on or are intolerant to crizotinib. Brigatinib may be administered in a 30 mg or 90 mg dosage form. In some embodiments, brigatinib is administered once daily up to a total daily dose of 180 mg. For example, when brigatinib is indicated for the treatment of patients with anaplastic lymphoma kinase (ALK)-positive metastatic non-small cell lung cancer (NSCLC) who have progressed on or are intolerant to crizotinib, the reference dose is 90 mg, administered once daily for the first 7 days and if tolerated, increased to 180 mg once daily (total daily reference dose is 90 mg or 180 mg). Thus, in various embodiments, the total daily reference dose of brigatinib may be, for example, 15 mg, 30 mg, 45 mg, 60 mg, 75 mg, 90 mg, 105 mg, 120 mg, 135 mg, 150 mg, 165 mg, or 180 mg. In accordance with certain embodiments of the present disclosure, when the total daily reference dose of brigatinib is, for example, 180 mg, the patient will take a reduced total daily dose of brigatinib (either concomitantly with posaconazole or after a delay period after stopping posaconazole). In some embodiments, the reduced total daily dose of brigatinib is, for example, 15 mg, 30 mg, 45 mg, 60 mg, 75 mg, 90 mg, 105 mg, 120 mg, 135 mg, 150 mg, or 165 mg, including all integers and ranges therebetween. When the total daily reference dose of brigatinib is 180 mg, the reduced total daily dose of brigatinib is, for example, 15 mg, 30 mg, 45 mg, 60 mg, 75 mg, 90 mg, 105 mg, 120 mg, 135 mg, 150 mg, 165 mg, including all integers and ranges therebetween. When the total daily reference dose of brigatinib is 120 mg, the reduced total daily dose of brigatinib is, for example, 15 mg, 30 mg, 45 mg, 60 mg, 75 mg, 90 mg, or 105 mg, including all integers and ranges therebetween. When the total daily reference dose of brigatinib is 90 mg, the reduced total daily dose of brigatinib is, for example, 15 mg, 30 mg, 45 mg, 60 mg, or 75 mg, including all integers and ranges therebetween. When the total daily reference dose of brigatinib is 60 mg, the reduced total daily dose of brigatinib is, for example, 15 mg, 30 mg, or 45 mg, including all integers and ranges therebetween. When the total daily reference dose of brigatinib is 30 mg, the reduced total daily dose of brigatinib is, for example, 7.5 mg or 15 mg, including all integers and ranges therebetween. Correspondingly, when the individual reference dose of brigatinib is 90 mg, the reduced individual reference dose of brigatinib is, for example, 15 mg, 30 mg, 45 mg, 60 mg, 75 mg, including all integers and ranges therebetween. When the individual reference dose of brigatinib is 30 mg, the reduced individual reference dose of brigatinib is, for example, 7.5 mg or 15 mg, including all integers and ranges therebetween.

In some embodiments, the CYP3A4 substrate drug is cabazitaxel. The disease or condition treated with cabazitaxel can include any disease or condition described herein or for which cabazitaxel is indicated. For example, in some embodiments, cabazitaxel is indicated in combination with prednisone for treatment of patients with metastatic castration-resistant prostate cancer previously treated with a docetaxel-containing treatment regimen. Cabazitaxel may be administered via injection in a 15 mg/m$^2$, 20 mg/m$^2$, or a 25 mg/m$^2$ dosage form (sold as a single dose vial of 60 mg/1.5 mL). In some embodiments, cabazitaxel is administered once every three weeks corresponding to a total dose of up to 25 mg/m$^2$ every three weeks. For example, when cabazitaxel is indicated for in combination with prednisone for treatment of patients with metastatic castration-resistant prostate cancer previously treated with a docetaxel-containing treatment regimen, the reference dose is 20 mg/m², administered once every 3 weeks (total reference dose is 20 mg/m² every 3 weeks). Thus, in various embodiments, the total reference dose of cabazitaxel may be, for example, 2.5 mg/m² every 3 weeks, 5 mg/m² every 3 weeks, 7.5 mg/m² every 3 weeks, 10 mg/m² every 3 weeks, 12.5 mg/m² every 3 weeks, 15 mg/m² every 3 weeks, 17.5 mg/m² every 3 weeks, 20 mg/m² every 3 weeks, 22.5 mg/m² every 3 weeks, or 25 mg/m² every 3 weeks. In accordance with certain embodiments of the present disclosure, when the total reference dose of cabazitaxel is, for example, 25 mg/m² every 3 weeks, the patient will take a reduced total dose of cabazitaxel (either concomitantly with posaconazole or after a delay period after stopping posaconazole). In some embodiments, the reduced total dose of cabazitaxel is, for example, 2.5 mg/m² every 3 weeks, 5 mg/m² every 3 weeks, 7.5 mg/m² every 3 weeks, 10 mg/m² every 3 weeks, 12.5 mg/m² every 3 weeks, 15 mg/m² every 3 weeks, 17.5 mg/m² every 3 weeks, 20 mg/m² every 3 weeks, or 22.5 mg/m² every 3 weeks, including all integers and ranges therebetween. When the total daily reference dose of cabazitaxel is 25 mg/m² every 3 weeks, the reduced total daily dose of cabazitaxel is, for example, 2.5 mg/m² every 3 weeks, 5 mg/m² every 3 weeks, 7.5 mg/m² every 3 weeks, 10 mg/m² every 3 weeks, 12.5 mg/m² every 3 weeks, 15 mg/m² every 3 weeks, 17.5 mg/m² every 3 weeks, 20 mg/m² every 3 weeks or 22.5 mg/m² every 3 weeks, including all integers and ranges therebetween. When the total daily reference dose of cabazitaxel is 20 mg/m² every 3 weeks, the reduced total daily dose of cabazitaxel is, for example, 2.5 mg/m² every 3 weeks, 5 mg/m² every 3 weeks, 7.5 mg/m² every 3 weeks, 10 mg/m² every 3 weeks, 12.5 mg/m² every 3 weeks, 15 mg/m² every 3 weeks, or 17.5 mg/m² every 3 weeks, including all integers and ranges therebetween. When the total daily reference dose of cabazitaxel is 15 mg/m² every 3 weeks, the reduced total daily dose of cabazitaxel is, for example, 2.5 mg/m² every 3 weeks, 5 mg/m² every 3 weeks, 7.5 mg/m² every 3 weeks, 10 mg/m² every 3 weeks, or 12.5 mg/m² every 3 weeks, including all integers and ranges therebetween.

In some embodiments, the CYP3A4 substrate drug is cannabidiol. The disease or condition treated with cannabidiol can include any disease or condition described herein or for which cannabidiol is indicated. For example, in some embodiments, cannabidiol is indicated for for the treatment of seizures associated with Lennox-Gastaut syndrome or Dravet syndrome in patients 2 years of age and older. Cannabidiol may be administered in a 100 mg/mL oral solution. In some embodiments, cannabidiol is administered once or twice daily up to a total daily dose of 20 mg/kg. For example, when cannabidiol is indicated for the treatment of seizures associated with Lennox-Gastaut syndrome or Dravet syndrome in patients 2 years of age and older, the starting reference dose is 2.5 mg/kg, administered twice daily (total daily reference dose is 5 mg/kg). After one week, the reference dose may be increased to 5 mg/kg, administered twice daily (total daily reference dose is 10 mg/kg). Based on individual clinical response and tolerability, cannabidiol may be increased to a maximum reference dose of 210 mg/kg, administered twice daily (total daily reference dose is 20 mg/kg). Thus, in various embodiments, the total daily reference dose of cannabidiol may be, for example, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg. In accordance with certain embodiments of the present disclosure, when the total daily reference dose of cannabidiol is, for example, 20 mg/kg, the patient will take a reduced total daily dose of cannabidiol (either concomitantly with posaconazole or after a delay period after stopping posaconazole). In some embodiments, the reduced total daily dose of cannabidiol is, for example, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, or 19 mg/kg, including all integers and ranges therebetween. When the total daily reference dose of cannabidiol is 20 mg/kg, the reduced total daily dose of cannabidiol is, for example, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, or 19 mg/kg, including all integers and ranges therebetween. When the total daily reference dose of cannabidiol is 10 mg/kg, the reduced total daily dose of cannabidiol is, for example, 1 mg/kg, 2 mg/kg, 3 mg/kg, 4 mg/kg, 5 mg/kg, 6 mg/kg, 7 mg/kg, 8 mg/kg, or 9 mg/kg, including all integers and ranges therebetween. When the total daily reference dose of cannabidiol is 5 mg/kg, the reduced total daily dose of cannabidiol is, for example, 1 mg/kg, 2 mg/kg, 3 mg/kg, or 4 mg/kg, including all integers and ranges therebetween.

In some embodiments, the CYP3A4 substrate drug is cariprazine. The disease or condition treated with cariprazine can include any disease or condition described herein or for which cariprazine is indicated. For example, in some embodiments, cariprazine is indicated for the treatment of schizophrenia in adults. In some embodiments, cariprazine is indicated for acute treatment of manic or mixed episodes associated with bipolar I disorder in adults. Cariprazine may be administered in a 1.5 mg, 3 mg, 4.5 mg, or 6 mg dosage form. In some embodiments, cariprazine is administered once daily up to a total daily dose of 6 mg. For example, when cariprazine is indicated for the treatment of schizophrenia, the starting reference dose is 1.5 mg, administered once daily (total daily reference dose is 1.5 mg). When cariprazine is indicated for the treatment of schizophrenia, the reference dose may be increased to up to 6 mg, administered once daily (total daily reference dose is 6 mg). For example, when cariprazine is indicated for acute treatment of manic or mixed episodes associated with bipolar I disorder in adults, the starting reference dose is 1.5 mg, administered once daily (total daily reference dose is 1.5 mg). When cariprazine is indicated for acute treatment of manic or mixed episodes associated with bipolar I disorder in adults, the reference dose may be increased to up to 6 mg, administered once daily (total daily reference dose is 6 mg). Thus, in various embodiments, the total daily reference dose of cariprazine may be, for example 0.75 mg, 1.5 mg, 2.25 mg, 3 mg, 3.75 mg, 4.5 mg, 5.25 mg, or 6 mg. In accordance with certain embodiments of the present disclosure, when the total daily reference dose of cariprazine is, for example, 6 mg, the patient will take a reduced total daily dose of cariprazine (either concomitantly with posaconazole or after a delay period after stopping posaconazole). In some embodiments, the reduced total daily dose of cariprazine is, for example, 0.75 mg, 1.5 mg, 2.25 mg, 3 mg, 3.75 mg, 4.5 mg, or 5.25 mg, including all integers and ranges therebetween. When the total daily reference dose of cariprazine is 6 mg, the reduced total daily dose of cariprazine is, for example, 0.75 mg, 1.5 mg, 2.25 mg, 3 mg, 3.75 mg, 4.5 mg, or 5.25 mg, including all integers and ranges therebetween. When the total daily reference dose of cariprazine is 4.5 mg, the reduced total daily dose of cariprazine is, for example, 0.75 mg, 1.5 mg, 2.25 mg, 3 mg, or 3.75 mg, including all integers and ranges therebetween. When the total daily reference dose of cariprazine is 3 mg, the reduced total daily dose of cariprazine is, for example, 0.75 mg, 1.5 mg, 2.25 mg, or 3 mg, including all integers and ranges therebetween. When the total daily reference dose of cariprazine is 1.5 mg, the reduced total daily dose of cariprazine is, for example, 0.75 mg. Correspondingly, when the individual reference dose of cariprazine is 6 mg, the reduced individual reference dose of cariprazine is, for example, 0.75 mg, 1.5 mg, 2.25 mg, 3 mg, 3.75 mg, 4.5 mg, or 5.25 mg, including all integers and ranges therebetween. When the individual reference dose of cariprazine is 4.5 mg, the reduced individual reference dose of cariprazine is, for example, 0.75 mg, 1.5 mg, 2.25 mg, 3 mg, or 3.75 mg, including all integers and ranges therebetween. When the individual reference dose of cariprazine is 3 mg, the reduced individual reference dose of cariprazine is, for example, 0.75 mg, 1.5 mg, or 2.25 mg, including all integers and ranges therebetween. When the individual reference dose of cariprazine is 1.5 mg, the reduced individual reference dose of cariprazine is, for example, 0.75 mg.

In some embodiments, the CYP3A4 substrate drug is cobimetinib. The disease or condition treated with cobimetinib can include any disease or condition described herein or for which cobimetinib is indicated. For example, in some embodiments, cobimetinib is indicated for the treatment of patients with unresectable or metastatic melanoma with a BRAF V600E or V600K mutation, in combination with vemurafenib. Cobimetinib may be administered in a 20 mg dosage form. In some embodiments, cobimetinib is administered once daily up to a total daily dose of 60 mg. For example, when cobimetinib is indicated for the treatment of patients with unresectable or metastatic melanoma with a BRAF V600E or V600K mutation, in combination with vemurafenib, the reference dose is 60 mg, administered once daily (total daily reference dose is 60 mg). Thus, in various embodiments, the total daily reference dose of cobimetinib may be, for example, 10 mg, 20 mg, 30 mg, 40 mg, 50 mg, or 60 mg. In accordance with certain embodiments of the present disclosure, when the total daily reference dose of cobimetinib is, for example, 60 mg, the patient will take a reduced total daily dose of cobimetinib (either concomitantly with posaconazole or after a delay period after stopping posaconazole). In some embodiments, the reduced total daily dose of cobimetinib is, for example, 10 mg, 20 mg, 30 mg, 40 mg, or 50 mg, including all integers and ranges therebetween. When the total daily reference dose of cobimetinib is 60 mg, the reduced total daily dose of cobimetinib is, for example, 10 mg, 20 mg, 30 mg, 40 mg, or 50 mg, including all integers and ranges therebetween. Correspondingly, when the individual reference dose of cobimetinib is 20 mg, the reduced individual reference dose of cobimetinib is, for example, 10 mg.

In some embodiments, the CYP3A4 substrate drug is copanlisib. The disease or condition treated with copanlisib can include any disease or condition described herein or for which copanlisib is indicated. For example, in some embodiments, copanlisib is indicated for the treatment of adult patients with relapsed follicular lymphoma (FL) who have received at least two prior systemic therapies. Copanlisib may be administered in a one-hour intravenous infusion as 30 mg, 45 mg, or 60 mg on days 1, 8 and 15 of a 28-day cycle dosage form. Thus, in some embodiments, copanlisib is administered on days 1, 8 and 15 of a 28-day cycle (three weeks on and one week off) up to a total dose of 180 mg/28 days. For example, when copanlisib is indicated for the treatment of adult patients with relapsed follicular lymphoma (FL) who have received at least two prior systemic therapies, the reference dose is 180 mg/28 days, administered on days 1, 8 and 15 of a 28-day cycle (three weeks on and one week off) (total reference dose is 180 mg/28 days). Thus, in various embodiments, the total daily reference dose of copanlisib may be, for example, 90 mg/28 days, 135 mg/28 days, or 180 mg/28 days. In accordance with certain embodiments of the present disclosure, when the total daily reference dose of copanlisib is, for example, 180 mg/28 days, the patient will take a reduced total daily dose of copanlisib (either concomitantly with posaconazole or after a delay period after stopping posaconazole). In some embodiments, the reduced total daily dose of copanlisib is, for example, 10 mg/28 days, 20 mg/28 days, 30 mg/28 days, 40 mg/28 days, 50 mg/28 days, 60 mg/28 days, 70 mg/28 days, 80 mg/28 days, 90 mg/28 days, 100 mg/28 days, 110 mg/28 days, 120 mg/28 days, 130 mg/28 days, 140 mg/28 days, 150 mg/28 days, 160 mg/28 days, or 170 mg/28 days, including all integers and ranges therebetween. When the total daily reference dose of copanlisib is 135 mg/28 days, the reduced total daily dose of copanlisib is, for example, 10 mg/28 days, 20 mg/28 days, 30 mg/28 days, 40 mg/28 days, 50 mg/28 days, 60 mg/28 days, 70 mg/28 days, 80 mg/28 days, 90 mg/28 days, 100 mg/28 days, 110 mg/28 days, or 120 mg/28 days, including all integers and ranges therebetween. When the total daily reference dose of copanlisib is 90 mg/28 days, the reduced total daily dose of copanlisib is, for example, 10 mg/28 days, 20 mg/28 days, 30 mg/28 days, 40 mg/28 days, 50 mg/28 days, 60 mg/28 days, 70 mg/28 days, or 80 mg/28 days, including all integers and ranges therebetween. Correspondingly, when the individual reference dose of copanlisib is 60 mg, the reduced individual reference dose of copanlisib is, for example, 10 mg, 20 mg, 30 mg, 40 mg, or 50 mg, including all integers and ranges therebetween. When the individual reference dose of copanlisib is 45 mg, the reduced individual reference dose of copanlisib is, for example, 10 mg, 20 mg, 30 mg, or 40 mg, including all integers and ranges therebetween. When the individual reference dose of copanlisib is 30 mg, the reduced individual reference dose of copanlisib is, for example, 10 mg or 20 mg, including all integers and ranges therebetween.

In some embodiments, the CYP3A4 substrate drug is crizotinib. The disease or condition treated with crizotinib can include any disease or condition described herein or for which crizotinib is indicated. For example, in some embodiments, crizotinib is indicated for the treatment of patients with metastatic non-small cell lung cancer (NSCLC) whose tumors are anaplastic lymphoma kinase (ALK) or ROS1-positive as detected by an FDA-approved test. Crizotinib may be administered in a 250 mg or 200 mg dosage form. In some embodiments, crizotinib is administered once daily up to a total daily dose of 250 mg. In some embodiments, crizotinib is administered twice daily up to a total daily dose of 500 mg. For example, when crizotinib is indicated for the treatment of patients with metastatic non-small cell lung cancer (NSCLC) whose tumors are anaplastic lymphoma kinase (ALK) or ROS1-positive as detected by an FDA-approved test, the reference dose is 250 mg, administered twice daily (total daily reference dose is 500 mg). In some embodiments, the patient has severe renal impairment (creatinine clearance <30 mL/min) not requiring dialysis and is administered 250 mg once daily. Thus, in various embodiments, the total daily reference dose of crizotinib may be, for example, 100 mg, 125 mg, 200 mg, 250 mg, 300 mg, 375 mg, 400 mg, or 500 mg. In accordance with certain embodiments of the present disclosure, when the total daily reference dose of crizotinib is, for example, 500 mg, the patient will take a reduced total daily dose of crizotinib (either concomitantly with posaconazole or after a delay period after stopping posaconazole). In some embodiments, the reduced total daily dose of crizotinib is, for example, 100 mg, 125 mg, 200 mg, 250 mg, 300 mg, 375 mg, or 400 mg, including all integers and ranges therebetween. When the total daily reference dose of crizotinib is 500 mg, the reduced total daily dose of crizotinib is, for example, 100 mg, 125 mg, 200 mg, 250 mg, 300 mg, 375 mg, or 400 mg, including all integers and ranges therebetween. When the total daily reference dose of crizotinib is 200 mg, the reduced total daily dose of crizotinib is, for example, 100 mg or 125 mg, including all integers and ranges therebetween. Correspondingly, when the individual reference dose of crizotinib is 250 mg, the reduced individual reference dose of crizotinib is, for example, 100 mg, 125 mg, or 200 mg, including all integers and ranges therebetween. When the individual reference dose of crizotinib is 200 mg, the reduced individual reference dose of crizotinib is, for example, 100 mg or 125 mg, including all integers and ranges therebetween.

In some embodiments, the CYP3A4 substrate drug is dabrafenib. The disease or condition treated with dabrafenib can include any disease or condition described herein or for which dabrafenib is indicated. For example, in some embodiments, dabrafenib is indicated as a single agent for the treatment of patients with unresectable or metastatic melanoma with BRAF V600E mutation as detected by an FDA-approved test. In some embodiments, dabrafenib is indicated in combination with trametinib, for the treatment of patients with unresectable or metastatic melanoma with BRAF V600E or V600K mutations as detected by an FDA-approved test. In some embodiments, dabrafenib is indicated in combination with trametinib, for the adjuvant treatment of patients with melanoma with BRAF V600E or V600K mutations, as detected by an FDA-approved test, and involvement of lymph node(s), following complete resection. In some embodiments, dabrafenib is indicated in combination with trametinib, for the treatment of patients with metastatic non-small cell lung cancer (NSCLC) with BRAF V600E mutation as detected by an FDA-approved test. In some embodiments, dabrafenib is indicated in combination with trametinib, for the treatment of patients with locally advanced or metastatic anaplastic thyroid cancer (ATC) with BRAF V600E mutation and with no satisfactory locoregional treatment options. Dabrafenib may be administered in a 50 mg or 75 mg dosage form. In some embodiments, dabrafenib is administered twice daily up to a total daily dose of 300 mg. In some embodiments, dabrafenib is administered 150 mg orally twice daily (total daily reference dose is 300 mg). For example, when dabrafenib is indicated for the treatment of patients with unresectable or metastatic melanoma with BRAF V600E mutation as detected by an FDA-approved test, the reference dose is 150 mg, administered twice daily (total daily reference dose is 300 mg). When dabrafenib is indicated in combination with trametinib, for the treatment of patients with unresectable or metastatic melanoma with BRAF V600E or V600K mutations as detected by an FDA-approved test, the reference dose is 150 mg, administered twice daily (total daily reference dose is 300 mg). When dabrafenib is indicated in combination with trametinib, for the treatment of patients with metastatic non-small cell lung cancer (NSCLC) with BRAF V600E mutation as detected by an FDA-approved test, the reference dose is 150 mg, administered twice daily (total daily reference dose is 300 mg). When dabrafenib is indicated in combination with trametinib, for the treatment of patients with locally advanced or metastatic anaplastic thyroid cancer (ATC) with BRAF V600E mutation and with no satisfactory locoregional treatment options, the reference dose is 150 mg, administered twice daily (total daily reference dose is 300 mg). Thus, in various embodiments, the total daily reference dose of dabrafenib may be, for example, 25 mg, 50 mg, 75 mg, 100 mg, 125 mg, 150 mg, 175 mg, 200 mg, 225 mg, 250 mg, 275 mg, or 300 mg. In accordance with certain embodiments of the present disclosure, when the total daily reference dose of dabrafenib is, for example, 300 mg, the patient will take a reduced total daily dose of dabrafenib (either concomitantly with posaconazole or after a delay period after stopping posaconazole). In some embodiments, the reduced total daily dose of dabrafenib may be, for example, 25 mg, 50 mg, 75 mg, 100 mg, 125 mg, 150 mg, 175 mg, 200 mg, 225 mg, 250 mg or 275 mg, including all the integers and ranges that lie therebetween. When the total daily reference dose of dabrafenib is 275 mg, the reduced total daily dose of dabrafenib may be, for example, 25 mg, 50 mg, 75 mg, 100 mg, 125 mg, 150 mg, 175 mg, 200 mg, 225 mg or 250 mg, including all the integers and ranges that lie therebetween. When the total daily reference dose of dabrafenib is 250 mg, the reduced total daily dose of dabrafenib may be, for example, 25 mg, 50 mg, 75 mg, 100 mg, 125 mg, 150 mg, 175 mg, 200 mg or 225 mg, including all the integers and ranges that lie therebetween. When the total daily reference dose of dabrafenib is 225 mg, the reduced total daily dose of dabrafenib may be, for example, 25 mg, 50 mg, 75 mg, 100 mg, 125 mg, 150 mg, 175 mg, or 200 mg, including all the integers and ranges that lie therebetween. Correspondingly, when the individual reference dose of dabrafenib is 150 mg, the reduced individual reference dose of dabrafenib may be, for example, 25 mg, 50 mg, 75 mg, 100 mg or 125 mg, including all the integers and ranges that lie therebetween.

In some embodiments, the CYP3A4 substrate drug is daclatasvir. The disease or condition treated with daclatasvir can include any disease or condition described herein or for which daclatasvir is indicated. For example, in some embodiments, daclatasvir is indicated for use with sofosbuvir for the treatment of chronic HCV genotype 1 or 3 infection. In some embodiments, daclatasvir is indicated for use with sofosbuvir and ribavirin, for the treatment of chronic HCV genotype 1 or 3 infection. Daclatasvir may be administered in a 30 mg, 60 mg or 90 mg dosage form. In some embodiments, daclatasvir is administered once daily up to a total daily dose of 90 mg. For example, when daclatasvir is indicated for use with sofosbuvir for the treatment of chronic HCV genotype 1 or 3 infection, the reference dose is 60 mg, administered orally once daily (total daily reference dose is 60 mg). When daclatasvir is indicated for use with sofosbuvir and ribavirin, for the treatment of chronic HCV genotype 1 or 3 infection, the reference dose is 60 mg, administered orally once daily (total daily reference dose is 60 mg). Thus, in various embodiments, the total daily reference dose of daclatasvir may be, for example, 2.5 mg, 5 mg, 10 mg, 15 mg, 30 mg, 45 mg, 60 mg, 75 mg or 90 mg. In accordance with certain embodiments of the present disclosure, when the total daily reference dose of daclatasvir is, for example, 90 mg, the patient will take a reduced total daily dose of daclatasvir (either concomitantly with posaconazole or after a delay period after stopping posaconazole). In some embodiments, the reduced total daily dose of daclatasvir may be, for example, 2.5 mg, 5 mg, 10 mg, 15 mg, 30 mg, 45 mg, 60 mg or 75 mg, including all the integers and ranges that lie therebetween. When the total daily reference dose of daclatasvir is 60 mg, the reduced total daily dose of daclatasvir may be, for example, 2.5 mg, 5 mg, 10 mg, 15 mg, 30 mg, or 45 mg, including all the integers and ranges that lie therebetween. When the total daily reference dose of daclatasvir is 30 mg, the reduced total daily dose of daclatasvir may be, for example, 2.5 mg, 5 mg, 10 mg, 15 mg, 30 mg or 45 mg, including all the integers and ranges that lie therebetween. Correspondingly, when the individual reference dose of daclatasvir is 30 mg, the reduced individual reference dose of daclatasvir may be, for example, 2.5 mg, 5 mg, 10 mg, 15 mg, including all the integers and ranges that lie therebetween. When the individual reference dose of daclatasvir is 60 mg, the reduced individual reference dose of daclatasvir may be, for example, 2.5 mg, 5 mg, 10 mg, 15 mg, 30 mg or 45 mg, including all the integers and ranges that lie therebetween. When the individual reference dose of daclatasvir is 90 mg, the reduced individual reference dose of daclatasvir may be, for example, 2.5 mg, 5 mg, 10 mg, 15 mg, 30 mg, 45 mg, 60 mg or 75 mg, including all the integers and ranges that lie therebetween.

In some embodiments, the CYP3A4 substrate drug is dapagliflozin and saxagliptin. The disease or condition treated with dapagliflozin and saxagliptin can include any disease or condition described herein or for which dapagliflozin and saxagliptin is indicated. For example, in some embodiments, dapagliflozin and saxagliptin is indicated as an adjunct to diet and exercise to improve glycemic control in adults with type 2 diabetes mellitus (T2DM) who have inadequate control with dapagliflozin or who are already treated with dapagliflozin and saxagliptin. Dapagliflozin and saxagliptin may be administered in 10 mg dapagliflozin/5 mg saxagliptin dosage form. In some embodiments, dapagliflozin and saxagliptin is administered once daily. Thus, in various embodiments, the total daily reference dose of dapagliflozin in the dapagliflozin/saxagliptin drug may be, for example, 2.5 mg, 5 mg, 7.5 mg, 10 mg, 15 mg or 20 mg and the total daily reference dose of saxagliptin in the dapagliflozin/saxagliptin drug may be, for example, 1 mg, 2 mg, 3 mg, 4 mg, 5 mg, 8 mg or 10 mg. In accordance with certain embodiments of the present disclosure, when the total daily reference dose of dapagliflozin and saxagliptin is, for example, 10 mg dapagliflozin/5 mg saxagliptin, the patient will take a reduced total daily dose of dapagliflozin and saxagliptin (either concomitantly with posaconazole or after a delay period after stopping posaconazole). In some embodiments, the reduced total daily dose of dapagliflozin in the dapagliflozin/saxagliptin drug may be, for example, 2.5 mg, 5 mg, or 7.5 mg, including all the integers and ranges that lie therebetween and the reduced total daily dose of saxagliptin in the dapagliflozin/saxagliptin drug may be, for example, 1 mg, 2 mg, 3 mg, or 4 mg, including all the integers and ranges that lie therebetween. In some embodiments, when the total daily reference dose of dapagliflozin and saxagliptin is, for example, 5 mg dapagliflozin/2.5 mg saxagliptin, the reduced total daily dose of dapagliflozin in the dapagliflozin/saxagliptin drug may be, for example, 1 mg, 1.5 mg, 2 mg, 2.5 mg, 3 mg, 3.5 mg, 4 mg, or 4.5 mg, including all the integers and ranges that lie therebetween; and the reduced total daily dose of saxagliptin in the dapagliflozin/saxagliptin drug may be, for example, 1 mg, 1.5 mg, or 2 mg, including all the integers and ranges that lie therebetween.

In some embodiments, the CYP3A4 substrate drug is deflazacort. The disease or condition treated with deflazacort can include any disease or condition described herein or for which deflazacort is indicated. For example, in some embodiments, deflazacort is indicated for the treatment of Duchenne muscular dystrophy (DMD) in patients 5 years of age and older. Deflazacort may be administered in a 6 mg, 18 mg, 30 mg, and 36 mg dosage form. In some embodiments, the recommended once-daily dosage of deflazacort is approximately 0.9 mg/kg/day administered orally. For example, when deflazacort is indicated for the treatment of Duchenne muscular dystrophy (DMD) in patients 5 years of age and older, the reference dose is 6 mg, administered once daily (total daily reference dose is 6 mg). In some embodiments, when deflazacort is indicated for the treatment of Duchenne muscular dystrophy (DMD) in patients 5 years of age and older, the reference dose is 18 mg, administered once daily (total daily reference dose is 18 mg). In some embodiments, when deflazacort is indicated for the treatment of Duchenne muscular dystrophy (DMD) in patients 5 years of age and older, the reference dose is 30 mg, administered once daily (total daily reference dose is 30 mg). In some embodiments, when deflazacort is indicated for the treatment of Duchenne muscular dystrophy (DMD) in patients 5 years of age and older, the reference dose is 36 mg, administered once daily (total daily reference dose is 36 mg). Thus, in various embodiments, the total daily reference dose of deflazacort may be, for example, 3 mg, 6 mg, 9 mg, 15 mg, 18 mg, 30 mg, or 36 mg. In accordance with certain embodiments of the present disclosure, when the total daily reference dose of deflazacort is, for example, 36 mg the patient will take a reduced total daily dose of deflazacort (either concomitantly with posaconazole or after a delay period after stopping posaconazole). In some embodiments, the reduced total daily dose of deflazacort may be, for example, 3 mg, 6 mg, 9 mg, 15 mg, 18 mg or 30 mg, including all the integers and ranges that lie therebetween. When the total daily reference dose of deflazacort is 30 mg, the reduced total daily dose of deflazacort may be, for example, 3 mg, 6 mg, 9 mg, 15 mg or 18 mg, including all the integers and ranges that lie therebetween. When the total daily reference dose of deflazacort is 18 mg, the reduced total daily dose of deflazacort may be, for example, 3 mg, 6 mg, 9 mg or 15 mg, including all the integers and ranges that lie therebetween. When the total daily reference dose of deflazacort is 6 mg, the reduced total daily dose of deflazacort may be, for example, 1 mg, 3 mg or 5 mg, including all the integers and ranges that lie therebetween.

In some embodiments, the CYP3A4 substrate drug is duvelisib. The disease or condition treated with duvelisib can include any disease or condition described herein or for which duvelisib is indicated. For example, in some embodiments, duvelisib is indicated for the treatment of adult patients with relapsed or refractory chronic lymphocytic leukemia (CLL) or small lymphocytic lymphoma (SLL) after at least two prior therapies. In some embodiments, duvelisib is indicated for the treatment of adult patients with relapsed or refractory follicular lymphoma (FL) after at least two prior systemic therapies. Duvelisib may be administered in a 15 mg or 25 mg dosage form. In some embodiments, duvelisib is administered orally twice daily. For example, when duvelisib is indicated for the treatment of adult patients with relapsed or refractory chronic lymphocytic leukemia (CLL) or small lymphocytic lymphoma (SLL) after at least two prior therapies, the reference dose is 25 mg administered twice daily (total daily reference dose is 50 mg). For example, when duvelisib is indicated for the treatment of adult patients with relapsed or refractory follicular lymphoma (FL) after at least two prior systemic therapies, the reference dose is 25 mg administered twice daily (total daily reference dose is 50 mg). Thus, in various embodiments, the total daily reference dose of duvelisib may be, for example, 2.5 mg 5 mg, 10 mg, 15 mg, 20 mg, 25 mg, 30 mg, 40 mg or 50 mg. In accordance with certain embodiments of the present disclosure, when the total daily reference dose of duvelisib is, for example, 50 mg, the patient will take a reduced total daily dose of duvelisib (either concomitantly with posaconazole or after a delay period after stopping posaconazole). In some embodiments, the reduced total daily dose of duvelisib may be, for example, 10 mg, 15 mg, 20 mg, 25 mg, 30 mg or 40 mg, including all the integers and ranges that lie therebetween. When the total daily reference dose of duvelisib is 40 mg, the reduced total daily dose of duvelisib may be, for example, 10 mg, 15 mg, 20 mg, 25 mg or 30 mg, including all the integers and ranges that lie therebetween. When the total daily reference dose of duvelisib is 30 mg, the reduced total daily dose of duvelisib may be, for example, 10 mg, 15 mg, 20 mg or 25 mg, including all the integers and ranges that lie therebetween. Correspondingly, when the individual reference dose of duvelisib is 15 mg g, the reduced individual reference dose of duvelisib may be, for example, 2.5 mg 5 mg or 10 mg, including all the integers and ranges that lie therebetween. When the individual reference dose of duvelisib is 25 mg, the reduced individual reference dose of duvelisib may be, for example, 2.5 mg 5 mg, 10 mg, 15 mg, 20 mg, including all the integers and ranges that lie therebetween.

In some embodiments, the CYP3A4 substrate drug is elbasvir and grazoprevir. The disease or condition treated with elbasvir and grazoprevir can include any disease or condition described herein or for which elbasvir and grazoprevir is indicated. For example, in some embodiments, elbasvir and grazoprevir is indicated for treatment of chronic HCV genotype 1 or 4 infection in adults. In some embodiments, elbasvir and grazoprevir is indicated for use with ribavirin in certain patient populations. Elbasvir and grazoprevir may be administered in a 50 mg elbasvir and 100 mg grazoprevir dosage form. In some embodiments, elbasvir and grazoprevir is administered once daily. For example, when elbasvir and grazoprevir is indicated for treatment of chronic HCV genotype 1 or 4 infection in adults, the reference dose is 50 mg elbasvir and 100 mg grazoprevir administered once daily (total daily reference dose is 50 mg elbasvir and 100 mg grazoprevir). For example, when elbasvir and grazoprevir is indicated for use with ribavirin in certain patient populations, the reference dose is 50 mg elbasvir and 100 mg grazoprevir administered once daily (total daily reference dose is 50 mg elbasvir and 100 mg grazoprevir). Thus, in various embodiments, the total daily reference dose of elbasvir and grazoprevir may be, for example, 5 mg elbasvir and 10 mg grazoprevir, 10 mg elbasvir and 25 mg grazoprevir, 25 mg elbasvir and 50 mg grazoprevir or 50 mg elbasvir and 100 mg grazoprevir. In accordance with certain embodiments of the present disclosure, when the total daily reference dose of elbasvir and grazoprevir is, for example, 50 mg elbasvir and 100 mg grazoprevir, the patient will take a reduced total daily dose of elbasvir and grazoprevir (either concomitantly with posaconazole or after a delay period after stopping posaconazole). In some embodiments, the reduced total daily dose of elbasvir in the elbasvir/grazoprevir drug may be, for example, 5 mg, 10 mg, 20 mg, 30 mg, or 40 mg, including all the integers and ranges that lie therebetween. In some embodiments, the reduced total daily dose of grazoprevir in the elbasvir/grazoprevir drug may be, for example, 10 mg, 20 mg, 30 mg, 40 mg, 50 mg, 60 mg, 70 mg, 80 mg or 90 mg, including all the integers and ranges that lie therebetween. In some embodiments, when the total daily reference dose of elbasvir and grazoprevir is, for example, 25 mg elbasvir and 50 mg grazoprevir, the reduced total daily dose of elbasvir may be, for example, 1 mg, 5 mg, 10 mg, 15 mg, or 20 mg, including all the integers and ranges that lie therebetween; and the reduced total daily dose of grazoprevir may be, for example, 10 mg, 20 mg, 30 mg, or 40 mg.

In some embodiments, the CYP3A4 substrate drug is encorafenib. The disease or condition treated with encorafenib can include any disease or condition described herein or for which encorafenib is indicated. For example, in some embodiments, encorafenib is indicated, in combination with binimetinib, for the treatment of patients with unresectable or metastatic melanoma with a BRAF V600E or V600K mutation, as detected by an FDA-approved test. Encorafenib may be administered in a 50 mg and 75 mg dosage form. In some embodiments, when encorafenib is indicated, in combination with binimetinib, for the treatment of patients with unresectable or metastatic melanoma with a BRAF V600E or V600K mutation, as detected by an FDA-approved test, the reference dose is 450 mg of encorafenib administered once daily (total daily reference dose is 450 mg). Thus, in various embodiments, the total daily reference dose of encorafenib may be, for example, 25 mg, 50 mg, 35 mg, 75 mg, 100 mg, 150 mg, 200 mg, 250 mg, 300 mg, 350 mg, 400 mg, 450 mg, or 500 mg. In accordance with certain embodiments of the present disclosure, when the total daily reference dose of encorafenib is, for example, 450 mg, the patient will take a reduced total daily dose of encorafenib (either concomitantly with posaconazole or after a delay period after stopping posaconazole). In some embodiments, the reduced total daily dose of encorafenib may be, for example, 25 mg, 35 mg, 50 mg, 75 mg, 100 mg, 150 mg, 200 mg, 250 mg, 300 mg, 350 mg, or 400 mg, including all integers and ranges therebetween. When the total daily reference dose of encorafenib is 450 mg, the reduced total daily dose of encorafenib may be, for example, 25 mg, 35 mg, 50 mg, 75 mg, 100 mg, 150 mg, 200 mg, 250 mg, 300 mg, 350 mg, or 400 mg, including all integers and ranges therebetween. When the total daily reference dose of encorafenib is 400 mg, the reduced total daily dose of encorafenib may be, for example, 25 mg, 35 mg, 50 mg, 75 mg, 100 mg, 150 mg, 200 mg, 250 mg, 300 mg or 350 mg, including all integers and ranges therebetween. When the total daily reference dose of encorafenib is 350 mg, the reduced total daily dose of encorafenib may be, for example, 25 mg, 35 mg, 50 mg, 75 mg, 100 mg, 150 mg, 200 mg, 250 mg or 300 mg, including all integers and ranges therebetween. Correspondingly, when the individual reference dose of encorafenib is 75 g, the reduced individual reference dose of encorafenib may be, for example, 25 mg, 35 mg or 50 mg, including all integers and ranges therebetween. When the individual reference dose of encorafenib is 50 mg, the reduced individual reference dose of encorafenib may be, for example, 10 mg, 25 mg or 35 mg, including all integers and ranges therebetween.

In some embodiments, the CYP3A4 substrate drug is flibanserin. The disease or condition treated with flibanserin can include any disease or condition described herein or for which flibanserin is indicated. For example, in some embodiments, flibanserin is indicated for the treatment of premenopausal women with acquired, generalized hypoactive sexual desire disorder (HSDD) as characterized by low sexual desire that causes marked distress or interpersonal difficulty and is not due to a co-existing medical or psychiatric condition; problems within the relationship; or the effects of a medication or other drug substance. Flibanserin may be administered in a 100 mg dosage form. In some embodiments, flibanserin is administered once daily. For example, when flibanserin is indicated for the treatment of premenopausal women with acquired, generalized hypoactive sexual desire disorder (HSDD) as characterized by low sexual desire that causes marked distress or interpersonal difficulty and is not due to a co-existing medical or psychiatric condition; problems within the relationship; or the effects of a medication or other drug substance, the reference dose is 100 mg, administered once daily (total daily reference dose is 100 mg). In various embodiments, the total daily reference dose of flibanserin may be, for example, 25 mg, 50 mg, 75 mg, or 100 mg. In accordance with certain embodiments of the present disclosure, when the total daily reference dose of flibanserin is, for example, 100 mg, the patient will take a reduced total daily dose of flibanserin (either concomitantly with posaconazole or after a delay period after stopping posaconazole). In some embodiments, the reduced total daily dose of flibanserin may be, for example, 25 mg, 50 mg, or 75 mg, including all integers and ranges therebetween. When the total daily reference dose of flibanserin is 100 mg, the reduced total daily dose of flibanserin may be, for example, 25 mg, 50 mg, or 75 mg, including all integers and ranges therebetween. Correspondingly, when the individual reference dose of flibanserin is 100 mg, the reduced individual reference dose of flibanserin may be, for example, 25 mg, 50 mg, or 75 mg, including all integers and ranges therebetween.

In some embodiments, the CYP3A4 substrate drug is fluticasone propionate and salmeterol. The disease or condition treated with fluticasone propionate and salmeterol can include any disease or condition described herein or for which fluticasone propionate and salmeterol is indicated. For example, in some embodiments, fluticasone propionate and salmeterol is indicated for treatment of asthma in patients aged 12 years or older. Fluticasone propionate may be administered in a 45, 115, or 230 mcg dosage form, in combination with salmeterol in a 21 mcg dosage form, as an aerosol formulation for oral inhalation. In some embodiments, fluticasone propionate and salmeterol is administered twice daily. For example, in some embodiments, when fluticasone propionate and salmeterol is indicated for treatment of asthma in patients aged 12 years or older, the reference dose is 45 mcg fluticasone propionate and 21 mcg salmeterol, administered twice daily (total daily reference dose is 90 mcg fluticasone propionate and 42 mcg salmeterol). In some embodiments, when fluticasone propionate and salmeterol is indicated for treatment of asthma in patients aged 12 years or older, the reference dose is 115 mcg fluticasone propionate and 21 mcg salmeterol, administered twice daily (total daily reference dose is 230 mcg fluticasone propionate and 42 mcg salmeterol). In some embodiments, when fluticasone propionate and salmeterol is indicated for treatment of asthma in patients aged 12 years or older, the reference dose is 230 mcg fluticasone propionate and 21 mcg salmeterol, administered twice daily (total daily reference dose is 460 mcg fluticasone propionate and 42 mcg salmeterol). Thus, in various embodiments, the total daily reference dose of fluticasone propionate may be, for example, 10 mcg, 20 mcg, 40 mcg, 45 mcg, 60 mcg, 90 mcg, 115 mcg, 230 mcg, 300 mcg, 400 mcg or 460 mcg and the total daily reference dose of salmeterol may be, for example, 5 mcg, 10 mcg, 15 mcg, 21 mcg, 42 mcg, 63 mcg, or 84 mcg. In accordance with certain embodiments of the present disclosure, when the total daily reference dose of fluticasone propionate is, for example, 460 mcg, and the total daily reference dose of salmeterol is 42 mcg, the patient will take a reduced total daily dose of fluticasone propionate and salmeterol (either concomitantly with posaconazole or after a delay period after stopping posaconazole). In some embodiments, the reduced total daily dose of fluticasone propionate may be, for example, 10 mcg, 20 mcg, 40 mcg, 45 mcg, 60 mcg, 90 mcg, 115 mcg, 230 mcg, 300 mcg, or 400 mcg, including all integers and ranges therebetween; and the reduced total daily dose of salmeterol may be, for example, 5 mcg, 10 mcg, 15 mcg, 21 mcg, 30 mcg, or 35 mcg, including all integers and ranges therebetween. When the total daily reference dose of fluticasone propionate is 230 mcg and the total daily reference dose of salmeterol is 42 mcg, the reduced total daily dose of fluticasone propionate may be, for example, 10 mcg, 20 mcg, 40 mcg, 45 mcg, 60 mcg, 90 mcg, or 115 mcg; and the reduced total daily dose of salmeterol may be, for example, 5 mcg, 10 mcg, 15 mcg or 21 mcg, 30 mcg, or 35 mcg, including all integers and ranges therebetween. When the total daily reference dose of fluticasone propionate is 90 mcg and the total daily dose of salmeterol is 42 mcg, the reduced total daily dose of fluticasone propionate may be, for example, 10 mcg, 20 mcg, 40 mcg, 45 mcg, or 60 mcg, including all integers and ranges therebetween and the reduced total daily dose of salmeterol is 5 mcg, 10 mcg, or 15 mcg, 30 mcg, or 35 mcg, including all integers and ranges therebetween. Correspondingly, when the individual reference dose of fluticasone propionate is 45 mcg and the individual reference dose of salmeterol is 21 mcg, the reduced individual reference dose of fluticasone propionate may be, for example, 5 mcg, 10 mcg, 15 mcg, 20 mcg, 30 mcg, or 40 mcg, including all integers and ranges therebetween and the reduced individual reference dose of salmeterol may be, for example, 5 mcg, 10 mcg or 15 mcg, including all integers and ranges therebetween. When the individual reference dose of fluticasone propionate is 115 mcg and the individual reference dose of salmeterol is 21 mcg, the reduced individual reference dose of fluticasone propionate may be, for example, 100 mcg, 90 mcg, 45 mcg, 30 mcg, 20 mcg, 10 mcg or 5 mcg, including all integers and ranges therebetween and the reduced individual reference dose of salmeterol may be, for example, 5 mcg, 10 mcg or 15 mcg, including all integers and ranges therebetween. When the individual reference dose of fluticasone propionate is 230 mcg and the individual reference dose of salmeterol is 21 mcg, the reduced individual reference dose of fluticasone propionate may be, for example, 5 mcg, 10 mcg, 20 mcg, 30 mcg, 45 mcg, 90 mcg, 100 mcg, 200 mcg, including all integers and ranges therebetween and the reduced individual reference dose of salmeterol may be, for example, 5 mcg, 10 mcg or 15 mcg, including all integers and ranges therebetween.

In some embodiments, the CYP3A4 substrate drug is ibrutinib. The disease or condition treated with ibrutinib can include any disease or condition described herein or for which ibrutinib is indicated. For example, in some embodiments, ibrutinib is indicated for the treatment of adult patients with mantle cell lymphoma (MCL) who have received at least one prior therapy. In some embodiments, ibrutinib is indicated for the treatment of chronic lymphocytic leukemia (CLL)/Small lymphocytic lymphoma (SLL). In some embodiments, ibrutinib is indicated for the treatment of chronic lymphocytic leukemia (CLL)/Small lymphocytic lymphoma (SLL) with 17p deletion. In some embodiments, ibrutinib is indicated for the treatment of waldenström's macroglobulinemia (WM). In some embodiments, ibrutinib is indicated for the treatment of Marginal zone lymphoma (MZL) who require systemic therapy and have received at least one prior anti-CD20-based therapy. In some embodiments, ibrutinib is indicated for the treatment of chronic graft versus host disease (cGVHD) after failure of one or more lines of systemic therapy. Ibrutinib may be administered as capsules in 70 mg or 140 mg dosage form; or as tablets in 140 mg, 280 mg, 420 mg, or 560 mg dosage forms. In some embodiments, ibrutinib is administered once daily. In some embodiments, when ibrutinib is indicated for the treatment of adult patients with mantle cell lymphoma (MCL) who have received at least one prior therapy, the reference dose 560 mg, administered once daily (total daily reference dose is 560 mg). In some embodiments, when ibrutinib is indicated for the treatment of Marginal zone lymphoma (MZL) who require systemic therapy and have received at least one prior anti-CD20-based therapy, the reference dose is 560 mg, administered once daily (total daily reference dose is 560 mg). In some embodiments, when ibrutinib is indicated for the treatment of chronic lymphocytic leukemia (CLL)/Small lymphocytic lymphoma (SLL), the reference dose is 420 mg, administered once daily (total daily reference dose is 420 mg). In some embodiments, when ibrutinib is indicated for the treatment of waldenström's macroglobulinemia (WM), the reference dose is 420 mg administered once daily (total daily reference dose is 420 mg). In some embodiments, when ibrutinib is indicated for the treatment of chronic graft versus host disease (cGVHD) after failure of one or more lines of systemic therapy, the reference dose is 420 mg, administered once daily (total daily reference dose is 420 mg). Thus, in various embodiments, the total daily reference dose of ibrutinib may be, for example, 25 mg, 50 mg, 70 mg, 100 mg, 140 mg, 200 mg, 280 mg, 300 mg, 350 mg, 400 mg, 420 mg, 450 mg, 500 mg or 550 mg or 560 mg. In accordance with certain embodiments of the present disclosure, when the total daily reference dose of ibrutinib is, for example, 560 mg, the patient will take a reduced total daily dose of ibrutinib (either concomitantly with posaconazole or after a delay period after stopping posaconazole). In some embodiments, the reduced total daily dose of ibrutinib may be, for example, 25 mg, 50 mg, 70 mg, 100 mg, 140 mg, 200 mg, 280 mg, 300 mg, 350 mg, 400 mg, 420 mg, 450 mg, 500 mg or 550 mg, including all integers and ranges therebetween. When the total daily reference dose of ibrutinib is 420 mg, the reduced total daily dose of ibrutinib may be, for example, 25 mg, 50 mg, 70 mg, 100 mg, 140 mg, 200 mg, 280 mg, 300 mg, 350 mg, or 400 mg, including all integers and ranges therebetween. When the total daily reference dose of ibrutinib is 280 mg, the reduced total daily dose of ibrutinib may be, for example, 25 mg, 50 mg, 70 mg, 100 mg, 140 mg, or 200 mg, including all integers and ranges therebetween. When the total daily reference dose of ibrutinib is 140 mg, the reduced total daily dose of ibrutinib may be, for example, 25 mg, 50 mg, 70 mg, or 100 mg, including all integers and ranges therebetween. When the total daily reference dose of ibrutinib is 70 mg, the reduced total daily dose of ibrutinib may be, for example, 25 mg or 50 mg, including all integers and ranges therebetween. Correspondingly, when the individual reference dose of ibrutinib is 70 mg, the reduced individual reference dose of ibrutinib may be, for example, 10 mg, 20 mg, 30 mg, 40 mg, 50 mg, or 60 mg, including all integers and ranges therebetween. When the individual reference dose of ibrutinib is 140 mg, the reduced individual reference dose of ibrutinib may be, for example, 10 mg, 20 mg, 30 mg, 40 mg, 50 mg, 60 mg, 70 mg, 80 mg, 90 mg, 100 mg, 110 mg, 120 mg, or 130 mg, including all integers and ranges therebetween. When the individual reference dose of ibrutinib is 280 mg, the reduced individual reference dose of ibrutinib may be, for example, 10 mg, 50 mg, 100 mg, 150 mg, 200 mg, or 250 mg, including all integers and ranges therebetween. When the individual reference dose of ibrutinib is 420 mg, the reduced individual reference dose of ibrutinib may be, for example, 50 mg, 100 mg, 150 mg, 200 mg, 250 mg, 300 mg or 400 mg including all integers and ranges therebetween. When the individual reference dose of ibrutinib is 560 mg, the reduced individual reference dose of ibrutinib may be, for example, 50 mg, 100 mg, 150 mg, 200 mg, 250 mg, 300 mg, 400 mg, 420 mg, 450 mg, 500 mg, or 550 mg, including all integers and ranges therebetween.

In some embodiments, the CYP3A4 substrate drug is ivabradine. The disease or condition treated with ivabradine can include any disease or condition described herein or for which ivabradine is indicated. For example, in some embodiments, ivabradine is indicated to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use. Ivabradine may be administered in a 5 mg or 7.5 mg dosage form. In some embodiments, ivabradine is administered twice daily. In some embodiments, when ivabradine is indicated to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the reference dose is 5 mg administered twice daily (total daily reference dose is 10 mg). In some embodiments, when ivabradine is indicated to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the reference dose is 7.5 mg, administered twice daily (total daily reference dose is 15 mg). In some embodiments, when ivabradine is indicated to reduce the risk of hospitalization for worsening heart failure in patients with stable, symptomatic chronic heart failure with left ventricular ejection fraction ≤35%, who are in sinus rhythm with resting heart rate ≥70 beats per minute; either are on maximally tolerated doses of beta-blockers or have a contraindication to beta-blocker use and with conduction defects or in whom bradycardia could lead to hemodynamic compromise, the reference dose is 2.5 mg, administered twice daily (total daily reference dose is 5 mg). In various embodiments, the total daily reference dose of ivabradine may be, for example, 1 mg, 2 mg, 3 mg, 4 mg, 5 mg, 10 mg, or 15 mg. In accordance with certain embodiments of the present disclosure, when the total daily reference dose of ivabradine is, for example, 15 mg, the patient will take a reduced total daily dose of ivabradine (either concomitantly with posaconazole or after a delay period after stopping posaconazole). In some embodiments, the reduced total daily dose of ivabradine may be, for example, 1 mg, 2 mg, 3 mg, 4 mg, 5 mg or 10 mg, including all integers and ranges therebetween. When the total daily reference dose of ivabradine is 10 mg, the reduced total daily dose of ivabradine may be, for example, 1 mg, 2 mg, 3 mg, 4 mg, 5 mg, 6 mg, 7 mg, 8 mg, 9 mg, including all integers and ranges therebetween. When the total daily reference dose of ivabradine is 5 mg, the reduced total daily dose of ivabradine may be, for example, 1 mg, 2 mg, 3 mg or 4 mg, including all integers and ranges therebetween. Correspondingly, when the individual reference dose of ivabradine is 7.5 g, the reduced individual reference dose of ivabradine may be, for example, 1 mg, 2 mg, 3 mg, 4 mg, 5 mg or 6 mg, including all integers and ranges therebetween. When the individual reference dose of ivabradine is 5 mg, the reduced individual reference dose of ivabradine may be, for example, 1 mg, 2 mg, 3 mg, or 4 mg, including all integers and ranges therebetween. When the individual reference dose of ivabradine is 2.5 mg, the reduced individual reference dose of ivabradine may be, for example, 0.5 mg, 1 mg, 1.5 mg or 2 mg, including all integers and ranges therebetween.

In some embodiments, the CYP3A4 substrate drug is ivacaftor. The disease or condition treated with ivacaftor can include any disease or condition described herein or for which ivacaftor is indicated. For example, in some embodiments, ivacaftor is indicated for the treatment of cystic fibrosis (CF) in patients age 12 months and older who have one mutation in the CFTR gene that is responsive to ivacaftor based on clinical and/or in vitro assay data. Ivacaftor may be administered as a tablet in a 150 mg dosage form or as oral granules in unit packets of 50 mg or 75 mg. In some embodiments, ivacaftor is administered twice daily up to a total daily dose of 300 mg to adults and pediatric patients age 6 years and older. In some embodiments, ivacaftor is administered twice daily up to a total daily dose of 100 mg to pediatric patients 12 months to less than 6 years of age and weighing 7 kg to less than 14 kg. In some embodiments, ivacaftor is administered twice daily up to a total daily dose of 150 mg to pediatric patients 12 months to less than 6 years of age and 14 kg or greater. In various embodiments, the total daily reference dose of ivacaftor may be, for example, 25 mg, 50 mg, 75 mg, 100 mg, 125 mg, 150 mg, 200 mg, 250 mg or 300 mg. In accordance with certain embodiments of the present disclosure, when the total daily reference dose of ivacaftor is, for example, 300 mg, the patient will take a reduced total daily dose of ivacaftor (either concomitantly with posaconazole or after a delay period after stopping posaconazole). In some embodiments, the reduced total daily dose of ivacaftor may be, for example, 25 mg, 50 mg, 75 mg, 100 mg, 125 mg, 150 mg, 200 mg, or 250 mg, including all integers and ranges therebetween. When the total daily reference dose of ivacaftor is 300 mg, the reduced total daily dose of ivacaftor may be, for example, 25 mg, 50 mg, 75 mg, 100 mg, 125 mg, 150 mg, 200 mg, or 250 mg, including all integers and ranges therebetween. When the total daily reference dose of ivacaftor is 150 mg, the reduced total daily dose of ivacaftor may be, for example, 25 mg, 50 mg, 75 mg, 100 mg, or 125 mg, including all integers and ranges therebetween. When the total daily reference dose of ivacaftor is 100 mg, the reduced total daily dose of ivacaftor may be, for example, 25 mg, 50 mg, or 75 mg, including all integers and ranges therebetween. Correspondingly, when the individual reference dose of ivacaftor is 150 mg, the reduced individual reference dose of ivacaftor may be, for example, 25 mg, 50 mg, 75 mg, 100 mg, or 125 mg, including all integers and ranges therebetween. When the individual reference dose of ivacaftor is 75 mg, the reduced individual reference dose of ivacaftor may be, for example, 5 mg, 10 mg, 15 mg, 20 mg, 25 mg or 50 mg, including all integers and ranges therebetween. When the individual reference dose of ivacaftor is 50 mg, the reduced individual reference dose of ivacaftor may be, for example, 5 mg, 10 mg, 15 mg, 20 mg, or 25 mg, including all integers and ranges therebetween.

In some embodiments, the CYP3A4 substrate drug is lumacaftor and ivacaftor. The disease or condition treated with lumacaftor and ivacaftor can include any disease or condition described herein or for which lumacaftor and ivacaftor is indicated. For example, in some embodiments, lumacaftor and ivacaftor is indicated for the treatment of cystic fibrosis (CF) in patients age 2 years and older who are homozygous for the F508del mutation in the CFTR gene. In some embodiments, lumacaftor and ivacaftor may be administered in the form of tablets containing a 100 mg lumacaftor and 125 mg ivacaftor; or 200 mg lumacaftor and 125 mg ivacaftor. In some embodiments, lumacaftor and ivacaftor may be administered as oral granules in unit-dose packets of 100 mg lumacaftor and 125 mg ivacaftor; or 150 mg lumacaftor and 188 mg ivacaftor. In some embodiments, lumacaftor and ivacaftor is administered as one packet of granules containing 100 mg lumacaftor and 125 mg ivacaftor twice daily (total daily reference dose is 200 mg lumacaftor and 250 mg ivacaftor) in pediatric patients of age 2 through 5 years and weighing less than 14 kg. In some embodiments, lumacaftor and ivacaftor is administered as one packet of granules containing 150 mg lumacaftor and 188 mg ivacaftor twice daily (total daily reference dose is 300 mg lumacaftor and 376 mg ivacaftor) in pediatric patients of age 2 through 5 years and weighing 14 kg or greater. In some embodiments, lumacaftor and ivacaftor is administered as two tablets each containing lumacaftor 100 mg/ivacaftor 125 mg twice daily (total daily reference dose of 400 mg lumacaftor and 500 mg ivacaftor) in pediatric patients of age 6 through 11 years. In some embodiments, lumacaftor and ivacaftor is administered as two tablets each containing lumacaftor 200 mg/ivacaftor 125 mg twice daily up (total daily reference dose is 800 mg lumacaftor and 500 mg ivacaftor) in adults and pediatric patients of age 12 years and older. Thus, in various embodiments, the total daily reference dose of lumacaftor is 200 mg, 300 mg, 400 mg or 800 mg and the total daily reference dose of ivacaftor is 250 mg, 376 mg or 500 mg. In accordance with certain embodiments of the present disclosure, when the total daily reference dose of lumacaftor is, for example, 800 mg, the patient will take a reduced total daily dose of lumacaftor (either concomitantly with posaconazole or after a delay period after stopping posaconazole). Therefore, in some embodiments, the reduced total daily dose of lumacaftor in the lumacaftor/ivacaftor drug may be, for example, 50 mg, 100 mg, 200 mg, 300 mg, 400 mg, 500 mg, 600 mg or 700 mg, including all integers and ranges therebetween. In some embodiments, when the total daily reference dose of lumacaftor is 400 mg, the reduced total daily dose of lumacaftor in the lumacaftor/ivacaftor drug may be, for example, 50 mg, 100 mg, 200 mg or 300 mg, including all integers and ranges therebetween. In some embodiments, when the total daily reference dose of lumacaftor is 300 mg, the reduced total daily dose of lumacaftor in the lumacaftor/ivacaftor drug may be, for example, 50 mg, 100 mg or 200 mg, including all integers and ranges therebetween. Correspondingly, in some embodiments, when the individual reference dose of lumacaftor is 100 mg then the reduced individual reference dose of lumacaftor in the lumacaftor/ivacaftor drug may be, for example, 10 mg, 25 mg, 50 mg or 75 mg, including all integers and ranges therebetween. In some embodiments, when the individual reference dose of lumacaftor is 150 mg then the reduced individual reference dose of lumacaftor in the lumacaftor/ivacaftor drug may be, for example, 10 mg, 25 mg, 50 mg, 75 mg, 100 mg or 125 mg, including all integers and ranges therebetween. In some embodiments, when the individual reference dose of lumacaftor is 188 mg then the reduced individual reference dose of lumacaftor in the lumacaftor/ivacaftor drug may be, for example, 10 mg, 25 mg, 50 mg, 75 mg, 100 mg, 125 mg or 150 mg, including all integers and ranges therebetween. In some embodiments, when the total daily reference dose of ivacaftor is for example, 500 mg, the patient will take a reduced total daily dose of ivacaftor (either concomitantly with posaconazole or after a delay period after stopping posaconazole). Thus, in some embodiments, the reduced total daily dose of ivacaftor in the lumacaftor/ivacaftor drug may be, for example, 50 mg, 100 mg, 150 mg, 200 mg, 250 mg, 300 mg, 350 mg, 376 mg 400 mg or 450 mg, including all integers and ranges therebetween. In some embodiments, when the total reference dose of ivacaftor is 376 mg, the reduced total daily dose of ivacaftor in the lumacaftor/ivacaftor drug may be, for example, 50 mg, 100 mg, 150 mg, 200 mg, 250 mg, 300 mg or 350 mg, including all integers and ranges therebetween. In some embodiments, when the total daily dose of ivacaftor is 250 mg, the reduced total daily dose of ivacaftor in the lumacaftor/ivacaftor drug may be, for example, 50 mg, 100 mg, 150 mg or 200 mg, including all integers and ranges therebetween. Correspondingly, in some embodiments, when the individual reference dose of ivacaftor is 188 mg, then the reduced individual reference dose of ivacaftor in the lumacaftor/ivacaftor drug may be, for example, 10 mg, 25 mg, 50 mg, 75 mg, 100 mg, 125 mg or 150 mg, including all integers and ranges therebetween. In some embodiments, when the individual reference dose of ivacaftor is 125 mg then the reduced individual reference dose of ivacaftor in the lumacaftor/ivacaftor drug may be, for example, 10 mg, 25 mg, 50 mg, 75 mg or 100 mg, including all integers and ranges therebetween.

In some embodiments, the CYP3A4 substrate drug is tezacaftor and ivacaftor. The disease or condition treated with tezacaftor and ivacaftor can include any disease or condition described herein or for which tezacaftor and ivacaftor is indicated. For example, in some embodiments, tezacaftor and ivacaftor is indicated for the treatment of patients with cystic fibrosis (CF) aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence. Tezacaftor and ivacaftor may be administered as fixed dose combination tablets containing 100 mg tezacaftor and 150 mg ivacaftor; and tablets containing 150 mg ivacaftor. In some embodiments, a tezacaftor/ivacaftor combination tablet and an ivacaftor tablet are administered about 12 hours apart in adults and pediatric patients ages 12 years and older. That is, when tezacaftor and ivacaftor is indicated for the treatment of patients with cystic fibrosis (CF) aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, the reference dose for tezacaftor is 100 mg administered once daily and the reference dose for ivacaftor is 150 mg administered twice daily (total daily reference dose of tezacaftor is 100 mg and total daily reference dose of ivacaftor is 300 mg). In various embodiments, the total daily reference dose of tezacaftor may be, for example, 10 mg, 25 mg, 50 mg, 75 mg, 100 mg, or 200 mg; and the total daily reference dose of ivacaftor may be, for example, 10 mg, 25 mg, 50 mg, 75 mg, 100 mg, 150 mg, 200 mg, 250 mg or 300 mg. In accordance with certain embodiments of the present disclosure, when the total daily reference dose of tezacaftor and ivacaftor is, for example, 100 mg tezacaftor/300 mg ivacaftor, the patient will take a reduced total daily dose of tezacaftor and ivacaftor (either concomitantly with posaconazole or after a delay period after stopping posaconazole). In some embodiments, the reduced total daily dose of tezacaftor may be, for example, 10 mg, 25 mg, 50 mg, or 75 mg, including all integers and ranges therebetween and the reduced total daily dose of ivacaftor may be, for example, 50 mg, 75 mg, 100 mg, 150 mg, 200 mg or 250 mg, including all integers and ranges therebetween. When the total daily reference dose of tezacaftor 75 mg, the reduced total daily dose of tezacaftor may be, for example, 10 mg, 25 mg or 50 mg, including all integers and ranges therebetween. When the total daily reference dose of ivacaftor is 200 mg, the reduced total daily dose of ivacaftor may be, for example, 50 mg, 75 mg, 100 mg, or 150 mg, including all integers and ranges therebetween. Correspondingly, when the individual reference dose of tezacaftor 100 mg, the reduced individual reference dose of tezacaftor may be, for example, 10 mg, 25 mg, 50 mg or 75 mg, including all integers and ranges therebetween. When the individual reference dose of ivacaftor is 150 mg, the reduced individual reference dose of ivacaftor may be, for example, 10 mg, 25 mg, 50 mg, 75 mg, or 100 mg, including all integers and ranges therebetween.

In some embodiments, the CYP3A4 substrate drug is ivosidenib. The disease or condition treated with ivosidenib can include any disease or condition described herein or for which ivosidenib is indicated. For example, in some embodiments, ivosidenib is indicated for the treatment of adult patients with relapsed or refractory acute myeloid leukemia (AML) with a susceptible IDH1 mutation as detected by an FDA-approved test. Ivosidenib may be administered in a 250 mg dosage form. In some embodiments, 500 mg of ivosidenib is administered once daily. For example, when ivosidenib is indicated for the treatment of adult patients with relapsed or refractory acute myeloid leukemia (AML) with a susceptible IDH1 mutation as detected by an FDA-approved test, the reference dose is 500 mg administered once daily (total daily reference dose is 500 mg). In various embodiments, the total daily reference dose of ivosidenib may be, for example, 125 mg, 250 mg, 375 mg, or 500 mg. In accordance with certain embodiments of the present disclosure, when the total daily reference dose of ivosidenib is, for example, 500 mg, the patient will take a reduced total daily dose of ivosidenib (either concomitantly with posaconazole or after a delay period after stopping posaconazole). In some embodiments, the reduced total daily dose of ivosidenib may be, for example, 10 mg, 25 mg, 50 mg, 100 mg, 125 mg, 150 mg, 200 mg, 250 mg, 300 mg, 375 mg, 400 mg, 450 mg, or 470 mg, including all integers and ranges therebetween. When the total daily reference dose of ivosidenib is 500 mg, the reduced total daily dose of ivosidenib may be, for example, 10 mg, 25 mg, 50 mg, 100 mg, 125 mg, 150 mg, 200 mg, 250 mg, 300 mg, 375 mg, 400 mg, 450 mg, or 470 mg, including all integers and ranges therebetween. When the total daily reference dose of ivosidenib is 250 mg, the reduced total daily dose of ivosidenib may be, for example, 10 mg, 25 mg, 50 mg, 100 mg, 125 mg, 150 mg, or 200 mg, including all integers and ranges therebetween. Correspondingly, when the individual reference dose of ivosidenib is 250 mg, the reduced individual reference dose of ivosidenib may be, for example, 10 mg, 25 mg, 50 mg, 100 mg, 125 mg, 150 mg, or 200 mg, including all integers and ranges therebetween.

In some embodiments, the CYP3A4 substrate drug is naloxegol. The disease or condition treated with naloxegol can include any disease or condition described herein or for which naloxegol is indicated. For example, in some embodiments, naloxegol is indicated for the treatment of opioid-induced constipation (OIC) in adult patients with chronic non-cancer pain, including patients with chronic pain related to prior cancer or its treatment who do not require frequent (e.g., weekly) opioid dosage escalation. Naloxegol may be administered in a 12.5 mg or 25 mg dosage form. In some embodiments, naloxegol is administered once daily up to a total daily dose of 25 mg. For example, when naloxegol is indicated for the treatment of opioid-induced constipation (OIC) in adult patients with chronic non-cancer pain, including patients with chronic pain related to prior cancer or its treatment who do not require frequent (e.g., weekly) opioid dosage escalation, the reference dose is 25 mg, administered once daily (total daily reference dose is 25 mg). If the reference dose of 25 mg is not tolerated, reduce to 12.5 mg once daily (total daily reference dose is 12.5 mg). For renal impairment (CLcr<60 mL/min), the reference dose is 12.5 mg once daily and increases to 25 mg once daily if tolerated and monitor for adverse reactions. Thus, in various embodiments, the total daily reference dose of naloxegol may be, for example, 5 mg, 10 mg, 15 mg, 20 mg, or 25 mg. In accordance with certain embodiments of the present disclosure, when the total daily reference dose of naloxegol is, for example, 25 mg, the patient will take a reduced total daily dose of naloxegol (either concomitantly with posaconazole or after a delay period after stopping posaconazole). In some embodiments, the reduced total daily dose of naloxegol is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, or 24 mg, including all integers and ranges therebetween. When the total daily reference dose of naloxegol is 25 mg, the reduced total daily dose of naloxegol is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, or 24 mg, including all integers and ranges therebetween. When the total daily reference dose of naloxegol is 12.5 mg, the reduced total daily dose of naloxegol is, for example, 1 mg, 2 mg, 3 mg, 4 mg, 5 mg, 6 mg, 7 mg, 8 mg, 9 mg, 10 mg, 11 mg, or 12 mg, including all integers and ranges therebetween. Correspondingly, when the individual reference dose of naloxegol is 25 mg, the reduced individual reference dose of naloxegol is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, or 24 mg, including all integers and ranges therebetween. When the individual reference dose of naloxegol is 12.5 mg, the reduced individual reference dose of naloxegol is, for example, 1 mg, 2 mg, 3 mg, 4 mg, 5 mg, 6 mg, 7 mg, 8 mg, 9 mg, 10 mg, 11 mg, or 12 mg, including all integers and ranges therebetween.

In some embodiments, the CYP3A4 substrate drug is nilotinib. The disease or condition treated with nilotinib can include any disease or condition described herein or for which nilotinib is indicated. For example, in some embodiments, nilotinib is indicated for the treatment of adult and pediatric patients greater than or equal to 1 year of age with newly diagnosed Philadelphia chromosome positive chronic myeloid leukemia (Ph+ CML) in chronic phase. In some embodiments, nilotinib is indicated for the treatment of adult patients with chronic phase (CP) and accelerated phase (AP) Ph+ CML resistant to or intolerant to prior therapy that included imatinib. In some embodiments, nilotinib is indicated for the treatment of pediatric patients greater than or equal to 1 year of age with Ph+ CML-CP resistant or intolerant to prior tyrosine-kinase inhibitor (TKI) therapy. Nilotinib may be administered in a 50 mg, 150 mg or 200 mg dosage form. In some embodiments, nilotinib is administered once daily up to a total daily dose of 400 mg. In some embodiments, nilotinib is administered twice daily up to a total daily dose of 800 mg. For example, when nilotinib is indicated for the treatment of adults newly diagnosed with Ph+ CML-CP, the reference dose is 300 mg, administered twice daily (total daily reference dose is 600 mg). For example, when nilotinib is indicated for the treatment of adults with resistant or intolerant to Ph+ CML-CP, the reference dose is 400 mg, administered twice daily (total daily reference dose is 800 mg). For example, when nilotinib is indicated for the treatment of pediatrics newly diagnosed with Ph+ CML-CP, the reference dose is 230 mg/m$^2$, administered twice daily, rounded to the nearest 50 mg dose (total daily reference dose is 400 mg). For example, when nilotinib is indicated for the treatment of adults with resistant or intolerant to Ph+ CML-CP, the reference dose is 400 mg, administered twice daily (total daily reference dose is 800 mg). Thus, in various embodiments, the total daily reference dose of nilotinib may be, for example, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, or 800 mg, including all integers and ranges therebetween. In accordance with certain embodiments of the present disclosure, when the total daily reference dose of nilotinib is, for example, 800 mg, the patient will take a reduced total daily dose of nilotinib (either concomitantly with posaconazole or after a delay period after stopping posaconazole). In some embodiments, the reduced total daily dose of nilotinib is, for example, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of nilotinib is 800 mg, the reduced total daily dose of nilotinib is, for example, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of nilotinib is 400 mg, the reduced total daily dose of nilotinib is, for example, 50 mg, 100 mg, 150 mg, 200 mg, 250 mg, 300 mg, or 350 mg, including all integers and ranges therebetween. Correspondingly, when the individual reference dose of nilotinib is 200 mg, the reduced individual reference dose of nilotinib is, for example, 50 mg, 100 mg, or 150 mg, including all integers and ranges therebetween. When the individual reference dose of nilotinib is 150 mg, the reduced individual reference dose of nilotinib is, for example, 50 mg or 100 mg, including all integers and ranges therebetween.

In some embodiments, the CYP3A4 substrate drug is olaparib (Capsules). The disease or condition treated with olaparib can include any disease or condition described herein or for which olaparib is indicated. For example, in some embodiments, olaparib is indicated for the treatment of adult patients with deleterious or suspected deleterious germline BRCA-mutated advanced ovarian cancer who have been treated with three or more prior lines of chemotherapy. Olaparib may be administered in a 50 mg dosage form. In some embodiments, olaparib is administered twice daily up to a total daily dose of 800 mg with or without food. For example, when olaparib is indicated for the treatment of adult patients with deleterious or suspected deleterious germline BRCA-mutated advanced ovarian cancer who have been treated with three or more prior lines of chemotherapy, the reference dose is 400 mg, administered twice daily (total daily reference dose is 800 mg) with or without food. For moderate renal impairment (CLcr 31-50 mL/min), the reference dose reduces to 300 mg twice daily (total daily reference dose is 600 mg). Thus, in various embodiments, the total daily reference dose of olaparib may be, for example, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, or 800 mg, including all integers and ranges therebetween. In accordance with certain embodiments of the present disclosure, when the total daily reference dose of olaparib is, for example, 800 mg, the patient will take a reduced total daily dose of olaparib (either concomitantly with posaconazole or after a delay period after stopping posaconazole). In some embodiments, the reduced total daily dose of olaparib is, for example, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of olaparib is 800 mg, the reduced total daily dose of olaparib is, for example, 25 mg, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of olaparib is 600 mg, the reduced total daily dose of olaparib is, for example, 25 mg, 50 mg, 100 mg, 150 mg, 200 mg, 250 mg, 300 mg, 350 mg, 400 mg, 450 mg, 500 mg, or 550 mg, including all integers and ranges therebetween. Correspondingly, when the individual reference dose of olaparib is 400 mg, the reduced individual reference dose of olaparib is, for example, 25 mg, 50 mg, 100 mg, 150 mg, 200 mg, 250 mg, 300 mg, or 350 mg, including all integers and ranges therebetween. When the individual reference dose of olaparib is 300 mg, the reduced individual reference dose of olaparib is, for example, 25 mg, 50 mg, 100 mg, 150 mg, 200 mg, or 250 mg, including all integers and ranges therebetween. When the individual reference dose of olaparib is 50 mg, the reduced individual reference dose of olaparib is, for example, 25 mg.

In some embodiments, the CYP3A4 substrate drug is olaparib (Tablets). The disease or condition treated with olaparib can include any disease or condition described herein or for which olaparib is indicated. For example, in some embodiments, olaparib is indicated for the maintenance treatment of adult patients with recurrent epithelial ovarian, fallopian tube or primary peritoneal cancer, who are in a complete or partial response to platinum-based chemotherapy. In some embodiments, olaparib is indicated for the treatment of adult patients with deleterious or suspected deleterious germline BRCA-mutated (gBRCAm) advanced ovarian cancer who have been treated with three or more prior lines of chemotherapy. In some embodiments, olaparib is indicated in patients with deleterious or suspected deleterious gBRCAm, human epidermal growth factor receptor 2 (HER2)-negative metastatic breast cancer who have been treated with chemotherapy in the neoadjuvant, adjuvant or metastatic setting. Olaparib may be administered in a 150 mg or 100 mg dosage form. In some embodiments, olaparib is twice daily up to a total daily dose of 600 mg with or without food. For example, when olaparib is indicated for the maintenance treatment of adult patients with recurrent epithelial ovarian, fallopian tube or primary peritoneal cancer, who are in a complete or partial response to platinum-based chemotherapy, the reference dose is 300 mg, administered twice daily (total daily reference dose is 600 mg). For example, when olaparib is indicated for the treatment of adult patients with deleterious or suspected deleterious germline BRCA-mutated (gBRCAm) advanced ovarian cancer who have been treated with three or more prior lines of chemotherapy, the reference dose is 300 mg, administered twice daily (total daily reference dose is 600 mg). For example, when olaparib is indicated for in patients with deleterious or suspected deleterious gBRCAm, human epidermal growth factor receptor 2 (HER2)-negative metastatic breast cancer who have been treated with chemotherapy in the neoadjuvant, adjuvant or metastatic setting, the reference dose is 300 mg, administered twice daily (total daily reference dose is 600 mg). For moderate renal impairment (CLcr 31-50 mL/min), the reference dose reduces to 200 mg twice daily (total daily reference dose is 400 mg). Thus, in various embodiments, the total daily reference dose of olaparib may be, for example, 50 mg, 100 mg, 150 mg, 200 mg, 250 mg, 300 mg, 350 mg, 400 mg, 450 mg, 500 mg, 550 mg, or 600 mg, including all integers and ranges therebetween. In accordance with certain embodiments of the present disclosure, when the total daily reference dose of olaparib is, for example, 600 mg, the patient will take a reduced total daily dose of olaparib (either concomitantly with posaconazole or after a delay period after stopping posaconazole). In some embodiments, the reduced total daily dose of olaparib is, for example, 50 mg, 100 mg, 150 mg, 200 mg, 250 mg, 300 mg, 350 mg, 400 mg, 450 mg, 500 mg, or 550 mg, including all integers and ranges therebetween. When the total daily reference dose of olaparib is 600 mg, the reduced total daily dose of olaparib is, for example, 50 mg, 100 mg, 150 mg, 200 mg, 250 mg, 300 mg, 350 mg, 400 mg, 450 mg, 500 mg, or 550 mg, including all integers and ranges therebetween. When the total daily reference dose of olaparib is 400 mg, the reduced total daily dose of olaparib is, for example, 50 mg, 100 mg, 150 mg, 200 mg, 250 mg, 300 mg, or 350 mg, including all integers and ranges therebetween. When the total daily reference dose of olaparib is 200 mg, the reduced total daily dose of olaparib is, for example, 50 mg, 100 mg, or 150 mg, including all integers and ranges therebetween. Correspondingly, when the individual reference dose of olaparib is 150 mg, the reduced individual reference dose of olaparib is, for example, 50 mg or 100 mg, including all integers and ranges therebetween. When the individual reference dose of olaparib is 100 mg, the reduced individual reference dose of olaparib is, for example, 50 mg.

In some embodiments, the CYP3A4 substrate drug is palbociclib. The disease or condition treated with palbociclib can include any disease or condition described herein or for which palbociclib is indicated. For example, in some embodiments, palbociclib is indicated for the treatment of hormone receptor (HR)-positive, human epidermal growth factor receptor 2 (HER2)-negative advanced or metastatic breast cancer in combination with an aromatase inhibitor as initial endocrine based therapy in postmenopausal women. For example, in some embodiments, palbociclib is indicated for the treatment of hormone receptor (HR)-positive, human epidermal growth factor receptor 2 (HER2)-negative advanced or metastatic breast cancer in combination with fulvestrant in women with disease progression following endocrine therapy. Palbociclib may be administered in a 125 mg, 100 mg or 75 mg dosage form. In some embodiments, palbociclib is administered once daily up to a total daily dose of 125 mg with food for 21 days followed by 7 days off treatment. For example, when palbociclib is indicated for the treatment of hormone receptor (HR)-positive, human epidermal growth factor receptor 2 (HER2)-negative advanced or metastatic breast cancer in combination with an aromatase inhibitor as initial endocrine based therapy in postmenopausal women, the reference dose is 125 mg, administered once daily (total daily reference dose is 125 mg). For example, when palbociclib is indicated for the treatment of hormone receptor (HR)-positive, human epidermal growth factor receptor 2 (HER2)-negative advanced or metastatic breast cancer in combination with fulvestrant in women with disease progression following endocrine therapy, the reference dose is 125 mg, administered once daily (total daily reference dose is 125 mg). Thus, in various embodiments, the total daily reference dose of palbociclib may be, for example, 25 mg, 50 mg, 75 mg, 100 mg or 125 mg, including all integers and ranges therebetween. In accordance with certain embodiments of the present disclosure, when the total daily reference dose of palbociclib is, for example, 125 mg, the patient will take a reduced total daily dose of palbociclib (either concomitantly with posaconazole or after a delay period after stopping posaconazole). In some embodiments, the reduced total daily dose of palbociclib is, for example, 25 mg, 50 mg, 75 mg, or 100 mg, including all integers and ranges therebetween. When the total daily reference dose of palbociclib is 125 mg, the reduced total daily dose of palbociclib is, for example, 25 mg, 50 mg, 75 mg, or 100 mg, including all integers and ranges therebetween. When the total daily reference dose of palbociclib is 125 mg, the reduced total daily dose of palbociclib is, for example, 25 mg, 50 mg, 75 mg, or 100 mg, including all integers and ranges therebetween. Correspondingly, when the individual reference dose of palbociclib is 125 mg, the reduced individual reference dose of palbociclib is, for example, 25 mg, 50 mg, 75 mg, or 100 mg, including all integers and ranges therebetween. When the individual reference dose of palbociclib is 100 mg, the reduced individual reference dose of palbociclib is, for example, 25 mg, 50 mg, or 75 mg, including all integers and ranges therebetween. When the individual reference dose of palbociclib is 75 mg, the reduced individual reference dose of palbociclib is, for example, 25 mg, or 50 mg, including all integers and ranges therebetween.

In some embodiments, the CYP3A4 substrate drug is panobinostat. The disease or condition treated with panobinostat can include any disease or condition described herein or for which panobinostat is indicated. For example, in some embodiments, panobinostat is indicated for the treatment of patients with multiple myeloma who have received at least 2 prior regimens, including bortezomib and an immunomodulatory agent. Panobinostat may be administered in a 10 mg, 15 mg, or 20 mg dosage form. In some embodiments, panobinostat is administered once every other day for 3 doses per week (on Days 1, 3, 5, 8, 10, and 12) of Weeks 1 and 2 of each 21-day cycle for 8 cycles, up to a total every other day dose of 20 mg. For example, when panobinostat is indicated for the treatment of patients with multiple myeloma who have received at least 2 prior regimens, including bortezomib and an immunomodulatory agent, the reference dose is 20 mg, administered once every other day for three times weekly (total every other day reference dose is 20 mg). Thus, in various embodiments, the total every other day reference dose of panobinostat may be, for example, 10 mg, 15 mg, or 20 mg, including all integers and ranges therebetween. In accordance with certain embodiments of the present disclosure, when the total every other day reference dose of panobinostat is, for example, 20 mg, the patient will take a reduced total every other day dose of panobinostat (either concomitantly with posaconazole or after a delay period after stopping posaconazole). In some embodiments, the reduced total every other day dose of panobinostat is, for example, 5 mg, 7.5 mg, 10 mg, or 15 mg, including all integers and ranges therebetween. When the total every other day reference dose of panobinostat is 20 mg, the reduced total every other day dose of panobinostat is, for example, 5 mg, 7.5 mg, 10 mg, or 15 mg, including all integers and ranges therebetween. Correspondingly, when the individual reference dose of panobinostat is 20 mg, the reduced individual reference dose of panobinostat is, for example, 5 mg, 7.5 mg, 10 mg, or 15 mg, including all integers and ranges therebetween. When the individual reference dose of panobinostat is 15 mg, the reduced individual reference dose of panobinostat is, for example, 5 mg, 7.5 mg, or 10 mg, including all integers and ranges therebetween. When the individual reference dose of panobinostat is 10 mg, the reduced individual reference dose of panobinostat is, for example, 5 mg, or 7.5 mg, including all integers and ranges therebetween.

In some embodiments, the CYP3A4 substrate drug is pazopanib. The disease or condition treated with pazopanib can include any disease or condition described herein or for which pazopanib is indicated. For example, in some embodiments, pazopanib is indicated for the treatment of patients with advanced renal cell carcinoma. For example, in some embodiments, pazopanib is indicated for the treatment of patients with advanced soft tissue sarcoma who have received prior chemotherapy. Pazopanib may be administered in a 200 mg dosage form. In some embodiments, pazopanib is administered once daily up to a total daily dose of 800 mg without food (at least 1 hour before or 2 hours after a meal). For baseline moderate hepatic impairment, pazopanib is administered once daily up to 200 mg. For example, when pazopanib is indicated for the treatment of patients with advanced renal cell carcinoma, the reference dose is 800 mg, administered once daily (total daily reference dose is 800 mg). For example, when pazopanib is indicated for the treatment of patients with advanced soft tissue sarcoma who have received prior chemotherapy, the reference dose is 800 mg, administered once daily (total daily reference dose is 800 mg). Thus, in various embodiments, the total daily reference dose of pazopanib may be, for example, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, or 800 mg. In accordance with certain embodiments of the present disclosure, when the total daily reference dose of pazopanib is, for example, 800 mg, the patient will take a reduced total daily dose of pazopanib (either concomitantly with posaconazole or after a delay period after stopping posaconazole). In some embodiments, the reduced total daily dose of pazopanib is, for example, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of pazopanib is 800 mg, the reduced total daily dose of pazopanib is, for example, 50 mg, 100 mg, 150 mg, 200 mg, 250 mg, 300 mg, 350 mg, 400 mg, 450 mg, 500 mg, 550 mg, 600 mg, 650 mg, 700 mg, or 750 mg, including all integers and ranges therebetween. When the total daily reference dose of pazopanib is 600 mg, the reduced total daily dose of pazopanib is, for example, 50 mg, 100 mg, 150 mg, 200 mg, 250 mg, 300 mg, 350 mg, 400 mg, 450 mg, 500 mg, or 550 mg, including all integers and ranges therebetween. When the total daily reference dose of pazopanib is 400 mg, the reduced total daily dose of pazopanib is, for example, 50 mg, 100 mg, 150 mg, 200 mg, 250 mg, 300 mg, or 350 mg, including all integers and ranges therebetween. When the total daily reference dose of pazopanib is 200 mg, the reduced total daily dose of pazopanib is, for example, 50 mg, 100 mg, or 150 mg, including all integers and ranges therebetween. Correspondingly, when the individual reference dose of pazopanib is 200 mg, the reduced individual reference dose of pazopanib is, for example, 50 mg, 100 mg, or 150 mg, including all integers and ranges therebetween.

In some embodiments, the CYP3A4 substrate drug is regorafenib. The disease or condition treated with regorafenib can include any disease or condition described herein or for which regorafenib is indicated. For example, in some embodiments, regorafenib is indicated for the treatment of patients with metastatic colorectal cancer (CRC) who have been previously treated with fluoropyrimidine-, oxaliplatin- and irinotecan-based chemotherapy, an anti-VEGF therapy, and, if RAS wild-type, an anti-EGFR therapy. In some embodiments, regorafenib is indicated for the treatment of patients with locally advanced, unresectable or metastatic gastrointestinal stromal tumor (GIST) who have been previously treated with imatinib mesylateand sunitinib malate. In some embodiments, regorafenib is indicated for the treatment of patients with hepatocellular carcinoma (HCC) who have been previously treated with sorafenib. Regorafenib may be administered in a 40 mg dosage form. In some embodiments, regorafenib is administered once daily up to a total daily dose of 160 mg for the first 21 days of each 28-day cycle. For example, when regorafenib is indicated for the treatment of patients with metastatic colorectal cancer (CRC) who have been previously treated with fluoropyrimidine-, oxaliplatin- and irinotecan-based chemotherapy, an anti-VEGF therapy, and, if RAS wild-type, an anti-EGFR therapy, the reference dose is 160 mg, administered once daily (total daily reference dose is 160 mg). For example, when regorafenib is indicated for the treatment of patients with locally advanced, unresectable or metastatic gastrointestinal stromal tumor (GIST) who have been previously treated with imatinib mesylateand sunitinib malate, the reference dose is 160 mg, administered once daily (total daily reference dose is 160 mg). For example, when regorafenib is indicated for the treatment of patients with hepatocellular carcinoma (HCC) who have been previously treated with sorafenib, the reference dose is 160 mg, administered once daily (total daily reference dose is 160 mg). Thus, in various embodiments, the total daily reference dose of regorafenib may be, for example, 20 mg, 40 mg, 60 mg, 80 mg, 100 mg, 120 mg, 140 mg, or 160 mg, including all integers and ranges therebetween. In accordance with certain embodiments of the present disclosure, when the total daily reference dose of regorafenib is, for example, 160 mg, the patient will take a reduced total daily dose of regorafenib (either concomitantly with posaconazole or after a delay period after stopping posaconazole). In some embodiments, the reduced total daily dose of regorafenib is 20 mg, 40 mg, 60 mg, 80 mg, 100 mg, 120 mg, or 140 mg. When the total daily reference dose of regorafenib is 160 mg, the reduced total daily dose of regorafenib is, for example, 20 mg, 40 mg, 60 mg, 80 mg, 100 mg, 120 mg, or 140 mg, including all integers and ranges therebetween. When the total daily reference dose of regorafenib is 120 mg, the reduced total daily dose of regorafenib is, for example, 20 mg, 40 mg, 60 mg, 80 mg, or 100 mg, including all integers and ranges therebetween. When the total daily reference dose of regorafenib is 80 mg, the reduced total daily dose of regorafenib is, for example, 20 mg, 40 mg, or 60 mg, including all integers and ranges therebetween. Correspondingly, when the individual reference dose of regorafenib is 40 mg, the reduced individual reference dose of regorafenib is, for example, 20 mg.

In some embodiments, the CYP3A4 substrate drug is rivaroxaban. The disease or condition treated with rivaroxaban can include any disease or condition described herein or for which rivaroxaban is indicated. For example, in some embodiments, rivaroxaban is indicated to reduce the risk of stroke and systemic embolism in patients with nonvalvular atrial fibrillation. In some embodiments, rivaroxaban is indicated for the treatment of deep vein thrombosis (DVT). In some embodiments, rivaroxaban is indicated for the treatment of pulmonary embolism (PE). In some embodiments, rivaroxaban is indicated for the reduction in the risk of recurrence of DVT and/or PE in patients at continued risk for recurrent DVT and/or PE after completion of initial treatment lasting at least 6 months. In some embodiments, rivaroxaban is indicated for the prophylaxis of DVT, which may lead to PE in patients undergoing knee or hip replacement surgery. In some embodiments, rivaroxaban is indicated in combination with aspirin, to reduce the risk of major cardiovascular events (cardiovascular (CV) death, myocardial infarction (MI) and stroke) in patients with chronic coronary artery disease (CAD) or peripheral artery disease (PAD). Rivaroxaban may be administered in a 2.5 mg, 10 mg, 15 mg, or 20 mg dosage form. In some embodiments, rivaroxaban is administered twice daily up to a total daily dose of 40 mg. In some embodiments, rivaroxaban is administered twice daily up to a total daily dose of 30 mg. In some embodiments, rivaroxaban is administered once daily up to a total daily dose of 20 mg. In some embodiments, rivaroxaban is administered once daily up to a total daily dose of 15 mg. In some embodiments, rivaroxaban is administered once daily up to a total daily dose of 10 mg. In some embodiments, rivaroxaban is administered once daily up to a total daily dose of 2.5 mg. For example, when rivaroxaban is indicated to reduce the risk of stroke and systemic embolism in patients with nonvalvular atrial fibrillation, the reference dose is 20 mg, administered once daily (total daily reference dose is 20 mg) with the evening meal for patients with CrCl>50 mL/min, while the reference dose is 15 mg, administered once daily (total daily reference dose is 15 mg) with the evening meal for patients with CrCl≤50 mL/min. For example, when rivaroxaban is indicated for the treatment of deep vein thrombosis (DVT), the reference dose is 15 mg administered twice daily (total daily reference dose is 30 mg) with food for the first 21 days and followed by 20 mg administered once daily (total daily reference dose is 20 mg) with food for the remaining treatment. For example, when rivaroxaban is indicated for the treatment of pulmonary embolism (PE), the reference dose is 15 mg administered twice daily (total daily reference dose is 30 mg) with food for the first 21 days and followed by 20 mg administered once daily (total daily reference dose is 20 mg) with food for the remaining treatment. For example, when rivaroxaban is indicated for the reduction in the risk of recurrence of DVT and/or PE in patients at continued risk for recurrent DVT and/or PE after completion of initial treatment lasting at least 6 months, the reference dose is 10 mg, administered once daily (total daily reference dose is 10 mg) with or without food. For example, when rivaroxaban is indicated for the prophylaxis of DVT, which may lead to PE in patients undergoing knee or hip replacement surgery, the reference dose is 10 mg, administered once daily (total daily reference dose is 10 mg) with or without food. For example, when rivaroxaban is indicated in combination with aspirin, to reduce the risk of major cardiovascular events (cardiovascular (CV) death, myocardial infarction (MI) and stroke) in patients with chronic coronary artery disease (CAD) or peripheral artery disease (PAD), the reference dose is 2.5 mg, administered twice daily (total daily reference dose is 5 mg) with or without food, in combination with aspirin (75-100 mg) once daily. Thus, in various embodiments, the total daily reference dose of rivaroxaban may be, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, or 40 mg, including all integers and ranges therebetween. In accordance with certain embodiments of the present disclosure, when the total daily reference dose of rivaroxaban is, for example, 40 mg, the patient will take a reduced total daily dose of rivaroxaban (either concomitantly with posaconazole or after a delay period after stopping posaconazole). In some embodiments, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, or 39 mg, including all integers and ranges therebetween. When the total daily reference dose of rivaroxaban is 40 mg, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, or 39 mg, including all integers and ranges therebetween. In accordance with certain embodiments of the present disclosure, when the total daily reference dose of rivaroxaban is, for example, 30 mg, the patient will take a reduced total daily dose of rivaroxaban (either concomitantly with posaconazole or after a delay period after stopping posaconazole). In some embodiments, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, or 29 mg, including all integers and ranges therebetween. When the total daily reference dose of rivaroxaban is 30 mg, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, or 29 mg, including all integers and ranges therebetween. When the total daily reference dose of rivaroxaban is 20 mg, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the total daily reference dose of rivaroxaban is 15 mg, the reduced total daily dose of rivaroxaban is 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, or 14 mg, including all integers and ranges therebetween. When the total daily reference dose of rivaroxaban is 10 mg, the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, or 9 mg, including all integers and ranges therebetween. When the total daily reference dose of rivaroxaban is 5 mg, the reduced total daily dose of rivaroxaban is 1 mg, 1.25 mg, 1.5 mg, 2 mg, 2.5 mg, 3 mg, or 4 mg, including all integers and ranges therebetween. Correspondingly, when the individual reference dose of rivaroxaban is 20 mg, the reduced individual reference dose of rivaroxaban is the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the individual reference dose of rivaroxaban is 15 mg, the reduced individual reference dose of rivaroxaban is the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, 9 mg, 10 mg, 11 mg, 12 mg, 13 mg, or 14 mg, including all integers and ranges therebetween. When the individual reference dose of rivaroxaban is 10 mg, the reduced individual reference dose of rivaroxaban is the reduced total daily dose of rivaroxaban is, for example, 1 mg, 1.25 mg, 1.5 mg, 2 mg, 2.5 mg, 3 mg, 4 mg, 5 mg, 6 mg, 7 mg, 8 mg, or 9 mg, including all integers and ranges therebetween. When the individual reference dose of rivaroxaban is 2.5 mg, the reduced individual reference dose of rivaroxaban is the reduced total daily dose of rivaroxaban is, for example, 1 mg, 1.25 mg, 1.5 mg, or 2 mg, including all integers and ranges therebetween.

In some embodiments, the CYP3A4 substrate drug is ruxolitinib. The disease or condition treated with ruxolitinib can include any disease or condition described herein or for which ruxolitinib is indicated. For example, in some embodiments, ruxolitinib is indicated for treatment of patients with intermediate or high-risk myelofibrosis, including primary myelofibrosis, post-polycythemia vera myelofibrosis and post-essential thrombocythemia myelofibrosis. In some embodiments, ruxolitinib is indicated for treatment of patients with polycythemia vera who have had an inadequate response to or are intolerant of hydroxyurea. Ruxolitinib may be administered in a 5 mg, 10 mg, 15 mg, 20 mg or 25 mg dosage form. In some embodiments, ruxolitinib is administered twice daily up to a total daily dose of 50 mg. For example, when ruxolitinib is indicated for treatment of patients with intermediate or high-risk myelofibrosis, including primary myelofibrosis, post-polycythemia vera myelofibrosis and post-essential thrombocythemia myelofibrosis, the reference dose is 20 mg, administered twice daily (total daily reference dose is 40 mg) when patient's baseline platelet count is greater than $200 \times 10^9$/L. For example, when ruxolitinib is indicated for treatment of patients with intermediate or high-risk myelofibrosis, including primary myelofibrosis, post-polycythemia vera myelofibrosis and post-essential thrombocythemia myelofibrosis, the reference dose is 15 mg, administered twice daily (total daily reference dose is 30 mg) when patient's baseline platelet count is $100 \times 10^9$/L to $200 \times 10^9$/L. For example, when ruxolitinib is indicated for treatment of patients with intermediate or high-risk myelofibrosis, including primary myelofibrosis, post-polycythemia vera myelofibrosis and post-essential thrombocythemia myelofibrosis, the reference dose is 5 mg, administered twice daily (total daily reference dose is 10 mg) when patient's baseline platelet count is $50 \times 10^9$/L to less than $100 \times 10^9$/L. For example, when ruxolitinib is indicated for treatment of patients with polycythemia vera who have had an inadequate response to or are intolerant of hydroxyurea, the reference dose is 10 mg, administered twice daily (total daily reference dose is 20 mg). Thus, in various embodiments, the total daily reference dose of ruxolitinib may be, for example, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45, 47.5 mg, or 50 mg. In accordance with certain embodiments of the present disclosure, when the total daily reference dose of ruxolitinib is, for example, 40 mg, the patient will take a reduced total daily dose of ruxolitinib (either concomitantly with posaconazole or after a delay period after stopping posaconazole). In some embodiments, the reduced total daily dose of ruxolitinib is, for example, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, or 37.5 mg, 40 mg, 42.5 mg, 45, or 47.5 mg, including all integers and ranges therebetween. When the total daily reference dose of ruxolitinib is 50 mg, the reduced total daily dose of ruxolitinib is, for example, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, or 37.5 mg, 40 mg, 42.5 mg, 45, or 47.5 mg, including all integers and ranges therebetween. When the total daily reference dose of ruxolitinib is 40 mg, the reduced total daily dose of ruxolitinib is, for example, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, or 37.5 mg, including all integers and ranges therebetween. When the total daily reference dose of ruxolitinib is 30 mg, the reduced total daily dose of ruxolitinib is, for example, 2.5 mg, 5 mg, 7.5 mg, 10 mg, 12.5 mg, 15 mg, 17.5 mg, 20 mg, 22.5 mg, 25 mg, or 27.5 mg, including all integers and ranges therebetween. When the total daily reference dose of ruxolitinib is 20 mg, the reduced total daily dose of ruxolitinib is, for example, 2.5 mg, 5 mg, 7.5 mg, 10 mg, 12.5 mg, 15 mg, or 17.5 mg, including all integers and ranges therebetween. When the total daily reference dose of ruxolitinib is 10 mg, the reduced total daily dose of ruxolitinib is, for example, 2.5 mg, 5 mg, or 7.5 mg, including all integers and ranges therebetween. Correspondingly, when the individual reference dose of ruxolitinib is 25 mg, the reduced individual reference dose of ruxolitinib is, for example, 2.5 mg, 5 mg, 7.5 mg, 10 mg, 12.5 mg, 15 mg, 17.5 mg, 20 mg, 22.5 mg, including all integers and ranges therebetween. When the individual reference dose of ruxolitinib is 20 mg, the reduced individual reference dose of ruxolitinib is, for example, 2.5 mg, 5 mg, 7.5 mg, 10 mg, 12.5 mg, 15 mg, or 17.5 mg, including all integers and ranges therebetween. When the individual reference dose of ruxolitinib is 15 mg, the reduced individual reference dose of ruxolitinib is, for example, 2.5 mg, 5 mg, 7.5 mg, 10 mg, or 12.5 mg, including all integers and ranges therebetween. When the individual reference dose of ruxolitinib is 10 mg, the reduced individual reference dose of ruxolitinib is, for example, 2.5 mg, 5 mg, or 7.5 mg, including all integers and ranges therebetween. When the individual reference dose of ruxolitinib is 5 mg, the reduced individual reference dose of ruxolitinib is, for example, 2.5 mg.

In some embodiments, the CYP3A4 substrate drug is sonidegib. The disease or condition treated with sonidegib can include any disease or condition described herein or for which sonidegib is indicated. For example, in some embodiments, sonidegib is indicated for treatment of adult patients with locally advanced basal cell carcinoma (BCC) that has recurred following surgery or radiation therapy, or those who are not candidates for surgery or radiation therapy. Sonidegib may be administered in a 200 mg dosage form. In some embodiments, sonidegib is administered once daily up to a total daily dose of 200 mg. For example, when sonidegib is indicated for treatment of adult patients with locally advanced basal cell carcinoma (BCC) that has recurred following surgery or radiation therapy, or those who are not candidates for surgery or radiation therapy, the reference dose is 200 mg, administered once daily (total daily reference dose is 200 mg). Thus, in various embodiments, the total daily reference dose of sonidegib may be, for example, 25 mg, 50 mg, 100 mg, 150 mg, or 200 mg. In accordance with certain embodiments of the present disclosure, when the total daily reference dose of sonidegib is, for example, 200 mg, the patient will take a reduced total daily dose of sonidegib (either concomitantly with posaconazole or after a delay period after stopping posaconazole). In some embodiments, the reduced total daily dose of sonidegib is, for example, 25 mg, 50 mg, 100 mg, or 150 mg, including all integers and ranges therebetween. When the total daily reference dose of sonidegib is 200 mg, the reduced total daily dose of sonidegib is, for example, 25 mg, 50 mg, 100 mg, or 150 mg, including all integers and ranges therebetween. Correspondingly, when the individual reference dose of sonidegib is 200 mg, the reduced individual reference dose of sonidegib is, for example, 25 mg, 50 mg, 100 mg, 150 mg, including all integers and ranges therebetween.

In some embodiments, the CYP3A4 substrate drug is sunitinib malate. The disease or condition treated with sunitinib malate can include any disease or condition described herein or for which sunitinib malate is indicated. For example, in some embodiments, sunitinib malate is indicated for the treatment of gastrointestinal stromal tumor (GIST) after disease progression on or intolerance to imatinib mesylate. In some embodiments, sunitinib malate is indicated for the treatment of advanced renal cell carcinoma (RCC). In some embodiments, sunitinib malate is indicated for the adjuvant treatment of adult patients at high risk of recurrent RCC following nephrectomy. In some embodiments, sunitinib malate is indicated for the treatment of progressive, well-differentiated pancreatic neuroendocrine tumors (pNET) in patients with unresectable locally advanced or metastatic disease. Sunitinib malate may be administered in a 12.5 mg, 25 mg, 37.5 mg, or 50 mg dosage form. In some embodiments, sunitinib malate is administered once daily up to a total daily dose of 87.5 mg. In some embodiments, sunitinib malate is administered once daily up to a total daily dose of 75 mg. In some embodiments, sunitinib malate is administered once daily up to a total daily dose of 62.5 mg. In some embodiments, sunitinib malate is administered once daily up to a total daily dose of 50 mg. For example, when sunitinib malate is indicated for the treatment of gastrointestinal stromal tumor (GIST) after disease progression on or intolerance to imatinib mesylate, the reference dose is 50 mg, administered once daily (total daily reference dose is 50 mg) with or without food, for 4 weeks on treatment followed by 2 weeks off. For example, when sunitinib malate is indicated for the treatment of advanced renal cell carcinoma (RCC), the reference dose is 50 mg, administered once daily (total daily reference dose is 50 mg) with or without food, for 4 weeks on treatment followed by 2 weeks off. For example, when sunitinib malate is indicated for the adjuvant treatment of adult patients at high risk of recurrent RCC following nephrectomy, the reference dose is 50 mg, administered once daily (total daily reference dose is 50 mg) with or without food, for 4 weeks on treatment followed by 2 weeks off for nine 6-week cycles. For example, when sunitinib malate is indicated for the treatment of progressive, well-differentiated pancreatic neuroendocrine tumors (pNET) in patients with unresectable locally advanced or metastatic disease, the reference dose is 37.5 mg, administered once daily (total daily reference dose is 37.5 mg) with or without food, continuously without a scheduled off-treatment period. Dose interruptions and/or dose adjustments of 12.5 mg recommended based on individual safety and tolerability. Thus, in various embodiments, the total daily reference dose of sunitinib malate may be, for example, 5 mg, 12.5 mg, 25 mg, 37.5 mg, 50 mg, 62.5 mg, 75 mg, or 87.5 mg, including all integers and ranges therebetween. In accordance with certain embodiments of the present disclosure, when the total daily reference dose of sunitinib malate is, for example, 87.5 mg, the patient will take a reduced total daily dose of sunitinib malate (either concomitantly with posaconazole or after a delay period after stopping posaconazole). In some embodiments, the reduced total daily dose of sunitinib malate is, for example, 5 mg, 12.5 mg, 25 mg, 37.5 mg, 50 mg, 62.5 mg, or 75 mg, including all integers and ranges therebetween. When the total daily reference dose of sunitinib malate is 87.5 mg, the reduced total daily dose of sunitinib malate is, for example, 5 mg, 12.5 mg, 25 mg, 37.5 mg, 50 mg, 62.5 mg, or 75 mg, including all integers and ranges therebetween. When the total daily reference dose of sunitinib malate is 50 mg, the reduced total daily dose of sunitinib malate is, for example, 5 mg, 12.5 mg, 25 mg or 37.5 mg, including all integers and ranges therebetween. When the total daily reference dose of sunitinib malate is 37.5 mg, the reduced total daily dose of sunitinib malate is, for example, 5 mg, 12.5 mg or 25 mg, including all integers and ranges therebetween. Correspondingly, when the individual reference dose of sunitinib malate is 50 mg, the reduced individual reference dose of sunitinib malate is, for example, 5 mg, 12.5 mg, 25 mg or 37.5 mg, including all integers and ranges therebetween. When the individual reference dose of sunitinib malate is 37.5 mg, the reduced individual reference dose of sunitinib malate is, for example, 5 mg, 12.5 mg or 25 mg, including all integers and ranges therebetween. When the individual reference dose of sunitinib malate is 25 mg, the reduced individual reference dose of sunitinib malate is, for example, 5 mg or 12.5 mg, including all integers and ranges therebetween. When the individual reference dose of sunitinib malate is 12.5 mg, the reduced individual reference dose of sunitinib malate is, for example, 5 mg.

In some embodiments, the CYP3A4 substrate drug is tofacitinib. The disease or condition treated with tofacitinib can include any disease or condition described herein or for which tofacitinib is indicated. For example, in some embodiments, tofacitinib is indicated for the treatment of adult patients with moderately to severely active rheumatoid arthritis who have had an inadequate response or intolerance to methotrexate. It may be used as monotherapy or in combination with methotrexate or other nonbiologic disease-modifying antirheumatic drugs (DMARDs). Use of tofacitinib in combination with biologic DMARDs or potent immunosuppressants such as azathioprine and cyclosporine is not recommended. In some embodiments, tofacitinib is indicated for the treatment of adult patients with active psoriatic arthritis who have had an inadequate response or intolerance to methotrexate or other disease-modifying antirheumatic drugs (DMARDs). Use of tofacitinib in combination with biologic DMARDs or potent immunosuppressants such as azathioprine and cyclosporine is not recommended. In some embodiments, tofacitinib is indicated for the treatment of adult patients with moderately to severely active ulcerative colitis (UC). Limitations of Use: Use of tofacitinib in combination with biological therapies for UC or with potent immunosuppressants such as azathioprine and cyclosporine is not recommended. Tofacitinib may be administered in a 5 mg, 10 mg, or 11 mg dosage form. In some embodiments, tofacitinib is administered twice daily up to a total daily dose of 20 mg. In some embodiments, tofacitinib is administered twice daily up to a total daily dose of 10 mg. In some embodiments, tofacitinib is administered once daily up to a total daily dose of 11 mg. For example, when tofacitinib is indicated for the treatment of adult patients with moderately to severely active rheumatoid arthritis who have had an inadequate response or intolerance to methotrexate, the reference dose is 5 mg, administered twice daily (total daily reference dose is 10 mg) or the reference dose is 11 mg, administered once daily (total daily reference dose is 11 mg). Recommended dosage in patients with moderate and severe renal impairment or moderate hepatic impairment is tofacitinib 5 mg once daily. For example, when tofacitinib is indicated for the treatment of adult patients with active psoriatic arthritis who have had an inadequate response or intolerance to methotrexate or other disease-modifying antirheumatic drugs (DMARDs), the reference dose is 5 mg, administered twice daily (total daily reference dose is 10 mg) or the reference dose is 11 mg, administered once daily (total daily reference dose is 11 mg). Recommended dosage in patients with moderate and severe renal impairment or moderate hepatic impairment is tofacitinib 5 mg once daily. For example, when tofacitinib is indicated for the treatment of adult patients with moderately to severely active ulcerative colitis (UC), the reference dose is 10 mg, administered twice daily (total daily reference dose is 20 mg) for at least 8 weeks and then 5 or 10 mg twice daily. Discontinue after 16 weeks of 10 mg twice daily, if adequate therapeutic benefit is not achieved. Use the lowest effective dose to maintain response. Recommended dosage in patients with moderate and severe renal impairment or moderate hepatic impairment: half the total daily dosage recommended for patients with normal renal and hepatic function. Thus, in various embodiments, the total daily reference dose of tofacitinib may be, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg, including all integers and ranges therebetween. In accordance with certain embodiments of the present disclosure, when the total daily reference dose of tofacitinib is, for example, 20 mg, the patient will take a reduced total daily dose of tofacitinib (either concomitantly with posaconazole or after a delay period after stopping posaconazole). In some embodiments, the reduced total daily dose of tofacitinib is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the total daily reference dose of tofacitinib is 20 mg, the reduced total daily dose of tofacitinib is, for example, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, or 19 mg, including all integers and ranges therebetween. When the total daily reference dose of tofacitinib is 11 mg, the reduced total daily dose of tofacitinib is, for example, 1 mg, 2 mg, 3 mg, 4 mg, 5 mg, 6 mg, 7 mg, 8 mg, 9 mg, or 10 mg, including all integers and ranges therebetween. When the total daily reference dose of tofacitinib is 10 mg, the reduced total daily dose of tofacitinib is, for example, 1 mg, 2 mg, 3 mg, 4 mg, 5 mg, 6 mg, 7 mg, 8 mg, or 9 mg, including all integers and ranges therebetween. Correspondingly, when the individual reference dose of tofacitinib is 11 mg, the reduced individual reference dose of tofacitinib is, for example, 1 mg, 2 mg, 3 mg, 4 mg, 5 mg, 6 mg, 7 mg, 8 mg, 9 mg, or 10 mg, including all integers and ranges therebetween. When the individual reference dose of tofacitinib is 10 mg, the reduced individual reference dose of tofacitinib is, for example, 1 mg, 2 mg, 3 mg, 4 mg, 5 mg, 6 mg, 7 mg, 8 mg, or 9 mg, including all integers and ranges therebetween. When the individual reference dose of tofacitinib is 5 mg, the reduced individual reference dose of tofacitinib is, for example, 1 mg, 2 mg, 3 mg, or 4 mg, including all integers and ranges therebetween.

In some embodiments, the CYP3A4 substrate drug is vemurafenib. The disease or condition treated with vemurafenib can include any disease or condition described herein or for which vemurafenib is indicated. For example, in some embodiments, vemurafenib is indicated for the treatment of patients with unresectable or metastatic melanoma with BRAF V600E mutation as detected by an FDA-approved test. In some embodiments, vemurafenib is indicated for the treatment of patients with Erdheim-Chester Disease with BRAF V600 mutation. Vemurafenib may be administered in a 240 mg dosage form. In some embodiments, vemurafenib is administered twice daily up to a total daily dose of 2000 mg. For example, when vemurafenib is indicated for the treatment of patients with unresectable or metastatic melanoma with BRAF V600E mutation as detected by an FDA-approved test, the reference dose is 960 mg, administered twice daily (total daily reference dose is 1920 mg) approximately 12 hours apart with or without a meal. For example, when vemurafenib is indicated for the treatment of patients with Erdheim-Chester Disease with BRAF V600 mutation, the reference dose is 960 mg, administered twice daily (total daily reference dose is 1920 mg) approximately 12 hours apart with or without a meal. Thus, in various embodiments, the total daily reference dose of vemurafenib may be, for example, 120 mg, 240 mg, 360 mg, 480 mg, 600 mg, 720 mg, 840 mg, 960 mg, 1080 mg, 1200 mg, 1320 mg, 1440 mg, 1560 mg, 1680 mg, 1800 mg, 1920 mg, or 2000 mg, including all integers and ranges therebetween. In accordance with certain embodiments of the present disclosure, when the total daily reference dose of vemurafenib is, for example, 2000 mg, the patient will take a reduced total daily dose of vemurafenib (either concomitantly with posaconazole or after a delay period after stopping posaconazole). In some embodiments, the reduced total daily dose of vemurafenib is, for example, 120 mg, 240 mg, 360 mg, 480 mg, 600 mg, 720 mg, 840 mg, 960 mg, 1080 mg, 1200 mg, 1320 mg, 1440 mg, 1560 mg, 1680 mg, or 1800 mg, or 1920, including all integers and ranges therebetween. When the total daily reference dose of vemurafenib is 2000 mg, the reduced total daily dose of vemurafenib is, for example, 120 mg, 240 mg, 360 mg, 480 mg, 600 mg, 720 mg, 840 mg, 960 mg, 1080 mg, 1200 mg, 1320 mg, 1440 mg, 1560 mg, 1680 mg, 1800 mg, or 1920 mg, including all integers and ranges therebetween. When the total daily reference dose of vemurafenib is 1920 mg, the reduced total daily dose of vemurafenib is, for example, 120 mg, 240 mg, 360 mg, 480 mg, 600 mg, 720 mg, 840 mg, 960 mg, 1080 mg, 1200 mg, 1320 mg, 1440 mg, 1560 mg, 1680 mg, or 1800 mg, including all integers and ranges therebetween. Correspondingly, when the individual reference dose of vemurafenib is 240 mg, the reduced individual reference dose of vemurafenib is, for example, 120 mg.

In some embodiments, the CYP3A4 substrate drug is venetoclax. The disease or condition treated with venetoclax can include any disease or condition described herein or for which venetoclax is indicated. For example, in some embodiments, venetoclax is indicated for the treatment of patients with chronic lymphocytic leukemia (CLL) or small lymphocytic lymphoma (SLL), with or without 17p deletion, who have received at least one prior therapy. Venetoclax may be administered in a 10 mg, 50 mg, or 100 mg dosage form. In some embodiments, venetoclax is administered once daily up to a total daily dose of 400 mg. For example, when venetoclax is indicated for the treatment of patients with chronic lymphocytic leukemia (CLL) or small lymphocytic lymphoma (SLL), with or without 17p deletion, who have received at least one prior therapy, the reference dose is 20 mg once daily for 7 days (total daily reference dose is 20 mg), followed by a weekly ramp-up dosing schedule to the recommended daily dose of 400 mg, administered once daily (total daily reference dose is 400 mg). Thus, in various embodiments, the total daily reference dose of venetoclax may be, for example, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, or 400 mg, including all integers and ranges therebetween. In accordance with certain embodiments of the present disclosure, when the total daily reference dose of venetoclax is, for example, 400 mg, the patient will take a reduced total daily dose of venetoclax (either concomitantly with posaconazole or after a delay period after stopping posaconazole). In some embodiments, the reduced total daily dose of venetoclax is, for example, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, or 390 mg, including all integers and ranges therebetween. When the total daily reference dose of venetoclax is 400 mg, the reduced total daily dose of venetoclax is, for example, 5 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, or 390 mg, including all integers and ranges therebetween. Correspondingly, when the individual reference dose of venetoclax is 100 mg, the reduced individual reference dose of venetoclax is, for example, 5 mg, 10 mg, 20 mg, 30 mg, 40 mg, 50 mg, 60 mg, 70 mg, 80 mg, or 90 mg, including all integers and ranges therebetween. When the individual reference dose of venetoclax is 50 mg, the reduced individual reference dose of venetoclax is, for example, 5 mg, 10 mg, 20 mg, 30 mg, or 40 mg, including all integers and ranges therebetween. When the individual reference dose of venetoclax is 20 mg, the reduced individual reference dose of venetoclax is, for example, 5 mg or 10 mg, including all integers and ranges therebetween. When the individual reference dose of venetoclax is 10 mg, the reduced individual reference dose of venetoclax is, for example, 5 mg.

In some embodiments, the CYP3A4 substrate drug is larotrectinib. The disease or condition treated with larotrectinib can include any disease or condition described herein or for which larotrectinib is indicated. For example, in some embodiments, larotrectinib is indicated for the treatment of adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment. Larotrectinib may be administered as a 25 mg or 100 mg oral capsule or 20 mg/ml oral solution. In some embodiments, larotrectinib is administered twice daily up to a total daily dose of 200 mg or 200 mg/m$^2$, depending on the age of the patient. For example, when larotrectinib is indicated for the treatment of adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, the reference dose is either 100 mg twice daily (total daily reference dose is 200 mg) in adult and pediatric patients with body surface area of at least 1.0 meter-squared, or 100 mg/m$^2$ twice daily (total daily reference dose is 200 mg/m$^2$) in pediatric patients with body surface area of less than 1.0 meter-squared. In accordance with certain embodiments of the present disclosure, when the total daily reference dose of larotrectinib is, for example, 200 mg, the patient will take a reduced total daily dose of larotrectinib (either concomitantly with posaconazole or after a delay period after stopping posaconazole). In some embodiments, the reduced total daily dose of larotrectinib is, for example, 25 mg, 50 mg, 75 mg, 100 mg, 125 mg, 150 mg, or 175 mg, including all integers and ranges therebetween. In accordance with certain embodiments of the present disclosure, when the total daily reference dose of larotrectinib is 200 mg/m$^2$, the reduced total daily dose of larotectinib is, for example, 20 mg/m$^2$, 40 mg/m$^2$, 60 mg/m$^2$, or 80 mg/m$^2$, including all integers and ranges therebetween. Correspondingly, when the individual reference dose is 100 mg, the reduced individual dose is, for example, 50 mg.

In some embodiments, the CYP3A4 substrate drug is irinotecan. The disease or condition treated with irinotecan can include any disease or condition described herein or for which irinotecan is indicated. For example, in some embodiments, irinotecan is indicated as a first-line therapy in combination with 5-fluorouracil and leucovorin for patients with metastatic carcinoma of the colon or rectum, or as treatment of patients with metastatic carcinoma of the colon or rectum whose disease has recurred or progressed following initial fluorouracil-based therapy. In some embodiments, irinotecan is indicated in combination with fluorouracil and leucovorin, for the treatment of patients with metastatic adenocarcinoma of the pancreas after disease progression following gemcitabine-based therapy. Irinotecan is available as a 40 mg/2 mL injection, 100 mg/5 mL injection, 300 mg/15 mL injection, or 43 mg/10 mL single dose vial. In some embodiments, irinotecan is administered as a 125 mg/m$^2$ intravenous infusion over 90 minutes on days 1, 8, 15, 22 with leucovorin 20 mg/m$^2$ intravenous bolus infusion on days 1, 8, 15, 22 followed by 5-fluorouracil intravenous bolus infusion on days 1, 8, 15, 22 every 6 weeks. In some embodiments, irinotecan is administered as a 180 mg/m$^2$ intravenous infusion over 90 minutes on days 1, 15, 29 with leucovorin 200 mg/m$^2$ intravenous bolus infusion on days 1, 2, 15, 16, 29, 30 followed by 5-fluorouracil 400 mg/m$^2$ intravenous bolus infusion on days 1, 2, 15, 16, 29, 30 and 5-fluorouracil 600 mg/m$^2$ intravenous infusion over 22 hours on days 1, 2, 15, 16, 29, 30. In some embodiments, irinotecan is administered as a 125 mg/m$^2$ intravenous infusion over 90 minutes on days 1, 8, 15, 22 followed by a 2-week rest. In some embodiments, irinotecan is administered as a 350 mg/m$^2$ intravenous infusion over 90 minutes on day 1 every 3 weeks. In some embodiments, irinotecan is administered as a 70 mg/m$^2$ intravenous infusion over 90 minutes every two weeks. For example, when irinotecan is indicated for the treatment of patients with metastatic carcinoma of the colon or rectum in combination with 5-fluorouracil and leucovorin, the reference dose is 125 mg/m$^2$, administered as an intravenous infusion over 90 minutes (total daily reference dose is 125 mg/m$^2$). For example, when irinotecan is indicated in combination with 5-fluorouracil and leucovorin in patients with metastatic carcinoma of the colon or rectum, the reference dose is 180 mg/m$^2$, administered as an intravenous infusion over 90 minutes (total daily reference dose is 180 mg/m$^2$). For example, when irinotecan is indicated for the treatment of patients with metastatic carcinoma of the colon or rectum whose disease has recurred or progressed following initial fluorouracil-based therapy, the reference dose is 125 mg/m$^2$, administered as an intravenous infusion over 90 minutes (total daily reference dose is 125 mg/m$^2$). For example, when irinotecan is indicated for the treatment of patients with metastatic carcinoma of the colon or rectum whose disease has recurred or progressed following initial fluorouracil-based therapy, the reference dose is 350 mg/m$^2$, administered as an intravenous infusion over 90 minutes (total daily reference dose is 350 mg/m$^2$). For example, when irinotecan is indicated, in combination with fluorouracil and leucovorin, for the treatment of patients with metastatic adenocarcinoma of the pancreas after disease progression following gemcitabine-based therapy, the reference dose is 70 mg/m$^2$. in patients homozygous for UGT1A1*28 the reference dose of irinotecan is 50 mg/m$^2$ every two weeks, and the dose is increased as tolerated in subsequent cycles. Thus, in various embodiments, the total daily reference dose of irinotecan may be, for example, 50 mg/m$^2$, 70 mg/m$^2$ 125 mg/m$^2$, 180 mg/m$^2$, or 350 mg/m$^2$, including all integers and ranges therebetween. In accordance with certain embodiments of the present disclosure, when the total daily reference dose of irinotecan is, for example, 125 mg/m$^2$, the patient will take a reduced total daily dose of irinotecan. In some embodiments, the reduced total daily dose of irinotecan is 20 mg/m$^2$, 40 mg/m$^2$, 60 mg/m$^2$, 80 mg/m$^2$, 100 mg/m$^2$, including all integers and ranges therebetween. When the total daily reference dose of irinotecan is 180 mg/m$^2$, the reduced total daily dose of irinotecan is, for example, 20 mg/m$^2$, 40 mg/m$^2$, 60 mg/m$^2$, 80 mg/m$^2$, 100 mg/m$^2$, 120 mg/m$^2$, 140 mg/m$^2$, or 160 mg/m$^2$, including all integers and ranges therebetween. When the total daily reference dose of irinotecan is 350 mg/m$^2$, the reduced total daily dose of irinotecan is, for example, 20 mg/m$^2$, 40 mg/m$^2$, 60 mg/m$^2$, 80 mg/m$^2$, 100 mg/m$^2$, 120 mg/m$^2$, 140 mg/m$^2$, 160 mg/m$^2$, 180 mg/m$^2$, 200 mg/m$^2$, 220 mg/m$^2$, 240 mg/m$^2$, 260 mg/m$^2$, 280 mg/m$^2$, 300 mg/m$^2$, 320 mg/m$^2$, or 340 mg/m$^2$, including all integers and ranges therebetween.

In some embodiments, the CYP3A4 substrate drug is siponimod. The disease or condition treated with siponimod can include any disease or condition described herein or for which siponimod is indicated. For example, in some embodiments, siponimod is indicated for the treatment of relapsing forms of multiple sclerosis (MS), to include clinically isolated syndrome, relapsing-remitting disease, and active secondary progressive disease, in adults. Siponimod may be administered in a 0.25 mg and 2 mg dosage form. For example, when siponimod is indicated for the treatment of relapsing forms of multiple sclerosis (MS), to include clinically isolated syndrome, relapsing-remitting disease, and active secondary progressive disease, in adults, the reference dose is 2 mg administered once daily after initiating treatment with the required titration. The reference dose in patients with a CYP2C9*1/*3 or *2/*3 genotype is 1 mg. In accordance with certain embodiments of the present disclosure, when the reference dose of siponimod is, for example, 2 mg, the patient will take a reduced dose of siponimod. In some embodiments, when the reference dose of siponimod is 2 mg, the reduced dose is, for example, 0.25 mg, 0.5 mg, 0.75 mg, 1.0 mg, 1.25 mg, 1.5 mg, or 1.75 mg, including all integers and ranges therebetween. When the reference dose of siponimod is 1 mg, the reduced dose is, for example, 0.25 mg, 0.5 mg, or 0.75 mg, including all integers and ranges therebetween.

In some embodiments, the CYP3A4 substrate drug is erdafitinib. The disease or condition treated with erdafitinib can include any disease or condition described herein or for which erdafitinib is indicated. For example, in some embodiments, erdafitinib is indicated for the treatment of adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy. Erdafitinib may be administered in a 3 mg, 4 mg, or 5 mg dosage form. For example, when erdafitinib is indicated for the treatment of adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, the reference dose is 8 mg once daily, with a dose increase to 9 mg (three 3 mg tablets) once daily based on serum phosphate (PO4) levels and tolerability at 14 to 21 days. In accordance with certain embodiments of the present disclosure, when the reference dose of erdafitinib is, for example, 8 mg, the patient will take a reduced dose of erdafitinib. In some embodiments, when the reference dose is 8 mg, the reduced dose is, for example, 3 mg, 4 mg, 5 mg, 6 mg, or 7 mg, including all integers and ranges therebetween. When the reference dose is 9 mg, the reduced dose is, for example, 3 mg, 4 mg, 5 mg, 6 mg, 7 mg, or 8 mg, including all integers and ranges therebetween.

In some embodiments, the CYP3A4 substrate drug is fostamatinib disodium. The disease or condition treated with fostamatinib disodium can include any disease or condition described herein or for which fostamatinib disodium is indicated. For example, in some embodiments, fostamatinib disodium is indicated for the treatment of thrombocytopenia in adult patients with chronic immune thrombocytopenia (ITP) who have had an insufficient response to a previous treatment. Fostamatinib disodium may be administered in a 100 mg, or 150 mg dosage form. In some embodiments, fostamatinib disodium is administered twice daily up to a total daily dose of 200 or 300 mg. For example, when fostamatinib disodium is indicated for the treatment of thrombocytopenia in adult patients with chronic immune thrombocytopenia (ITP) who have had an insufficient response to a previous treatment, the reference dose is 100 mg twice daily (total daily reference dose is 200 mg), with an increase to 150 mg twice daily (total daily reference dose is 300 mg) if needed after 4 weeks. In accordance with certain embodiments of the present disclosure, when the total daily reference dose of fostamatinib disodium is, for example, 200 mg, the patient will take a reduced total daily dose of fostamatinib. In some embodiments, when the total daily reference dose is 200 mg, the reduced daily dose is, for example, 100 mg or 150 mg, including all integers and ranges therebetween. When the total daily reference dose is 300 mg, the reduced daily dose is, for example, 100 mg, 150 mg, 200 mg, or 250 mg, including all integers and ranges therebetween. Correspondingly, when the reference dose is 100 mg, the reduced dose is, for example, 50 mg or 75 mg, including all integers and ranges therebetween. When the reference dose is 150 mg, the reduced dose is, for example, 50 mg, 75 mg, or 100 mg, including all integers and ranges therebetween.

In some embodiments, the CYP3A4 substrate drug is elagolix sodium. The disease or condition treated with elagolix sodium can include any disease or condition described herein or for which elagolix sodium is indicated. For example, in some embodiments, elagolix sodium is indicated for the management of moderate to severe pain associated with endometriosis. Elagolix sodium may be administered in a 150 mg or 200 mg dosage form. In some embodiments, elagolix sodium is administered twice daily up to a total daily dose of 400 mg. For example, when elagolix sodium is indicated for the management of moderate to severe pain associated with endometriosis, the reference dose is either 150 mg once daily or 200 mg twice daily (total daily reference dose is 400 mg). The reference dose is 150 mg once daily if there is no coexisting condition or if the coexisting condition is moderate hepatic impairment (Child-Pugh Class B). The reference dose is 200 mg twice daily (total daily reference dose is 400 mg) when the coexisting condition is dyspareunia. In accordance with certain embodiments of the present disclosure, when the total daily reference dose of elagolix sodium is, for example, 400 mg, the patient will take a reduced total daily dose of elagolix sodium. In some embodiments, when the total daily reference dose is 400 mg, the reduced daily dose is, for example, 150 mg, 200 mg, 300 mg, or 350 mg, including all integers and ranges therebetween. When the reference dose is 200 mg, the reduced dose is, for example, 50 mg, 75 mg, 100 mg, 125 mg, or 150 mg, including all integers and ranges therebetween. When the reference dose is 150 mg, the reduced dose is, for example, 50 mg, 75 mg, or 100 mg, including all integers and ranges therebetween.

In some embodiments, the CYP3A4 substrate drug is lorlatinib. The disease or condition treated with lorlatinib can include any disease or condition described herein or for which lorlatinib is indicated. For example, in some embodiments, lorlatinib is indicated for the treatment of patients with anaplastic lymphoma kinase (ALK)-positive metastatic non-small cell lung cancer (NSCLC) whose disease has progressed on crizotinib and at least one other ALK inhibitor for metastatic disease. In some embodiments, lorlatinib is indicated for the treatment of patients with anaplastic lymphoma kinase (ALK)-positive metastatic non-small cell lung cancer (NSCLC) whose disease has progressed on alectinib as the first ALK inhibitor therapy for metastatic disease. In some embodiments, lorlatinib is indicated for the treatment of patients with anaplastic lymphoma kinase (ALK)-positive metastatic non-small cell lung cancer (NSCLC) whose disease has progressed on ceritinib as the first ALK inhibitor therapy for metastatic disease. Lorlatinib may be administered in a 25 mg or 100 mg dosage form. For example, when lorlatinib is indicated for the treatment of patients with anaplastic lymphoma kinase (ALK)-positive metastatic non-small cell lung cancer (NSCLC) whose disease has progressed on crizotinib and at least one other ALK inhibitor for metastatic disease, the reference dose is 100 mg once daily. When lorlatinib is indicated for the treatment of patients with anaplastic lymphoma kinase (ALK)-positive metastatic non-small cell lung cancer (NSCLC) whose disease has progressed on alectinib as the first ALK inhibitor therapy for metastatic disease, the reference dose is 100 mg once daily. When lorlatinib is indicated for the treatment of patients with anaplastic lymphoma kinase (ALK)-positive metastatic non-small cell lung cancer (NSCLC) whose disease has progressed on ceritinib as the first ALK inhibitor therapy for metastatic disease, the reference dose is 100 mg once daily. In accordance with certain embodiments of the present disclosure, when the reference dose of lorlatinib is, for example, 100 mg, the patient will take a reduced dose of irinotecan. In some embodiments, when the reference dose is 100 mg once daily, the reduced dose is, for example, 25 mg, 50 mg, or 75 mg, including all integers and ranges therebetween.

In some embodiments, the CYP3A4 substrate drug is glasdegib. The disease or condition treated with glasdegib can include any disease or condition described herein or for which glasdegib is indicated. For example, in some embodiments, glasdegib is indicated, in combination with low-dose cytarabine, for the treatment of newly-diagnosed acute myeloid leukemia (AML) in adult patients who are ≥75 years old or who have comorbidities that preclude use of intensive induction chemotherapy. Glasdegib may be administered in a 25 mg or 100 mg dosage form. For example, when glasdegib is indicated, in combination with low-dose cytarabine, for the treatment of newly-diagnosed acute myeloid leukemia (AML) in adult patients who are ≥75 years old or who have comorbidities that preclude use of intensive induction chemotherapy, the reference dose is 100 mg once daily. In accordance with certain embodiments of the present disclosure, when the reference dose of glasdegib is, for example, 100 mg, the patient will take a reduced dose of glasdegib. In some embodiments, when the reference dose is 100 mg, the reduced dose is, for example, 25 mg, 50 mg, or 75 mg, including all integers and ranges therebetween.

In some embodiments, the CYP3A4 substrate drug is gilteritinib. The disease or condition treated with gilteritinib can include any disease or condition described herein or for which gilteritinib is indicated. For example, in some embodiments, gilteritinib is indicated for the treatment of adult patients who have relapsed or refractory acute myeloid leukemia (AML) with a FLT3 mutation as detected by an FDA-approved test. Gilteritinib may be administered in 40 mg dosage form. For example, when gilteritinib is indicated for the treatment of adult patients who have relapsed or refractory acute myeloid leukemia (AML) with a FLT3 mutation as detected by an FDA-approved test, the reference dose is 120 mg once daily. In accordance with certain embodiments of the present disclosure, when the reference dose of gilteritinib is, for example, 120 mg, the patient will take a reduced dose of gilteritinib. In some embodiments, when the reference dose is 120 mg, the reduced dose is, for example, 40 mg or 80 mg, including all integers and ranges therebetween.

In some embodiments, the CYP3A4 substrate drug is naldemedine. The disease or condition treated with naldemedine can include any disease or condition described herein or for which naldemedine is indicated. For example, in some embodiments, naldemedine is indicated for the treatment of opioid-induced constipation (OIC) in adult patients with chronic non-cancer pain, including patients with chronic pain related to prior cancer or its treatment who do not require frequent (e.g., weekly) opioid dosage escalation. Naldemedine may be administered in a 0.2 mg dosage form. For example, when naldemedine is indicated for the treatment of opioid-induced constipation (OIC) in adult patients with chronic non-cancer pain, including patients with chronic pain related to prior cancer or its treatment who do not require frequent (e.g., weekly) opioid dosage escalation, the reference dose is 0.2 mg once daily. In accordance with certain embodiments of the present disclosure, when the reference dose of naldemedine is, for example, 0.2 mg, the patient will take a reduced dose of naldemedine. In some embodiments, when the reference dose is 0.2 mg, the reduced dose is, for example, 0.05 mg, 0.1 mg, or 0.15 mg, including all integers and ranges therebetween.

In some embodiments, the CYP3A4 substrate drug is valbenazine. The disease or condition treated with valbenazine can include any disease or condition described herein or for which valbenazine is indicated. For example, in some embodiments, valbenazine is indicated for the treatment of adults with tardive dyskinesia. Valbenazine may be administered in a 40 mg or 80 mg dosage form. For example, when valbenazine is indicated for the treatment of adults with tardive dyskinesia, the reference dose is either 40 or 80 mg once daily. The initial dose for valbenazine is 40 once daily. After one week, the dose should be increased to the recommended dose of 80 mg once daily. Continuation of 40 mg once daily may be considered for some patients. The reference dose for patients with moderate or severe hepatic impairment is 40 mg once daily. In accordance with certain embodiments of the present disclosure, when the reference dose of valbenazine is, for example, 40 mg, the patient will take a reduced dose of valbenazine. In some embodiments, when the reference dose is 40 mg, the reduced dose is 10 mg, 20 mg, or 30 mg, including all integers and ranges therebetween. In some embodiments, when the reference dose is 80 mg, the reduced dose is 10 mg, 20 mg, 30 mg, 40 mg, 50 mg, 60 mg, or 70 mg, including all integers and ranges therebetween.

In some embodiments, the CYP3A4 substrate drug is midostaurin. The disease or condition treated with midostaurin can include any disease or condition described herein or for which midostaurin is indicated. For example, in some embodiments, midostaurin is indicated for the treatment of adult patients with newly diagnosed acute myeloid leukemia (AML) that is FLT3 mutation-positive as detected by an FDA-approved test, in combination with standard cytarabine and daunorubicin induction and cytarabine consolidation. In some embodiments, midostaurin is indicated for the treatment of adult patients with aggressive systemic mastocytosis (ASM), systemic mastocytosis with associated hematological neoplasm (SM-AHN), or mast cell leukemia (MCL). Midostaurin may be administered in a 25 mg dosage form. In some embodiments, midostaurin is administered twice daily up to a total daily dose of 100 or 200 mg. For example, when midostaurin is indicated for the treatment of adult patients with newly diagnosed acute myeloid leukemia (AML) that is FLT3 mutation positive as detected by an FDA-approved test, in combination with standard cytarabine and daunorubicin induction and cytarabine consolidation, the reference dose is 50 mg twice daily (total daily reference dose is 100 mg). When midostaurin is indicated for the treatment of adult patients with aggressive systemic mastocytosis (ASM), systemic mastocytosis with associated hematological neoplasm (SM-AHN), or mast cell leukemia (MCL), the reference dose is 100 mg twice daily (total daily reference dose is 200 mg). In accordance with certain embodiments of the present disclosure, when the total daily reference dose of midostaurin is, for example, 100 mg, the patient will take a reduced total daily dose of midostaurin. In some embodiments, when the total daily reference dose is 100 mg, the reduced total daily dose is, for example, 25 mg, 50 mg, or 75 mg, including all integers and ranges therebetween. In some embodiments, when the total daily reference dose is 200 mg, the reduced total daily dose is, for example, 25 mg, 50 mg, 75 mg, 100 mg, 125 mg, 150 mg, or 175 mg. Correspondingly, when the reference dose is 50 mg, the reduced dose is 25 mg. When the reference dose is 100 mg, the reduced dose is, for example, 25 mg, 50 mg, or 75 mg, including all integers and ranges therebetween.

In some embodiments, the CYP3A4 substrate drug is neratinib. The disease or condition treated with neratinib can include any disease or condition described herein or for which neratinib is indicated. For example, in some embodiments, neratinib is indicated for the extended adjuvant treatment of adult patients with early stage HER2-overexpressed/amplified breast cancer, to follow adjuvant trastuzumab-based therapy. Neratinib may be administered in a 40 mg dosage form. For example, when neratinib is indicated for the extended adjuvant treatment of adult patients with early stage HER2-overexpressed/amplified breast cancer, to follow adjuvant trastuzumab-based therapy, the reference dose is 240 mg once daily. The reference dose for patients with severe hepatic impairment is 80 mg once daily. In accordance with certain embodiments of the present disclosure, when the reference dose of neratinib is, for example, 240 mg, the patient will take a reduced dose of neratinib. In some embodiments, when the reference dose of neratinib is 240 mg, the reduced dose is, for example, 40 mg, 80 mg, 120 mg, 160 mg, or 200 mg, including all integers and ranges therebetween. When the reference dose of neratinib is 80 mg, the reduced dose is, for example, 40 mg.

In some embodiments, the CYP3A4 substrate drug is acalabrutinib. The disease or condition treated with acalabrutinib can include any disease or condition described herein or for which acalabrutinib is indicated. For example, in some embodiments, acalabrutinib is indicated for the treatment of adult patients with mantle cell lymphoma (MCL) who have received at least one prior therapy. Acalabrutinib may be administered in a 100 mg dosage form. In some embodiments, acalabrutinib is administered every twelve hours up to a total daily dose of 200 mg. For example, when acalabrutinib is indicated for the treatment of adult patients with mantle cell lymphoma (MCL) who have received at least one prior therapy, the reference dose is 100 mg every twelve hours (total daily reference dose is 200 mg). In accordance with certain embodiments of the present disclosure, when the total daily reference dose of acalabrutinib is, for example, 200 mg, the patient will take a reduced total daily dose of acalabrutinib. In some embodiments, when the total daily reference dose of acalabrutinib is 200 mg, the reduced total daily dose is, for example, 50 mg, 100 mg, or 150 mg, including all integers and ranges therebetween. Correspondingly, when the reference dose is 100 mg, the reduced dose is, for example, 25 mg, 50 mg, or 75 mg, including all integers and ranges therebetween.

In some embodiments, the CYP3A4 substrate drug is pimavanserin. The disease or condition treated with pimavanserin can include any disease or condition described herein or for which pimavanserin is indicated. For example, in some embodiments, pimavanserin is indicated for the treatment of the treatment of hallucinations and delusions associated with Parkinson's disease psychosis. Pimavanserin may be administered in a 34 mg or 10 mg dosage form. For example, when pimavanserin is indicated for the treatment of the treatment of hallucinations and delusions associated with Parkinson's disease psychosis, the reference dose is 34 mg once daily. In accordance with certain embodiments of the present disclosure, when the reference dose of pimavanserin is, for example, 34 mg, the patient will take a reduced dose of pimavanserin. In some embodiments, when the reference dose of pimavanserin is 34 mg, the reduced dose is, for example, 10 mg, 17 mg, 20 mg, or 30 mg, including all integers and ranges therebetween.

In some embodiments, the CYP3A4 substrate drug is trabectedin. The disease or condition treated with trabectedin can include any disease or condition described herein or for which trabectedin is indicated. For example, in some embodiments, trabectedin is indicated for the treatment of patients with unresectable or metastatic liposarcoma or leiomyosarcoma who received a prior anthracycline-containing regimen. Trabectedin is available as a 1 mg sterile lyophilized powder in a single-dose vial. For example, when trabectedin is indicated for the treatment of patients with unresectable or metastatic liposarcoma or leiomyosarcoma who received a prior anthracycline-containing regimen, the reference dose is 1.5 mg/m$^2$ body surface area as a 24-hour intravenous infusion every 3 weeks through a central venous line. In patients with moderate hepatic impairment, the reference dose is 0.9 mg/m$^2$ body surface area as a 24-hour intravenous infusion, every 3 weeks through a central venous line. In accordance with certain embodiments of the present disclosure, when the reference dose of trabectedin is, for example, 1.5 mg/m$^2$, the patient will take a reduced dose of trabectedin. In some embodiments, when the reference dose of trabectedin is 1.5 mg/m$^2$, the reduced dose is, for example, 0.5 mg/m$^2$, 0.6 mg/m$^2$, 0.7 mg/m$^2$, 0.8 mg/m$^2$, 0.9 mg/m$^2$, 1.0 mg/m$^2$, 1.1 mg/m$^2$, 1.2 mg/m$^2$, 1.3 mg/m$^2$, or 1.4 mg/m$^2$, including all integers and ranges therebetween. When the reference dose of trabectedin is 0.9 mg/m$^2$, the reduced dose is, for example, 0.5 mg/m$^2$, 0.6 mg/m$^2$, 0.7 mg/m$^2$, or 0.8 mg/m$^2$, including all integers and ranges therebetween.

In some embodiments, the CYP3A4 substrate drug is upadacitinib. The disease or condition treated with upadacitinib can include any disease or condition described herein or for which upadacitinib is indicated. For example, in some embodiments, upadacitinib is indicated for the treatment of patients with moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients. In some embodiments, upadacitinib is indicated for the treatment of patients with ulcerative colitis. In some embodiments, upadacitinib is indicated for the treatment of patients with psoriatic arthritis. In some embodiments, upadacitinib is indicated for the treatment of patients with Crohn's disease. In some embodiments, upadacitinib is indicated for the treatment of patients with atopic dermatitis. In some embodiments, upadacitinib is indicated for the treatment of patients with ankylosing spondylitis. In some embodiments, upadacitinib is indicated for the treatment of patients with and giant cell arteritis.

In some embodiments, the CYP3A4 substrate drug is roxadustat. The disease or condition treated with roxadustat can include any disease or condition described herein or for which roxadustat is indicated. For example, in some embodiments, roxadustat is indicated for the treatment of CKD-related anemia in patients dependent on kidney dialysis and not on kidney dialysis.

In some embodiments, the CYP3A4 substrate drug is AR101. The disease or condition treated with AR101 can include any disease or condition described herein or for which AR101 is indicated. For example, in some embodiments, AR101 is indicated to reduce peanut allergy in children and adolescents aged from 4 to 17, and children aged between 1 and 3 years.

In some embodiments, the CYP3A4 substrate drug is trastuzumab deruxtecan (DS-8201). The disease or condition treated with deruxtecan (DS-8201) can include any disease or condition described herein or for which deruxtecan (DS-8201) is indicated. For example, in some embodiments, rastuzumab deruxtecan (DS-8201) is indicated, as monotherapy or as part of a combination, for the treatment of patients with HER2-expressing cancers, including breast cancer, gastric cancer, non-small cell lung cancer, and colorectal cancer In some embodiments, the CYP3A4 substrate drug is VK2809. The disease or condition treated with VK2809 can include any disease or condition described herein or for which VK2809 is indicated. For example, in some embodiments, VK2809 is indicated for the treatment of non-alcoholic fatty liver disease (NAFLD) and elevated low-density lipoprotein cholesterol (LDL-C). In some embodiments, VK2809 is indicated for the treatment of glycogen storage disease type I (GSD I). In some embodiments, VK2809 is indicated for the treatment of non-alcoholic steatohepatitis (NASH). In some embodiments, VK2809 is indicated for the treatment of hypercholesterolemia.

In some embodiments, the CYP3A4 substrate drug is MGL-3196 (resmetirom). The disease or condition treated with MGL-3196 can include any disease or condition described herein or for which MGL-3196 is indicated. For example, in some embodiments, MGL-3196 is indicated for the treatment of non-alcoholic steatohepatitis (NASH). In some embodiments, MGL-3196 is indicated for the treatment of dyslipidemias, including heterozygous familial hypercholesterolemia (HeFH).

In some embodiments, the CYP3A4 substrate drug is MGL-3745. The disease or condition treated with MGL-3745 can include any disease or condition described herein or for which MGL-3745 is indicated. For example, in some embodiments, MGL-3745 is indicated for the treatment of non-alcoholic steatohepatitis (NASH). In some embodiments, MGL-3745 is indicated for the treatment of dyslipidemias, including heterozygous familial hypercholesterolemia (HeFH).

In some embodiments, the time period for delaying treatment of the CYP3A4 substrate drug, or the time period during which the patient is treated with a reduced dose (e.g., no more than about 90%, about 75%, about 50%, about 25%, etc. of the reference dose) of the CYP3A4 substrate, is at least about 1.5 times the reported average $t_{1/2}$ of posaconazole, e.g., about 2 times, about 2.5 times, about 3 times, about 3.5 times, about 4 times, about 4.5 times, about 5 times, about 5.5 times, about 6 times, about 6.5 times, about 7 times, about 7.5 times, about 8 times, about 8.5 times, about 9 times, about 9.5 times, about 10 times, about 11 times, about 12 times, about 13 times, about 14 times, about 15 times, about 16 times, about 17 times, about 18 times, about 19 times, about 20 times, about 21 times, about 22 times, about 23 times, about 24 times, about 25 times, about 26 times, about 27 times, about 28 times, about 29 times, and about 30 times inclusive of all values and subranges therebetween.

The present disclosure also provides methods for treating, or prescribing treatment, with a CYP3A4 substrate drug intended to treat any of the disorders or conditions described herein, to a patient who has been administered posaconazole prior to the administration of the CYP3A4 substrate drug. In addition to treating the disorder or condition treatable with the CYP3A4 substrate drug, in some embodiments the methods of the present invention reduce the severity or incidence of side effects associated with administration of the CYP3A4 substrate drug after stopping administration of posaconazole. In embodiments, these methods include (a) treating a patient with multiple doses of posaconazole, (b) not administering the CYP3A4 substrate drug during the administration of the posaconazole regimen, (c) stopping administration of posaconazole, (d) delaying treatment of a CYP3A4 substrate drug, or prescribing treatment of the CYP3A4 substrate drug to be delayed, for at least 2-42 days after stopping the posaconazole regimen, and then (e) treating with a CYP3A4 substrate drug. In other embodiments, the methods include (a) treating a patient with multiple doses of posaconazole, (b) not treating the patient with the CYP3A4 substrate drug during the posaconazole regimen, (c) stopping the posaconazole regimen; and (d) for at least about 2-42 days after stopping the posaconazole regimen, treating the patient with the CYP3A4 substrate drug at a dose which is no more than about 50% of the reference dose of the CYP3A4 substrate drug (e.g., an amount in the range of about 10% to about 50%, or about 10% to about 90%, of the reference dose, as described above). The disease or condition treated with the CYP3A4 substrate drug can include any disease or condition described herein or for which CYP3 substrate drug is administered. In some embodiments, the disease or condition is selected from the group consisting of schizophrenia in adults and adolescents (13 to 17 years), depressive episodes associated with Bipolar I Disorder (bipolar depression) in adults and pediatrics (10 to 17 years) as monotherapy or as adjunctive therapy with lithium or valproate, moderate bipolar depression, severe bipolar depression, severe bipolar depression with acute suicidal ideation and behavior (ASIB), chronic angina, erectile dysfunction (ED), benign prostatic hyperplasia (BPH), and pulmonary arterial hypertension (PAH) (WHO Group 1) to improve exercise ability. In other embodiments, the disease or condition is selected from the group consisting of non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, and tuberous sclerosis complex. In other embodiments, the disease or condition is selected from the group consisting of in combination with fulvestrant for the treatment of women with hormone receptor (HR)-positive, human epidermal growth factor receptor 2 (HER2)-negative advanced or metastatic breast cancer with disease progression following endocrine therapy, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, use with sofosbuvir, with or without ribavirin, for the treatment of chronic HCV genotype 1 or 3 infection, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma with BRAF V600E mutation as detected by an FDA-approved test, in combination with trametinib, for the treatment of patients with unresectable or metastatic melanoma with BRAF V600E or V600K mutations as detected by an FDA-approved test, adjuvant treatment of patients with melanoma with BRAF V600E or V600K mutations, as detected by an FDA-approved test, and involvement of lymph node(s), following complete resection, metastatic non-small cell lung cancer (NSCLC) with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

In some embodiments, the time period for delaying administration of the CYP3A4 substrate drug, or the time period during which the CYP3A4 substrate drug is administered at no more than 50% of the reference dose, is greater than about 21 days, such as 22, 23, 24, 25, 26, 27, 28, 29, 30, 31, 32, 33, 34, 35, 36, 37, 38, 39, 40, 41, 42, 43, 44, or 45 days, e.g., for patients with one or more physiological characteristics described herein.

INCORPORATION BY REFERENCE

The entire contents of each of U.S. application Ser. No. 15/596,585, filed May 16, 2017; U.S. application Ser. No. 15/670,262, filed Aug. 7, 2017; U.S. application Ser. No. 15/670,267, filed Aug. 7, 2017; U.S. application Ser. No. 15/670,268, filed Aug. 7, 2017; U.S. application Ser. No. 15/670,271, filed Aug. 7, 2017; U.S. application Ser. No. 15/036,678, filed Jul. 16, 2018; U.S. application Ser. No. 16/191,351, filed Nov. 14, 2018; and U.S. application Ser. No. 16/351,198, filed Mar. 12, 2019, are hereby incorporated by reference for all purposes.

Other particular embodiments are provided herein below:

Embodiments I

1. A method of treating a patient who has previously been administered a therapeutically effective regimen of posaconazole, with a CYP3A4 substrate drug contraindicated for concomitant administration with a strong CYP3A4 inhibitor, said method comprising:
first treating the patient, or prescribing a first treatment to begin, with the CYP3A4 substrate drug at least 2-42 days after stopping administration of posaconazole.

2. The method of embodiment 1, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

3. The method of embodiment 2, wherein the CYP3A4 substrate drug is lurasidone.

4. The method of embodiment 2, wherein the CYP3A4 substrate drug is ranolazine.

5. The method of embodiment 2, wherein the CYP3A4 substrate drug is tadalafil.

6. The method of any of embodiments 1-5, wherein the patient is obese.

7. The method of embodiment 6, wherein the patient has at least one of the following characteristics:
  i) BMI of at least about 35;
  ii) % IBW of at least about 150%;
  iii) waist size greater than about 42 inches;
  iv) % body fat greater than about 40%;
  v) total body fat greater than about 40 kg; and
  vi) medically diagnosed as obese.

8. The method of any of embodiments 1-7, wherein the CYP3A4 substrate drug is ranolazine, and the AUC of ranolazine is maintained at a level of no more than about 150% of a normal baseline AUC of ranolazine.

9. The method of any of embodiments 1-7, wherein the CYP3A4 substrate drug is ranolazine, and the $C_{max}$ of ranolazine is maintained at a level of no more than about 150% of a normal baseline $C_{max}$ of ranolazine.

10. The method of any of embodiments 1-7, wherein the CYP3A4 substrate drug is lurasidone, and the AUC of lurasidone is maintained at a level of no more than about 216% of a normal baseline AUC of lurasidone.

11. The method of any of embodiments 1-7, wherein the CYP3A4 substrate drug is lurasidone, and the $C_{max}$ of lurasidone is maintained at a level of no more than about 210% of a normal baseline $C_{max}$ of lurasidone.

12. The method of any of embodiments 1-7, wherein the CYP3A4 substrate drug is tadalafil, and the AUC of tadalafil is maintained at a level of no more than about 410% of a normal baseline AUC of tadalafil.

13. The method of any of embodiments 1-7, wherein the CYP3A4 substrate drug is tadalafil, and the a $C_{max}$ of tadalafil is maintained at a level of no more than about 120% of a normal baseline $C_{max}$ of tadalafil.

14. The method of embodiments 1-10, wherein the patient is a poor or intermediate CYP3A4 metabolizer.

15. A method of treating a patient with a CYP3A4 substrate drug contraindicated for concomitant administration with a strong CYP3A4 inhibitor, comprising:
treating or prescribing a therapeutically effective amount of a CYP3A4 substrate drug to a patient in need thereof, wherein:
said patient has previously been administered a therapeutically effective regimen of posaconazole, and
for at least about 2-42 days after discontinuation of the posaconazole regimen, said patient is treated with the CYP3A4 substrate drug is at a dose which is no more than about 50% of the reference dose.

16. The method of embodiment 15, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

17. The method of embodiment 16, wherein the CYP3A4 substrate drug is lurasidone.

18. The method of embodiment 16, wherein the CYP3A4 substrate drug is ranolazine.

19. The method of embodiment 16, wherein the CYP3A4 substrate drug is tadalafil.

20. The method of any of embodiments 15-19, wherein the patient is obese.

21. The method of embodiment 20, wherein the patient has at least one of the following characteristics:
i) BMI of at least about 35;
ii) % IBW of at least about 150%;
iii) waist size greater than about 42 inches;
iv) % body fat greater than about 40%;
v) total body fat greater than about 40 kg; and
vi) medically diagnosed as obese.

22. The method of any of embodiments 15-21, wherein the CYP3A4 substrate drug is ranolazine, and the AUC of ranolazine is maintained at a level of no more than about a normal baseline AUC of ranolazine to about 150% of the normal baseline AUC of ranolazine.

23. The method of any of embodiments 15-21, wherein the CYP3A4 substrate drug is ranolazine, and the $C_{max}$ of ranolazine is maintained at a level of no more than about a normal baseline $C_{max}$ of ranolazine to about 150% of the normal baseline $C_{max}$ of ranolazine.

24. The method of any of embodiments 15-21, wherein the CYP3A4 substrate drug is lurasidone, and the AUC of lurasidone is maintained at a level of no more than about a normal baseline AUC of lurasidone to about 216% of the normal baseline AUC of lurasidone.

25. The method of any of embodiments 15-21, wherein the CYP3A4 substrate drug is lurasidone, and the $C_{max}$ of lurasidone is maintained at a level of no more than about a normal baseline $C_{max}$ of lurasidone to about 210% of the normal baseline $C_{max}$ of lurasidone.

26. The method of any of embodiments 15-21, wherein the CYP3A4 substrate drug is tadalafil, and the AUC of tadalafil is maintained at a level of no more than about 410% of a normal baseline AUC of tadalafil.

27. The method of any of embodiments 15-21, wherein the CYP3A4 substrate drug is tadalafil, and the a $C_{max}$ of tadalafil is maintained at a level of no more than about 120% of a normal baseline $C_{max}$ of tadalafil.

28. The method of embodiments 15-27, wherein the patient is a poor or intermediate CYP3A4 metabolizer.

29. The method of embodiment 15, wherein the CYP3A4 substrate drug is ranolazine and the daily dose is no more than about 500 mg for at least about 2-42 days after discontinuation of the posaconazole regimen.

30. A method of treating a disease or condition in a patient with a CYP3A4 substrate drug which is contraindicated for concomitant use with a strong CYP3A4 inhibitor, wherein the patient is also in need of treatment with posaconazole, comprising:
(a) treating a patient with a therapeutically effective regimen of posaconazole;
(b) not treating the patient with the CYP3A4 substrate drug during the posaconazole regimen, and for at least 2-42 days after stopping the posaconazole regimen; and then
(c) treating, or prescribing treatment to begin, with a therapeutically effective amount of the CYP3A4 substrate drug;
wherein the disease or condition treated with the CYP3A4 substrate drug is selected from the group consisting of schizophrenia in adults and adolescents (13 to 17 years), depressive episodes associated with Bipolar I Disorder (bipolar depression) in adults and pediatrics (10 to 17 years) as monotherapy or as adjunctive therapy with lithium or valproate, moderate bipolar depression, severe bipolar depression, severe bipolar depression with acute suicidal ideation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, in combination with fulvestrant for the treatment of women with hormone receptor (HR)-positive, human epidermal growth factor receptor 2 (HER2)-negative advanced or metastatic breast cancer with disease progression following endocrine therapy, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, use with sofosbuvir, with or without ribavirin, for the treatment of chronic HCV genotype 1 or 3 infection, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma with BRAF V600E mutation as detected by an FDA-approved test, in combination with trametinib, for the treatment of patients with unresectable or metastatic melanoma with BRAF V600E or V600K mutations as detected by an FDA-approved test, adjuvant treatment of patients with melanoma with BRAF V600E or V600K mutations, as detected by an FDA-approved test, and involvement of lymph node(s), following complete resection, metastatic non-small cell lung cancer (NSCLC) with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)- positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

31. The method of embodiment 30, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

32. The method of embodiment 31, wherein the CYP3A4 substrate drug is lurasidone.

33. The method of embodiment 31, wherein the CYP3A4 substrate drug is ranolazine.

34. The method of embodiment 31, wherein the CYP3A4 substrate drug is tadalafil.

35. The method of any of embodiments 30-34, wherein the patient is obese.

36. The method of embodiment 35, wherein the patient has at least one of the following characteristics:
   i) BMI of at least about 35;
   ii) % IBW of at least about 150%;
   iii) waist size greater than about 42 inches;
   iv) % body fat greater than about 40%;
   v) total body fat greater than about 40 kg; and
   vi) medically diagnosed as obese.

37. The method of any of embodiments 30-36, wherein the CYP3A4 substrate drug is ranolazine, and the AUC of ranolazine is maintained at a level of no more than about 150% of a normal baseline AUC of ranolazine.

38. The method of any of embodiments 30-36, wherein the CYP3A4 substrate drug is ranolazine, and the $C_{max}$ of ranolazine is maintained at a level of no more than about 150% of a normal baseline $C_{max}$ of ranolazine.

39. The method of any of embodiments 30-36, wherein the CYP3A4 substrate drug is lurasidone, and the AUC of lurasidone is maintained at a level of no more than about 216% of a normal baseline AUC of lurasidone.

40. The method of any of embodiments 30-36, wherein the CYP3A4 substrate drug is lurasidone, and the $C_{max}$ of lurasidone is maintained at a level of no more than about 210% of a normal baseline $C_{max}$ of lurasidone.

41. The method of any of embodiments 30-36, wherein the CYP3A4 substrate drug is tadalafil, and the AUC of tadalafil is maintained at a level of no more than about 410% of a normal baseline AUC of tadalafil.

42. The method of any of embodiments 30-36, wherein the CYP3A4 substrate drug is tadalafil, and the a $C_{max}$ of tadalafil is maintained at a level of no more than about 120% of a normal baseline $C_{max}$ of tadalafil.

43. The method of any of embodiments 30-42, wherein the patient is a poor or intermediate CYP3A4 metabolizer.

44. A method of treating a disease or condition in a patient with a CYP3A4 substrate drug which is contraindicated for concomitant use with a strong CYP3A4 inhibitor, wherein the patient is also in need of treatment with posaconazole, comprising:
  (a) treating a patient with a therapeutically effective regimen of posaconazole to the patient;
  (b) not administering the CYP3A4 substrate drug during the administration of the posaconazole regimen;
  (c) for at least about 2-42 days after stopping the posaconazole regimen, treating the patient with, or prescribing, the CYP3A4 substrate drug at a dose which is no more than about 50% of the reference dose;
wherein the disease or condition treated with the CYP3A4 substrate drug is selected from the group consisting of schizophrenia in adults and adolescents (13 to 17 years), depressive episodes associated with Bipolar I Disorder (bipolar depression) in adults and pediatrics (10 to 17 years) as monotherapy or as adjunctive therapy with lithium or valproate, moderate bipolar depression, severe bipolar depression, severe bipolar depression with acute suicidal ideation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, nonfunctional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, in combination with fulvestrant for the treatment of women with hormone receptor (HR)-positive, human epidermal growth factor receptor 2 (HER2)-negative advanced or metastatic breast cancer with disease progression following endocrine therapy, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, use with sofosbuvir, with or without ribavirin, for the treatment of chronic HCV genotype 1 or 3 infection, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma with BRAF V600E mutation as detected by an FDA-approved test, in combination with trametinib, for the treatment of patients with unresectable or metastatic melanoma with BRAF V600E or V600K mutations as detected by an FDA-approved test, adjuvant treatment of patients with melanoma with BRAF V600E or V600K mutations, as detected by an FDA-approved test, and involvement of lymph node(s), following complete resection, metastatic non-small cell lung cancer (NSCLC) with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

45. The method of embodiment 44, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

46. The method of embodiment 45, wherein the CYP3A4 substrate drug is lurasidone.

47. The method of embodiment 45, wherein the CYP3A4 substrate drug is ranolazine.

48. The method of embodiment 45, wherein the CYP3A4 substrate drug is tadalafil.

49. The method of any of embodiments 44-48, wherein the patient is obese.

50. The method of embodiment 49, wherein the patient has at least one of the following characteristics:
   i) BMI of at least about 35;
   ii) % IBW of at least about 150%;
   iii) waist size greater than about 42 inches;
   iv) % body fat greater than about 40%;
   v) total body fat greater than about 40 kg; and
   vi) medically diagnosed as obese.

51. The method of any of embodiments 44-50, wherein the CYP3A4 substrate drug is ranolazine, and the AUC of ranolazine is maintained at a level of no more than about a normal baseline AUC of ranolazine to about 150% of the normal baseline AUC of ranolazine.

52. The method of any of embodiments 44-50, wherein the CYP3A4 substrate drug is ranolazine, and the $C_{max}$ of ranolazine is maintained at a level of no more than about a normal baseline $C_{max}$ of ranolazine to about 150% of the normal baseline $C_{max}$ of ranolazine.

53. The method of any of embodiments 44-50, wherein the CYP3A4 substrate drug is lurasidone, and the AUC of lurasidone is maintained at a level of no more than about a normal baseline AUC of lurasidone to about 216% of the normal baseline AUC of lurasidone.

54. The method of any of embodiments 44-50, wherein the CYP3A4 substrate drug is lurasidone, and the $C_{max}$ of lurasidone is maintained at a level of no more than about a normal baseline $C_{max}$ of lurasidone to about 210% of the normal baseline $C_{max}$ of lurasidone.

55. The method of any of embodiments 44-50, wherein the CYP3A4 substrate drug is tadalafil, and the AUC of tadalafil is maintained at a level of no more than about 410% of a normal baseline AUC of tadalafil.

56. The method of any of embodiments 44-50, wherein the CYP3A4 substrate drug is tadalafil, and the a $C_{max}$ of tadalafil is maintained at a level of no more than about 120% of a normal baseline $C_{max}$ of tadalafil.

57. The method of embodiments 44-56, wherein the patient is a poor or intermediate CYP3A4 metabolizer.

58. The method of embodiment 44, wherein the CYP3A4 substrate drug is ranolazine and the daily dose is no more than about 500 mg for at least about 2-42 days after discontinuation of the posaconazole regimen.

59. A method of treating a patient in need thereof comprising delaying a first treatment of a CYP3A4 substrate drug until about 2-42 days after stopping administration of posaconazole.

60. The method of embodiment 59, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

61. The method of embodiment 60, wherein the CYP3A4 substrate drug is lurasidone.

62. The method of embodiment 60, wherein the CYP3A4 substrate drug is ranolazine.

63. The method of embodiment 60, wherein the CYP3A4 substrate drug is tadalafil.

64. The method of any of embodiments 59-63, wherein the patient is obese.

65. The method of embodiment 64, wherein the patient has at least one of the following characteristics:
   i) BMI of at least about 35;
   ii) % IBW of at least about 150%;
   iii) waist size greater than about 42 inches;
   iv) % body fat greater than about 40%;
   v) total body fat greater than about 40 kg; and
   vi) medically diagnosed as obese.

66. The method of any of embodiments 59-65, wherein the CYP3A4 substrate drug is ranolazine, and the AUC of ranolazine is maintained at a level of no more than about 150% of a normal baseline AUC of ranolazine.

67. The method of any of embodiments 59-65, wherein the CYP3A4 substrate drug is ranolazine, and the $C_{max}$ of ranolazine is maintained at a level of no more than about 150% of a normal baseline $C_{max}$ of ranolazine.

68. The method of any of embodiments 59-65, wherein the CYP3A4 substrate drug is lurasidone, and the AUC of lurasidone is maintained at a level of no more than about 216% of a normal baseline AUC of lurasidone.

68. The method of any of embodiments 59-65, wherein the CYP3A4 substrate drug is lurasidone, and the $C_{max}$ of lurasidone is maintained at a level of no more than about 210% of a normal baseline $C_{max}$ of lurasidone.

69. The method of any of embodiments 59-65, wherein the CYP3A4 substrate drug is tadalafil, and the AUC of tadalafil is maintained at a level of no more than about 410% of a normal baseline AUC of tadalafil.

70. The method of any of embodiments 59-65, wherein the CYP3A4 substrate drug is tadalafil, and the a $C_{max}$ of tadalafil is maintained at a level of no more than about 120% of a normal baseline $C_{max}$ of tadalafil.

80. The method of embodiments 59-70, wherein the patient is a poor or intermediate CYP3A4 metabolizer.

81. A method of treating a patient previously on posaconazole with a CYP3A4 substrate drug which is contraindicated for concomitant use with a strong CYP3A4 inhibitor comprising, delaying a first treatment, or prescribing a first treatment to be delayed, of the CYP3A4 substrate drug for at least about 2-42 days after posaconazole administration has ceased.

82. The method of embodiment 81, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

83. The method of embodiment 82, wherein the CYP3A4 substrate drug is lurasidone.

84. The method of embodiment 82, wherein the CYP3A4 substrate drug is ranolazine.

85. The method of embodiment 45, wherein the CYP3A4 substrate drug is tadalafil.

86. The method of any of embodiments 81-85, wherein the patient is obese.

87. The method of embodiment 86, wherein the patient has at least one of the following characteristics:
  i) BMI of at least about 35;
  ii) % IBW of at least about 150%;
  iii) waist size greater than about 42 inches;
  iv) % body fat greater than about 40%;
  v) total body fat greater than about 40 kg; and
  vi) medically diagnosed as obese.

88. The method of any of embodiments 81-87, wherein the CYP3A4 substrate drug is ranolazine, and the AUC of ranolazine is maintained at a level of no more than about 150% of a normal baseline AUC of ranolazine.

89. The method of any of embodiments 81-87, wherein the CYP3A4 substrate drug is ranolazine, and the $C_{max}$ of ranolazine is maintained at a level of no more than about 150% of a normal baseline $C_{max}$ of ranolazine.

90. The method of any of embodiments 81-87, wherein the CYP3A4 substrate drug is lurasidone, and the AUC of lurasidone is maintained at a level of no more than about 216% of a normal baseline AUC of lurasidone.

91. The method of any of embodiments 81-87, wherein the CYP3A4 substrate drug is lurasidone, and the $C_{max}$ of lurasidone is maintained at a level of no more than about 210% of a normal baseline $C_{max}$ of lurasidone.

92. The method of any of embodiments 81-87, wherein the CYP3A4 substrate drug is tadalafil, and the AUC of tadalafil is maintained at a level of no more than about 410% of a normal baseline AUC of tadalafil.

93. The method of any of embodiments 81-87, wherein the CYP3A4 substrate drug is tadalafil, and the a $C_{max}$ of tadalafil is maintained at a level of no more than about 120% of a normal baseline $C_{max}$ of tadalafil.

94. The method of embodiments 81-93, wherein the patient is a poor or intermediate CYP3A4 metabolizer.

95. A method of treating a patient with a CYP3A4 substrate drug contraindicated for concomitant use with a strong CYP3A4 inhibitor, comprising treating the patient, or prescribing a treatment of, the CYP3A4 substrate drug at a dose which is less than or equal to about 50% of the reference dose for a period of at least about 2-42 days after stopping administration of posaconazole.

96. The method of embodiment 95, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib. larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

97. The method of embodiment 96, wherein the CYP3A4 substrate drug is lurasidone.

98. The method of embodiment 96, wherein the CYP3A4 substrate drug is ranolazine.

99. The method of embodiment 96, wherein the CYP3A4 substrate drug is tadalafil.

100. The method of any of embodiments 95-99, wherein the patient is obese.

101. The method of embodiment 100, wherein the patient has at least one of the following characteristics:
  i) BMI of at least about 35;
  ii) % IBW of at least about 150%;
  iii) waist size greater than about 42 inches;
  iv) % body fat greater than about 40%;
  v) total body fat greater than about 40 kg; and
  vi) medically diagnosed as obese.

102. The method of any of embodiments 95-101, wherein the CYP3A4 substrate drug is ranolazine, and the AUC of ranolazine is maintained at a level of no more than about a normal baseline AUC of ranolazine to about 150% of the normal baseline AUC of ranolazine.

103. The method of any of embodiments 95-101, wherein the CYP3A4 substrate drug is ranolazine, and the $C_{max}$ of ranolazine is maintained at a level of no more than about a normal baseline $C_{max}$ of ranolazine to about 150% of the normal baseline $C_{max}$ of ranolazine.

104. The method of any of embodiments 95-101, wherein the CYP3A4 substrate drug is lurasidone, and the AUC of lurasidone is maintained at a level of no more than about a normal baseline AUC of lurasidone to about 216% of the normal baseline AUC of lurasidone.

105. The method of any of embodiments 95-101, wherein the CYP3A4 substrate drug is lurasidone, and the $C_{max}$ of lurasidone is maintained at a level of no more than about a normal baseline $C_{max}$ of lurasidone to about 210% of the normal baseline $C_{max}$ of lurasidone.

106. The method of any of embodiments 95-101, wherein the CYP3A4 substrate drug is tadalafil, and the AUC of tadalafil is maintained at a level of no more than about 410% of a normal baseline AUC of tadalafil.

107. The method of any of embodiments 95-101, wherein the CYP3A4 substrate drug is tadalafil, and the a $C_{max}$ of tadalafil is maintained at a level of no more than about 120% of a normal baseline $C_{max}$ of tadalafil.

108. The method of embodiments 95-107, wherein the patient is a poor or intermediate CYP3A4 metabolizer.

109. The method of embodiment 95, wherein the CYP3A4 substrate drug is ranolazine and the daily dose is no more than about 500 mg for at least about 2-42 days after discontinuation of the posaconazole regimen.

110. A method of treating a disease or condition in a patient with a CYP3A4 substrate drug which is contraindicated for concomitant use with a strong CYP3A4 inhibitor, comprising:
 (a) delaying a first treatment, or prescribing a delay of the first treatment, of the CYP3A4 substrate drug for at least 2-42 days after stopping administration of posaconazole; and then
 (b) administering the CYP3A4 substrate drug;
wherein the disease or condition treated with the CYP3A4 substrate drug is selected from the group consisting of schizophrenia in adults and adolescents (13 to 17 years), depressive episodes associated with Bipolar I Disorder (bipolar depression) in adults and pediatrics (10 to 17 years) as monotherapy or as adjunctive therapy with lithium or valproate, moderate bipolar depression, severe bipolar depression, severe bipolar depression with acute suicidal ideation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever, antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, in combination with fulvestrant for the treatment of women with hormone receptor (HR)-positive, human epidermal growth factor receptor 2 (HER2)-negative advanced or metastatic breast cancer with disease progression following endocrine therapy, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, use with sofosbuvir, with or without ribavirin, for the treatment of chronic HCV genotype 1 or 3 infection, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma with BRAF V600E mutation as detected by an FDA-approved test, in combination with trametinib, for the treatment of patients with unresectable or metastatic melanoma with BRAF V600E or V600K mutations as detected by an FDA-approved test, adjuvant treatment of patients with melanoma with BRAF V600E or V600K mutations, as detected by an FDA-approved test, and involvement of lymph node(s), following complete resection, metastatic non-small cell lung cancer (NSCLC) with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

111. The method of embodiment 110, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

112. The method of embodiment 111, wherein the CYP3A4 substrate drug is lurasidone.

113. The method of embodiment 111, wherein the CYP3A4 substrate drug is ranolazine.

114. The method of embodiment 111, wherein the CYP3A4 substrate drug is tadalafil.

115. The method of any of embodiments 110-114, wherein the patient is obese.

116. The method of embodiment 115, wherein the patient has at least one of the following characteristics:
  i) BMI of at least about 35;
  ii) % IBW of at least about 150%;
  iii) waist size greater than about 42 inches;
  iv) % body fat greater than about 40%;
  v) total body fat greater than about 40 kg; and
  vi) medically diagnosed as obese.

117. The method of any of embodiments 110-116, wherein the CYP3A4 substrate drug is ranolazine, and the AUC of ranolazine is maintained at a level of no more than about 150% of a normal baseline AUC of ranolazine.

118. The method of any of embodiments 110-116, wherein the CYP3A4 substrate drug is ranolazine, and the $C_{max}$ of ranolazine is maintained at a level of no more than about 150% of a normal baseline $C_{max}$ of ranolazine.

119. The method of any of embodiments 110-116, wherein the CYP3A4 substrate drug is lurasidone, and the AUC of lurasidone is maintained at a level of no more than about 216% of a normal baseline AUC of lurasidone.

120. The method of any of embodiments 110-116, wherein the CYP3A4 substrate drug is lurasidone, and the $C_{max}$ of lurasidone is maintained at a level of no more than about 210% of a normal baseline $C_{max}$ of lurasidone.

121. The method of any of embodiments 110-116, wherein the CYP3A4 substrate drug is tadalafil, and the AUC of tadalafil is maintained at a level of no more than about 410% of a normal baseline AUC of tadalafil.

122. The method of any of embodiments 110-116, wherein the CYP3A4 substrate drug is tadalafil, and the a $C_{max}$ of tadalafil is maintained at a level of no more than about 120% of a normal baseline $C_{max}$ of tadalafil.

123. The method of embodiments 110-122, wherein the patient is a poor or intermediate CYP3A4 metabolizer.

124. A method of treating a patient with a CYP3A4 substrate drug which is contraindicated for concomitant use with a strong CYP3A4 inhibitor, comprising:
  (a) delaying a first treatment, or prescribing a delay in the first treatment, of the CYP3A4 substrate drug for at least about 2-21 days after stopping administration of the posaconazole regimen; and then
  (d) treating the patient with the CYP3A4 substrate drug at a dose which is less than or equal to about 50% of the reference dose for at least about 2-21 days after stopping administration of the posaconazole regimen;
  wherein the disease or condition treated with the CYP3A4 substrate drug is selected from the group consisting of schizophrenia in adults and adolescents (13 to 17 years), depressive episodes associated with Bipolar I Disorder (bipolar depression) in adults and pediatrics (10 to 17 years) as monotherapy or as adjunctive therapy with lithium or valproate, moderate bipolar depression, severe bipolar depression, severe bipolar depression with acute suicidal ideation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever, antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, in combination with fulvestrant for the treatment of women with hormone receptor (HR)-positive, human epidermal growth factor receptor 2 (HER2)-negative advanced or metastatic breast cancer with disease progression following endocrine therapy, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, use with sofosbuvir, with or without ribavirin, for the treatment of chronic HCV genotype 1 or 3 infection, metastatic non-small cell lung cancer (NSCLC) patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma with BRAF V600E mutation as detected by an FDA-approved test, in combination with trametinib, for the treatment of patients with unresectable or metastatic melanoma with BRAF V600E or V600K mutations as detected by an FDA-approved test, adjuvant treatment of patients with melanoma with BRAF V600E or V600K mutations, as detected by an FDA-approved test, and involvement of lymph node(s), following complete resection, metastatic non-small cell lung cancer (NSCLC) with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

125. The method of embodiment 124, wherein said CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab ematansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilnacipran hydrochloride, pimozide, pomalidomide, abemaciclib, ivacaftor, ruxolitinib phosphate, brexpiprazole, ivacaftor/tezacaftor, regorafenib, daclatasvir, crizotinib, naloxegol oxalate, dabrafenib, olaparib, elbasvir and grazoprevir, apalutamide, brigatinib, cannabidiol, copanlisib, duvelisib, encorafenib, flibanserin, ivabradine, ivosidenib, panobinostat, sonidegib, vemurafenib larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

126. The method of embodiment 125, wherein the CYP3A4 substrate drug is lurasidone.

127. The method of embodiment 125, wherein the CYP3A4 substrate drug is ranolazine.

128. The method of embodiment 125, wherein the CYP3A4 substrate drug is tadalafil.

129. The method of any of embodiments 124-128, wherein the patient is obese.

130. The method of embodiment 129, wherein the patient has at least one of the following characteristics:
 i) BMI of at least about 35;
 ii) % IBW of at least about 150%;
 iii) waist size greater than about 42 inches;
 iv) % body fat greater than about 40%;
 v) total body fat greater than about 40 kg; and
 vi) medically diagnosed as obese.

131. The method of any of embodiments 124-132, wherein the CYP3A4 substrate drug is ranolazine, and the AUC of ranolazine is maintained at a level of no more than about a normal baseline AUC of ranolazine to about 150% of the normal baseline AUC of ranolazine.

132. The method of any of embodiments 124-132, wherein the CYP3A4 substrate drug is ranolazine, and the $C_{max}$ of ranolazine is maintained at a level of no more than about a normal baseline $C_{max}$ of ranolazine to about 150% of the normal baseline $C_{max}$ of ranolazine.

133. The method of any of embodiments 124-132, wherein the CYP3A4 substrate drug is lurasidone, and the AUC of lurasidone is maintained at a level of no more than about a normal baseline AUC of lurasidone to about 216% of the normal baseline AUC of lurasidone.

134. The method of any of embodiments 124-132, wherein the CYP3A4 substrate drug is lurasidone, and the $C_{max}$ of lurasidone is maintained at a level of no more than about a normal baseline $C_{max}$ of lurasidone to about 210% of the normal baseline $C_{max}$ of lurasidone.

135. The method of any of embodiments 124-132, wherein the CYP3A4 substrate drug is tadalafil, and the AUC of tadalafil is maintained at a level of no more than about 410% of a normal baseline AUC of tadalafil.

136. The method of any of embodiments 124-132, wherein the CYP3A4 substrate drug is tadalafil, and the a $C_{max}$ of tadalafil is maintained at a level of no more than about 120% of a normal baseline $C_{max}$ of tadalafil.

137. The method of any one of embodiments 134-136, wherein the patient is a poor or intermediate CYP3A4 metabolizer.

138. The method of any of embodiments 2, 16, 31, 45, 60, 82, 96, 111, or 125, wherein the wherein the CYP3A4 substrate drug is erlotinib.

139. The method of any of embodiments 2, 16, 31, 45, 60, 82, 96, 111, or 125, wherein the wherein the CYP3A4 substrate drug is solifenacin succinate.

140. The method of any of embodiments 2, 16, 31, 45, 60, 82, 96, 111, or 125, wherein the wherein the CYP3A4 substrate drug is everolimus.

141, The method of any of embodiments 2, 16, 31, 45, 60, 82, 96, 111, or 125, wherein the wherein the CYP3A4 substrate drug is abemaciclib.

142. The method of any of embodiments 2, 16, 31, 45, 60, 82, 96, 111, or 125, wherein the wherein the CYP3A4 substrate drug is ivacaftor.

143. The method of any of embodiments 2, 16, 31, 45, 60, 82, 96, 111, or 125, wherein the wherein the CYP3A4 substrate drug is ruxolitinib phosphate.

144. The method of any of embodiments 2, 16, 31, 45, 60, 82, 96, 111, or 125, wherein the wherein the CYP3A4 substrate drug is brexpiprazole.

145. The method of any of embodiments 2, 16, 31, 45, 60, 82, 96, 111, or 125, wherein the wherein the CYP3A4 substrate drug is ivacaftor/tezacaftor.

146. The method of any of embodiments 2, 16, 31, 45, 60, 82, 96, 111, or 125, wherein the wherein the CYP3A4 substrate drug is regorafenib.

147. The method of any of embodiments 2, 16, 31, 45, 60, 82, 96, 111, or 125, wherein the wherein the CYP3A4 substrate drug is daclatasvir.

148. The method of any of embodiments 2, 16, 31, 45, 60, 82, 96, 111, or 125, wherein the wherein the CYP3A4 substrate drug is crizotinib.

149. The method of any of embodiments 2, 16, 31, 45, 60, 82, 96, 111, or 125, wherein the wherein the CYP3A4 substrate drug is naloxegol oxalate.

150. The method of any of embodiments 2, 16, 31, 45, 60, 82, 96, 111, or 125, wherein the wherein the CYP3A4 substrate drug is dabrafenib.

151. The method of any of embodiments 2, 16, 31, 45, 60, 82, 96, 111, or 125, wherein the wherein the CYP3A4 substrate drug is elbasvir and grazoprevir.

152. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is erlotinib, and the AUC of erlotinib is maintained at a level of no more than about 164% of the normal baseline AUC of erlotinib.

153. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is erlotinib, and the $C_{max}$ of erlotinib is maintained at a level of no more than about 167% of the normal baseline $C_{max}$ of erlotinib.

154. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is solifenacin succinate, and the AUC of solifenacin succinate is maintained at a level of no more than about 270% of the normal baseline AUC of solifenacin succinate.

155. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is solifenacin succinate, and the $C_{max}$ of solifenacin succinate is maintained at a level of no more than about 150% of the normal baseline $C_{max}$ of solifenacin succinate.

156. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is everolimus, and the AUC of everolimus is maintained at a level of no more than about 440% of a normal baseline AUC of everolimus.

157. The method of any of embodiments 1, 2, 6, 7, 14-16, 20, 21, 28-31, 35, 36, 43-45, 49, 50, 57-60, 64, 65, 80-82, 86, 87, 94-96, 100, 101, 108-111, 115, 116, 123-125, 129, 130, or 137-140, wherein the CYP3A4 substrate drug is everolimus, and the a $C_{max}$ of everolimus is maintained at a level of no more than about 200% of a normal baseline $C_{max}$ of everolimus.

Embodiments II

1A. A method of treating a patient in need thereof with a CYP3A4 substrate drug, wherein the patient is treated with posaconazole, comprising:
(a) selecting a reference dose of the CYP3A4 substrate drug based on the patient's age and/or condition;
(b) stopping posaconazole treatment;
(c) waiting at least two days after stopping posaconazole treatment; and then
(d) administering the CYP3A4 substrate drug as soon as it is safe to do so.

1B. The method of embodiment 1A, wherein the CYP3A4 substrate drug is administered in step (d) as soon as at least one of the patient's AUC, $C_{max}$, AUC GMR, or $C_{max}$ GMR reaches a target safe level disclosed herein, e.g., as provided in Table A for the CYP3A4 substrate drug.

2A. A method of treating a patient in need thereof with a CYP3A4 substrate drug, wherein the patient is treated with posaconazole, comprising:
(a) selecting a reference dose of the CYP3A4 substrate drug based on the patient's age and/or condition;
(b) stopping posaconazole treatment;
(c) waiting at least two days after stopping posaconazole treatment; and then
(d) administering the CYP3A4 substrate drug to achieve an AUC of the CYP3A4 substrate that is at least about 105% of a predicted AUC for the day on which that CYP3A4 substrate drug is administered.

2B. The method of embodiment 2A, wherein the AUC of the CYP3A4 substrate drug in step (d) ranges from 105% to a target safe level disclosed herein, e.g., as provided in Table A for the CYP3A4 substrate drug.

3A. A method of treating a patient in need thereof with a CYP3A4 substrate drug, wherein the patient is treated with posaconazole, comprising:
(a) selecting a reference dose of the CYP3A4 substrate drug based on the patient's age and/or condition;
(b) stopping posaconazole treatment;
(c) waiting at least two days after stopping posaconazole treatment; and then
(d) administering the CYP3A4 substrate drug to achieve a GMR AUC of the CYP3A4 substrate which is at least about 1.05 fold of the expected AUC.

3B. The method of embodiment 3A, wherein the AUC of the CYP3A4 substrate drug in step (d) ranges from about 1.05 fold to a target safe level disclosed herein, e.g., as provided in Table A for the CYP3A4 substrate drug.

4A. A method of treating a patient in need thereof with a CYP3A4 substrate drug, wherein the patient is treated with posaconazole, comprising:
(a) selecting a reference dose of the CYP3A4 substrate drug based on the patient's age and/or condition;
(b) stopping posaconazole treatment;
(c) waiting at least two days after stopping posaconazole treatment; and then
(d) administering the CYP3A4 substrate drug to achieve an AUC of the CYP3A4 substrate that does not exceed a maximum level where benefits of treating the patient outweigh risks of elevated exposure to the CYP3A4 substrate drug.

4B. The method of embodiment 4A, wherein the AUC of the CYP3A4 substrate drug in step (d) does not exceed a target safe level disclosed herein, e.g., as provided in Table A for the CYP3A4 substrate drug.

5A. A method of treating a patient in need thereof with a CYP3A4 substrate drug, wherein the patient is treated with posaconazole, comprising:
(a) selecting a reference dose of the CYP3A4 substrate drug based on the patient's age and/or condition;
(b) stopping posaconazole treatment;
(c) waiting at least two days after stopping posaconazole treatment; and then
(d) administering the CYP3A4 substrate drug to achieve a GMR AUC of the CYP3A4 substrate that does not exceed a maximum level where benefits of treating the patient outweigh risks of elevated exposure to the CYP3A4 substrate drug.

5B. The method of embodiment 5A, wherein the AUC of the CYP3A4 substrate drug in step (d) does not exceed a target safe level disclosed herein, e.g., as provided in Table A for the CYP3A4 substrate drug.

6A. A method of treating a patient in need thereof with a CYP3A4 substrate drug, wherein the patient is treated with posaconazole, comprising:
(a) selecting a reference dose of the CYP3A4 substrate drug based on the patient's age and/or condition;

(b) stopping posaconazole treatment
(c) waiting at least two days after stopping posaconazole treatment; and then and then
(d) administering the CYP3A4 substrate drug to achieve at least one of a GMR AUC or GMR $C_{max}$ of the CYP3A4 substrate which is:
  (i) at least about 1.05 fold greater than the predicted AUC or $C_{max}$; and
  (ii) does not exceed maximum level where benefits of treating the patient outweigh risks of elevated exposure to the CYP3A4 substrate drug.

6B. The method of embodiment 6A, wherein the GMR AUC or GMR $C_{max}$ of the CYP3A4 substrate drug in step (d)(ii) does not exceed a target safe level disclosed herein, e.g., as listed in Table A for the CYP3A4 substrate drug.

7A. A method of treating a patient in need thereof with a CYP3A4 substrate drug, wherein the patient is treated with posaconazole, comprising:
  (a) selecting a reference dose of the CYP3A4 substrate drug based on the patient's age and/or condition;
  (b) stopping posaconazole treatment
  (c) waiting at least two days after stopping posaconazole treatment; and then
  (d) administering the CYP3A4 substrate drug:
    (i) as soon as steady state posaconazole levels ($C_{ss}$ ng/mL) are reduced by at least about 50%; and
    (ii) the at least one of the AUC, Cmax, GMR AUC, or GMR Cmax are at or below a target safe level (e.g., as disclosed in Table A) but above the expected level.

8. The method of any one of embodiments 1A-1B, 2A-2B, 3A-3B, 4A-4B, 5A-5B, 6A-6B, or 7 wherein the CYP3A4 substrate drug is selected from the group consisting of lurasidone, ranolazine, lumacaftor/ivacaftor, venetoclax, trabectedin, ribociclib succinate, deflazacort, cinacalcet hydrochloride, pimavanserin tartrate, aripiprazole lauroxil, cariprazine hydrochloride, simeprevir sodium, everolimus, saxagliptin hydrochloride, saxagliptin/metformin hydrochloride, ticagrelor, vilazodone hydrochloride, apixaban, tofacitinib citrate, eletriptan hydrobromide, nilotinib hydrochloride monohydrate, dronedarone hydrochloride, fluticasone propionate/salmeterol xinafoate, rivaroxaban, tadalafil, ibrutinib, cobimetinib, colchicine, cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilacipran hydrochloride, pimozide, pomalidomide, abemaciclib, ivacaftor, olaparib, ruxolitinib phosphate, brexpiprazole, ivacaftor/tezacaftor, regorafenib, daclatasvir, crizotinib, naloxegol oxalate, dabrafenib, elbasvir/grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

9. The method of any one of embodiments 1A-1B, 2A-2B, 3A-3B, 4A-4B, 5A-5B, 6A-6B, 7 or 8 wherein the CYP3A4 substrate drug is selected from the group consisting of cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilacipran hydrochloride, pimozide, pomalidomide, abemaciclib, ivacaftor, olaparib, ruxolitinib phosphate, brexpiprazole, ivacaftor/tezacaftor, regorafenib, daclatasvir, crizotinib, naloxegol oxalate, dabrafenib, elbasvir/grazoprevir, apalutamide, brigatinib, cannabidiol, copanlisib, duvelisib, encorafenib, flibanserin, ivabradine, ivosidenib, panobinostat, sonidegib, vemurafenib, pimavanserin, trabectedin, larotrectinib, irinotecan, siponimod, erdafitinib, fostamatinib disodium, elagolix sodium, lorlatinib, glasdegib, gilteritinib, naldemedine, valbenazine, midostaurin, neratinib, acalabrutinib, pimavanserin, trabectedin, upadacitinib, roxadustat, AR101, trastuzumab deruxtecan, VK2809, MGL-3196, and MGL-3745.

10. The method of any one of embodiments 1A-1B, 2A-2B, 3A-3B, 4A-4B, 5A-5B, 6A-6B, 7, 8, or 9 wherein the CYP3A4 substrate drug is selected from the group consisting of cabazitaxel, tolvaptan, fosaprepitant dimeglumine, aprepitant, solifenacin succinate, erlotinib hydrochloride, ado-trastuzumab emtansine, bosutinib monohydrate, sunitinib malate, fesoterodine fumarate, maraviroc, pazopanib hydrochloride, aripiprazole, axitinib, dapagliflozin/saxagliptin, cabozantinib S-malate, ponatinib hydrochloride, isavuconazonium sulfate, lomitapide mesylate, iloperidone, palbociclib, levomilacipran hydrochloride, pimozide, and pomalidomide.

11. The method of any one of embodiments 1A-1B, 2A-2B, 3A-3B, 4A-4B, 5A-5B, 6A-6B, 7, 8, 9, or 10 wherein the CYP3A4 substrate drug is selected from the group consisting of abemaciclib, ivacaftor, olaparib, ruxolitinib phosphate, brexpiprazole, ivacaftor/tezacaftor, regorafenib, daclatasvir, crizotinib, naloxegol oxalate, dabrafenib, and elbasvir/grazoprevir.

12. The method of any one of embodiments 1A-1B, 2A-2B, 3A-3B, 4A-4B, 5A-5B, 6A-6B, 7, 8, 9, 10, or 11 wherein the CYP3A4 substrate drug is selected from the group consisting of apalutamide, brigatinib, cannabidiol, copanlisib, duvelisib, encorafenib, flibanserin, ivabradine, ivosidenib, panobinostat, sonidegib, and vemurafenib.

13. The method of any of embodiments 1A-1B, 2A-2B, 3A-3B, 4A-4B, 5A-5B, 6A-6B, 7, or 8 wherein the patient is treated for disease or condition selected from the group consisting of schizophrenia in adults and adolescents (13 to 17 years), depressive episodes associated with Bipolar I Disorder (bipolar depression) in adults and pediatric patients (10-17 years) as monotherapy or adjunctive therapy with lithium or valproate, moderate bipolar depression, severe bipolar depression, and severe bipolar depression with acute suicidal idealation and behavior (ASIB), chronic angina, cystic fibrosis in patients 6 years and older who are homozygous for the F508del mutation in the CFTR gene, chronic lymphocytic leukemia in patients with 17p deletion, who have received at least one prior therapy, unresectable or metastatic liposarcoma or leiomyosarcoma in patients who received a prior anthracycline-containing regimen, advanced or metastatic breast cancer in postmenopausal women with hormone receptor (HR)-positive, human epidermal growth factor receptor 2 (HER2)-negative advanced or metastatic breast cancer, negative advanced or metastatic breast cancer in combination with an aromatase inhibitor for postmenopausal women, Duchenne muscular dystrophy (DMD), secondary hyperparathyroidism (HPT) in patients with chronic kidney disease (CKD) on dialysis, hypercalcemia in patients with parathyroid carcinoma or in patients with primary HPT for who parathyroidectomy would be indicated on the basis of serum calcium levels, but who are unable to undergo parathyroidectomy, hallucinations and delusions associated with Parkinson's disease psychosis, schizophrenia, acute manic or mixed episodes associated with bipolar I disorder, chronic hepatitis C (CHC) infection as a component of a combination antiviral treatment regimen with peginterferon alfa and ribavirin in HCV genotype 1 infected subjects with compensated liver disease, postmenopausal women with advanced hormone receptor-positive, HER2-negative breast cancer (advanced HR+ BC), e.g., in combination with exemestane after failure of treatment with letrozole or anastrozole, progressive neuroendocrine tumors of pancreatic origin (PNET), progressive, well-differentiated, non-functional neuroendocrine tumors (NET) of gastrointestinal (GI) or lung origin that are unresectable, locally advanced or metastatic, advanced renal cell carcinoma (RCC), e.g., after failure of treatment with sunitinib or sorafenib, renal angiomyolipoma and tuberous sclerosis complex (TSC), not requiring immediate surgery, TSC in patients who have subependymal giant cell astrocytoma (SEGA) that require therapeutic intervention but are not candidates for surgical resection, type 2 diabetes mellitus in adults as an adjunct to diet and exercise to improve glycemic control, major depressive disorder (MDD), thrombotic cardiovascular events (e.g., cardiovascular death, myocardial infarction, or stroke) in patients with acute coronary syndrome (ACS), stroke and systemic embolism in patients with nonvalvular atrial fibrillation, deep vein thrombosis (DVT), which may lead to pulmonary embolism (PE) in patients who have undergone hip or knee replacement surgery, DVT, PE, recurrent DVT and PE following initial therapy, moderate to severe active rheumatoid arthritis in patients who have had inadequate response or tolerance to methotrexate, acute migraine with or without aura, chronic phase and accelerated phase Philadelphia chromosome positive chronic myeloid leukemia (Ph+ CML) in newly diagnosed patients or in patients resistant to or intolerant to prior therapy that included imatinib, atrial fibrillation (AF) in patients with a history of paroxysmal or persistent AF or atrial flutter (AFK), who are in sinus rhythm or will be cardioverted, asthma in patients aged 4 years and older, airflow obstruction and reducing exacerbations in patients with chronic obstructive pulmonary disease, erectile dysfunction (ED), benign prostatic hyperplasia (BPH), pulmonary arterial hypertension (PAH) (WHO Group 1) to improve exercise ability, gout flares, Familial Mediterranean fever, antiretroviral therapy, anxiety disorders, panic disorders, seizures, insomnia, hypertension, cardiovascular disease, hyperlipidemia, cancer, such as primary kidney cancer, advanced primary liver cancer, radioactive iodine resistant advanced thyroid carcinoma, renal cell carcinoma, imatinib-resistant gastrointestinal stromal tumor, mantle cell lymphoma in patients who have received at least one prior therapy, chronic lymphocytic leukemia/small lymphocytic lymphoma, chronic lymphocytic leukemia/small lymphocytic lymphoma with 17p deletion, Waldenström's macroglobulinemia, marginal zone lymphoma who require systemic therapy and have received at least one prior anti-CD20-based therapy, unresectable or metastatic melanoma with a BRAF V600E or V600K mutation, allergies, transplantation, hormone-refractory metastatic prostate cancer previously treated with a docetaxel-containing treatment regimen, hormone-refractory metastatic prostate cancer previously treated with a docetaxel-containing treatment regimen, treatment of clinically significant hypervolemic and euvolemic hyponatremia, including patients with heart failure and Syndrome of Inappropriate Antidiuretic Hormone (SIADH), prevention of acute and delayed nausea and vomiting associated with initial and repeat courses of highly emetogenic cancer chemotherapy (HEC) including high-dose cisplatin, prevention of delayed nausea and vomiting associated with initial and repeat courses of moderately emetogenic cancer chemotherapy (MEC), over-active bladder with symptoms of urge urinary incontinence, urgency, and urinary frequency, metastatic non-small cell lung cancer (NSCLC) whose tumors have epidermal growth factor receptor (EGFR) exon 19 deletions or exon 21 (L858R) substitution mutations as detected by an FDA-approved test receiving first-line, maintenance, or second or greater line treatment after progression, locally advanced, unresectable or metastatic pancreatic cancer, in combination with gemcitabine, HER2-positive, metastatic breast cancer who previously received trastuzumab and a taxane, separately or in combination in patients who have either: received prior therapy for metastatic disease or developed disease recurrence during or within six months of completing adjuvant therapy, chronic, accelerated, or blast phase Ph+ chronic myelogenous leukemia (CML) in adults with resistance or intolerance to prior therapy, gastrointestinal stromal tumor (GIST) after disease progression on or intolerance to imatinib mesylate, advanced renal cell carcinoma (RCC), progressive, well-differentiated pancreatic neuroendocrine tumors (pNET) in patients with unresectable locally advanced or metastatic disease, CCR5-tropic HIV-1 infection in patients 2 years of age and older weighing at least 10 kg in combination with other antiretroviral agents, advanced renal cell carcinoma, advanced soft tissue sarcoma who have received prior chemotherapy, manic and mixed episodes associated with Bipolar I, Major Depressive Disorder, irritability associated with Autistic Disorder, Tourette's disorder, agitation associated with schizophrenia or bipolar mania, advanced renal cell carcinoma after failure of one prior systemic therapy, to improve glycemic control in adults with type 2 diabetes mellitus (T2DM) who have inadequate control with dapagliflozin or who are already treated with dapagliflozin and saxagliptin, progressive, metastatic medullary thyroid cancer (MTC), advanced renal cell carcinoma (RCC) who have received prior anti-angiogenic therapy, chronic phase, accelerated phase, or blast phase chronic myeloid leukemia (CML) or Ph+ ALL in adults for whom no other tyrosine kinase inhibitor (TKI) therapy is indicated, T315I-positive CML (chronic phase, accelerated phase, or blast phase) or T315I-positive Philadelphia chromosome in adults, positive acute lymphoblastic leukemia (Ph+ ALL), invasive aspergillosis, invasive mucormycosis, to reduce low-density lipoprotein cholesterol (LDL-C), total cholesterol (TC), apolipoprotein B (apo B), and non-high density lipoprotein cholesterol (non-HDL-C) in patients with homozygous familial hypercholesterolemia (HoFH), schizophrenia in adults, hormone receptor (HR)-positive, human epidermal growth factor receptor 2 (HER2)-negative advanced or metastatic breast cancer in combination with an aromatase inhibitor as initial endocrine based therapy in postmenopausal women, or fulvestrant in women with disease progression following endocrine therapy, Major Depressive Disorder (MDD), suppression of motor and phonic tics in patients with Tourette's Disorder who have failed to respond satisfactorily to standard treatment, treatment of multiple myeloma in patients who have received at least two prior therapies including lenalidomide and a proteasome inhibitor and have demonstrated disease progression on or within 60 days of completion of the last therapy, non-small cell lung cancer (NSCLC) whose disease has not progressed after four cycles of platinum-based first-line chemotherapy, locally advanced or metastatic NSCLC after failure of at least one prior chemotherapy regimen, locally advanced, unresectable or metastatic pancreatic cancer, overactive bladder with symptoms of urge urinary incontinence, urgency, and urinary frequency, advanced renal cell carcinoma (RCC) after failure of treatment with sunitinib or sorafenib, subependymal giant cell astrocytoma (SEGA) associated with tuberous sclerosis (TS) who require therapeutic intervention but are not candidates for curative surgical resection, renal angiomyolipoma, tuberous sclerosis complex, hormone receptor (HR)-positive, human epidermal growth factor receptor 2 (HER2)-negative advanced or metastatic breast cancer with disease progression following endocrine therapy in women in combination with fulvestrant, as monotherapy for the treatment of adult patients with HRpositive, HER2-negative advanced or metastatic breast cancer with disease progression following endocrine therapy and prior chemotherapy in the metastatic setting, cystic fibrosis (CF) in patients age 2 years and older who have one mutation in the CFTR gene that is responsive to ivacaftor based on clinical and/or in vitro assay data, deleterious or suspected deleterious germline BRCA-mutated advanced ovarian cancer in adult patients who have been treated with three or more prior lines of chemotherapy, intermediate or high-risk myelofibrosis, including primary myelofibrosis, post-polycythemia vera myelofibrosis and post-essential thrombocythemia myelofibrosis, polycythemia vera patients who have had an inadequate response to or are intolerant of hydroxyurea, as an adjunctive therapy to antidepressants for the treatment of major depressive disorder (MDD), schizophrenia, cystic fibrosis (CF) patients aged 12 years and older who are homozygous for the F508del mutation or who have at least one mutation in the cystic fibrosis transmembrane conductance regulator (CFTR) gene that is responsive to tezacaftor/ivacaftor based on in vitro data and/or clinical evidence, metastatic colorectal cancer (CRC) patients who have been previously treated with fluoropyrimidine-, oxaliplatin- and irinotecan-based chemotherapy, an antiVEGF therapy, and, if RAS wild-type, an anti-EGFR therapy, locally advanced, unresectable or metastatic gastrointestinal stromal tumor (GIST) patients who have been previously treated with imatinib mesylate and sunitinib malate, hepatocellular carcinoma (HCC) who have been previously treated with sorafenib, chronic HCV genotype 1 or 3 infection with sofosbuvir and with or without ribavirin, metastatic non-small cell lung cancer (NSCLC) in patients whose tumors are anaplastic lymphoma kinase (ALK) or ROS1-positive as detected by an FDA-approved test, opioid induced constipation (OIC) in adult patients with chronic non-cancer pain, including patients with chronic pain related to prior cancer or its treatment who do not require frequent (e.g., weekly) opioid dosage escalation, unresectable or metastatic melanoma in patients with BRAF V600E mutation as detected by an FDA-approved test, in combination with trametinib, for the treatment of unresectable or metastatic melanoma in patients with BRAF V600E or V600K mutations as detected by an FDA-approved test, melanoma in patients with BRAF V600E or V600K mutations, as detected by an FDA-approved test, and involvement of lymph node(s), following complete resection, metastatic non-small cell lung cancer (NSCLC) in patients with BRAF V600E mutation as detected by an FDA-approved test, locally advanced or metastatic anaplastic thyroid cancer (ATC) in patients with BRAF V600E mutation and with no satisfactory locoregional treatment options, with or without ribavirin for treatment of chronic HCV genotypes 1 or 4 infection in adults, the treatment of patients with non-metastatic castration-resistant prostate cancer, the treatment of patients with anaplastic lymphoma kinase (ALK)-positive metastatic non-small cell lung cancer (NSCLC) who have progressed on or are intolerant to crizotinib, the treatment of seizures associated with Lennox-Gastaut syndrome or Dravet syndrome in patients 2 years of age and older, the treatment of adult patients with relapsed follicular lymphoma (FL) who have received at least two prior systemic therapies, the treatment of adult patients with relapsed or refractory chronic lymphocytic leukemia (CLL) or small lymphocytic lymphoma (SLL) after at least two prior therapies, the treatment of adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use, the treatment of adult patients with relapsed or refractory acute myeloid leukemia (AML) with a susceptible IDH1 mutation as detected by an FDA-approved test, the treatment of patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy, the treatment of patients with unresectable or metastatic melanoma with BRAF V600E mutation as detected by an FDA-approved test, the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

14. The method of any of embodiments 1A-1B, 2A-2B, 3A-3B, 4A-4B, 5A-5B, 6A-6B, 7, 8, 11, or 12, wherein the patient is treated for a disease or condition selected from the group consisting of: non-metastatic castration-resistant prostate cancer; anaplastic lymphoma kinase (ALK)-positive metastatic non-small cell lung cancer (NSCLC) who have progressed on or are intolerant to crizotinib; seizures associated with Lennox-Gastaut syndrome or Dravet syndrome in patients 2 years of age and older; relapsed follicular lymphoma (FL) in adults who have received at least two prior systemic therapies; adults with relapsed or refractory chronic lymphocytic leukemia (CLL) or small lymphocytic lymphoma (SLL) after at least two prior therapies; adult patients with relapsed or refractory follicular lymphoma (FL) after at least two prior systemic therapies, in combination with binimetinib; unresectable or metastatic melanoma with a BRAF V600E or V600K mutation, as detected by an FDA-approved test, the treatment of premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance, to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use; adult patients with relapsed or refractory acute myeloid leukemia (AML) with a susceptible IDH1 mutation as detected by an FDA-approved test; multiple myeloma who have received at least 2 prior regimens, including bortezomib and an immunomodulatory agent; adult patients with locally advanced basal cell carcinoma (BCC) that has recurred following surgery or radiation therapy, or those who are not candidates for surgery or radiation therapy; unresectable or metastatic melanoma with BRAF V600E mutation as detected by an FDA-approved test; Erdheim-Chester Disease with BRAF V600 mutation; non-metastatic castration-resistant prostate cancer; anaplastic lymphoma kinase (ALK)-positive metastatic non-small cell lung cancer (NSCLC) who have progressed on or are intolerant to crizotinib; seizures associated with Lennox-Gastaut syndrome or Dravet syndrome in patients 2 years of age and older; adult patients with relapsed follicular lymphoma (FL) who have received at least two prior systemic therapies; adult patients with relapsed or refractory chronic lymphocytic leukemia (CLL) or small lymphocytic lymphoma (SLL) after at least two prior therapies; adult patients with relapsed or refractory follicular lymphoma (FL) after at least two prior systemic therapies, in combination with binimetinib, for the treatment of patients with unresectable or metastatic melanoma with a BRAF V600E or V600K mutation, as detected by an FDA-approved test; premenopausal women with acquired, generalized hypoactive sexual desire disorder (HSDD) as characterized by low sexual desire that causes marked distress or interpersonal difficulty and is not due to a co-existing medical or psychiatric condition, problems within the relationship, or the effects of a medication or other drug substance; to reduce the risk of hospitalization for worsening heart failure in patients with stable, symptomatic chronic heart failure with left ventricular ejection fraction ≤35%, who are in sinus rhythm with resting heart rate ≥70 beats per minute and either are on maximally tolerated doses of beta-blockers or have a contraindication to beta-blocker use; adult patients with relapsed or refractory acute myeloid leukemia (AML) with a susceptible IDH1 mutation as detected by an FDA-approved test; patients with multiple myeloma who have received at least 2 prior regimens, including bortezomib and an immunomodulatory agent, the treatment of adult patients with locally advanced basal cell carcinoma (BCC) that has recurred following surgery or radiation therapy, or those who are not candidates for surgery or radiation therapy; patients with unresectable or metastatic melanoma with BRAF V600E mutation as detected by an FDA-approved test; and the treatment of patients with Erdheim-Chester Disease with BRAF V600 mutation, adult and pediatric patients with solid tumors that have a neurotrophic receptor tyrosine kinase (NTRK) gene fusion without a known acquired resistance mutation, are metastatic or where surgical resection is likely to result in severe morbidity, and have no satisfactory alternative treatments or that have progressed following treatment, relapsing forms of multiple sclerosis (MS), to include clinically isolated syndrome, relapsing-remitting disease, and active secondary progressive disease, in adults, adult patients with locally advanced or metastatic urothelial carcinoma that has susceptible FGFR3 or FGFR2 genetic alterations and progressed during or following at least one line of prior platinum containing chemotherapy including within 12 months of neoadjuvant or adjuvant platinum-containing chemotherapy, thrombocytopenia in adult patients with chronic immune thrombocytopenia (ITP) who have had an insufficient response to a previous treatment, management of moderate to severe pain associated with endometriosis, treatment of patients with anaplastic lymphoma kinase (ALK)-positive metastatic non-small cell lung cancer (NSCLC) whose disease has progressed on crizotinib and at least one other ALK inhibitor for metastatic disease, anaplastic lymphoma kinase (ALK)-positive metastatic non-small cell lung cancer (NSCLC) whose disease has progressed on alectinib as the first ALK inhibitor therapy for metastatic disease, anaplastic lymphoma kinase (ALK)-positive metastatic non-small cell lung cancer (NSCLC) whose disease has progressed on ceritinib as the first ALK inhibitor therapy for metastatic disease, in combination with low-dose cytarabine, for the treatment of newly-diagnosed acute myeloid leukemia (AML) in adult patients who are ≥75 years old or who have comorbidities that preclude use of intensive induction chemotherapy, adult patients who have relapsed or refractory acute myeloid leukemia (AML) with a FLT3 mutation as detected by an FDA-approved test, opioid-induced constipation (OIC) in adult patients with chronic non-cancer pain, including patients with chronic pain related to prior cancer or its treatment who do not require frequent (e.g., weekly) opioid dosage escalation, adults with tardive dyskinesia, adult patients with newly diagnosed acute myeloid leukemia (AML) that is FLT3 mutation-positive as detected by an FDA-approved test, in combination with standard cytarabine and daunorubicin induction and cytarabine consolidation, adult patients with aggressive systemic mastocytosis (ASM), systemic mastocytosis with associated hematological neoplasm (SM-AHN), or mast cell leukemia (MCL), extended adjuvant treatment of adult patients with early stage HER2-overexpressed/amplified breast cancer, to follow adjuvant trastuzumab-based therapy, adult patients with mantle cell lymphoma (MCL) who have received at least one prior therapy, moderate to severe rheumatoid arthritis, including patients not responding adequately to conventional synthetic disease-modifying anti-rheumatic drugs (DMARDs), patients not adequately responding to or intolerant of biologic DMARDs, in patients switching from methotrexate monotherapy after inadequate responses, in combination with methotrexate, in patients with inadequate responses, and in methotrexate-naive patients, ulcerative colitis, psoriatic arthritis, Crohn's disease, atopic dermatitis, ankylosing spondylitis, and giant cell arteritis, CKD-related anemia in patients dependent on kidney dialysis and not on kidney dialysis, to reduce peanut allergy in children and adolescents aged from 4 to 17, and children aged between 1 and 3 years, as monotherapy or as part of a combination with HER2-expressing cancers, including breast cancer, gastric cancer, non-small cell lung cancer, and colorectal cancer, non-alcoholic fatty liver disease (NAFLD), elevated low-density lipoprotein cholesterol (LDL-C), Glycogen storage disease type I (GSD I), non-alcoholic steatohepatitis (NASH), hypercholesterolemia, non-alcoholic steatohepatitis (NASH), dyslipidemias, including heterozygous familial hypercholesterolemia (HeFH), in combination with fluorouracil and leucovorin, for the treatment of patients with metastatic adenocarcinoma of the pancreas after disease progression following gemcitabine-based therapy, first-line therapy in combination with 5-fluorouracil and leucovorin for patients with metastatic carcinoma of the colon or rectum, metastatic carcinoma of the colon or rectum whose disease has recurred or progressed following initial fluorouracil-based therapy, hallucinations and delusions associated with Parkinson's disease psychosis, and unresectable or metastatic liposarcoma or leiomyosarcoma who received a prior anthracycline-containing regimen.

15. The method of any one of embodiments 1A-14, wherein the waiting in step (c) is at least 5 days.

16. The method of any one of embodiments 1A-14, wherein the waiting in step (c) is at least 7 days.

17. The method of any one of embodiments 1A-14, wherein the waiting in step (c) is at least 14 days.

18. The method of any one of embodiments 1-14, wherein the waiting in step (c) is in the range of from 2-42 days.

19. The method of any one of embodiments 1-12, wherein the waiting in step (c) is in the range of from 5-42 days.

20. The method of any one of embodiments 1-13, wherein the waiting in step (c) is in the range of from 7-21 days.

21. The method of any one of embodiments 1-13, wherein the waiting in step (b) is in the range of from 14-28 days.

22. The method of any one of embodiments 1A-21, wherein the reference dose of the CYP3A4 substrate drug is administered or a reduced dose of the CYP3A4 substrate drug is administered.

EXAMPLES

Example 1. Pharmacokinetic Studies with Posaconazole and Lurasidone

Inventors studied 6 obese male and female subjects (ages 18-50, BMI>35) taking Posaconazole oral tablets (300 mg qd) and Lurasidone (20 mg qd). Body weights and BMI measurements for the 6 subjects are provided below in Table 1.

TABLE 1

| Subject Demographics | | |
| --- | --- | --- |
| Subject # | Weight (kg) | BMI (kg/m$^2$) |
| 101-001 | 111.8 | 45 |
| 101-002 | 136.8 | 44.4 |
| 101-005 | 137.7 | 51.2 |
| 101-007 | 103.7 | 36.8 |
| 101-008 | 122.3 | 39.8 |
| 101-010 | 120.0 | 43.9 |

Subjects were dosed with Lurasidone alone on Day 1, then subsequently dosed to steady-state Posaconazole levels, with a loading dose of 300 mg twice a day on Day 2 and 300 mg once a day thereafter over a period of 14 days. Posaconazole administration was then stopped and Lurasidone (20 mg qd) administered 2, 4, and 6 days after administration had ceased (studies days 17, 19, and 21 respectively). Lurasidone AUC was measured for 24 hours after each administration. Table 2 shows subject Lurasidone AUC levels 2, 4 and 6 days after Posaconazole was stopped, Posaconazole AUC levels 2, 4, and 6 days after Posaconazole was stopped, and the ratio of post-Posaconazole Lurasidone AUC to the baseline Lurasidone AUC measured before Posaconazole treatment:

These results indicate that post-Posaconazole treatment mean AUC ratio values for Lurasidone are in the range of from 3.6-4.3× for 2-6 days after ceasing Posaconazole treatment.

In conclusion, the results from the clinical trials reported in Example 1 indicate that the Posaconazole accumulates in the body of obese patients after treatment has stopped, and patients should delay a first dose of Lurasidone or reduce the first dose of Lurasidone to achieve safe blood plasma levels of Lurasidone.

TABLE 2

| Subject | | Lurasidone AUC (ng*h/mL) | | | Posaconazole AUC (ng*h/mL) | | | Lurasidone AUC Ratio relative to Day 1 | | | Subject Data | |
| | | Day 1 | Day 17 | Day 19 | Day 21 | Day 17 | Day 19 | Day 21 | Day 17 | Day 19 | Day 21 | BMI (kg/m$^2$) | Weight (kg) |
| --- | --- | --- | --- | --- | --- | --- | --- | --- | --- | --- | --- | --- | --- |
| HMS001 | 101-001 | 92.8 | 284 | 234.4 | 204.5 | 2886 | 2019 | 1365 | 3.06 | 2.53 | 2.20 | 45.0 | 111.8 |
| DES005 | 101-005 | 26 | 167.3 | 186 | 168 | 2512 | 1954 | 1563 | 6.43 | 7.15 | 6.46 | 51.2 | 137.7 |
| TRB007 | 101-007 | 38.3 | 173.8 | 89.5 | 124.7 | 824 | 542 | 285 | 4.54 | 2.34 | 3.26 | 36.8 | 103.7 |
| NNJ010 | 101-010 | 71 | 211.7 | 163 | 226 | 4551 | 3688 | 3081 | 2.98 | 2.30 | 3.18 | 43.9 | 120.0 |
| KDH002 | 101-002 | 110 | 195.5 | 146 | 186.3 | 1299 | 626 | 284 | 1.78 | 1.33 | 1.69 | 44.4 | 136.8 |
| DTG008 | 101-008 | 45.6 | 57 | 36.2 | 27.8 | 190 | 78 | 31 | 1.25 | 0.79 | 0.61 | 39.8 | 122.3 |

Table 3 compares Lurasidone AUC levels after Posaconazole treatment to baseline Lurasidone AUC levels.

TABLE 3

Lurasidone Levels vs. Base Line Days After Posaconazole Was Ceased

| | Day 2 | Day 4 | Day 6 |
| --- | --- | --- | --- |
| Mean | 3.3x | 2.7x | 2.9x |
| Min | 1.3x | 0.8x | 0.6x |
| Max | 6.4x | 7.2x | 6.5x |
| Median | 3.0x | 2.3x | 2.7x |

As shown above in Table 3, the post-Posaconazole treatment mean AUC ratios of Lurasidone are about 3 times higher than the baseline. This data indicates that Posaconazole accumulates in obese subjects, and results in significantly higher Lurasidone AUC levels compared to baseline levels measured before Posaconazole treatment.

The AUC measurements from two patients (DTG008 and KDH002) indicates that these patients were non-compliant with the Posaconazole treatment regimen, and the corresponding AUC measurements were removed from the study. The results are shown below in Table 4.

TABLE 4

Lurasidone Levels vs. Base Line Days After Posaconazole Was Ceased Excluding DTG008 & KDH002

| | Day 2 | Day 4 | Day 6 |
| --- | --- | --- | --- |
| Mean | 4.3x | 3.6x | 3.8x |
| Min | 3.0x | 2.3x | 2.2x |
| Max | 6.4x | 7.2x | 6.5x |
| Median | 3.8x | 2.4x | 3.2x |

Example 2. Sustained Impairment of Lurasidone Clearance after Discontinuation of Posaconazole. Impact of Obesity, and Implications for Patient Safety The following studies were reported by Greenblatt et al., J. Clin. Psychopharmacol., 2018; 38(4):289-295 (doi: 10.1097/JCP.0000000000000892), which is herein incorporated by reference in its entirety for all purposes.

The antipsychotic agent lurasidone is metabolized by Cytochrome P450-3A (CYP3A) enzymes. Coadministration with strong CYP3A inhibitors (such as ketoconazole, posaconazole, and ritonavir) is contraindicated due to the risk of sedation and movement disorders from high levels of lurasidone. This study evaluated the time-course of recovery from the posaconazole drug interaction, and the effect of obesity on the recovery process.

With posaconazole coadministration, lurasidone area under the concentration curve (AUC) increased by an arithmetic mean factor of 6.2 in normals, and by 4.9 in obese subjects. Post-treatment washout of posaconazole was slow in normals (mean half-life 31 hours), and further prolonged in obese subjects (53 hours). Recovery of lurasidone AUC toward baseline was correspondingly slow, and was incomplete. AUC remained significantly elevated above baseline both in normals (factor of 2.1) and obese subjects (factor of 3.4) even at 2 weeks after stopping posaconazole.

Product labeling does not address the necessary delay after discontinuation of a strong CYP3A inhibitor before lurasidone can be safely administered. It is recommended that normal-weight and obese patients be required to limit the dosage of lurasidone, or undergo a washout period after discontinuation of posaconazole, as set forth in the present disclosure.

Methods. Study Site and Institutional Review Board. The study was conducted at Avail Clinical Research, located in DeLand, Fla. The study protocol and consent document were reviewed and approved by IntegReview, Austin, Tex. All study participants provided written informed consent prior to initiation of any study procedures. In addition, this study was performed in accordance with the Declaration of Helsinki, International Conference on Harmonization Good Clinical Practice guidelines, and applicable regulatory requirements.

Subjects. The study participants consisted of two cohorts, with a total of 34 subjects receiving at least one dose of study drug, and a total of 24 subjects completing the entire study with evaluable pharmacokinetic data. In the first cohort were those of normal body habitus (n=11 completed; BMI 18.5-24.9 kg/m$^2$, inclusive); the second group consisted of subjects of obese body habitus (n=13 completed; BMI≥35 kg/m$^2$). Subjects were previously known to the research center, or were recruited through notices in the public media. Subjects were matched by gender and age when possible. Sample sizes were based on power calculations.

Potential participants underwent screening and evaluation within 30 days of study initiation. Procedures included medical and psychiatric history, physical examination, electrocardiogram if indicated, hematologic and biochemical screening (including liver function tests such as alanine transaminase, asparagine transaminase, and bilirubin), and urine testing for drugs of abuse. All study participants were healthy, active, non-smoking adults with no history of significant medical or psychiatric disease and taking no prescription medications. Obese subjects were free of metabolic or other complications of obesity. Potentially child-bearing women in both groups had negative pregnancy tests and agreed to avoid the risk of pregnancy during the course of the study. Subjects were instructed to avoid alcohol use throughout the course of the study and underwent a breath alcohol analysis prior to initiation of the study protocol.

Subjects' waist circumference was measured manually. Percent android fat for all subjects was determined by dual energy X-ray absorptiometry (DXA). For three subjects whose weight exceeded the limits of the DXA instrumentation, percent android fat was imputed using population data available from the National Health and Nutrition Evaluation Survey (NHANES). Total android fat (termed total body fat) was calculated as the product of body weight and percent android fat. Ideal body weight (IBW) was determined from actuarial data based on height and gender, and percent ideal body weight calculated as the ratio of actual weight divided by IBW.

Procedures. Subjects received lurasidone (20 mg tablet) on the mornings of study Days 1, 14, 20, 23, 26, and 30. Lurasidone doses were given immediately prior to a continental breakfast provided in the clinical research unit. Venous blood samples were drawn into ethylenediaminetetraacetic acid (EDTA)-containing tubes from an indwelling catheter, or by separate venipuncture, prior to the lurasidone dose and at 1, 2, 3, 4, 8, 12, 18, 24, 48, and 72 hours post-dose. Samples were centrifuged and the plasma was separated and frozen at −70° C. until the time of assay.

On study Day 4, subjects received two doses of posaconazole (300 mg BID). On the mornings of Days 5-17, they received posaconazole 300 mg once daily. As posaconazole is to be taken with food, subjects were fed a continental breakfast in the clinical research unit after receiving posaconazole and prior to discharge from the unit. Venous blood samples were drawn into EDTA containing tubes prior to the posaconazole dose on Days 4, 7, 11, and prior to the lurasidone dose on Days 14, 20, 23, 26 and 30. An additional blood sample was taken 5 hours after posaconazole dosage on Day 17, for approximate determination of maximum posaconazole plasma concentrations, and on Day 33. Samples were centrifuged and the plasma was separated and frozen at −70° C. until the time of assay.

Analytic Methods. All bioassay analyses were performed by Keystone Bioanalytical, North Wales, Pa. For analysis of posaconazole, the internal standard (posaconazole-D4) was added to the biological samples. Plasma samples were precipitated using formic acid in acetonitrile and isolated using a Phree phospholipid removal tube. An aliquot of the sample was injected onto a high-pressure liquid chromatograph with tandem mass spectrometry triple quadrupole mass spectrometer (SCIEX API-5500). The analytical column was a Unison CK-218, 3 µm particle size HPLC column (50×2 mm) from Imtakt USA (Portland, Oreg.). The mobile phase consisted of an aqueous component (0.25% formic acid and 10 mM ammonium formate in water) and an organic component (0.1% formic acid in acetonitrile) and was delivered by gradient, with the organic component going from 35% to 100%. The m/z transitions monitored were 701.6>614.4 for posaconazole and 705.6>618.4 for the internal standard. The calibration curve ranged from 1-1000 ng/mL (8 concentrations in duplicate).

For analysis of lurasidone, the internal standard (lurasidone-D8) was added to the biological samples. Plasma samples were isolated using a Phree phospholipid removal tube. An aliquot of the sample was injected onto a high-pressure liquid chromatograph with tandem mass spectrometry triple quadrupole mass spectrometer (SCIEX API-5500). The analytical column was a Unison UK-C18, 3 µm particle size HPLC column (50×2 mm) from Imtakt USA (Portland, Oreg.). The mobile phase consisted of an aqueous component (0.025% formic acid and 10 mM ammonium formate in water) and an organic component (0.1% formic acid in acetonitrile) and was delivered by gradient, with the organic component going from 35% to 100%. The m/z transitions monitored were 493.4>166.1 for lurasidone and 501.4>166.1 for the internal standard. The calibration curve ranged from 0.25-200 ng/mL (8 concentrations in duplicate).

Pharmacokinetic and Statistical Methods. For each subject, pre-dose plasma posaconazole concentrations on study Days 14 and 17 were averaged, and used as a steady-state concentration ($C_{ss}$) to calculate apparent steady-state clearance of posaconazole according to the relation: Clearance= (dosing rate)/$C_{ss}$. The apparent washout half-life of posaconazole was calculated by log-linear regression analysis starting with the plasma concentration on Day 20 and ending with the last non-zero value. Differences between normal-weight and obese cohorts were evaluated by Student's t-test for independent groups. The relation between measures of body habitus and posaconazole washout half-life for individual subjects was evaluated by linear regression analysis.

For each lurasidone trial for each subject, the terminal log-linear phase of the plasma concentration curve was identified visually, and the terminal rate constant (beta) was determined by log-linear regression analysis. This was used to calculate the elimination half-life. Area under the plasma concentration curve from time zero until the last non-zero point was determined by the linear trapezoidal method. To this was added the residual area, calculated as the final non-zero concentration divided by beta, yielding the total area under the plasma concentration curve extrapolated to infinity (AUC). Also tabulated was the observed maximum plasma concentration ($C_{max}$). AUC and $C_{max}$ both were adjusted, where necessary, for non-zero baseline (pre-dose) concentrations measured in some subjects on the Day 20, 23, 26, and 30 trials.

Variables were aggregated as arithmetic mean and SD or SE. Lurasidone $C_{max}$ and AUC were also aggregated as geometric mean and 90% confidence interval (90% CI). Differences in kinetic variables between study Day 1 and Days 14, 20, 23, 26, and 30 (control vs after posaconazole administration) were evaluated either from the untransformed data using Dunnett's t-test, or by comparison of geometric means and the 90% CI of the difference.

The relation between lurasidone AUC and plasma posaconazole concentration for individual subjects across the 5 DDI trials (Days 14, 20, 23, 26, and 30) was analyzed by nonlinear regression (SAS PROC NLIN). The following function was fitted to data points:

$$Y = Y_0 + B\ X^A$$

where Y is the lurasidone AUC value corresponding to X, the plasma posaconazole concentration at the start of relevant AUC measurement period. Iterated variables were: $Y_0$, A, and B.

Results

Subject Characteristics. Screening procedures yielded 34 subjects who were potential study participants. Of these, 8 initiated participation but did not complete the study for personal or administrative reasons not related to the study or study medications. Data from 2 other subjects could not be analyzed due to apparent protocol deviations. A total of 24 subjects (11 normal-weight and 13 obese) completed the study and were included in the pharmacokinetic analysis (Table 5). The groups were comparable in age, gender composition, height, and IBW. The obese group had significantly higher values of weight, percent IBW, BMI, waist circumference, percent android fat, and total body (android) fat (Table 5). The mean weight in the obese group s 140 kg (309 pounds), and the mean BMI was 49.3 kg.

TABLE 5

DEMOGRAPHIC CHARACTERISTICS OF STUDY PARTICIPANTS

| | Normal-weight* | Obese* | Independent t-test: Normal vs obese |
|---|---|---|---|
| Number | 11 | 13 | |
| Age (years) | 34 ± 8 | 33 ± 7 | N.S. |
| Male/female | 6/5 | 6/7 | |
| Weight | | | |
| (Kg) | 67.9 ± 9.1 | 140.4 ± 32 | P < 0.001 |
| (Pounds) | 149 ± 29 | 309 ± 70 | P < 0.001 |
| Height | | | |
| (Cm) | 171 ± 10 | 168 ± 11 | N.S. |
| (Inches) | 67.3 ± 4.0 | 66.3 ± 4.3 | N.S. |
| BMI (kg/m$^2$) | 23.1 ± 1.8 | 49.3 ± 9.6 | P < 0.001 |
| Waist circumference | | | |
| (Cm) | 80.4 ± 6.8 | 129.3 ± 22.4 | P < 0.001 |
| (Inches) | 31.7 ± 2.7 | 50.9 ± 8.8 | P < 0.001 |
| Ideal body weight (kg) | 64.5 ± 12.3 | 61.9 ± 11.4 | N.S. |
| Percent ideal body weight | 106 ± 11 | 230 ± 46 | P < 0.001 |
| Percent android fat | 33 ± 12 | 66 ± 4 | P < 0.001 |
| Total body fat (kg) | 22.5 ± 8.0 | 81.3 ± 25.8 | P < 0.001 |

*Mean ± SD

Adverse Events. Five subjects experienced adverse events considered possibly or probably related to one or both study medications. These were gastrointestinal disturbances in two cases, and one each of dry mouth, somnolence, and headache. All resolved without specific treatment.

Posaconazole Pharmacokinetics. Plasma posaconazole concentrations had reached steady-state by study Day 14 (FIG. 1). Mean $C_{ss}$ was significantly lower, and posaconazole clearance was significantly higher, in the obese cohort compared to controls (Table 6). However, weight-normalized posaconazole clearance was not significantly different between the groups.

Washout of posaconazole after discontinuation of treatment was significantly slower in the obese group compared to controls (P<0.005) (FIG. 1). Mean washout half-life values in the two groups were 2.19 days (52.5 hours) and 1.28 days (31 hours), respectively (Table 6). Among all subjects, the correlation between posaconazole washout half-life and each of the measures of body habitus was statistically significant, but the degree of obesity explained only a small fraction of variance in washout half-life (r2<0.32). The attenuated associations were in part attributable to two obese subjects with very long half-life values (121 hours).

TABLE 6

POSACONAZOLE PHARMACOKINETICS

| | Mean ± SD value for Group: | | Value of Student's t: Normal vs Obese |
|---|---|---|---|
| | Normal | Obese | |
| Steady-state concentration (ng/mL) | 2377 ± 1188 | 1462 ± 649 | 3.33 (P < 0.005) |
| Steady-state clearance | | | |
| mL/min | 101 ± 71 | 175 ± 91 | 2.19 (P < 0.04) |
| mL/min/kg | 1.48 ± 1.02 | 1.25 ± 0.61 | N.S. |
| Washout half-life (hours) | 31 ± 6.7 | 52.5 ± 31.1 | 2.25 (P < 0.04) |

Figure 2:
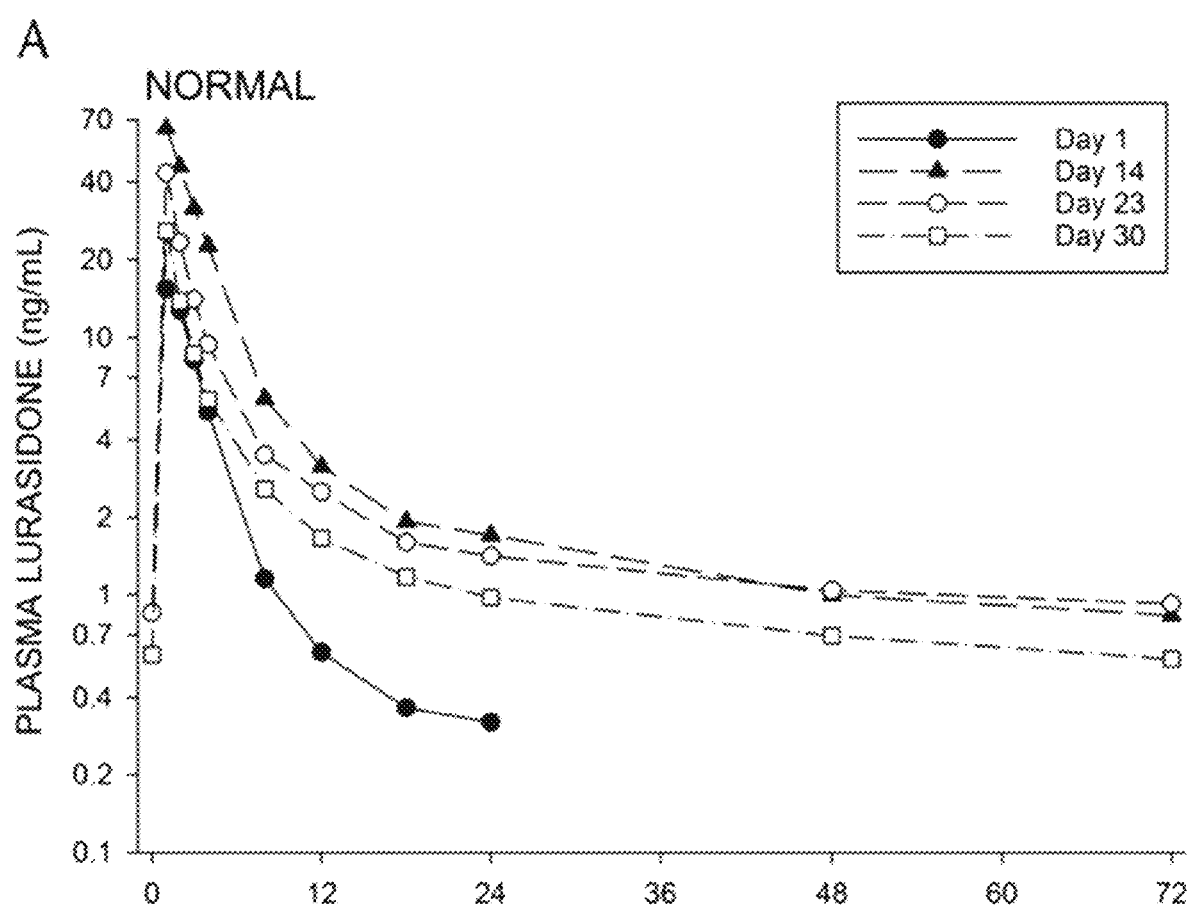
FIG. 2 shows mean plasma lurasidone concentrations in normal-weight subjects (FIGS. 2A and 2B) and in obese subjects (FIGS. 2C and 2D).
Figure 2:
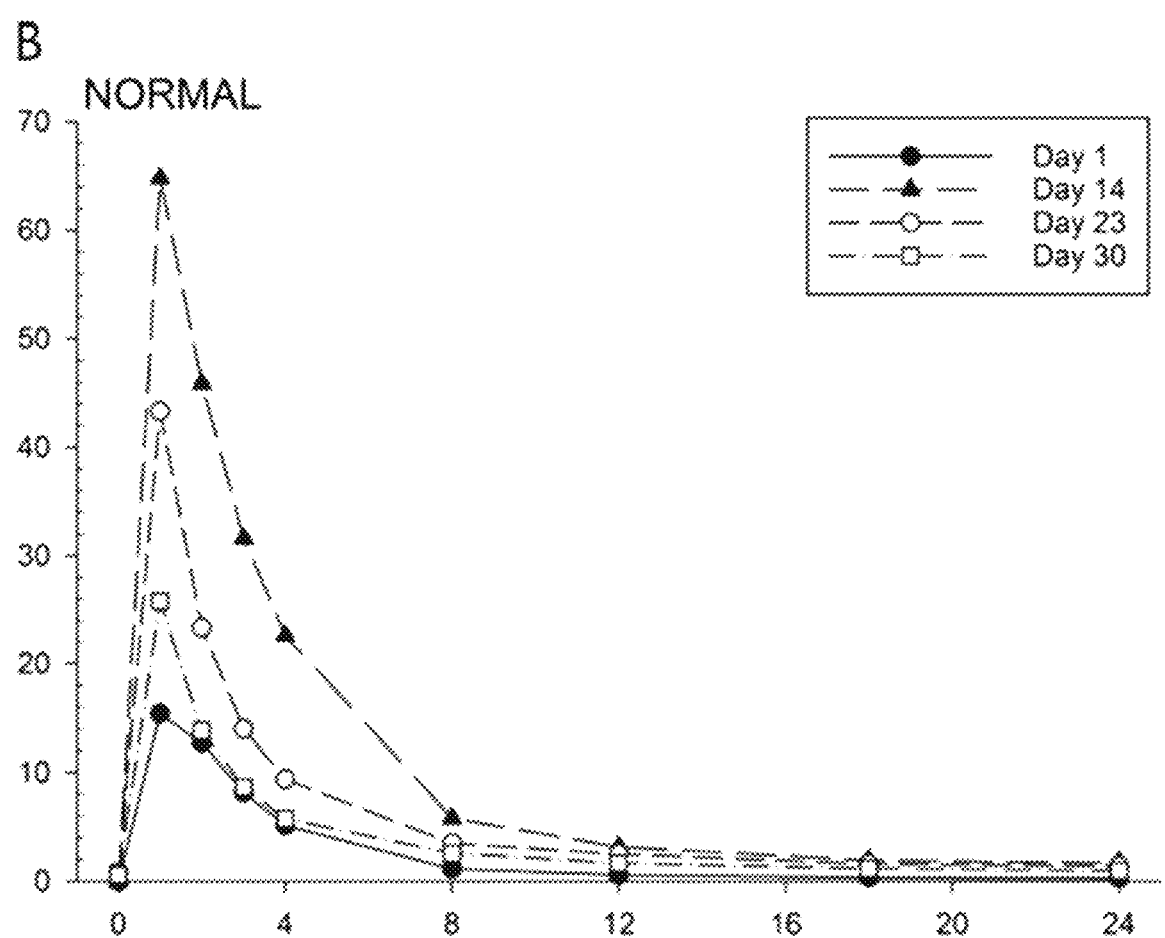
Figure 2:
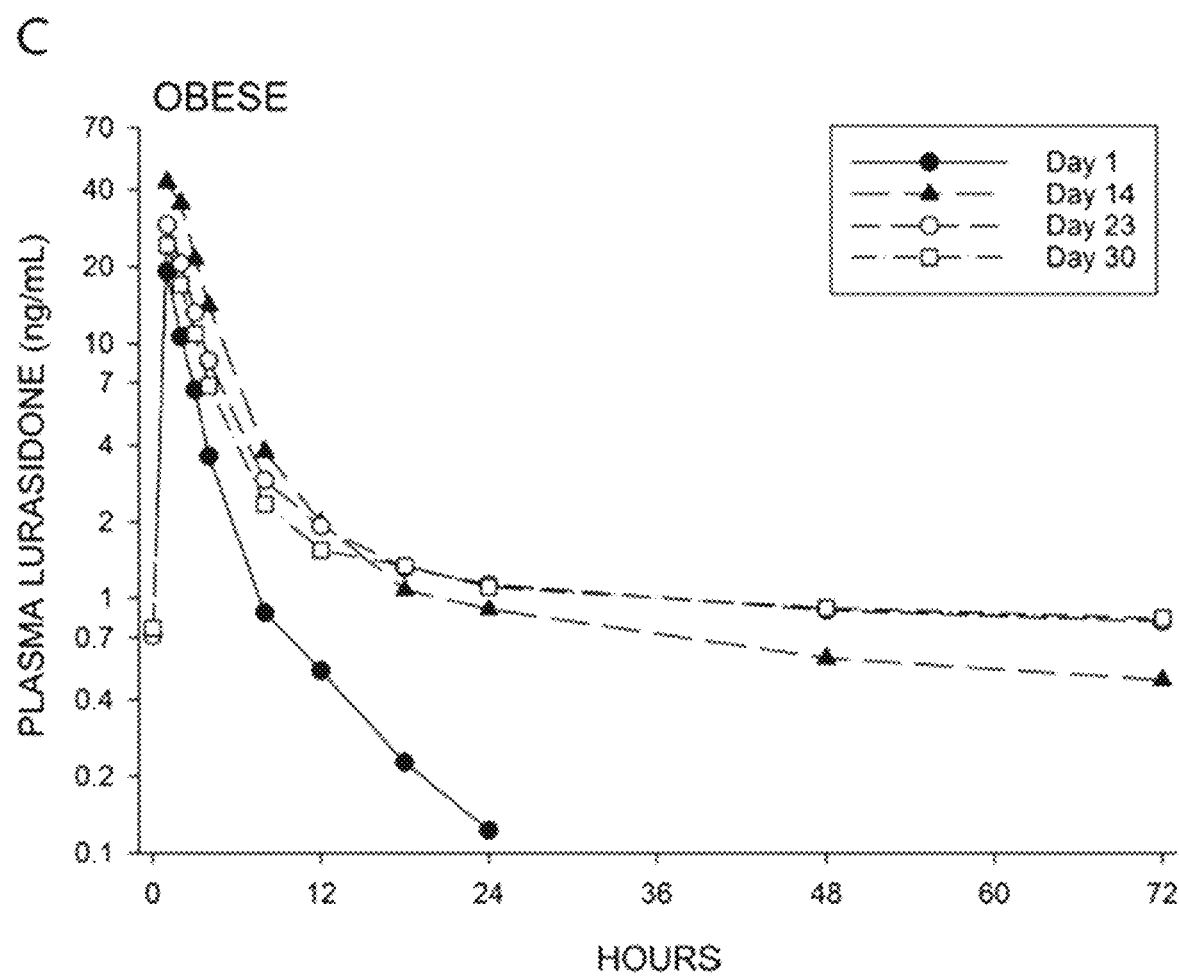
Figure 2:
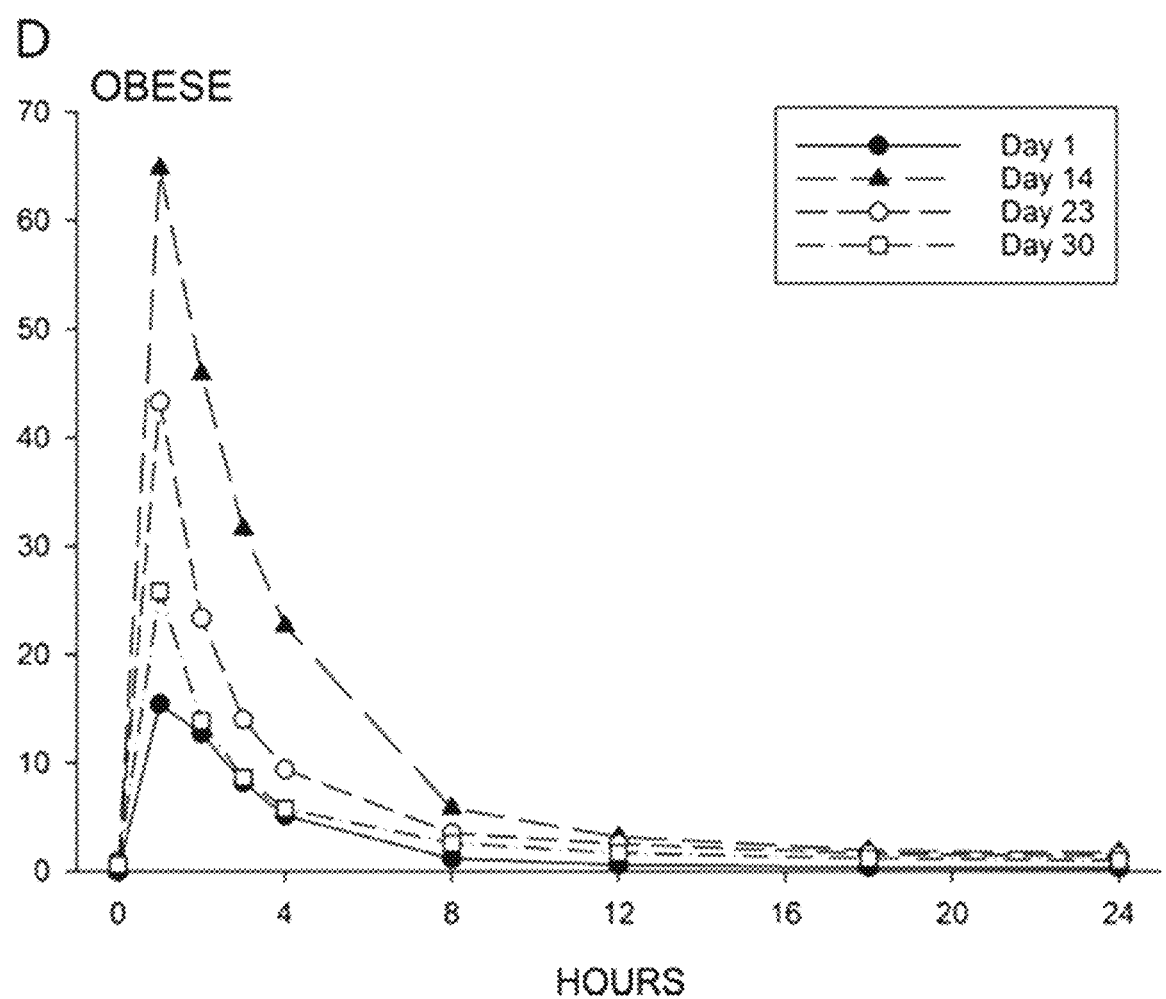

Lurasidone Pharmacokinetics. Coadministration of lurasidone with posaconazole resulted in a highly significant increase in lurasidone $C_{max}$ and AUC (FIG. 2, Table 7). Comparing Day 14 values to the Day 1 pre-posaconazole values based on ratio of geometric means, $C_{max}$ increased by a factor of 4.0 in normal-weight subjects and by 2.9 in the obese subjects. Corresponding increases in AUC were greater than increases in $C_{max}$. Geometric mean AUC increased by a factor of 5.75 in the normal-weight cohort, and by 4.34 in the obese cohort (Table 7). When calculated as arithmetic mean ratios, values were 6.2 in controls and 4.9 in obese subjects.

TABLE 7

SUMMARY OF LURASIDONE PHARMACOKINETICS

| | Arithmetic mean ± standard error Corrected Cmax (ng/mL) | | Geometric mean (90% CI) Corrected Cmax (ng/mL) | | | Ratio of geometric means (RGM) vs Day 1 (90% CI) Corrected Cmax | |
|---|---|---|---|---|---|---|---|
| | Normal | Obese | Normal | Obese | | Normal | Obese |
| Day 1 | 17.1 ± 1.6 | 19.8 ± 4 | 16.3 (13.5-19.6) | 15.1 (10.2-22.6) | | | |
| Day 14 | 69.4 ± 8.3* | 47.0 ± 5* | 65.2 (53.5-79.5) | 44.1 (35.9-54.2) | Day 14 | 4.00 (3.09-5.19) | 2.91 (1.89-4.47) |
| Day 20 | 55.9 ± 7.8* | 40.0 ± 5* | 48.6 (34.6-68.4) | 36.6 (29-46.3) | Day 20 | 2.98 (2.06-4.33) | 2.42 (1.55-3.76) |
| Day 23 | 42.5 ± 6.3* | 30.0 ± 3 | 37.8 (28.5-50.2) | 28.0 (22.7-34.6) | Day 23 | 2.32 (1.68-3.21) | 1.85 (1.2-2.84) |
| Day 26 | 32.2 ± 6.6 | 30.0 ± 4 | 26.5 (18.3-30.9) | 26.9 (21-34.5) | Day 26 | 1.63 (1.1-2.4) | 1.78 (1.13-2.79) |
| Day 30 | 26.2 ± 3.2 | 25.0 ± 4.4 | 24.0 (18.6-30.9) | 21.6 (16.4-28.4) | Day 30 | 1.47 (1.09-1.99) | 1.42 (0.89-2.26) |

| | Total AUC (ng/mL × hr) | | Total AUC (ng/mL × hr) | | | Total AUC | |
|---|---|---|---|---|---|---|---|
| | Normal | Obese | Normal | Obese | | Normal | Obese |
| Day 1 | 57.9 ± 5.8 | 50.8 ± 9 | 54.5 (43.3-68.6) | 42.0 (30.4-57.9) | | | |
| Day 14 | 333 ± 24* | 205 ± 19* | 324 (282-372) | 195 (166-230) | Day 14 | 5.94 (4.64-7.46) | 4.66 (3.28-6.59) |
| Day 20 | 265 ± 34* | 217 ± 20* | 237 (175-321) | 205 (173-244) | Day 20 | 4.34 (3-6.28) | 4.90 (3.45-6.96) |
| Day 23 | 204 ± 27* | 170 ± 17* | 184 (139-242) | 160 (133-193) | Day 23 | 3.38 (2.39-4.78) | 3.82 (2.68-5.47) |
| Day 26 | 148 ± 27* | 152 ± 19* | 122 (83-179) | 140 (113-173) | Day 26 | 2.24 (1.45-3.46) | 3.33 (2.3-4.83) |
| Day 30 | 129 ± 20* | 150 ± 17* | 114 (85-154) | 140 (116-170) | Day 30 | 2.10 (1.46-3.01) | 3.34 (2.33-4.78) |

*P < 0.05 compared to Day 1 value, Dunnett's t test

Figure 3:
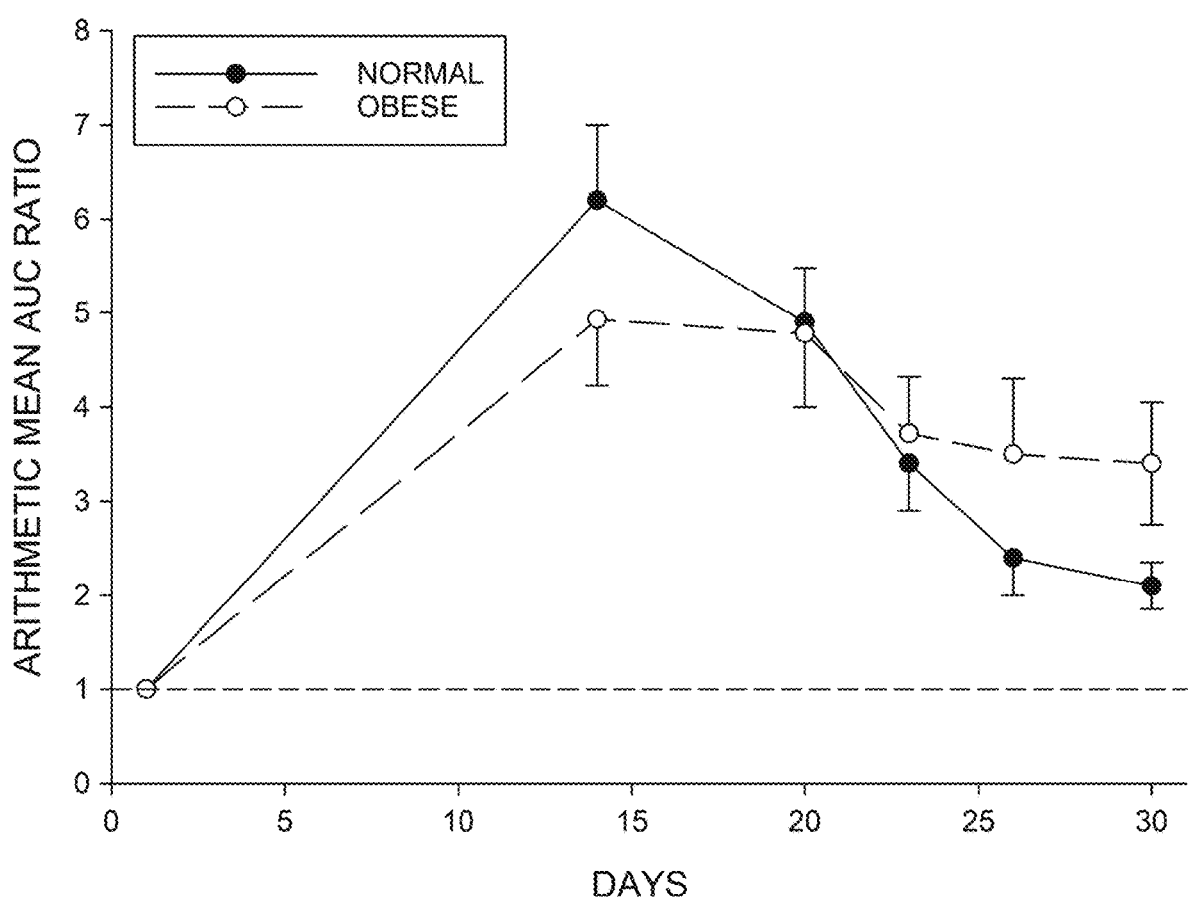
FIG. 3 shows the arithmetic mean (±standard error) ratio of lurasidone AUC during and after posaconazole dosage divided by the AUC in the baseline control condition in normal-weight and obese subject groups. At all time points, the ratios were significantly different from 1.0.

Kinetic variables for lurasidone recovered toward the pre-posaconazole baseline values during the posaconazole washout period. Based on ratios of geometric mean values versus the Day 1 baseline, $C_{max}$ remained elevated above Day 1 even on Day 30 (ratio=1.47, 90% CI=1.09-1.99) in the normal-weight control subjects. In the obese cohort, $C_{max}$ remained above baseline up to Day 26. Recovery of AUC in both groups was even less complete, with Day 30 ratios of 1.9 in the normal-weight group and 2.8 in the obese subjects (arithmetic mean ratios: 2.1 and 3.4, respectively). Consistent with the slower washout of posaconazole in the obese group, the rate of recovery of lurasidone AUC toward baseline values was correspondingly slower in the obese cohort compared to controls (FIG. 3).

Baseline values of lurasidone elimination half-life averaged 9.4 hours in normal-weight subjects and 10.9 hours in the obese group. These values are in the range of what has been reported previously. The half-life values were significantly prolonged during and after administration of posaconazole, and were still substantially longer than baseline values even on the Day 30 trial (FIG. 2, Table 8). Mean half-life values were longer in obese subjects compared to controls. However, half-life determinations were complicated by estimates that exceeded the sampling duration in some subjects.

TABLE 8

LURASIDONE ELIMINATION HALF-LIFE (HOURS)
Arithmetic mean ± S.E.

| | Normal | Obese |
|---|---|---|
| Day 1 | 9.4 ± 1.5 | 10.9 ± 4 |
| Day 14 | 37 ± 4* | 38 ± 2* |
| Day 20 | 39 ± 3* | 48 ± 4* |
| Day 23 | 48 ± 5* | 52 ± 3* |
| Day 26 | 50 ± 7* | 61 ± 4* |
| Day 30 | 45 ± 9* | 71 ± 5* |

*P < 0.05 compared to Day 1 based on Dunnett's t test

Figure 4:
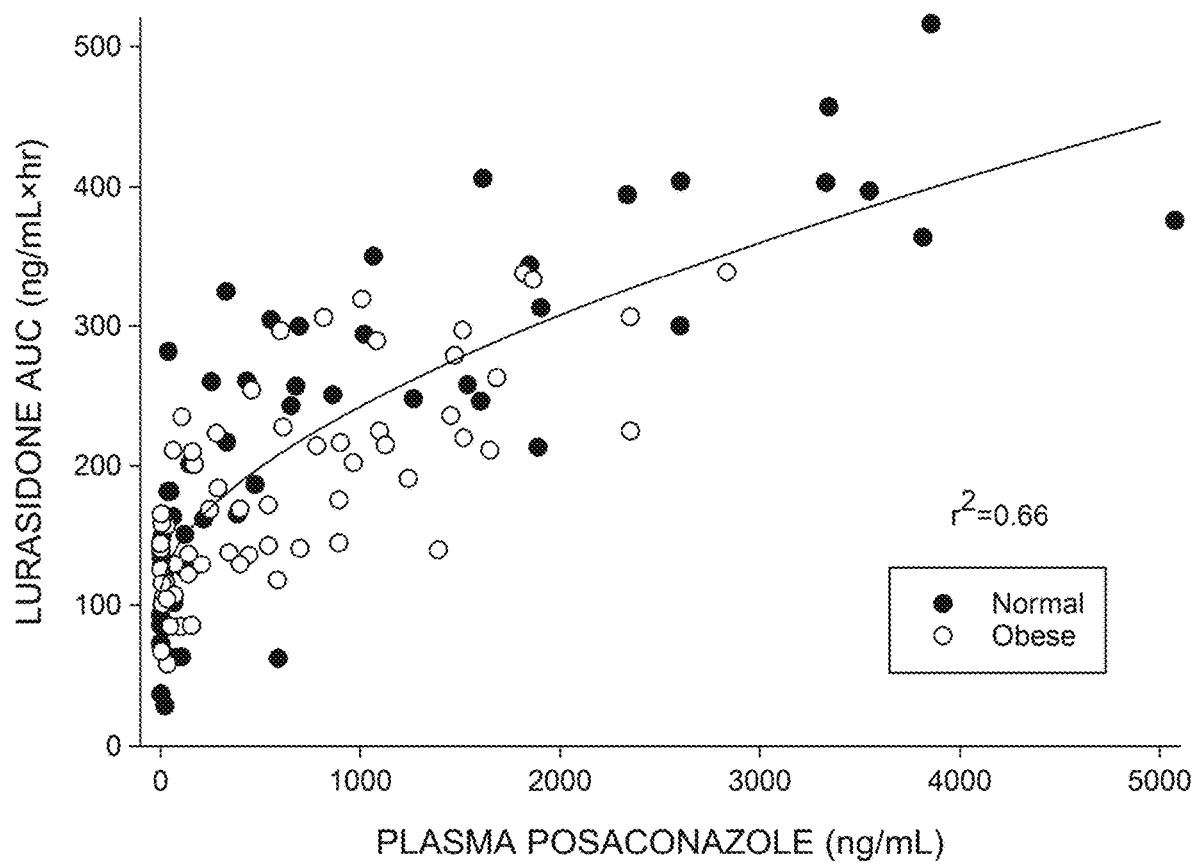
FIG. 4 shows the relation of plasma posaconazole concentration (X-axis) to lurasidone AUC (Y-axis). Solid line represents the function of best fit as determined by linear regression analysis. The fitted function is: $Y=2.38\ X^{0.58}+110.6$.

Relation of Plasma Posaconazole to Lurasidone AUC. Based on analysis of data from all subjects, individual variations in plasma posaconazole concentrations accounted for 66% of the variance in lurasidone AUC at the corresponding times ($r^2=0.66$), indicating that posaconazole exposure is a principal determinant of the magnitude of the posaconazole-lurasidone DDI (FIG. 4).

Discussion. The present study evaluated the pharmacokinetic DDI between lurasidone as victim (substrate) and the strong CYP3A inhibitor posaconazole as perpetrator (precipitant), both in volunteers of normal body weight and in an otherwise healthy group of subjects with BMI≥35 kg/m2. A particular focus of the study was the time-course of recovery from the DDI during the two weeks after discontinuation of posaconazole.

Coadministration of lurasidone with typical doses of posaconazole resulted in increased lurasidone exposure (total AUC) by a factor averaging in the range of 4 to 6 in both groups of subjects. After posaconazole was discontinued, the effect on lurasidone exposure did not return quickly to baseline. Rather, the DDI persisted for at least 2 weeks after the last dose of posaconazole, and probably well beyond the study duration. The slow recovery from the DDI was consistent with the long elimination half-life of posaconazole. With all data aggregated, plasma posaconazole concentration accounted for 66% of the variability in lurasidone AUC associated with the DDI.

The pharmacokinetic properties of posaconazole were significantly modified in the cohort of obese subjects compared to those of normal body size. The clearance of posaconazole—not corrected for body weight—was higher in obese subjects compared to controls, resulting in lower values of $C_{ss}$ when the same daily dosage was administered to both groups. Despite the higher clearance, the washout half-life was significantly prolonged in the obese subjects compared to controls. This is likely explained by the disproportionate distribution of the lipophilic drug posaconazole into excess adipose tissue, thereby causing a prolongation of elimination half-life. As a result of the longer half-life and persistence of posaconazole in blood, the duration of the lurasidone DDI was correspondingly longer. At two weeks after the last dose of posaconazole, lurasidone AUC was still elevated above baseline by a mean factor of 3.3 in the obese subject group.

This study involved a relatively small number of subjects, but the findings were statistically robust. Although lurasidone was administered as single test doses, the kinetics of lurasidone are linear, and single-dose kinetic properties will be predictive of behavior during multiple dosing as is customary in the treatment of schizophrenia.

Conclusions. The posaconazole-lurasidone DDI persists long after posaconazole is discontinued, resulting in a sustained risk of a potentially hazardous DDI. The duration of persistent risk is further prolonged in obese individuals due to the effect of obesity on the elimination kinetics of posaconazole. Revision of product labeling is needed to assure patient safety. Based on the findings of this study, it is recommended to require normal-weight and obese patients to limit the dosage of lurasidone, or undergo a washout period, as set forth in the present disclosure.

Example 3. Persistence of a Posaconazole-Mediated Drug-Drug Interaction with Ranolazine after Cessation of Posaconazole Administration: Impact of Obesity and Implications for Patient Safety The following studies were reported by Chow et al., J. Clin. Pharmacology. 2018; 0(0):1-7 (doi: 10.1002/jcph.1257), which is herein incorporated by reference in its entirety for all purposes.

The antianginal agent ranolazine is metabolized primarily by cytochrome P450-3A (CYP3A) enzymes. Coadministration with strong CYP3A inhibitors, such as ketoconazole and posaconazole, is contraindicated due to risk of QT prolongation from high levels of ranolazine. This study evaluated the time course of recovery from the posaconazole drug interaction in normal-weight and otherwise healthy obese subjects. Subjects received single doses of ranolazine in the baseline control condition, again during coadministration of posaconazole, and at 4 additional time points during the 2 weeks after posaconazole discontinuation. With posaconazole coadministration, the geometric mean ratio of ranolazine area under the concentration curve (AUC) increased by a factor of 3.9 in normals and by 2.8 in obese subjects. Posttreatment washout of posaconazole was slow in normals (mean half-life 36 hours) and further prolonged in obese subjects (64 hours). Recovery of ranolazine AUC toward baseline was delayed. AUC remained significantly elevated above baseline in normal-weight and obese subjects for 7-14 days after stopping posaconazole. Current product labeling does not address the need for delay or a reduced dose of ranolazine after discontinuation of a strong CYP3A inhibitor before ranolazine can be safely administered. It is recommended that administration of ranolazine should be limited, for example to 500 mg twice daily for 7 days after posaconazole discontinuation in patients with body mass index 18.5-24.9 kg/m$^2$ and for 12 days in patients with body mass index≥35 kg/m$^2$ after ranolazine is resumed.

Methods. Study Site and Institutional Review Board. The study was conducted at Avail Clinical Research, located in DeLand, Fla. The study protocol and consent document were reviewed and approved by IntegReview, Austin, Tex. All study participants provided written informed consent prior to initiation of any study procedures. In addition, this study was performed in accordance with the Declaration of Helsinki, International Conference on Harmonisation Good Clinical Practice guidelines, and applicable regulatory requirements.

Subjects. A total of 30 subjects, aged 19 to 50, were enrolled in the study (Table 9). All were healthy adults without evidence of active medical disease, with the exception of obesity, and taking no prescription medications; 43% of the study subjects were male.

The study included 2 cohorts of volunteers. The first consisted of subjects of normal body habitus (BMI 18.5-24.9 kg/m$^2$, inclusive, n 15); the second consisted of subjects of obese body habitus (BMI 2:35 kg/m$^2$, n 15). Subjects were matched by sex and age when possible. Sample sizes were based on power calculations.

Potential study participants underwent screening and evaluation within 30 days of study initiation. Procedures included medical and psychiatric history, physical examination, electrocardiogram (ECG), hematologic and biochemical screening, and urine testing for drugs of abuse. All study participants were healthy active nonsmoking adults with no history of significant medical or psychiatric disease and taking no prescription medications. Obese subjects were free of metabolic or other complications of obesity. Potentially child-bearing women in both groups had a negative pregnancy test and agreed to avoid the risk of pregnancy during the course of the study. Subjects were also administered 12-lead ECGs in triplicate on study days 1 and 15 before and 4 hours after the ranolazine dose as well as before discharge on day 30.

Subjects' waist circumference was measured manually. Percentage android fat for all subjects was determined by dual-energy x-ray absorptiometry. Total android fat (total body fat) was calculated as the product of body weight and percentage android fat.

Procedures. Subjects received ranolazine (500 mg extended-release tablet) on the mornings of study days 1, 15, 18, 22, 25, and 29. Venous blood samples were drawn into ethylenediaminetetraacetic acid (EDTA)-containing tubes from an indwelling catheter or by separate venipuncture prior to the ranolazine dose and at 1, 2, 4, 6, 8, 12, 18, 24, and 32 hours postdose. Samples were centrifuged, and the plasma was separated and frozen at −70° C. until the time of assay of plasma ranolazine concentrations.

On study day 2, subjects received posaconazole (300 mg delayed-release tablet twice a day), and on the mornings of days 3-15, subjects received posaconazole (300 mg delayed-release tablet daily). Because posaconazole is to be taken with food,[6] subjects were fed a continental breakfast in the clinical research unit after receiving posaconazole and before discharge from the unit. Venous blood samples were drawn into EDTA-containing tubes before the posaconazole dose on days 2, 5, 8, 12, and 15, and before the ranolazine dose on days 18, 22, 25, and 29. One additional blood sample was taken 5 hours after the posaconazole dose on day 15 for approximate determination of maximum plasma posaconazole concentrations. Samples were centrifuged, and the plasma was separated and frozen at −70° C. until the time of assay of plasma posaconazole concentrations.

Analytic Methods. All bioassay analysis was performed by Keystone Bioanalytical (North Wales, Pa.). For analysis of posaconazole, the internal standard (posaconazole-d$_4$) was added to the biological samples. Plasma samples were precipitated using formic acid in acetonitrile and isolated using a Phree phospholipid removal tube, and then an aliquot of the sample was injected onto a high-pressure liquid chromatography with tandem mass spectrometry triple quadrupole mass spectrometer (Sciex API-5500). The analytical column was a Unison CK-218, 3 μm particle size HPLC column (50×2 mm) from Imtakt USA (Portland, Oreg.). The mobile phase consisted of an aqueous component (0.25% formic acid and 10 mmol/L ammonium formate in water) and an organic component (0.1% formic acid in acetonitrile) and was delivered by gradient, with the organic component going from 35% to 100%. The m/z transitions monitored were 701.6→614.4 for posaconazole and 705.6→618.4 for the internal standard. The calibration curve ranged from 1 to 1000 ng/mL (8 concentrations in duplicate). The interassay precision of this method (as percentage coefficient of variance) was 4.28% to 7.14%, and the interassay accuracy (as percentage relative error) was 7.02% to 3.12%.

For analysis of ranolazine in plasma samples, the internal standard (ranolazine-d3) was added to the biological samples. Plasma samples were extracted by methyl tertiary butyl ether, centrifuged, and the upper layer was transferred to plastic injection vials with MeOH/water (50:50). An aliquot of the sample was then injected onto a high-pressure liquid chromatography with tandem mass spectrometry triple quadrupole mass spectrometer (Sciex API-5500). The analytical column was a Unison CK-218, 3 μm particle size HPLC column (50×2 mm) from Imtakt USA (Portland, Oreg.). The mobile phase consisted of an aqueous component (0.025% formic acid and 10 mmol/L ammonium formate in water) and organic component (0.1% formic acid in acetonitrile) and was delivered by gradient, with the organic component going from 15% to 45%. The m/z transitions monitored were 428.3→279.2 for ranolazine and 431.3→282.2 for the internal standard. The calibration curve ranged from 5 to 2500 ng/mL (8 concentrations in duplicate). The interassay precision of this method (as percentage coefficient of variance) was 1.49% to 4.88%, and the intra-assay accuracy (as percentage relative error) was −3.07% to 1.83%.

Pharmacokinetic and Statistical Methods. For each ranolazine trial in each subject, the terminal log-linear phase of the plasma concentration curve was identified visually, and the terminal rate constant (β) was determined by log-linear regression analysis. This was used to calculate the half-life ($t_{1/2}$) The area under the plasma concentration curve from time 0 until the last nonzero point was determined by the linear trapezoidal method. To this was added the residual area, calculated as the final nonzero concentration divided by β, yielding the total area under the plasma concentration curve extrapolated to infinity (AUC). Also tabulated was the observed maximum plasma concentration ($C_{max}$). Variables were aggregated as arithmetic mean and SD. Ranolazine $C_{max}$ and AUC were also aggregated as geometric mean and 90% CI.

For each subject, the predose plasma posaconazole concentration on study day 15 was used as a steady-state concentration. The apparent washout half-life of posaconazole was calculated by log-linear regression analysis starting with the plasma concentration on day 15 and ending with the last nonzero value. Differences between normal-weight and obese cohorts were evaluated by Student t-test for independent groups.

Differences in kinetic variables between study days 1 and 15, 18, 22, 25, and 29 (control versus after posaconazole administration) were evaluated either from the untransformed data using Dunnett's t-test or by comparison of geometric means and the 90% CI of the difference.

QTcF values were determined electronically from 12-lead ECG readings taken for safety purposes. This protocol did not involve a thorough QT study; however, safety data were recorded, and the mean, standard deviation, and standard error of QT and QTcF values were tabulated. Differences between baseline and study days 1, 15, and 30 were evaluated by Student's t-test for independent groups.

Results. All 30 subjects completed day 1 of the study, and 27 completed the full study protocol. (One subject was inadvertently given an incorrect dosage of study drug on day 1; this subject was allowed to re-enroll with a new subject number after an appropriate washout period.) Two obese subjects and 1 normal-weight subject withdrew from the study before completion of all study procedures. In the normal-weight group, 1 subject discontinued due to abdominal pain that was possibly related to ranolazine treatment. In the obese group, 1 subject withdrew consent for personal reasons, and 1 subject discontinued due to an adverse event (paresthesia) that was unrelated to the study drug.

Obese subjects were similar in height to normal-weight subjects but were significantly higher in age, weight, BMI, and percentage of total body fat (Table 9).

TABLE 9

Demographic characteristics of study participants (mean ± SD)

| | Normal-weight | Obese |
|---|---|---|
| Number | 14 | 13 |
| Age (years) | 27.7 ± 10.6 | 33.9 ± 7.7 |
| Male/female | 7/7 | 4/9 |
| Weight | | |
| (Kg) | 71.2 ± 8.2 | 116.8 ± 19.6 |
| (Pounds) | 157 ± 18.1 | 257.5 ± 43.2 |
| Height | | |
| (Cm) | 174.0 ± 8.6 | 169.0 ± 11.8 |
| (Inches) | 68.5 ± 3.4 | 66.5 ± 4.6 |
| BMI (kg/m$^2$) | 23.5 ± 1.6 | 40.9 ± 5.7 |

Posaconazole plasma concentrations were lower in obese subjects than in normal-weight subjects (FIG. 5); however, this difference did not reach significance. This is consistent with previous observations of altered posaconazole pharmacokinetics in obese subjects compared to normal-weight subjects, where posaconazole plasma concentrations were observed to be lower in obese patients. Trough (predose) steady-state posaconazole concentrations on day 15 were 3071±1422 ng/mL in normal-weight subjects and 2258±952 ng/mL in obese subjects. Surprisingly, however, it was also observed that the postdosage washout half-life of posaconazole in obese subjects was significantly increased relative to that in normal-weight subjects (64.3 hours and 35.8 hours, respectively). Posaconazole plasma concentrations persisted for at least 2 weeks after stopping treatment in most subjects (FIG. 5).

The geometric mean AUC for ranolazine on day 1 was similar in normal-weight and obese subjects (6454 ng h/mL and 6955 ng h/mL, respectively). Similarly, the geometric mean $C_{max}$ on day 1 did not differ significantly between groups (664.7±318.2 ng/mL and 559.1±270.7 ng/mL in normal-weight and obese subjects, respectively). The geometric mean AUC and Cmax for ranolazine in both normal-weight and obese subjects on days 15, 18, and 22 increased significantly compared to day 1 (FIG. 6, Table 10). AUC and Cmax did not differ significantly between groups. $t_{1/2}$ on day 1 was slightly prolonged in obese subjects (4.99±1.50 hours and 6.02±1.75 hours in normal-weight and obese subjects, respectively), but this difference did not reach significance (P=0.126, Table 10).

TABLE 10

Pharmacokinetic parameters of ranolazine (mean ± SD)

| | | Normal-weight | Obese |
|---|---|---|---|
| Day 1 | $C_{max}$ (ng/mL) | 665 ± 318 | 559 ± 271 |
| | $AUC_{0-inf}$ (ng/mL × h) | 7085 ± 3603 | 8126 ± 4840 |
| | $T_{1/2}$ (h) | 4.98 ± 1.50$^a$ | 6.02 ± 1.75$^a$ |

TABLE 10-continued

Pharmacokinetic parameters of ranolazine (mean ± SD)

|  |  | Normal-weight | Obese |
|---|---|---|---|
| Day 15 | $C_{max}$ (ng/mL) | 1429 ± 666* | 1177 ± 512* |
|  | $AUC_{0-inf}$ (ng/mL × h) | 27477 ± 14895* | 25842 ± 21638* |
|  | $T_{1/2}$ (h) | 9.54 ± 4.3 | 8.78 ± 5.58 |
| Day 18 | $C_{max}$ (ng/mL) | 1188 ± 469* | 1096 ± 502* |
|  | $AUC_{0-inf}$ (ng/mL × h) | 17310 ± 10263* | 19294 ± 14150* |
|  | $T_{1/2}$ (h) | 5.73 ± 1.53 | 7.93 ± 2.98 |
| Day 22 | $C_{max}$ (ng/mL) | 974 ± 400* | 1063 ± 508* |
|  | $AUC_{0-inf}$ (ng/mL × h) | 13414 ± 6252* | 15920 ± 11832* |
|  | $T_{1/2}$ (h) | 6.47 ± 3.14 | 6.09 ± 2.10 |
| Day 25 | $C_{max}$ (ng/mL) | 928 ± 482* | 976 ± 487* |
|  | $AUC_{0-inf}$ (ng/mL × h) | 9385 ± 4591 | 13846 ± 10600 |
|  | $T_{1/2}$ (h) | 5.05 ± 1.82 | 6.07 ± 2.10 |
| Day 29 | $C_{max}$ (ng/mL) | 751 ± 276 | 719 ± 333 |
|  | $AUC_{0-inf}$ (ng/mL × h) | 8568 ± 3802 | 10171 ± 7942 |
|  | $T_{1/2}$ (h) | 4.45 ± 1.38 | 6.38 ± 3.05 |

Figure 7:
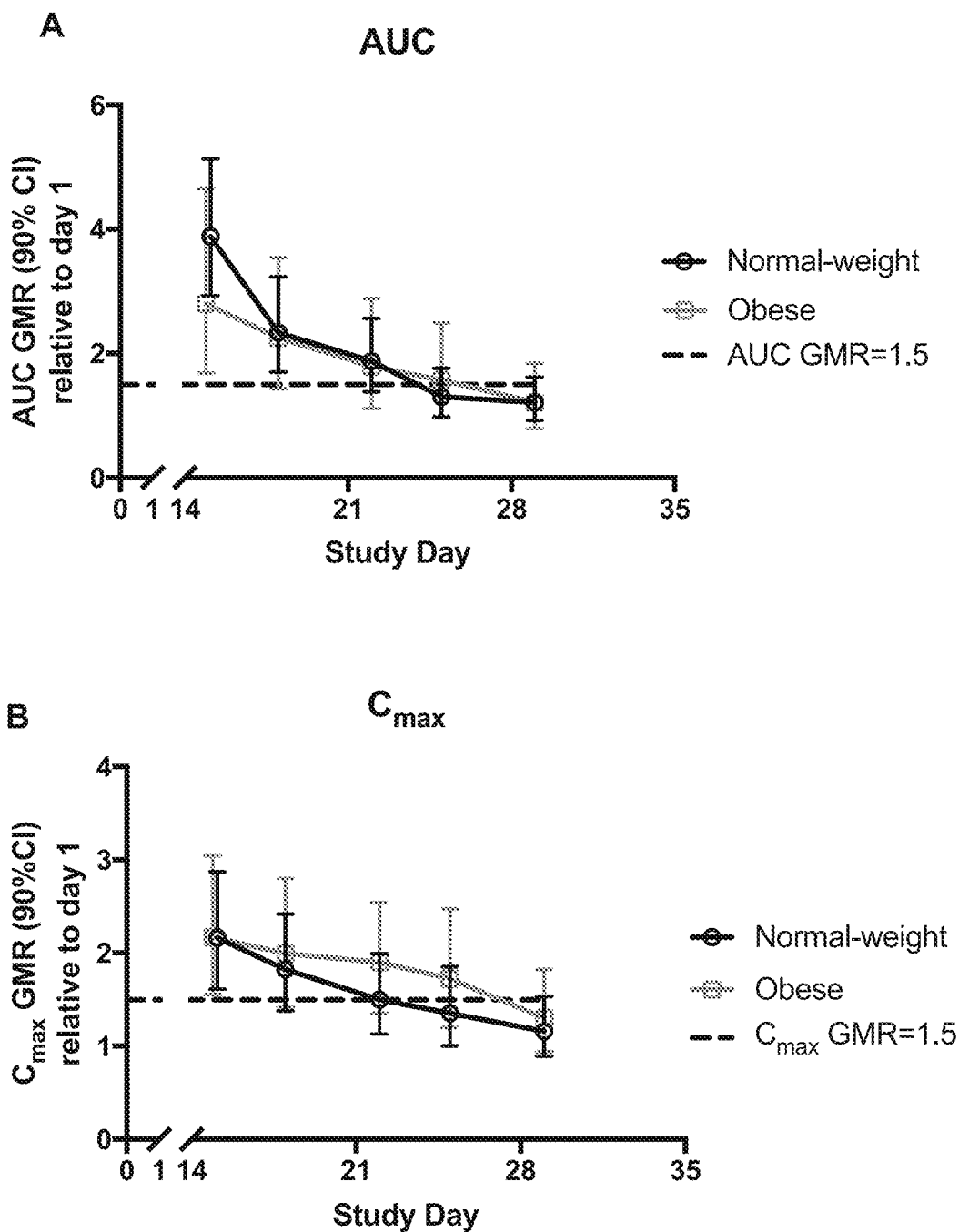
FIG. 7 shows the geometric mean ratios (GMR) and 90% CI of ranolazine AUC (FIG. 7A) and $C_{max}$ (FIG. 7B) relative to day 1. GMR=1.5 line refers to the levels observed during ranolazine coadministration with diltiazem in preapproval studies. AUC indicates area under the concentration-time curve; $C_{max}$, peak concentration.

*Significance vs Day 1 determined by Dunnett's t-test
<sup>a</sup>Not significant between normal-weight and obese groups (p = 0.126) by Student's t-test Within each cohort, the interaction between posaconazole and ranolazine was greatest on day 15 relative to day 1 as determined by the AUC geometric mean ratio (GMR) and 90% CI. The magnitude of the interaction decreased from days 18 to 29; however, plasma ranolazine concentrations on day 29 were still increased relative to day 1 (FIGS. 7A and 7B, Table 11). The lower bound of the AUC GMR 90% CI also remained above 1.0 for 7 days in both normal-weight and obese subjects. Cmax GMRs and 90% CIs followed a similar trend and can be found in Table 11.

TABLE 11

Geometric mean ratios (90% CI) of plasma ranolazine

|  |  | Normal-weight | Obese |
|---|---|---|---|
| Day 15/Day 1 | $AUC_{0-inf}$ | 3.88 (2.94-5.13) | 2.80 (1.68-4.66) |
|  | $C_{max}$ | 2.16 (1.61-2.87) | 2.18 (1.55-3.04) |
| Day 18/Day 1 | $AUC_{0-inf}$ | 2.34 (1.70-3.22) | 2.25 (1.41-3.58) |
|  | $C_{max}$ | 1.82 (1.38-2.42) | 1.97 (1.42-2.80) |
| Day 22/Day 1 | $AUC_{0-inf}$ | 1.88 (1.38-2.54) | 1.79 (1.11-2.88) |
|  | $C_{max}$ | 1.50 (1.13-1.99) | 1.90 (1.35-2.54) |
| Day 25/Day 1 | $AUC_{0-inf}$ | 1.30 (0.97-1.76) | 1.57 (0.99-2.50) |
|  | $C_{max}$ | 1.36 (1.00-1.85) | 1.72 (1.20-2.47) |
| Day 29/Day 1 | $AUC_{0-inf}$ | 1.22 (0.92-1.62) | 1.21 (0.79-1.85) |
|  | $C_{max}$ | 1.16 (0.89-1.53) | 1.30 (0.94-1.82) |

ECG data revealed that, on study day 30, the average change in QTcF interval from screening values was 12.9±16 milliseconds in normal-weight subjects who completed the study and 2.6±11 milliseconds in obese subjects who completed the study (Table 12).

TABLE 12

QTcF values relative to baseline (msec, mean ± SD)

|  | Normal-weight | Obese |
|---|---|---|
| Day 1, predose | 2.14 ± 10 | 7.50 ± 9.2 |
| Day 1, 4 h post-dose | 9.85 ± 12 | 3.83 ± 11 |
| Day 15, predose | 6.29 ± 16 | 2.64 ± 11 |
| Day 15, 4 h post-dose | 4.36 ± 16 | −3.33 ± 13 |
| Day 30 | 12.9 ± 16** | 2.58 ± 11 |

**p = 0.012 compared to baseline

Discussion. The present study evaluated the effects of obesity on the plasma concentration of ranolazine in otherwise healthy adults during or after cessation of posaconazole administration. Due to the known linear correlation between ranolazine plasma concentration and increases in the QTc interval, the lower marketed dose of 500 mg was chosen for testing in this study to minimize safety risks.

Without or during concomitant dosing of posaconazole, obese and normal-weight subjects had similar $C_{max}$, AUC, and $t_{1/2}$ (Table 10). After cessation of posaconazole administration, both obese and normal-weight subjects demonstrated persistence of elevated ranolazine levels for several days. Interestingly, the $t_{1/2}$ of ranolazine increased slightly with the magnitude of the interaction. The magnitude of the effect of posaconazole on day 15 $C_{max}$ was similar between normal-weight and obese subjects ($C_{max}$ GMR=2.16 and 2.18, respectively). The interaction persisted above a $C_{max}$ GMR of 1.5 for 7 and 10 days in normal-weight and obese subjects, respectively. The magnitude of the interaction on day 15 AUC was greater in normal-weight subjects than in obese subjects (AUC GMR, day 15/day 1=3.88 and 2.90, respectively). After day 15, however, the magnitude of the interaction was similar in obese and normal-weight subjects and decreased as posaconazole was eliminated from the body (FIGS. 7A and 7B). The interaction between ranolazine and residual posaconazole persisted above an AUC GMR of 1.5 for at least 7 and 10 days after cessation of posaconazole administration in normal-weight and obese subjects, respectively.

$C_{max}$ and AUC GMRs of 1.5 were also observed in preapproval drug-drug interaction studies between ranolazine and diltiazem, a moderate CYP3A inhibitor.

Based on the results of these preapproval studies, current prescribing instructions for ranolazine state that the maximum dosage of ranolazine should be limited to 500 mg twice a day when taken concomitantly with moderate CYP3A inhibitors, and ranolazine is contraindicated for concomitant use with strong CYP3A inhibitors such as posaconazole. These dosing recommendations are based on the linear correlation between ranolazine plasma concentrations and QT interval because risk of cardiac arrhythmias increases as the QT interval increases.

Among the 27 subjects who completed this study, an average increase in the QTcF interval of 12.9 milliseconds was observed in normal-weight patients on day 30 compared to screening. The average QTcF interval in obese subjects was 2.6 milliseconds. The increase of 12.9 milliseconds in normal subjects was statistically significant (P=0.012) (Table 12). The changes in QTcF were observed from safety ECG data and were not derived from a thorough QT study; however, given current FDA guidance on QT-prolonging drugs, it is important to note this finding.

This study is one of the first reports of a sustained drug-drug interaction with posaconazole. Although time-dependent inhibition of CYP3A by posaconazole is minimal, the results of these studies suggest that inhibition of CYP3A by posaconazole persists after cessation of administration and should be accounted for in clinical practice.

In current clinical practice, a patient on ranolazine in need of treatment with posaconazole would stop taking ranolazine while being treated with posaconazole, and then resume ranolazine shortly after finishing the posaconazole regimen to recommence treatment for chronic angina. The results of this study suggest that physicians should instruct their patients to delay/limit the dose of ranolazine for an extended period after stopping posaconazole to avoid drug-drug interactions due to residual posaconazole levels.

CONCLUSION

Posaconazole, a known CYP3A strong inhibitor, increases ranolazine concentrations to a clinically relevant and potentially hazardous extent during concomitant administration and for several days following its discontinuation. Although steady-state posaconazole concentrations are lower in obese subjects than in normal-weight subjects, its half-life is increased in obese subjects such that the persistence of the interaction is observed in both obese and normal-weight people. The magnitude of the interaction between ranolazine and residual posaconazole elevates ranolazine plasma concentrations to the extent that they are at risk for significant QTc prolongation and potentially fatal cardiac arrhythmias. Based on the results of this study, administration of ranolazine should be limited to 500 mg twice daily for 7 days after posaconazole discontinuation in patients with BMI 18.5-24.9 kg/m$^2$ and for 12 days in patients with BMI≥35 kg/m$^2$ after ranolazine is resumed.

The invention claimed is:

1. A method of treating lung cancer in a patient in need thereof with an antineoplastic drug which is a CYP3A4 substrate, wherein the patient is treated with a strong CYP3A4 inhibitor, comprising:
   (a) discontinuing the strong CYP3A4 inhibitor treatment;
   (b) delaying administering, for at least about 4 days after discontinuing the strong CYP3A4 inhibitor treatment, a dose of the anti-neoplastic drug that the patient would have received based on the patient's age and condition if the patient had not been treated with the strong CYP3A4 inhibitor; and then
   (c) administering the anti-neoplastic drug;
   wherein the strong CYP3A4 inhibitor is posaconazole.

2. The method of claim 1, wherein the patient is not obese.

3. The method of claim 1, wherein the patient has at least one characteristic selected from the group consisting of the following:
   i) body mass index (BMI) of at least about 35;
   ii) waist size greater than about 42 inches;
   iii) % body fat greater than about 40%;
   iv) total body fat greater than about 40 kg; and,
   v) medically diagnosed as obese.

4. The method of claim 1, wherein said administering in step (c) is about 4 days to about 11 days after stopping posaconazole in step (a).

5. The method of claim 1, wherein said administering in step (c) is about 4 days to about 9 days after stopping posaconazole in step (a).

6. The method of claim 1, wherein said administering in step (c) is about 4 days after stopping posaconazole in step (a).

7. The method of claim 1, wherein said administering in step (c) is about 5 days after stopping posaconazole in step (a).

8. The method of claim 1, wherein said administering in step (c) is about 6 days after stopping posaconazole in step (a).

9. The method of claim 1, wherein said administering in step (c) is about 7 days after stopping posaconazole in step (a).

10. The method of claim 1, wherein said administering in step (c) is about 8 days after stopping posaconazole in step (a).

11. The method of claim 1, wherein said administering in step (c) is about 9 days after stopping posaconazole in step (a).

12. The method of claim 1, wherein said administering of step (c) is about 10 days after stopping posaconazole in step (a).

13. The method of claim 1, wherein said administering in step (c) is about 11 days after stopping posaconazole in step (a).

14. The method of claim 1, wherein said administering in step (c) is about 12 days after stopping posaconazole in step (a).

15. The method of claim 1, wherein the lung cancer is non-small cell lung cancer (NSCLC).

16. The method of claim 1, wherein the anti-neoplastic drug is selected from the group consisting of erlotinib, crizotinib, dabrafenib, brigatinib, lorlatinib, and trastuzumab deruxtecan.

17. The method of claim 1, wherein the anti-neoplastic drug is erlotinib.

18. The method of claim 1, wherein the anti-neoplastic drug is crizotinib.

19. The method of claim 1, wherein the anti-neoplastic drug is dabrafenib.

20. The method of claim 1, wherein the anti-neoplastic drug is brigatinib.

21. The method of claim 1, wherein the anti-neoplastic drug is lorlatinib.

22. The method of claim 1, wherein the anti-neoplastic drug is trastuzumab deruxtecan.

23. The method of claim 15, wherein the NSCLC is metastatic NSCLC.

24. The method of claim 23, wherein the metastatic NSCLC tumors are ROS1-positive.

25. The method of claim 23, wherein the metastatic NSCLC tumors are anaplastic lymphoma kinase (ALK)-positive.

26. The method of claim 25, wherein said administering in step (c) is about 5 days after stopping posaconazole in step (a).

27. The method of claim 25, wherein said administering in step (c) is about 6 days after stopping posaconazole in step (a).

28. The method of claim 25, wherein said administering in step (c) is about 7 days after stopping posaconazole in step (a).

29. The method of claim 25, wherein said administering in step (c) is about 8 days after stopping posaconazole in step (a).

30. The method of claim 25, wherein said administering in step (c) is about 9 days after stopping posaconazole in step (a).

* * * * *